United States Patent
Armstrong et al.

(10) Patent No.: US 10,221,250 B2
(45) Date of Patent: Mar. 5, 2019

(54) INTERNALIZING MOIETIES

(71) Applicant: Valerion Therapeutics, LLC, Concord, MA (US)

(72) Inventors: Dustin D. Armstrong, Quincy, MA (US); Jeffrey C. Way, Cambridge, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 0 days.

(21) Appl. No.: 15/111,160

(22) PCT Filed: Jan. 13, 2015

(86) PCT No.: PCT/US2015/011269
§ 371 (c)(1),
(2) Date: Jul. 12, 2016

(87) PCT Pub. No.: WO2015/106290
PCT Pub. Date: Jul. 16, 2015

(65) Prior Publication Data
US 2017/0174790 A1    Jun. 22, 2017

Related U.S. Application Data

(60) Provisional application No. 62/042,755, filed on Aug. 27, 2014, provisional application No. 62/042,771, filed on Aug. 27, 2014, provisional application No. 61/926,863, filed on Jan. 13, 2014, provisional application No. 61/926,865, filed on Jan. 13, 2014.

(51) Int. Cl.
| | |
|---|---|
| *C07K 16/44* | (2006.01) |
| *C07K 14/47* | (2006.01) |
| *A61K 38/00* | (2006.01) |

(52) U.S. Cl.
CPC .............. *C07K 16/44* (2013.01); *C07K 14/47* (2013.01); *A61K 38/00* (2013.01); *C07K 2317/24* (2013.01); *C07K 2317/55* (2013.01); *C07K 2317/565* (2013.01); *C07K 2317/567* (2013.01); *C07K 2317/622* (2013.01); *C07K 2317/77* (2013.01); *C07K 2317/92* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 7,189,396 B1 | 3/2007 | Weisbart |
| 8,609,615 B2 | 12/2013 | Armstrong |
| 8,834,866 B2 | 9/2014 | Armstrong |
| 9,114,178 B2 | 8/2015 | Armstrong |
| 9,447,394 B2 | 9/2016 | Armstrong |
| 2008/0292618 A1 | 11/2008 | Weisbart |
| 2010/0143358 A1 | 6/2010 | Weisbart |
| 2013/0266570 A1 | 10/2013 | Weisbart et al. |
| 2015/0064181 A1 | 3/2015 | Armstrong |
| 2015/0152170 A1 | 6/2015 | Armstrong et al. |
| 2016/0089451 A1 | 3/2016 | Armstrong |
| 2016/0108133 A1 | 4/2016 | Armstrong et al. |

FOREIGN PATENT DOCUMENTS

| | | |
|---|---|---|
| WO | WO-97/32602 A1 | 9/1997 |
| WO | WO-2008/091911 A2 | 7/2008 |
| WO | WO-2008/148063 A1 | 12/2008 |
| WO | WO-2010/044894 | 4/2010 |
| WO | WO-2010/148010 A1 | 12/2010 |
| WO | WO-2012/145125 A1 | 10/2012 |
| WO | WO-2013/138662 A1 | 9/2013 |
| WO | WO-2013/177428 | 11/2013 |
| WO | WO-2014/130722 A1 | 8/2014 |
| WO | WO-2014/130723 A1 | 8/2014 |
| WO | WO-2015/106290 A1 | 7/2015 |
| WO | WO-2015/192092 A1 | 12/2015 |
| WO | WO-2016/033324 A1 | 3/2016 |

OTHER PUBLICATIONS

Rudikoff et al., PNAS 79: 1979-1983, 1982.*
Kussie et al., J. Immunol. 152: 146-152, 1994.*
Chen et al., EMBO J., 14: 2784-2794, 1995.*
Wu et al., J. Mol. Biol. 294: 151-162, 1999.*
Abhinandan and Martin, "Analyzing the "Degree of Humanness" of Antibody Sequences," Journal Molecular Biology, vol. 369:852-862 (2007).
Ducancel, "Molecular Engineering of Antibodies for Therapeutic and Diagnostic Purposes," Landes Bioscience, 4(4): 445-457 (2012).
Hansen et al., Antibody-mediated Hsp70 Protein Therapy, Brain Research, 1088(1):187-196 (2006).
Hansen et al., Intranuclear Protein Transduction Through a Nucleoside Salvage Pathway, The Journal of Biological Chemistry, vol. 282(29):20790-20793 (2007).
Kunik et al., "Structural Consensus Among Antibodies Defines the Antigen Binding Site," PLoS Computational Biology, vol. 8(2): (12 pages) (2012).
Pennycooke et al., "Differential Expression of Human Nucleoside Transporters in Normal and Tumor Tissue," Biochemical and Biophysical Research Communications, vol. 280(3):951-959 (2001).
Weisbart RH et al., "An Autoantibody is Modified for Use as a Delivery System to Target the Cell Nucleus: Therapeutic Implications," Journal of Autoimmunity, vol. 11(5):539-546 (1998).

(Continued)

*Primary Examiner* — Phuong Huynh
(74) *Attorney, Agent, or Firm* — Lisa M. Warren, Esq.; Morse, Barnes-Brown & Pendleton, P.C.

(57) ABSTRACT

The present disclosure provides antibodies and antigen-binding fragments capable of penetrating cells via an ENT transporter, such as humanized antibodies. The disclosure also provides conjugates comprising the antibodies or antigen-binding fragments and a heterologous agent. The disclosure further provides methods for making and using the antibodies, antigen-binding fragments and conjugates, including humanized antibodies.

16 Claims, 6 Drawing Sheets
(3 of 6 Drawing Sheet(s) Filed in Color)
Specification includes a Sequence Listing.

(56) References Cited

OTHER PUBLICATIONS

Weisbart RH et al., "An intracellular Delivery Vehicle for Pprotein Tansduction of Micro-Dystrophin," Journal of Drug Targeting, vol. 13(2):81-87 (2005).
Weisbart RH et al., "Novel Protein Transfection of Primary Rat Cortical Neurons Using an Antibody that Penetrates Living Cells," The Journal of Immunology, vol. 164:6020-6026 (2000).
Weisbart RH et al., "Nuclear delivery of p53 C-terminal peptides into cancer calls using scFv fragments of a monoclonal antibody that penetrates living cells," Cancer Letters, vol. 195(2):211-219 (2003).
Weisbart RH, et al., "Cell type specific targeted intracellular delivery into muscle of a monoclonal antibody that binds myosin llb," Molecular Immunology, vol. 39(13):783-789 (2003).
Yamane-Ohnuki,"Production of Therapeutic Antibodies with Controlled Fucosylation," Landes Bioscience, 1(3): 230-236 (2009).
Zack DJ et al., "Mechanisms of Cellular Penetration and Nuclear Localization of an Anti-Double Strand DNA Autoantibody," Journal of Immunology, vol. 157(5):2082-2088 (1996).
Zack, et al., "DNA Mimics a Self-Protein That May Be a Target for Some Anti-DNA Antibodies in Systemic Lupus Erythematosus," *The Journal of Immunology*, 154:1987-1994, (Feb. 15, 1995).
Extended European Search Report from EP 15735467.1, dated Jun. 1, 2017.
International Search Report from PCT/US2015/011269, dated Apr. 14, 2015.

\* cited by examiner

Figure 1

```
MH1  EVQLVESGGGLVKPGGSRKLSCAASGFTFSNYGMHWVRQAPEKGLEWVAYISSGSSTIYY  60
HH1  EVQLVESGGGLIQPGGSLRLSCAASGFTFSNYGMHWVRQAPGKGLEWVSYISSGSSTIYY  60
HH2  EVQLVESGGGLIQPGGSLRLSCAASGFTFSNYGMHWVRQAPGKGLEWVSYISSGSSTIYY  60
HH3  EVQLVESGGGVQPGGSLRLSCAASGFTFSNYGMHWVRQAPGKGLEWVSYISSGSSTIYY  60
     **********  ******  **:***********:*** ******.*** ***.*********

MH1  ADTVKGRFTISRDNAKNTLFLQMTSLRSEDTAMYYCARPGLLDYWGQGTTLTVSS  116
HH1  ADSVKGRFTISRDNSKNTLYLQMMSLRAEDTAVYYCARPGLLDYWGQGTTLVTVSS  116
HH2  ADSVKGRFTISRDNSKNTLYLQMNSLRAEDTAVYYCARPGLLDYWGQGTTLVTVSS  116
HH3  ADSVKGRFTISRDNSKNTLYLQMNSLRAEDTAVYYCARPGLLDYWGQGTTLVTVSS  116
     **:**********:**** ***.***:****:*************  *********

ML1  DIVLTQSPASLAVSLGQRATISCRASKSVSTSGYSYMHWYQQKPGQPPKLLIKASYLES  60
HL1  DIQMTQSPSSLSASVGDRVTITCRASKSVSTSGYSYLAWYQQKPEKAPKLLIKASYLQS  60
HL2  DIQMTQSPSSLSASVGDRVTISCRASKSVSTSGYSYLAWYQQKPEKAPKLLIFASYLQS  60
     **  ****:**:**:** **::*****************:***:*:******:****:*

ML1  GVPARFSGSGSGTDFHLNIHPVEEEDAATYYCQHSRELPWFGGGTKLEIK  111
HL1  GVPSRFSGSGSGTDFTLTISSLQPEDFATYYCQHSRELPWFGAGTKLELK  111
HL2  GVPSRFSGSGSGTDFTLTISSLQPEDVATYYCQHSRELPWFGAGTKLELK  111
     ***:***********.*.*.*  ***:***************.****:*
```

| Sample | Visual | | A280 (mg/mL) | | X Fold | Recovery | Turbidity | pH | | Area% Main Peak | | SDS-PAGE | |
|---|---|---|---|---|---|---|---|---|---|---|---|---|---|
| | Pre-Conc. | Conc. | Pre-Conc. | Conc. | | % | Δ 600nm | Pre-Conc. | Conc. | Pre-Conc. | Conc. | Red | Non-red |
| MH1/ML1 | Clear | Opal | 2.02 | 28.9 | 14.3 | 99.2 | 0.0233 | 7.17 | 7.17 | 98.8 | 98.8 | NC | NC |
| HH1/HL1 | Clear | Opal, hazy | 1.59 | 25.9 | 16.3 | 89.0 | 0.0449 | 7.14 | 7.17 | 99.9 | 99.9 | NC | NC |
| HH1/HL2 | Clear | Opal, Low VP | 0.87 | 33.6 | 38.6 | 95.3 | 0.2165 | 7.51 | 7.42 | 99.9 | 98.8 | NC | NC |
| HH2/HL1 | slight hazy | Opal, hazy Low VP | 1.26 | 33.4 | 26.5 | 96.7 | 0.1295 | 7.24 | 7.24 | 99.3 | 99.3 | NC | NC |
| HH2/HL2 | slight hazy, high VP | Opal, high VP | 1.34 | 25.4 | 19.0 | 69.3 | 0.4345 | 7.29 | 7.24 | 99.9 | 99.9 | NC | NBTG |
| HH3/HL1 | Clear | Opal, hazy | 1.27 | 30.9 | 24.3 | 85.2 | 0.0554 | 7.20 | 7.23 | 99.9 | 99.9 | NC | NBTG |
| HH3/HL2 | Clear | Opal | 1.33 | 30.0 | 22.6 | 87.5 | 0.0490 | 7.24 | 7.20 | 100.0 | 99.9 | NC | NBTG |

Fig. 4

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Ser Gly Ser Ser Thr Ile
1               5

<210> SEQ ID NO 3
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 3

Ala Arg Arg Gly Leu Leu Leu Asp Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ser Val Ser Thr Ser Ser Tyr Ser Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Ser Arg Glu Phe Pro Trp Thr
1               5

<210> SEQ ID NO 7
<211> LENGTH: 111
<212> TYPE: PRT
<213> ORGANISM: Mus sp.

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
                100                 105                 110
```

-continued

```
<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Leu Ser Ala Ser Val Gly
1               5                   10                  15

Asp Arg Val Thr Ile Ser Cys Arg Ala Ser Lys Ser Val Ser Thr Ser
            20                  25                  30

Ser Tyr Ser Tyr Met His Trp Tyr Gln Gln Lys Pro Glu Lys Ala Pro
        35                  40                  45

Lys Leu Leu Ile Lys Tyr Ala Ser Tyr Leu Gln Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln His Ser Arg
                85                  90                  95

Glu Phe Pro Trp Thr Phe Gly Ala Gly Thr Lys Leu Glu Leu Lys
            100                 105                 110

<210> SEQ ID NO 9
<211> LENGTH: 116
<212> TYPE: PRT
<213> ORGANISM: Mus sp.

<400> SEQUENCE: 9

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met His Trp Ile Arg Gln Ala Pro Gly Lys Gly Leu Glu Trp Val
            35                  40                  45

Ser Tyr Ile Ser Ser Gly Ser Ser Thr Ile Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ser Glu Asp Thr Ala Val Tyr Tyr Cys
                 85                  90                  95

Ala Arg Arg Gly Leu Leu Leu Asp Tyr Trp Gly Gln Gly Thr Leu Val
             100                 105                 110

Thr Val Ser Ser
            115

<210> SEQ ID NO 11
<211> LENGTH: 602
<212> TYPE: PRT
<213> ORGANISM: Homo sapiens

<400> SEQUENCE: 11

Ala Ser Ala Ser Thr Ser Lys Tyr Asn Ser His Ser Leu Glu Asn Glu
1               5                   10                  15

Ser Ile Lys Arg Thr Ser Arg Asp Gly Val Asn Arg Asp Leu Thr Glu
                20                  25                  30

Ala Val Pro Arg Leu Pro Gly Glu Thr Leu Ile Thr Asp Lys Glu Val
             35                  40                  45

Ile Tyr Ile Cys Pro Phe Asn Gly Pro Ile Lys Gly Arg Val Tyr Ile
         50                  55                  60

Thr Asn Tyr Arg Leu Tyr Leu Arg Ser Leu Glu Thr Asp Ser Ser Leu
 65                  70                  75                  80

Ile Leu Asp Val Pro Leu Gly Val Ile Ser Arg Ile Glu Lys Met Gly
                 85                  90                  95

Gly Ala Thr Ser Arg Gly Glu Asn Ser Tyr Gly Leu Asp Ile Thr Cys
             100                 105                 110

Lys Asp Met Arg Asn Leu Arg Phe Ala Leu Lys Gln Glu Gly His Ser
         115                 120                 125

Arg Arg Asp Met Phe Glu Ile Leu Thr Arg Tyr Ala Phe Pro Leu Ala
130                 135                 140

His Ser Leu Pro Leu Phe Ala Phe Leu Asn Glu Glu Lys Phe Asn Val
145                 150                 155                 160

Asp Gly Trp Thr Val Tyr Asn Pro Val Glu Glu Tyr Arg Arg Gln Gly
                165                 170                 175

Leu Pro Asn His His Trp Arg Ile Thr Phe Ile Asn Lys Cys Tyr Glu
            180                 185                 190

Leu Cys Asp Thr Tyr Pro Ala Leu Leu Val Val Pro Tyr Arg Ala Ser
        195                 200                 205

Asp Asp Asp Leu Arg Arg Val Ala Thr Phe Arg Ser Arg Asn Arg Ile
210                 215                 220

Pro Val Leu Ser Trp Ile His Pro Glu Asn Lys Thr Val Ile Val Arg
225                 230                 235                 240

Cys Ser Gln Pro Leu Val Gly Met Ser Gly Lys Arg Asn Lys Asp Asp
                245                 250                 255

Glu Lys Tyr Leu Asp Val Ile Arg Glu Thr Asn Lys Gln Ile Ser Lys
            260                 265                 270

Leu Thr Ile Tyr Asp Ala Arg Pro Ser Val Asn Ala Val Ala Asn Lys
        275                 280                 285
```

```
Ala Thr Gly Gly Gly Tyr Glu Ser Asp Asp Ala Tyr His Asn Ala Glu
    290                 295                 300

Leu Phe Phe Leu Asp Ile His Asn Ile His Val Met Arg Glu Ser Leu
305                 310                 315                 320

Lys Lys Val Lys Asp Ile Val Tyr Pro Asn Val Glu Glu Ser His Trp
                325                 330                 335

Leu Ser Ser Leu Glu Ser Thr His Trp Leu Glu His Ile Lys Leu Val
                340                 345                 350

Leu Thr Gly Ala Ile Gln Val Ala Asp Lys Val Ser Ser Gly Lys Ser
            355                 360                 365

Ser Val Leu Val His Cys Ser Asp Gly Trp Asp Arg Thr Ala Gln Leu
        370                 375                 380

Thr Ser Leu Ala Met Leu Met Leu Asp Ser Phe Tyr Arg Ser Ile Glu
385                 390                 395                 400

Gly Phe Glu Ile Leu Val Gln Lys Glu Trp Ile Ser Phe Gly His Lys
                405                 410                 415

Phe Ala Ser Arg Ile Gly His Gly Asp Lys Asn His Thr Asp Ala Asp
            420                 425                 430

Arg Ser Pro Ile Phe Leu Gln Phe Ile Asp Cys Val Trp Gln Met Ser
        435                 440                 445

Lys Gln Phe Pro Thr Ala Phe Glu Phe Asn Glu Gln Phe Leu Ile Ile
    450                 455                 460

Ile Leu Asp His Leu Tyr Ser Cys Arg Phe Gly Thr Phe Leu Phe Asn
465                 470                 475                 480

Cys Glu Ser Ala Arg Glu Arg Gln Lys Val Thr Glu Arg Thr Val Ser
                485                 490                 495

Leu Trp Ser Leu Ile Asn Ser Asn Lys Glu Lys Phe Lys Asn Pro Phe
            500                 505                 510

Tyr Thr Lys Glu Ile Asn Arg Val Leu Tyr Pro Val Ala Ser Met Arg
        515                 520                 525

His Leu Glu Leu Trp Val Asn Tyr Tyr Ile Arg Trp Asn Pro Arg Ile
    530                 535                 540

Lys Gln Gln Gln Pro Asn Pro Val Glu Gln Arg Tyr Met Glu Leu Leu
545                 550                 555                 560

Ala Leu Arg Asp Glu Tyr Ile Lys Arg Leu Glu Glu Leu Gln Leu Ala
                565                 570                 575

Asn Ser Ala Lys Leu Ser Asp Pro Pro Thr Ser Pro Ser Pro Ser
            580                 585                 590

Gln Met Met Pro His Val Gln Thr His Phe
        595                 600

<210> SEQ ID NO 12
<211> LENGTH: 381
<212> TYPE: PRT
<213> ORGANISM: Homo sapiens

<400> SEQUENCE: 12

Ala Val Ser Val Thr Pro Ile Arg Asp Thr Lys Trp Leu Thr Leu Glu
1               5                   10                  15

Val Cys Arg Glu Phe Gln Arg Gly Thr Cys Ser Arg Pro Asp Thr Glu
                20                  25                  30

Cys Lys Phe Ala His Pro Ser Lys Ser Cys Gln Val Glu Asn Gly Arg
            35                  40                  45

Val Ile Ala Cys Phe Asp Ser Leu Lys Gly Arg Cys Ser Arg Glu Asn
        50                  55                  60
```

```
Cys Lys Tyr Leu His Pro Pro His Leu Lys Thr Gln Leu Glu Ile
 65                  70                  75                  80

Asn Gly Arg Asn Asn Leu Ile Gln Gln Lys Asn Met Ala Met Leu Ala
             85                  90                  95

Gln Gln Met Gln Leu Ala Asn Ala Met Met Pro Gly Ala Pro Leu Gln
            100                 105                 110

Pro Val Pro Met Phe Ser Val Ala Pro Ser Leu Ala Thr Asn Ala Ser
            115                 120                 125

Ala Ala Ala Phe Asn Pro Tyr Leu Gly Pro Val Pro Ser Leu Val
        130                 135                 140

Pro Ala Glu Ile Leu Pro Thr Ala Pro Met Leu Val Thr Gly Asn Pro
145                 150                 155                 160

Gly Val Pro Val Pro Ala Ala Ala Ala Ala Ala Gln Lys Leu Met
            165                 170                 175

Arg Thr Asp Arg Leu Glu Val Cys Arg Glu Tyr Gln Arg Gly Asn Cys
            180                 185                 190

Asn Arg Gly Glu Asn Asp Cys Arg Phe Ala His Pro Ala Asp Ser Thr
        195                 200                 205

Met Ile Asp Thr Asn Asp Asn Thr Val Thr Val Cys Met Asp Tyr Ile
210                 215                 220

Lys Gly Arg Cys Ser Arg Glu Lys Cys Lys Tyr Phe His Pro Pro Ala
225                 230                 235                 240

His Leu Gln Ala Lys Ile Lys Ala Ala Gln Tyr Gln Val Asn Gln Ala
                245                 250                 255

Ala Ala Ala Gln Ala Ala Ala Thr Ala Ala Met Gly Ile Pro Gln
        260                 265                 270

Ala Val Leu Pro Pro Leu Pro Lys Arg Pro Ala Leu Glu Lys Thr Asn
        275                 280                 285

Gly Ala Thr Ala Val Phe Asn Thr Gly Ile Phe Gln Tyr Gln Gln Ala
        290                 295                 300

Leu Ala Asn Met Gln Leu Gln Gln His Thr Ala Phe Leu Pro Pro Gly
305                 310                 315                 320

Ser Ile Leu Cys Met Thr Pro Ala Thr Ser Val Val Pro Met Val His
                325                 330                 335

Gly Ala Thr Pro Ala Thr Val Ser Ala Ala Thr Thr Ser Ala Thr Ser
                340                 345                 350

Val Pro Phe Ala Ala Thr Ala Thr Ala Asn Gln Ile Pro Ile Ile Ser
            355                 360                 365

Ala Glu His Leu Thr Ser His Lys Tyr Val Thr Gln Met
        370                 375                 380

<210> SEQ ID NO 13
<211> LENGTH: 370
<212> TYPE: PRT
<213> ORGANISM: Homo sapiens

<400> SEQUENCE: 13

Met Ala Val Ser Val Thr Pro Ile Arg Asp Thr Lys Trp Leu Thr Leu
  1               5                  10                  15

Glu Val Cys Arg Glu Phe Gln Arg Gly Thr Cys Ser Arg Pro Asp Thr
             20                  25                  30

Glu Cys Lys Phe Ala His Pro Ser Lys Ser Cys Gln Val Glu Asn Gly
         35                  40                  45

Arg Val Ile Ala Cys Phe Asp Ser Leu Lys Gly Arg Cys Ser Arg Glu
     50                  55                  60
```

```
Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
             85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Phe Asn Pro Tyr Leu Gly Pro Val Ser Pro Ser Leu
130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
                180                 185                 190

Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
        210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Ala Thr Ala Ala Ala Met Gly Ile Pro
            260                 265                 270

Gln Ala Val Leu Pro Pro Leu Pro Lys Arg Pro Ala Leu Glu Lys Thr
        275                 280                 285

Asn Gly Ala Thr Ala Val Phe Asn Thr Gly Ile Phe Gln Tyr Gln Gln
290                 295                 300

Ala Leu Ala Asn Met Gln Leu Gln Gln His Thr Ala Phe Leu Pro Pro
305                 310                 315                 320

Val Pro Met Val His Gly Ala Thr Pro Ala Thr Val Ser Ala Ala Thr
                325                 330                 335

Thr Ser Ala Thr Ser Val Pro Phe Ala Ala Thr Ala Thr Ala Asn Gln
            340                 345                 350

Ile Pro Ile Ile Ser Ala Glu His Leu Thr Ser His Lys Tyr Val Thr
        355                 360                 365

Gln Met
    370

<210> SEQ ID NO 14
<211> LENGTH: 388
<212> TYPE: PRT
<213> ORGANISM: Homo sapiens

<400> SEQUENCE: 14

Met Ala Val Ser Val Thr Pro Ile Arg Asp Thr Lys Trp Leu Thr Leu
1               5                  10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60
```

```
Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
             85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
            115                 120                 125

Ser Ala Ala Phe Asn Pro Tyr Leu Gly Pro Val Ser Pro Ser Leu
        130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
            165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
        210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
            245                 250                 255

Ala Ala Ala Ala Gln Ala Ala Thr Ala Ala Ala Met Thr Gln Ser
        260                 265                 270

Ala Val Lys Ser Leu Lys Arg Pro Leu Glu Ala Thr Phe Asp Leu Gly
            275                 280                 285

Ile Pro Gln Ala Val Leu Pro Pro Leu Pro Lys Arg Pro Ala Leu Glu
            290                 295                 300

Lys Thr Asn Gly Ala Thr Ala Val Phe Asn Thr Gly Ile Phe Gln Tyr
305                 310                 315                 320

Gln Gln Ala Leu Ala Asn Met Gln Leu Gln Gln His Thr Ala Phe Leu
            325                 330                 335

Pro Pro Val Pro Met Val His Gly Ala Thr Pro Ala Thr Val Ser Ala
            340                 345                 350

Ala Thr Thr Ser Ala Thr Ser Val Pro Phe Ala Ala Thr Ala Thr Ala
            355                 360                 365

Asn Gln Ile Pro Ile Ile Ser Ala Glu His Leu Thr Ser His Lys Tyr
        370                 375                 380

Val Thr Gln Met
385

<210> SEQ ID NO 15
<211> LENGTH: 302
<212> TYPE: PRT
<213> ORGANISM: Homo sapiens

<400> SEQUENCE: 15

Met Ala Val Ser Val Thr Pro Ile Arg Asp Thr Lys Trp Leu Thr Leu
  1               5                  10                  15

Glu Val Cys Arg Glu Phe Gln Arg Gly Thr Cys Ser Arg Pro Asp Thr
             20                  25                  30

Glu Cys Lys Phe Ala His Pro Ser Lys Ser Cys Gln Val Glu Asn Gly
         35                  40                  45
```

```
Arg Val Ile Ala Cys Phe Asp Ser Leu Lys Gly Arg Cys Ser Arg Glu
 50                  55                  60

Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
                 85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
            115                 120                 125

Glu Asn Asp Cys Arg Phe Ala His Pro Ala Asp Ser Thr Met Ile Asp
130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met Gly Ile Pro Gln Ala Val Leu
            195                 200                 205

Pro Pro Leu Pro Lys Arg Pro Ala Leu Glu Lys Thr Asn Gly Ala Thr
210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Val Pro Met Val
                245                 250                 255

His Gly Ala Thr Pro Ala Thr Val Ser Ala Ala Thr Thr Ser Ala Thr
            260                 265                 270

Ser Val Pro Phe Ala Ala Thr Ala Thr Ala Asn Gln Ile Pro Ile Ile
            275                 280                 285

Ser Ala Glu His Leu Thr Ser His Lys Tyr Val Thr Gln Met
290                 295                 300

<210> SEQ ID NO 16
<211> LENGTH: 314
<212> TYPE: PRT
<213> ORGANISM: Homo sapiens

<400> SEQUENCE: 16

Met Ala Val Ser Val Thr Pro Ile Arg Asp Thr Lys Trp Leu Thr Leu
 1               5                  10                  15

Glu Val Cys Arg Glu Phe Gln Arg Gly Thr Cys Ser Arg Pro Asp Thr
                20                  25                  30

Glu Cys Lys Phe Ala His Pro Ser Lys Ser Cys Gln Val Glu Asn Gly
            35                  40                  45

Arg Val Ile Ala Cys Phe Asp Ser Leu Lys Gly Arg Cys Ser Arg Glu
 50                  55                  60

Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
                 85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
            115                 120                 125
```

```
Glu Asn Asp Cys Arg Phe Ala His Pro Ala Asp Ser Thr Met Ile Asp
130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met Gly Ile Pro Gln Ala Val Leu
        195                 200                 205

Pro Pro Leu Pro Lys Arg Pro Ala Leu Glu Lys Thr Asn Gly Ala Thr
210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Gly Ser Ile Leu
                245                 250                 255

Cys Met Thr Pro Ala Thr Ser Val Val Pro Met Val His Gly Ala Thr
                260                 265                 270

Pro Ala Thr Val Ser Ala Ala Thr Thr Ser Ala Thr Ser Val Pro Phe
            275                 280                 285

Ala Ala Thr Ala Thr Ala Asn Gln Ile Pro Ile Ile Ser Ala Glu His
        290                 295                 300

Leu Thr Ser His Lys Tyr Val Thr Gln Met
305                 310

<210> SEQ ID NO 17
<211> LENGTH: 340
<212> TYPE: PRT
<213> ORGANISM: Homo sapiens

<400> SEQUENCE: 17

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
                20                  25                  30

Glu Cys Lys Phe Ala His Pro Ser Lys Ser Cys Gln Val Glu Asn Gly
            35                  40                  45

Arg Val Ile Ala Cys Phe Asp Ser Leu Lys Gly Arg Cys Ser Arg Glu
50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190
```

```
Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
            245                 250                 255

Ala Ala Ala Ala Gln Ala Ala Ala Thr Ala Ala Ala Met Phe Pro Trp
            260                 265                 270

Cys Thr Val Leu Arg Gln Pro Leu Cys Pro Gln Gln Gln His Leu Pro
            275                 280                 285

Gln Val Phe Pro Ser Leu Gln Gln Pro Gln Thr Ser Pro Ile Leu
290                 295                 300

Asp Ala Ser Thr Leu Leu Gly Ala Thr Ser Cys Pro Ala Ala Ala Gly
305                 310                 315                 320

Lys Met Ile Pro Ile Ile Ser Ala Glu His Leu Thr Ser His Lys Tyr
            325                 330                 335

Val Thr Gln Met
            340

<210> SEQ ID NO 18
<211> LENGTH: 342
<212> TYPE: PRT
<213> ORGANISM: Homo sapiens

<400> SEQUENCE: 18

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
            85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
            165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220
```

```
Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
            245                 250                 255

Ala Ala Ala Ala Gln Ala Ala Thr Ala Ala Met Gly Ile Pro
            260                 265                 270

Gln Ala Val Leu Pro Pro Leu Pro Lys Arg Pro Ala Leu Glu Lys Thr
            275                 280                 285

Asn Gly Ala Thr Ala Val Phe Asn Thr Gly Ile Phe Gln Tyr Gln Gln
            290                 295                 300

Ala Leu Ala Asn Met Gln Leu Gln Gln His Thr Ala Phe Leu Pro Pro
305                 310                 315                 320

Gly Ser Ile Leu Cys Met Thr Pro Ala Thr Ser Val Asp Thr His Asn
                325                 330                 335

Ile Cys Arg Thr Ser Asp
                340

<210> SEQ ID NO 19
<211> LENGTH: 1532
<212> TYPE: PRT
<213> ORGANISM: Homo sapiens

<400> SEQUENCE: 19

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255
```

```
Phe Ser Cys Asp Val Ala Glu Gly Lys Tyr Lys Glu Lys Gly Ile Pro
                260                 265                 270

Ala Leu Ile Glu Asn Asp His His Met Asn Ser Ile Arg Lys Ile Ile
            275                 280                 285

Trp Glu Asp Ile Phe Pro Lys Leu Lys Leu Trp Glu Phe Phe Gln Val
        290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Lys Gly Pro Ala Ala Ile Glu
        355                 360                 365

Glu Cys Cys Asn Trp Phe His Lys Arg Met Glu Glu Leu Asn Ser Glu
370                 375                 380

Lys His Arg Leu Ile Asn Tyr His Gln Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Ile Asp Phe Ser Met Glu Glu Ser Met Ile His Leu
        435                 440                 445

Pro Asn Lys Ala Cys Phe Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asn Ser His Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Ile Ser Val Val Ser
            660                 665                 670
```

```
Glu Glu Arg Phe Tyr Thr Lys Trp Asn Pro Glu Ala Leu Pro Ser Asn
            675                 680                 685

Thr Gly Glu Val Asn Phe Gln Ser Gly Ile Ile Ala Ala Arg Cys Ala
690                 695                 700

Ile Ser Lys Leu His Gln Glu Leu Gly Ala Lys Gly Phe Ile Gln Val
705                 710                 715                 720

Tyr Val Asp Gln Val Asp Glu Asp Ile Val Ala Val Thr Arg His Ser
                725                 730                 735

Pro Ser Ile His Gln Ser Val Val Val Ser Arg Thr Ala Phe Arg
            740                 745                 750

Asn Pro Lys Thr Ser Phe Tyr Ser Lys Glu Val Pro Gln Met Cys Ile
            755                 760                 765

Pro Gly Lys Ile Glu Glu Val Val Leu Glu Ala Arg Thr Ile Glu Arg
770                 775                 780

Asn Thr Lys Pro Tyr Arg Lys Asp Glu Asn Ser Ile Asn Gly Thr Pro
785                 790                 795                 800

Asp Ile Thr Val Glu Ile Arg Glu His Ile Gln Leu Asn Glu Ser Lys
                805                 810                 815

Ile Val Lys Gln Ala Gly Val Ala Thr Lys Gly Pro Asn Glu Tyr Ile
            820                 825                 830

Gln Glu Ile Glu Phe Glu Asn Leu Ser Pro Gly Ser Val Ile Ile Phe
            835                 840                 845

Arg Val Ser Leu Asp Pro His Ala Gln Val Ala Val Gly Ile Leu Arg
            850                 855                 860

Asn His Leu Thr Gln Phe Ser Pro His Phe Lys Ser Gly Ser Leu Ala
865                 870                 875                 880

Val Asp Asn Ala Asp Pro Ile Leu Lys Ile Pro Phe Ala Ser Leu Ala
                885                 890                 895

Ser Arg Leu Thr Leu Ala Glu Leu Asn Gln Ile Leu Tyr Arg Cys Glu
            900                 905                 910

Ser Glu Glu Lys Glu Asp Gly Gly Cys Tyr Asp Ile Pro Asn Trp
            915                 920                 925

Ser Ala Leu Lys Tyr Ala Gly Leu Gln Gly Leu Met Ser Val Leu Ala
            930                 935                 940

Glu Ile Arg Pro Lys Asn Asp Leu Gly His Pro Phe Cys Asn Asn Leu
945                 950                 955                 960

Arg Ser Gly Asp Trp Met Ile Asp Tyr Val Ser Asn Arg Leu Ile Ser
                965                 970                 975

Arg Ser Gly Thr Ile Ala Glu Val Gly Lys Trp Leu Gln Ala Met Phe
            980                 985                 990

Phe Tyr Leu Lys Gln Ile Pro Arg Tyr Leu Ile Pro Cys Tyr Phe Asp
            995                 1000                1005

Ala Ile Leu Ile Gly Ala Tyr Thr Thr Leu Leu Asp Thr Ala Trp
    1010                1015                1020

Lys Gln Met Ser Ser Phe Val Gln Asn Gly Ser Thr Phe Val Lys
    1025                1030                1035

His Leu Ser Leu Gly Ser Val Gln Leu Cys Gly Val Gly Lys Phe
    1040                1045                1050

Pro Ser Leu Pro Ile Leu Ser Pro Ala Leu Met Asp Val Pro Tyr
    1055                1060                1065

Arg Leu Asn Glu Ile Thr Lys Glu Lys Glu Gln Cys Cys Val Ser
    1070                1075                1080
```

Leu Ala Ala Gly Leu Pro His Phe Ser Ser Gly Ile Phe Arg Cys
1085                    1090                    1095

Trp Gly Arg Asp Thr Phe Ile Ala Leu Arg Gly Ile Leu Leu Ile
1100                    1105                    1110

Thr Gly Arg Tyr Val Glu Ala Arg Asn Ile Ile Leu Ala Phe Ala
1115                    1120                    1125

Gly Thr Leu Arg His Gly Leu Ile Pro Asn Leu Leu Gly Glu Gly
1130                    1135                    1140

Ile Tyr Ala Arg Tyr Asn Cys Arg Asp Ala Val Trp Trp Trp Leu
1145                    1150                    1155

Gln Cys Ile Gln Asp Tyr Cys Lys Met Val Pro Asn Gly Leu Asp
1160                    1165                    1170

Ile Leu Lys Cys Pro Val Ser Arg Met Tyr Pro Thr Asp Asp Ser
1175                    1180                    1185

Ala Pro Leu Pro Ala Gly Thr Leu Asp Gln Pro Leu Phe Glu Val
1190                    1195                    1200

Ile Gln Glu Ala Met Gln Lys His Met Gln Gly Ile Gln Phe Arg
1205                    1210                    1215

Glu Arg Asn Ala Gly Pro Gln Ile Asp Arg Asn Met Lys Asp Glu
1220                    1225                    1230

Gly Phe Asn Ile Thr Ala Gly Val Asp Glu Glu Thr Gly Phe Val
1235                    1240                    1245

Tyr Gly Gly Asn Arg Phe Asn Cys Gly Thr Trp Met Asp Lys Met
1250                    1255                    1260

Gly Glu Ser Asp Arg Ala Arg Asn Arg Gly Ile Pro Ala Thr Pro
1265                    1270                    1275

Arg Asp Gly Ser Ala Val Glu Ile Val Gly Leu Ser Lys Ser Ala
1280                    1285                    1290

Val Arg Trp Leu Leu Glu Leu Ser Lys Lys Asn Ile Phe Pro Tyr
1295                    1300                    1305

His Glu Val Thr Val Lys Arg His Gly Lys Ala Ile Lys Val Ser
1310                    1315                    1320

Tyr Asp Glu Trp Asn Arg Lys Ile Gln Asp Asn Phe Glu Lys Leu
1325                    1330                    1335

Phe His Val Ser Glu Asp Pro Ser Asp Leu Asn Glu Lys His Pro
1340                    1345                    1350

Asn Leu Val His Lys Arg Gly Ile Tyr Lys Asp Ser Tyr Gly Ala
1355                    1360                    1365

Ser Ser Pro Trp Cys Asp Tyr Gln Leu Arg Pro Asn Phe Thr Ile
1370                    1375                    1380

Ala Met Val Val Ala Pro Glu Leu Phe Thr Thr Glu Lys Ala Trp
1385                    1390                    1395

Lys Ala Leu Glu Ile Ala Glu Lys Lys Leu Leu Gly Pro Leu Gly
1400                    1405                    1410

Met Lys Thr Leu Asp Pro Asp Asp Met Val Tyr Cys Gly Ile Tyr
1415                    1420                    1425

Asp Asn Ala Leu Asp Asn Asp Asn Tyr Asn Leu Ala Lys Gly Phe
1430                    1435                    1440

Asn Tyr His Gln Gly Pro Glu Trp Leu Trp Pro Ile Gly Tyr Phe
1445                    1450                    1455

Leu Arg Ala Lys Leu Tyr Phe Ser Arg Leu Met Gly Pro Glu Thr
1460                    1465                    1470

```
Thr Ala Lys Thr Ile Val Leu Val Lys Asn Val Leu Ser Arg His
    1475                1480                1485

Tyr Val His Leu Glu Arg Ser Pro Trp Lys Gly Leu Pro Glu Leu
    1490                1495                1500

Thr Asn Glu Asn Ala Gln Tyr Cys Pro Phe Ser Cys Glu Thr Gln
    1505                1510                1515

Ala Trp Ser Ile Ala Thr Ile Leu Glu Thr Leu Tyr Asp Leu
    1520                1525                1530

<210> SEQ ID NO 20
<211> LENGTH: 1515
<212> TYPE: PRT
<213> ORGANISM: Homo sapiens

<400> SEQUENCE: 20

Met Ser Leu Leu Thr Cys Ala Phe Tyr Leu Gly Tyr Glu Leu Gln Phe
1               5                   10                  15

Arg Leu Gly Pro Thr Leu Gln Gly Lys Ala Val Thr Val Tyr Thr Asn
            20                  25                  30

Tyr Pro Phe Pro Gly Glu Thr Phe Asn Arg Glu Lys Phe Arg Ser Leu
        35                  40                  45

Asp Trp Glu Asn Pro Thr Glu Arg Glu Asp Ser Asp Lys Tyr Cys
    50                  55                  60

Lys Leu Asn Leu Gln Gln Ser Gly Ser Phe Gln Tyr Tyr Phe Leu Gln
65                  70                  75                  80

Gly Asn Glu Lys Ser Gly Gly Gly Tyr Ile Val Val Asp Pro Ile Leu
                85                  90                  95

Arg Val Gly Ala Asp Asn His Val Leu Pro Leu Asp Cys Val Thr Leu
            100                 105                 110

Gln Thr Phe Leu Ala Lys Cys Leu Gly Pro Phe Asp Glu Trp Glu Ser
        115                 120                 125

Arg Leu Arg Val Ala Lys Glu Ser Gly Tyr Asn Met Ile His Phe Thr
    130                 135                 140

Pro Leu Gln Thr Leu Gly Leu Ser Arg Ser Cys Tyr Ser Leu Ala Asn
145                 150                 155                 160

Gln Leu Glu Leu Asn Pro Asp Phe Ser Arg Pro Asn Arg Lys Tyr Thr
                165                 170                 175

Trp Asn Asp Val Gly Gln Leu Val Glu Lys Leu Lys Lys Glu Trp Asn
            180                 185                 190

Val Ile Cys Ile Thr Asp Val Val Tyr Asn His Thr Ala Ala Asn Ser
        195                 200                 205

Lys Trp Ile Gln Glu His Pro Glu Cys Ala Tyr Asn Leu Val Asn Ser
    210                 215                 220

Pro His Leu Lys Pro Ala Trp Val Leu Asp Arg Ala Leu Trp Arg Phe
225                 230                 235                 240

Ser Cys Asp Val Ala Glu Gly Lys Tyr Lys Glu Lys Gly Ile Pro Ala
                245                 250                 255

Leu Ile Glu Asn Asp His His Met Asn Ser Ile Arg Lys Ile Ile Trp
            260                 265                 270

Glu Asp Ile Phe Pro Lys Leu Lys Leu Trp Glu Phe Phe Gln Val Asp
        275                 280                 285

Val Asn Lys Ala Val Glu Gln Phe Arg Arg Leu Leu Thr Gln Glu Asn
    290                 295                 300

Arg Arg Val Thr Lys Ser Asp Pro Asn Gln His Leu Thr Ile Ile Gln
305                 310                 315                 320
```

-continued

```
Asp Pro Glu Tyr Arg Arg Phe Gly Cys Thr Val Asp Met Asn Ile Ala
            325                 330                 335

Leu Thr Thr Phe Ile Pro His Asp Lys Gly Pro Ala Ala Ile Glu Glu
        340                 345                 350

Cys Cys Asn Trp Phe His Lys Arg Met Glu Glu Leu Asn Ser Glu Lys
            355                 360                 365

His Arg Leu Ile Asn Tyr His Gln Glu Gln Ala Val Asn Cys Leu Leu
370                 375                 380

Gly Asn Val Phe Tyr Glu Arg Leu Ala Gly His Gly Pro Lys Leu Gly
385                 390                 395                 400

Pro Val Thr Arg Lys His Pro Leu Val Thr Arg Tyr Phe Thr Phe Pro
                405                 410                 415

Phe Glu Glu Ile Asp Phe Ser Met Glu Glu Ser Met Ile His Leu Pro
                420                 425                 430

Asn Lys Ala Cys Phe Leu Met Ala His Asn Gly Trp Val Met Gly Asp
            435                 440                 445

Asp Pro Leu Arg Asn Phe Ala Glu Pro Gly Ser Glu Val Tyr Leu Arg
        450                 455                 460

Arg Glu Leu Ile Cys Trp Gly Asp Ser Val Lys Leu Arg Tyr Gly Asn
465                 470                 475                 480

Lys Pro Glu Asp Cys Pro Tyr Leu Trp Ala His Met Lys Lys Tyr Thr
                485                 490                 495

Glu Ile Thr Ala Thr Tyr Phe Gln Gly Val Arg Leu Asp Asn Cys His
            500                 505                 510

Ser Thr Pro Leu His Val Ala Glu Tyr Met Leu Asp Ala Ala Arg Asn
        515                 520                 525

Leu Gln Pro Asn Leu Tyr Val Val Ala Glu Leu Phe Thr Gly Ser Glu
        530                 535                 540

Asp Leu Asp Asn Val Phe Val Thr Arg Leu Gly Ile Ser Ser Leu Ile
545                 550                 555                 560

Arg Glu Ala Met Ser Ala Tyr Asn Ser His Glu Glu Gly Arg Leu Val
                565                 570                 575

Tyr Arg Tyr Gly Gly Glu Pro Val Gly Ser Phe Val Gln Pro Cys Leu
                580                 585                 590

Arg Pro Leu Met Pro Ala Ile Ala His Ala Leu Phe Met Asp Ile Thr
            595                 600                 605

His Asp Asn Glu Cys Pro Ile Val His Arg Ser Ala Tyr Asp Ala Leu
        610                 615                 620

Pro Ser Thr Thr Ile Val Ser Met Ala Cys Cys Ala Ser Gly Ser Thr
625                 630                 635                 640

Arg Gly Tyr Asp Glu Leu Val Pro His Gln Ile Ser Val Val Ser Glu
                645                 650                 655

Glu Arg Phe Tyr Thr Lys Trp Asn Pro Glu Ala Leu Pro Ser Asn Thr
            660                 665                 670

Gly Glu Val Asn Phe Gln Ser Gly Ile Ile Ala Ala Arg Cys Ala Ile
        675                 680                 685

Ser Lys Leu His Gln Glu Leu Gly Ala Lys Gly Phe Ile Gln Val Tyr
        690                 695                 700

Val Asp Gln Val Asp Glu Asp Ile Val Ala Val Thr Arg His Ser Pro
705                 710                 715                 720
```

```
Ser Ile His Gln Ser Val Ala Val Ser Arg Thr Ala Phe Arg Asn
            725                 730                 735

Pro Lys Thr Ser Phe Tyr Ser Lys Glu Val Pro Gln Met Cys Ile Pro
        740                 745                 750

Gly Lys Ile Glu Glu Val Val Leu Glu Ala Arg Thr Ile Glu Arg Asn
        755                 760                 765

Thr Lys Pro Tyr Arg Lys Asp Glu Asn Ser Ile Asn Gly Thr Pro Asp
        770                 775                 780

Ile Thr Val Glu Ile Arg Glu His Ile Gln Leu Asn Glu Ser Lys Ile
785                 790                 795                 800

Val Lys Gln Ala Gly Val Ala Thr Lys Gly Pro Asn Glu Tyr Ile Gln
                805                 810                 815

Glu Ile Glu Phe Glu Asn Leu Ser Pro Gly Ser Val Ile Ile Phe Arg
                820                 825                 830

Val Ser Leu Asp Pro His Ala Gln Val Ala Val Gly Ile Leu Arg Asn
                835                 840                 845

His Leu Thr Gln Phe Ser Pro His Phe Lys Ser Gly Ser Leu Ala Val
        850                 855                 860

Asp Asn Ala Asp Pro Ile Leu Lys Ile Pro Phe Ala Ser Leu Ala Ser
865                 870                 875                 880

Arg Leu Thr Leu Ala Glu Leu Asn Gln Ile Leu Tyr Arg Cys Glu Ser
                885                 890                 895

Glu Glu Lys Glu Asp Gly Gly Gly Cys Tyr Asp Ile Pro Asn Trp Ser
                900                 905                 910

Ala Leu Lys Tyr Ala Gly Leu Gln Gly Leu Met Ser Val Leu Ala Glu
        915                 920                 925

Ile Arg Pro Lys Asn Asp Leu Gly His Pro Phe Cys Asn Asn Leu Arg
        930                 935                 940

Ser Gly Asp Trp Met Ile Asp Tyr Val Ser Asn Arg Leu Ile Ser Arg
945                 950                 955                 960

Ser Gly Thr Ile Ala Glu Val Gly Lys Trp Leu Gln Ala Met Phe Phe
                965                 970                 975

Tyr Leu Lys Gln Ile Pro Arg Tyr Leu Ile Pro Cys Tyr Phe Asp Ala
            980                 985                 990

Ile Leu Ile Gly Ala Tyr Thr Thr Leu Leu Asp Thr Ala Trp Lys Gln
        995                 1000                1005

Met Ser  Ser Phe Val Gln  Asn  Gly Ser Thr Phe Val  Lys His Leu
        1010                1015                1020

Ser Leu  Gly Ser Val Gln  Leu  Cys Gly Val Gly Lys  Phe Pro Ser
        1025                1030                1035

Leu Pro  Ile Leu Ser Pro  Ala  Leu Met Asp Val Pro  Tyr Arg Leu
        1040                1045                1050

Asn Glu  Ile Thr Lys Glu  Lys  Glu Gln Cys Cys Val  Ser Leu Ala
        1055                1060                1065

Ala Gly  Leu Pro His Phe  Ser  Ser Gly Ile Phe Arg  Cys Trp Gly
        1070                1075                1080

Arg Asp  Thr Phe Ile Ala  Leu  Arg Gly Ile Leu Leu  Ile Thr Gly
        1085                1090                1095

Arg Tyr  Val Glu Ala Arg  Asn  Ile Ile Leu Ala Phe  Ala Gly Thr
        1100                1105                1110

Leu Arg  His Gly Leu Ile  Pro  Asn Leu Leu Gly Glu  Gly Ile Tyr
        1115                1120                1125
```

```
Ala Arg Tyr Asn Cys Arg Asp Ala Val Trp Trp Trp Leu Gln Cys
1130                1135                1140

Ile Gln Asp Tyr Cys Lys Met Val Pro Asn Gly Leu Asp Ile Leu
1145                1150                1155

Lys Cys Pro Val Ser Arg Met Tyr Pro Thr Asp Ser Ala Pro
1160                1165                1170

Leu Pro Ala Gly Thr Leu Asp Gln Pro Leu Phe Glu Val Ile Gln
1175                1180                1185

Glu Ala Met Gln Lys His Met Gln Gly Ile Gln Phe Arg Glu Arg
1190                1195                1200

Asn Ala Gly Pro Gln Ile Asp Arg Asn Met Lys Asp Glu Gly Phe
1205                1210                1215

Asn Ile Thr Ala Gly Val Asp Glu Glu Thr Gly Phe Val Tyr Gly
1220                1225                1230

Gly Asn Arg Phe Asn Cys Gly Thr Trp Met Asp Lys Met Gly Glu
1235                1240                1245

Ser Asp Arg Ala Arg Asn Arg Gly Ile Pro Ala Thr Pro Arg Asp
1250                1255                1260

Gly Ser Ala Val Glu Ile Val Gly Leu Ser Lys Ser Ala Val Arg
1265                1270                1275

Trp Leu Leu Glu Leu Ser Lys Lys Asn Ile Phe Pro Tyr His Glu
1280                1285                1290

Val Thr Val Lys Arg His Gly Lys Ala Ile Lys Val Ser Tyr Asp
1295                1300                1305

Glu Trp Asn Arg Lys Ile Gln Asp Asn Phe Glu Lys Leu Phe His
1310                1315                1320

Val Ser Glu Asp Pro Ser Asp Leu Asn Glu Lys His Pro Asn Leu
1325                1330                1335

Val His Lys Arg Gly Ile Tyr Lys Asp Ser Tyr Gly Ala Ser Ser
1340                1345                1350

Pro Trp Cys Asp Tyr Gln Leu Arg Pro Asn Phe Thr Ile Ala Met
1355                1360                1365

Val Val Ala Pro Glu Leu Phe Thr Thr Glu Lys Ala Trp Lys Ala
1370                1375                1380

Leu Glu Ile Ala Glu Lys Lys Leu Leu Gly Pro Leu Gly Met Lys
1385                1390                1395

Thr Leu Asp Pro Asp Asp Met Val Tyr Cys Gly Ile Tyr Asp Asn
1400                1405                1410

Ala Leu Asp Asn Asp Asn Tyr Asn Leu Ala Lys Gly Phe Asn Tyr
1415                1420                1425

His Gln Gly Pro Glu Trp Leu Trp Pro Ile Gly Tyr Phe Leu Arg
1430                1435                1440

Ala Lys Leu Tyr Phe Ser Arg Leu Met Gly Pro Glu Thr Thr Ala
1445                1450                1455

Lys Thr Ile Val Leu Val Lys Asn Val Leu Ser Arg His Tyr Val
1460                1465                1470

His Leu Glu Arg Ser Pro Trp Lys Gly Leu Pro Glu Leu Thr Asn
1475                1480                1485

Glu Asn Ala Gln Tyr Cys Pro Phe Ser Cys Glu Thr Gln Ala Trp
1490                1495                1500

Ser Ile Ala Thr Ile Leu Glu Thr Leu Tyr Asp Leu
1505                1510                1515
```

<210> SEQ ID NO 21
<211> LENGTH: 1516
<212> TYPE: PRT
<213> ORGANISM: Homo sapiens

<400> SEQUENCE: 21

```
Met Ala Pro Ile Leu Ser Ile Asn Leu Phe Ile Gly Tyr Glu Leu Gln
1               5                   10                  15

Phe Arg Leu Gly Pro Thr Leu Gln Gly Lys Ala Val Thr Val Tyr Thr
            20                  25                  30

Asn Tyr Pro Phe Pro Gly Glu Thr Phe Asn Arg Glu Lys Phe Arg Ser
        35                  40                  45

Leu Asp Trp Glu Asn Pro Thr Glu Arg Glu Asp Ser Asp Lys Tyr
    50                  55                  60

Cys Lys Leu Asn Leu Gln Gln Ser Gly Ser Phe Gln Tyr Tyr Phe Leu
65                  70                  75                  80

Gln Gly Asn Glu Lys Ser Gly Gly Tyr Ile Val Val Asp Pro Ile
                85                  90                  95

Leu Arg Val Gly Ala Asp Asn His Val Leu Pro Leu Asp Cys Val Thr
            100                 105                 110

Leu Gln Thr Phe Leu Ala Lys Cys Leu Gly Pro Phe Asp Glu Trp Glu
        115                 120                 125

Ser Arg Leu Arg Val Ala Lys Glu Ser Gly Tyr Asn Met Ile His Phe
    130                 135                 140

Thr Pro Leu Gln Thr Leu Gly Leu Ser Arg Ser Cys Tyr Ser Leu Ala
145                 150                 155                 160

Asn Gln Leu Glu Leu Asn Pro Asp Phe Ser Arg Pro Asn Arg Lys Tyr
                165                 170                 175

Thr Trp Asn Asp Val Gly Gln Leu Val Glu Lys Leu Lys Lys Glu Trp
            180                 185                 190

Asn Val Ile Cys Ile Thr Asp Val Val Tyr Asn His Thr Ala Ala Asn
        195                 200                 205

Ser Lys Trp Ile Gln Glu His Pro Glu Cys Ala Tyr Asn Leu Val Asn
    210                 215                 220

Ser Pro His Leu Lys Pro Ala Trp Val Leu Asp Arg Ala Leu Trp Arg
225                 230                 235                 240

Phe Ser Cys Asp Val Ala Glu Gly Lys Tyr Lys Glu Lys Gly Ile Pro
                245                 250                 255

Ala Leu Ile Glu Asn Asp His His Met Asn Ser Ile Arg Lys Ile Ile
            260                 265                 270

Trp Glu Asp Ile Phe Pro Lys Leu Lys Leu Trp Glu Phe Phe Gln Val
        275                 280                 285

Asp Val Asn Lys Ala Val Glu Gln Phe Arg Arg Leu Leu Thr Gln Glu
    290                 295                 300

Asn Arg Arg Val Thr Lys Ser Asp Pro Asn Gln His Leu Thr Ile Ile
305                 310                 315                 320

Gln Asp Pro Glu Tyr Arg Arg Phe Gly Cys Thr Val Asp Met Asn Ile
                325                 330                 335

Ala Leu Thr Thr Phe Ile Pro His Asp Lys Gly Pro Ala Ala Ile Glu
            340                 345                 350

Glu Cys Cys Asn Trp Phe His Lys Arg Met Glu Glu Leu Asn Ser Glu
        355                 360                 365

Lys His Arg Leu Ile Asn Tyr His Gln Glu Gln Ala Val Asn Cys Leu
    370                 375                 380
```

```
Leu Gly Asn Val Phe Tyr Glu Arg Leu Ala Gly His Gly Pro Lys Leu
385                 390                 395                 400

Gly Pro Val Thr Arg Lys His Pro Leu Val Thr Arg Tyr Phe Thr Phe
            405                 410                 415

Pro Phe Glu Glu Ile Asp Phe Ser Met Glu Glu Ser Met Ile His Leu
        420                 425                 430

Pro Asn Lys Ala Cys Phe Leu Met Ala His Asn Gly Trp Val Met Gly
        435                 440                 445

Asp Asp Pro Leu Arg Asn Phe Ala Glu Pro Gly Ser Glu Val Tyr Leu
450                 455                 460

Arg Arg Glu Leu Ile Cys Trp Gly Asp Ser Val Lys Leu Arg Tyr Gly
465                 470                 475                 480

Asn Lys Pro Glu Asp Cys Pro Tyr Leu Trp Ala His Met Lys Lys Tyr
            485                 490                 495

Thr Glu Ile Thr Ala Thr Tyr Phe Gln Gly Val Arg Leu Asp Asn Cys
            500                 505                 510

His Ser Thr Pro Leu His Val Ala Glu Tyr Met Leu Asp Ala Ala Arg
        515                 520                 525

Asn Leu Gln Pro Asn Leu Tyr Val Val Ala Glu Leu Phe Thr Gly Ser
530                 535                 540

Glu Asp Leu Asp Asn Val Phe Val Thr Arg Leu Gly Ile Ser Ser Leu
545                 550                 555                 560

Ile Arg Glu Ala Met Ser Ala Tyr Asn Ser His Glu Glu Gly Arg Leu
            565                 570                 575

Val Tyr Arg Tyr Gly Gly Glu Pro Val Gly Ser Phe Val Gln Pro Cys
        580                 585                 590

Leu Arg Pro Leu Met Pro Ala Ile Ala His Ala Leu Phe Met Asp Ile
        595                 600                 605

Thr His Asp Asn Glu Cys Pro Ile Val His Arg Ser Ala Tyr Asp Ala
610                 615                 620

Leu Pro Ser Thr Thr Ile Val Ser Met Ala Cys Cys Ala Ser Gly Ser
625                 630                 635                 640

Thr Arg Gly Tyr Asp Glu Leu Val Pro His Gln Ile Ser Val Val Ser
            645                 650                 655

Glu Glu Arg Phe Tyr Thr Lys Trp Asn Pro Glu Ala Leu Pro Ser Asn
            660                 665                 670

Thr Gly Glu Val Asn Phe Gln Ser Gly Ile Ile Ala Ala Arg Cys Ala
        675                 680                 685

Ile Ser Lys Leu His Gln Glu Leu Gly Ala Lys Gly Phe Ile Gln Val
        690                 695                 700

Tyr Val Asp Gln Val Asp Glu Asp Ile Val Ala Val Thr Arg His Ser
705                 710                 715                 720

Pro Ser Ile His Gln Ser Val Val Ala Val Ser Arg Thr Ala Phe Arg
            725                 730                 735

Asn Pro Lys Thr Ser Phe Tyr Ser Lys Glu Val Pro Gln Met Cys Ile
            740                 745                 750

Pro Gly Lys Ile Glu Glu Val Val Leu Glu Ala Arg Thr Ile Glu Arg
        755                 760                 765

Asn Thr Lys Pro Tyr Arg Lys Asp Glu Asn Ser Ile Asn Gly Thr Pro
        770                 775                 780

Asp Ile Thr Val Glu Ile Arg Glu His Ile Gln Leu Asn Glu Ser Lys
785                 790                 795                 800
```

```
Ile Val Lys Gln Ala Gly Val Ala Thr Lys Gly Pro Asn Glu Tyr Ile
            805                 810                 815

Gln Glu Ile Glu Phe Glu Asn Leu Ser Pro Gly Ser Val Ile Ile Phe
            820                 825                 830

Arg Val Ser Leu Asp Pro His Ala Gln Val Ala Val Gly Ile Leu Arg
            835                 840                 845

Asn His Leu Thr Gln Phe Ser Pro His Phe Lys Ser Gly Ser Leu Ala
    850                 855                 860

Val Asp Asn Ala Asp Pro Ile Leu Lys Ile Pro Phe Ala Ser Leu Ala
865                 870                 875                 880

Ser Arg Leu Thr Leu Ala Glu Leu Asn Gln Ile Leu Tyr Arg Cys Glu
            885                 890                 895

Ser Glu Glu Lys Glu Asp Gly Gly Cys Tyr Asp Ile Pro Asn Trp
            900                 905                 910

Ser Ala Leu Lys Tyr Ala Gly Leu Gln Gly Leu Met Ser Val Leu Ala
            915                 920                 925

Glu Ile Arg Pro Lys Asn Asp Leu Gly His Pro Phe Cys Asn Asn Leu
    930                 935                 940

Arg Ser Gly Asp Trp Met Ile Asp Tyr Val Ser Asn Arg Leu Ile Ser
945                 950                 955                 960

Arg Ser Gly Thr Ile Ala Glu Val Gly Lys Trp Leu Gln Ala Met Phe
            965                 970                 975

Phe Tyr Leu Lys Gln Ile Pro Arg Tyr Leu Ile Pro Cys Tyr Phe Asp
            980                 985                 990

Ala Ile Leu Ile Gly Ala Tyr Thr Thr Leu Leu Asp Thr Ala Trp Lys
            995                 1000                1005

Gln Met Ser Ser Phe Val Gln Asn Gly Ser Thr Phe Val Lys His
    1010                1015                1020

Leu Ser Leu Gly Ser Val Gln Leu Cys Gly Val Gly Lys Phe Pro
    1025                1030                1035

Ser Leu Pro Ile Leu Ser Pro Ala Leu Met Asp Val Pro Tyr Arg
    1040                1045                1050

Leu Asn Glu Ile Thr Lys Glu Lys Glu Gln Cys Cys Val Ser Leu
    1055                1060                1065

Ala Ala Gly Leu Pro His Phe Ser Ser Gly Ile Phe Arg Cys Trp
    1070                1075                1080

Gly Arg Asp Thr Phe Ile Ala Leu Arg Gly Ile Leu Leu Ile Thr
    1085                1090                1095

Gly Arg Tyr Val Glu Ala Arg Asn Ile Ile Leu Ala Phe Ala Gly
    1100                1105                1110

Thr Leu Arg His Gly Leu Ile Pro Asn Leu Leu Gly Glu Gly Ile
    1115                1120                1125

Tyr Ala Arg Tyr Asn Cys Arg Asp Ala Val Trp Trp Trp Leu Gln
    1130                1135                1140

Cys Ile Gln Asp Tyr Cys Lys Met Val Pro Asn Gly Leu Asp Ile
    1145                1150                1155

Leu Lys Cys Pro Val Ser Arg Met Tyr Pro Thr Asp Asp Ser Ala
    1160                1165                1170

Pro Leu Pro Ala Gly Thr Leu Asp Gln Pro Leu Phe Glu Val Ile
    1175                1180                1185

Gln Glu Ala Met Gln Lys His Met Gln Gly Ile Gln Phe Arg Glu
    1190                1195                1200
```

Arg Asn Ala Gly Pro Gln Ile Asp Arg Asn Met Lys Asp Glu Gly
    1205                1210                1215

Phe Asn Ile Thr Ala Gly Val Asp Glu Glu Thr Gly Phe Val Tyr
    1220                1225                1230

Gly Gly Asn Arg Phe Asn Cys Gly Thr Trp Met Asp Lys Met Gly
    1235                1240                1245

Glu Ser Asp Arg Ala Arg Asn Arg Gly Ile Pro Ala Thr Pro Arg
    1250                1255                1260

Asp Gly Ser Ala Val Glu Ile Val Gly Leu Ser Lys Ser Ala Val
    1265                1270                1275

Arg Trp Leu Leu Glu Leu Ser Lys Lys Asn Ile Phe Pro Tyr His
    1280                1285                1290

Glu Val Thr Val Lys Arg His Gly Lys Ala Ile Lys Val Ser Tyr
    1295                1300                1305

Asp Glu Trp Asn Arg Lys Ile Gln Asp Asn Phe Glu Lys Leu Phe
    1310                1315                1320

His Val Ser Glu Asp Pro Ser Asp Leu Asn Glu Lys His Pro Asn
    1325                1330                1335

Leu Val His Lys Arg Gly Ile Tyr Lys Asp Ser Tyr Gly Ala Ser
    1340                1345                1350

Ser Pro Trp Cys Asp Tyr Gln Leu Arg Pro Asn Phe Thr Ile Ala
    1355                1360                1365

Met Val Val Ala Pro Glu Leu Phe Thr Thr Glu Lys Ala Trp Lys
    1370                1375                1380

Ala Leu Glu Ile Ala Glu Lys Lys Leu Leu Gly Pro Leu Gly Met
    1385                1390                1395

Lys Thr Leu Asp Pro Asp Asp Met Val Tyr Cys Gly Ile Tyr Asp
    1400                1405                1410

Asn Ala Leu Asp Asn Asp Asn Tyr Asn Leu Ala Lys Gly Phe Asn
    1415                1420                1425

Tyr His Gln Gly Pro Glu Trp Leu Trp Pro Ile Gly Tyr Phe Leu
    1430                1435                1440

Arg Ala Lys Leu Tyr Phe Ser Arg Leu Met Gly Pro Glu Thr Thr
    1445                1450                1455

Ala Lys Thr Ile Val Leu Val Lys Asn Val Leu Ser Arg His Tyr
    1460                1465                1470

Val His Leu Glu Arg Ser Pro Trp Lys Gly Leu Pro Glu Leu Thr
    1475                1480                1485

Asn Glu Asn Ala Gln Tyr Cys Pro Phe Ser Cys Glu Thr Gln Ala
    1490                1495                1500

Trp Ser Ile Ala Thr Ile Leu Glu Thr Leu Tyr Asp Leu
    1505                1510                1515

<210> SEQ ID NO 22
<211> LENGTH: 952
<212> TYPE: PRT
<213> ORGANISM: Homo sapiens

<400> SEQUENCE: 22

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

-continued

```
Leu Glu Glu Thr His Pro Ala His Gln Gln Gly Ala Ser Arg Pro Gly
 50                  55                  60

Pro Arg Asp Ala Gln Ala His Pro Gly Arg Pro Arg Ala Val Pro Thr
 65                  70                  75                  80

Gln Cys Asp Val Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
                100                 105                 110

Ala Lys Gln Gly Leu Gln Gly Ala Gln Met Gly Gln Pro Trp Cys Phe
                115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
                180                 185                 190

Val Pro Leu Glu Thr Pro His Val His Ser Arg Ala Pro Ser Pro Leu
                195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
                275                 280                 285

Ala Asn Leu Tyr Gly Ser His Pro Phe Tyr Leu Ala Leu Glu Asp Gly
                290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Thr
                370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
450                 455                 460
```

-continued

```
Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
            530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu Gln Leu
                610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
                690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Val Glu Ala Leu Gly
                770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880
```

```
Arg Asn Asn Thr Ile Val Asn Glu Leu Val Arg Val Thr Ser Glu Gly
                    885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 23
<211> LENGTH: 957
<212> TYPE: PRT
<213> ORGANISM: Homo sapiens

<400> SEQUENCE: 23

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300
```

-continued

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
            325                 330                 335

Leu Asp Val Tyr Ile Phe Leu Gly Pro Glu Pro Lys Ser Val Val Gln
        340                 345                 350

Gln Tyr Leu Asp Val Val Gly Tyr Pro Phe Met Pro Pro Tyr Trp Gly
    355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
        420                 425                 430

Gln Gly Gly Arg Arg Tyr Met Met Ile Val Asp Pro Ala Ile Ser Ser
    435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
        500                 505                 510

Asp Gly Met Trp Ile Asp Met Asn Glu Pro Ser Asn Phe Ile Arg Gly
    515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
        580                 585                 590

Thr Arg Pro Phe Val Ile Ser Arg Ser Thr Phe Ala Gly His Gly Arg
    595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
        660                 665                 670

Asn His Asn Ser Leu Leu Ser Leu Pro Gln Glu Pro Tyr Ser Phe Ser
    675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

```
Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
        740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
        770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
            850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Ala Arg Gly Pro Arg Val Leu Asp Ile Cys Val
        930                 935                 940

Ser Leu Leu Met Gly Glu Gln Phe Leu Val Ser Trp Cys
945                 950                 955

<210> SEQ ID NO 24
<211> LENGTH: 660
<212> TYPE: PRT
<213> ORGANISM: Homo sapiens

<400> SEQUENCE: 24

Gly Gln Pro Trp Cys Phe Phe Pro Pro Ser Tyr Pro Ser Tyr Lys Leu
1               5                   10                  15

Glu Asn Leu Ser Ser Ser Glu Met Gly Tyr Thr Ala Thr Leu Thr Arg
            20                  25                  30

Thr Thr Pro Thr Phe Phe Pro Lys Asp Ile Leu Thr Leu Arg Leu Asp
        35                  40                  45

Val Met Met Glu Thr Glu Asn Arg Leu His Phe Thr Ile Lys Asp Pro
    50                  55                  60

Ala Asn Arg Arg Tyr Glu Val Pro Leu Glu Thr Pro His Val His Ser
65                  70                  75                  80

Arg Ala Pro Ser Pro Leu Tyr Ser Val Glu Phe Ser Glu Glu Pro Phe
                85                  90                  95

Gly Val Ile Val Arg Arg Gln Leu Asp Gly Arg Val Leu Leu Asn Thr
            100                 105                 110

Thr Val Ala Pro Leu Phe Phe Ala Asp Gln Phe Leu Gln Leu Ser Thr
        115                 120                 125

Ser Leu Pro Ser Gln Tyr Ile Thr Gly Leu Ala Glu His Leu Ser Pro
        130                 135                 140
```

```
Leu Met Leu Ser Thr Ser Trp Thr Arg Ile Thr Leu Trp Asn Arg Asp
145                 150                 155                 160

Leu Ala Pro Thr Pro Gly Ala Asn Leu Tyr Gly Ser His Pro Phe Tyr
            165                 170                 175

Leu Ala Leu Glu Asp Gly Gly Ser Ala His Gly Val Phe Leu Leu Asn
            180                 185                 190

Ser Asn Ala Met Asp Val Val Leu Gln Pro Ser Pro Ala Leu Ser Trp
        195                 200                 205

Arg Ser Thr Gly Gly Ile Leu Asp Val Tyr Ile Phe Leu Gly Pro Glu
        210                 215                 220

Pro Lys Ser Val Val Gln Gln Tyr Leu Asp Val Val Gly Tyr Pro Phe
225                 230                 235                 240

Met Pro Pro Tyr Trp Gly Leu Gly Phe His Leu Cys Arg Trp Gly Tyr
            245                 250                 255

Ser Ser Thr Ala Ile Thr Arg Gln Val Val Glu Asn Met Thr Arg Ala
            260                 265                 270

His Phe Pro Leu Asp Val Gln Trp Asn Asp Leu Asp Tyr Met Asp Ser
        275                 280                 285

Arg Arg Asp Phe Thr Phe Asn Lys Asp Gly Phe Arg Asp Phe Pro Ala
        290                 295                 300

Met Val Gln Glu Leu His Gln Gly Gly Arg Arg Tyr Met Met Ile Val
305                 310                 315                 320

Asp Pro Ala Ile Ser Ser Gly Pro Ala Gly Ser Tyr Arg Pro Tyr
            325                 330                 335

Asp Glu Gly Leu Arg Arg Gly Val Phe Ile Thr Asn Glu Thr Gly Gln
            340                 345                 350

Pro Leu Ile Gly Lys Val Trp Pro Gly Ser Thr Ala Phe Pro Asp Phe
        355                 360                 365

Thr Asn Pro Thr Ala Leu Ala Trp Trp Glu Asp Met Val Ala Glu Phe
        370                 375                 380

His Asp Gln Val Pro Phe Asp Gly Met Trp Ile Asp Met Asn Glu Pro
385                 390                 395                 400

Ser Asn Phe Ile Arg Gly Ser Glu Asp Gly Cys Pro Asn Asn Glu Leu
            405                 410                 415

Glu Asn Pro Pro Tyr Val Pro Gly Val Val Gly Gly Thr Leu Gln Ala
            420                 425                 430

Ala Thr Ile Cys Ala Ser Ser His Gln Phe Leu Ser Thr His Tyr Asn
        435                 440                 445

Leu His Asn Leu Tyr Gly Leu Thr Glu Ala Ile Ala Ser His Arg Ala
450                 455                 460

Leu Val Lys Ala Arg Gly Thr Arg Pro Phe Val Ile Ser Arg Ser Thr
465                 470                 475                 480

Phe Ala Gly His Gly Arg Tyr Ala Gly His Trp Thr Gly Asp Val Trp
            485                 490                 495

Ser Ser Trp Glu Gln Leu Ala Ser Ser Val Pro Glu Ile Leu Gln Phe
            500                 505                 510

Asn Leu Leu Gly Val Pro Leu Val Gly Ala Asp Val Cys Gly Phe Leu
        515                 520                 525

Gly Asn Thr Ser Glu Glu Leu Cys Val Arg Trp Thr Gln Leu Gly Ala
        530                 535                 540

Phe Tyr Pro Phe Met Arg Asn His Asn Ser Leu Leu Ser Leu Pro Gln
545                 550                 555                 560
```

Glu Pro Tyr Ser Phe Ser Glu Pro Ala Gln Ala Met Arg Lys Ala
                565                 570                 575

Leu Thr Leu Arg Tyr Ala Leu Leu Pro His Leu Tyr Thr Leu Phe His
            580                 585                 590

Gln Ala His Val Ala Gly Glu Thr Val Ala Arg Pro Leu Phe Leu Glu
        595                 600                 605

Phe Pro Lys Asp Ser Ser Thr Trp Thr Val Asp His Gln Leu Leu Trp
    610                 615                 620

Gly Glu Ala Leu Leu Ile Thr Pro Val Leu Gln Ala Gly Lys Ala Glu
625                 630                 635                 640

Val Thr Gly Tyr Phe Pro Leu Gly Thr Trp Tyr Asp Leu Gln Thr Val
                645                 650                 655

Pro Val Glu Ala
            660

<210> SEQ ID NO 25
<211> LENGTH: 495
<212> TYPE: PRT
<213> ORGANISM: Homo sapiens

<400> SEQUENCE: 25

Gly Ala Asn Leu Tyr Gly Ser His Pro Phe Tyr Leu Ala Leu Glu Asp
1               5                   10                  15

Gly Gly Ser Ala His Gly Val Phe Leu Leu Asn Ser Asn Ala Met Asp
            20                  25                  30

Val Val Leu Gln Pro Ser Pro Ala Leu Ser Trp Arg Ser Thr Gly Gly
        35                  40                  45

Ile Leu Asp Val Tyr Ile Phe Leu Gly Pro Glu Pro Lys Ser Val Val
    50                  55                  60

Gln Gln Tyr Leu Asp Val Val Gly Tyr Pro Phe Met Pro Pro Tyr Trp
65                  70                  75                  80

Gly Leu Gly Phe His Leu Cys Arg Trp Gly Tyr Ser Ser Thr Ala Ile
                85                  90                  95

Thr Arg Gln Val Val Glu Asn Met Thr Arg Ala His Phe Pro Leu Asp
            100                 105                 110

Val Gln Trp Asn Asp Leu Asp Tyr Met Asp Ser Arg Arg Asp Phe Thr
        115                 120                 125

Phe Asn Lys Asp Gly Phe Arg Asp Phe Pro Ala Met Val Gln Glu Leu
    130                 135                 140

His Gln Gly Gly Arg Arg Tyr Met Met Ile Val Asp Pro Ala Ile Ser
145                 150                 155                 160

Ser Ser Gly Pro Ala Gly Ser Tyr Arg Pro Tyr Asp Glu Gly Leu Arg
                165                 170                 175

Arg Gly Val Phe Ile Thr Asn Glu Thr Gly Gln Pro Leu Ile Gly Lys
            180                 185                 190

Val Trp Pro Gly Ser Thr Ala Phe Pro Asp Phe Thr Asn Pro Thr Ala
        195                 200                 205

Leu Ala Trp Trp Glu Asp Met Val Ala Glu Phe His Asp Gln Val Pro
    210                 215                 220

Phe Asp Gly Met Trp Ile Asp Met Asn Glu Pro Ser Asn Phe Ile Arg
225                 230                 235                 240

Gly Ser Glu Asp Gly Cys Pro Asn Asn Glu Leu Glu Asn Pro Pro Tyr
                245                 250                 255

Val Pro Gly Val Val Gly Gly Thr Leu Gln Ala Ala Thr Ile Cys Ala
            260                 265                 270

```
Ser Ser His Gln Phe Leu Ser Thr His Tyr Asn Leu His Asn Leu Tyr
        275                 280                 285

Gly Leu Thr Glu Ala Ile Ala Ser His Arg Ala Leu Val Lys Ala Arg
    290                 295                 300

Gly Thr Arg Pro Phe Val Ile Ser Arg Ser Thr Phe Ala Gly His Gly
305                 310                 315                 320

Arg Tyr Ala Gly His Trp Thr Gly Asp Val Trp Ser Ser Trp Glu Gln
                325                 330                 335

Leu Ala Ser Ser Val Pro Glu Ile Leu Gln Phe Asn Leu Leu Gly Val
            340                 345                 350

Pro Leu Val Gly Ala Asp Val Cys Gly Phe Leu Gly Asn Thr Ser Glu
        355                 360                 365

Glu Leu Cys Val Arg Trp Thr Gln Leu Gly Ala Phe Tyr Pro Phe Met
    370                 375                 380

Arg Asn His Asn Ser Leu Leu Ser Leu Pro Gln Glu Pro Tyr Ser Phe
385                 390                 395                 400

Ser Glu Pro Ala Gln Gln Ala Met Arg Lys Ala Leu Thr Leu Arg Tyr
                405                 410                 415

Ala Leu Leu Pro His Leu Tyr Thr Leu Phe His Gln Ala His Val Ala
            420                 425                 430

Gly Glu Thr Val Ala Arg Pro Leu Phe Leu Glu Phe Pro Lys Asp Ser
        435                 440                 445

Ser Thr Trp Thr Val Asp His Gln Leu Leu Trp Gly Glu Ala Leu Leu
    450                 455                 460

Ile Thr Pro Val Leu Gln Ala Gly Lys Ala Glu Val Thr Gly Tyr Phe
465                 470                 475                 480

Pro Leu Gly Thr Trp Tyr Asp Leu Gln Thr Val Pro Val Glu Ala
                485                 490                 495

<210> SEQ ID NO 26
<211> LENGTH: 892
<212> TYPE: PRT
<213> ORGANISM: Homo sapiens

<400> SEQUENCE: 26

Ser Arg Pro Gly Pro Arg Asp Ala Gln Ala His Pro Gly Arg Pro Arg
1               5                   10                  15

Ala Val Pro Thr Gln Cys Asp Val Pro Pro Asn Ser Arg Phe Asp Cys
                20                  25                  30

Ala Pro Asp Lys Ala Ile Thr Gln Glu Gln Cys Glu Ala Arg Gly Cys
            35                  40                  45

Cys Tyr Ile Pro Ala Lys Gln Gly Leu Gln Gly Ala Gln Met Gly Gln
    50                  55                  60

Pro Trp Cys Phe Phe Pro Pro Ser Tyr Pro Tyr Lys Leu Glu Asn
65                  70                  75                  80

Leu Ser Ser Ser Glu Met Gly Tyr Thr Ala Thr Leu Thr Arg Thr Thr
                85                  90                  95

Pro Thr Phe Phe Pro Lys Asp Ile Leu Thr Leu Arg Leu Asp Val Met
            100                 105                 110

Met Glu Thr Glu Asn Arg Leu His Phe Thr Ile Lys Asp Pro Ala Asn
        115                 120                 125

Arg Arg Tyr Glu Val Pro Leu Glu Thr Pro His Val His Ser Arg Ala
    130                 135                 140

Pro Ser Pro Leu Tyr Ser Val Glu Phe Ser Glu Glu Pro Phe Gly Val
145                 150                 155                 160
```

```
Ile Val Arg Arg Gln Leu Asp Gly Arg Val Leu Leu Asn Thr Thr Val
                165                 170                 175
Ala Pro Leu Phe Phe Ala Asp Gln Phe Leu Gln Leu Ser Thr Ser Leu
            180                 185                 190
Pro Ser Gln Tyr Ile Thr Gly Leu Ala Glu His Leu Ser Pro Leu Met
        195                 200                 205
Leu Ser Thr Ser Trp Thr Arg Ile Thr Leu Trp Asn Arg Asp Leu Ala
    210                 215                 220
Pro Thr Pro Gly Ala Asn Leu Tyr Gly Ser His Pro Phe Tyr Leu Ala
225                 230                 235                 240
Leu Glu Asp Gly Gly Ser Ala His Gly Val Phe Leu Leu Asn Ser Asn
                245                 250                 255
Ala Met Asp Val Val Leu Gln Pro Ser Pro Ala Leu Ser Trp Arg Ser
            260                 265                 270
Thr Gly Gly Ile Leu Asp Val Tyr Ile Phe Leu Gly Pro Glu Pro Lys
        275                 280                 285
Ser Val Val Gln Gln Tyr Leu Asp Val Val Gly Tyr Pro Phe Met Pro
    290                 295                 300
Pro Tyr Trp Gly Leu Gly Phe His Leu Cys Arg Trp Gly Tyr Ser Ser
305                 310                 315                 320
Thr Ala Ile Thr Arg Gln Val Val Glu Asn Met Thr Arg Ala His Phe
                325                 330                 335
Pro Leu Asp Val Gln Trp Asn Asp Leu Asp Tyr Met Asp Ser Arg Arg
            340                 345                 350
Asp Phe Thr Phe Asn Lys Asp Gly Phe Arg Asp Phe Pro Ala Met Val
        355                 360                 365
Gln Glu Leu His Gln Gly Arg Arg Tyr Met Met Ile Val Asp Pro
    370                 375                 380
Ala Ile Ser Ser Ser Gly Pro Ala Gly Ser Tyr Arg Pro Tyr Asp Glu
385                 390                 395                 400
Gly Leu Arg Arg Gly Val Phe Ile Thr Asn Glu Thr Gly Gln Pro Leu
                405                 410                 415
Ile Gly Lys Val Trp Pro Gly Ser Thr Ala Phe Pro Asp Phe Thr Asn
            420                 425                 430
Pro Thr Ala Leu Ala Trp Trp Glu Asp Met Val Ala Glu Phe His Asp
        435                 440                 445
Gln Val Pro Phe Asp Gly Met Trp Ile Asp Met Asn Glu Pro Ser Asn
    450                 455                 460
Phe Ile Arg Gly Ser Glu Asp Gly Cys Pro Asn Asn Glu Leu Glu Asn
465                 470                 475                 480
Pro Pro Tyr Val Pro Gly Val Val Gly Gly Thr Leu Gln Ala Ala Thr
                485                 490                 495
Ile Cys Ala Ser Ser His Gln Phe Leu Ser Thr His Tyr Asn Leu His
            500                 505                 510
Asn Leu Tyr Gly Leu Thr Glu Ala Ile Ala Ser His Arg Ala Leu Val
        515                 520                 525
Lys Ala Arg Gly Thr Arg Pro Phe Val Ile Ser Arg Ser Thr Phe Ala
    530                 535                 540
Gly His Gly Arg Tyr Ala Gly His Trp Thr Gly Asp Val Trp Ser Ser
545                 550                 555                 560
Trp Glu Gln Leu Ala Ser Ser Val Pro Glu Ile Leu Gln Phe Asn Leu
                565                 570                 575
```

Leu Gly Val Pro Leu Val Gly Ala Asp Val Cys Gly Phe Leu Gly Asn
            580                 585                 590

Thr Ser Glu Glu Leu Cys Val Arg Trp Thr Gln Leu Gly Ala Phe Tyr
        595                 600                 605

Pro Phe Met Arg Asn His Asn Ser Leu Leu Ser Leu Pro Gln Glu Pro
    610                 615                 620

Tyr Ser Phe Ser Glu Pro Ala Gln Gln Ala Met Arg Lys Ala Leu Thr
625                 630                 635                 640

Leu Arg Tyr Ala Leu Leu Pro His Leu Tyr Thr Leu Phe His Gln Ala
                645                 650                 655

His Val Ala Gly Glu Thr Val Ala Arg Pro Leu Phe Leu Glu Phe Pro
            660                 665                 670

Lys Asp Ser Ser Thr Trp Thr Val Asp His Gln Leu Leu Trp Gly Glu
        675                 680                 685

Ala Leu Leu Ile Thr Pro Val Leu Gln Ala Gly Lys Ala Glu Val Thr
    690                 695                 700

Gly Tyr Phe Pro Leu Gly Thr Trp Tyr Asp Leu Gln Thr Val Pro Val
705                 710                 715                 720

Glu Ala Leu Gly Ser Leu Pro Pro Pro Ala Ala Pro Arg Glu Pro
                725                 730                 735

Ala Ile His Ser Glu Gly Gln Trp Val Thr Leu Pro Ala Pro Leu Asp
            740                 745                 750

Thr Ile Asn Val His Leu Arg Ala Gly Tyr Ile Ile Pro Leu Gln Gly
        755                 760                 765

Pro Gly Leu Thr Thr Thr Glu Ser Arg Gln Gln Pro Met Ala Leu Ala
    770                 775                 780

Val Ala Leu Thr Lys Gly Gly Glu Ala Arg Gly Glu Leu Phe Trp Asp
785                 790                 795                 800

Asp Gly Glu Ser Leu Glu Val Leu Glu Arg Gly Ala Tyr Thr Gln Val
                805                 810                 815

Ile Phe Leu Ala Arg Asn Asn Thr Ile Val Asn Glu Leu Val Arg Val
            820                 825                 830

Thr Ser Glu Gly Ala Gly Leu Gln Leu Gln Lys Val Thr Val Leu Gly
        835                 840                 845

Val Ala Thr Ala Pro Gln Gln Val Leu Ser Asn Gly Val Pro Val Ser
850                 855                 860

Asn Phe Thr Tyr Ser Pro Asp Thr Lys Val Leu Asp Ile Cys Val Ser
865                 870                 875                 880

Leu Leu Met Gly Glu Gln Phe Leu Val Ser Trp Cys
                885                 890

<210> SEQ ID NO 27
<211> LENGTH: 886
<212> TYPE: PRT
<213> ORGANISM: Homo sapiens

<400> SEQUENCE: 27

Asp Ala Gln Ala His Pro Gly Arg Pro Arg Ala Val Pro Thr Gln Cys
1               5                   10                  15

Asp Val Pro Pro Asn Ser Arg Phe Asp Cys Ala Pro Asp Lys Ala Ile
            20                  25                  30

Thr Gln Glu Gln Cys Glu Ala Arg Gly Cys Cys Tyr Ile Pro Ala Lys
        35                  40                  45

Gln Gly Leu Gln Gly Ala Gln Met Gly Gln Pro Trp Cys Phe Phe Pro
    50                  55                  60

-continued

```
Pro Ser Tyr Pro Ser Tyr Lys Leu Glu Asn Leu Ser Ser Ser Glu Met
 65                  70                  75                  80

Gly Tyr Thr Ala Thr Leu Thr Arg Thr Thr Pro Thr Phe Phe Pro Lys
                 85                  90                  95

Asp Ile Leu Thr Leu Arg Leu Asp Val Met Met Glu Thr Glu Asn Arg
            100                 105                 110

Leu His Phe Thr Ile Lys Asp Pro Ala Asn Arg Arg Tyr Glu Val Pro
        115                 120                 125

Leu Glu Thr Pro His Val His Ser Arg Ala Pro Ser Pro Leu Tyr Ser
130                 135                 140

Val Glu Phe Ser Glu Glu Pro Phe Gly Val Ile Val Arg Arg Gln Leu
145                 150                 155                 160

Asp Gly Arg Val Leu Leu Asn Thr Thr Val Ala Pro Leu Phe Phe Ala
                165                 170                 175

Asp Gln Phe Leu Gln Leu Ser Thr Ser Leu Pro Ser Gln Tyr Ile Thr
            180                 185                 190

Gly Leu Ala Glu His Leu Ser Pro Leu Met Leu Ser Thr Ser Trp Thr
        195                 200                 205

Arg Ile Thr Leu Trp Asn Arg Asp Leu Ala Pro Thr Pro Gly Ala Asn
210                 215                 220

Leu Tyr Gly Ser His Pro Phe Tyr Leu Ala Leu Glu Asp Gly Gly Ser
225                 230                 235                 240

Ala His Gly Val Phe Leu Leu Asn Ser Asn Ala Met Asp Val Val Leu
                245                 250                 255

Gln Pro Ser Pro Ala Leu Ser Trp Arg Ser Thr Gly Gly Ile Leu Asp
            260                 265                 270

Val Tyr Ile Phe Leu Gly Pro Glu Pro Lys Ser Val Val Gln Gln Tyr
        275                 280                 285

Leu Asp Val Val Gly Tyr Pro Phe Met Pro Pro Tyr Trp Gly Leu Gly
290                 295                 300

Phe His Leu Cys Arg Trp Gly Tyr Ser Ser Thr Ala Ile Thr Arg Gln
305                 310                 315                 320

Val Val Glu Asn Met Thr Arg Ala His Phe Pro Leu Asp Val Gln Trp
                325                 330                 335

Asn Asp Leu Asp Tyr Met Asp Ser Arg Arg Asp Phe Thr Phe Asn Lys
            340                 345                 350

Asp Gly Phe Arg Asp Phe Pro Ala Met Val Gln Glu Leu His Gln Gly
        355                 360                 365

Gly Arg Arg Tyr Met Met Ile Val Asp Pro Ala Ile Ser Ser Ser Gly
370                 375                 380

Pro Ala Gly Ser Tyr Arg Pro Tyr Asp Glu Gly Leu Arg Arg Gly Val
385                 390                 395                 400

Phe Ile Thr Asn Glu Thr Gly Gln Pro Leu Ile Gly Lys Val Trp Pro
                405                 410                 415

Gly Ser Thr Ala Phe Pro Asp Phe Thr Asn Pro Thr Ala Leu Ala Trp
            420                 425                 430

Trp Glu Asp Met Val Ala Glu Phe His Asp Gln Val Pro Phe Asp Gly
        435                 440                 445

Met Trp Ile Asp Met Asn Glu Pro Ser Asn Phe Ile Arg Gly Ser Glu
450                 455                 460

Asp Gly Cys Pro Asn Asn Glu Leu Glu Asn Pro Pro Tyr Val Pro Gly
465                 470                 475                 480
```

```
Val Val Gly Gly Thr Leu Gln Ala Ala Thr Ile Cys Ala Ser Ser His
            485                 490                 495

Gln Phe Leu Ser Thr His Tyr Asn Leu His Asn Leu Tyr Gly Leu Thr
            500                 505                 510

Glu Ala Ile Ala Ser His Arg Ala Leu Val Lys Ala Arg Gly Thr Arg
            515                 520                 525

Pro Phe Val Ile Ser Arg Ser Thr Phe Ala Gly His Gly Arg Tyr Ala
            530                 535                 540

Gly His Trp Thr Gly Asp Val Trp Ser Ser Trp Glu Gln Leu Ala Ser
545                 550                 555                 560

Ser Val Pro Glu Ile Leu Gln Phe Asn Leu Leu Gly Val Pro Leu Val
                565                 570                 575

Gly Ala Asp Val Cys Gly Phe Leu Gly Asn Thr Ser Glu Glu Leu Cys
                580                 585                 590

Val Arg Trp Thr Gln Leu Gly Ala Phe Tyr Pro Phe Met Arg Asn His
                595                 600                 605

Asn Ser Leu Leu Ser Leu Pro Gln Glu Pro Tyr Ser Phe Ser Glu Pro
            610                 615                 620

Ala Gln Gln Ala Met Arg Lys Ala Leu Thr Leu Arg Tyr Ala Leu Leu
625                 630                 635                 640

Pro His Leu Tyr Thr Leu Phe His Gln Ala His Val Ala Gly Glu Thr
                645                 650                 655

Val Ala Arg Pro Leu Phe Leu Glu Phe Pro Lys Asp Ser Ser Thr Trp
                660                 665                 670

Thr Val Asp His Gln Leu Leu Trp Gly Glu Ala Leu Leu Ile Thr Pro
            675                 680                 685

Val Leu Gln Ala Gly Lys Ala Glu Val Thr Gly Tyr Phe Pro Leu Gly
            690                 695                 700

Thr Trp Tyr Asp Leu Gln Thr Val Pro Val Glu Ala Leu Gly Ser Leu
705                 710                 715                 720

Pro Pro Pro Pro Ala Ala Pro Arg Glu Pro Ala Ile His Ser Glu Gly
                725                 730                 735

Gln Trp Val Thr Leu Pro Ala Pro Leu Asp Thr Ile Asn Val His Leu
                740                 745                 750

Arg Ala Gly Tyr Ile Ile Pro Leu Gln Gly Pro Gly Leu Thr Thr Thr
            755                 760                 765

Glu Ser Arg Gln Gln Pro Met Ala Leu Ala Val Ala Leu Thr Lys Gly
            770                 775                 780

Gly Glu Ala Arg Gly Glu Leu Phe Trp Asp Asp Gly Glu Ser Leu Glu
785                 790                 795                 800

Val Leu Glu Arg Gly Ala Tyr Thr Gln Val Ile Phe Leu Ala Arg Asn
                805                 810                 815

Asn Thr Ile Val Asn Glu Leu Val Arg Val Thr Ser Glu Gly Ala Gly
            820                 825                 830

Leu Gln Leu Gln Lys Val Thr Val Leu Gly Val Ala Thr Ala Pro Gln
            835                 840                 845

Gln Val Leu Ser Asn Gly Val Pro Val Ser Asn Phe Thr Tyr Ser Pro
            850                 855                 860

Asp Thr Lys Val Leu Asp Ile Cys Val Ser Leu Leu Met Gly Glu Gln
865                 870                 875                 880

Phe Leu Val Ser Trp Cys
            885
```

```
<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Gly Ile His
1

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Gly Ile His
1               5

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Thr Ser Gly Ser Gly Lys Ser Ser Glu Gly Lys Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Tyr Gly Met His
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Tyr Ile Ser Ser Gly Ser Ser Thr Ile Tyr Tyr Ala Asp Thr Val Lys
1               5                   10                  15

Gly

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gly Leu Leu Leu Asp Tyr
1               5

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Ser Lys Ser Val Ser Thr Ser Ser Tyr Ser Tyr Met His
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ala Ser Tyr Leu Glu Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln His Ser Arg Glu Phe Pro Trp Thr
1               5

<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Phe Ser Asn Tyr
            20                  25                  30
```

Gly Met His Trp Val Arg Gln Ala Pro Gly Lys Gly Leu Glu Trp Val
         35                  40                  45

Ser Tyr Ile Ser Ser Gly Ser Ser Thr Ile Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Val
             100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ser Tyr Ile Ser Ser Gly Ser Ser Thr Ile Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Thr Ser Leu Arg Ala Glu Asp Thr Ala Val Tyr Tyr Cys
                 85                  90                  95

Ala Arg Arg Gly Leu Leu Leu Asp Tyr Trp Gly Gln Gly Thr Thr Leu
             100                 105                 110

Thr Val Ser Ser
        115

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Ser Val Ser Thr Ser
             20                  25                  30

Ser Tyr Ser Tyr Leu Ala Trp Tyr Gln Gln Lys Pro Glu Lys Ala Pro
         35                  40                  45

Lys Leu Leu Ile Lys Tyr Ala Ser Tyr Leu Gln Ser Gly Val Pro Ser
 50                      55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Ala Gly Thr Lys Leu Glu Leu Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Tyr Leu Glu Ser Gly Val Pro Ala
 50                 55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 42
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Gly Met His Trp Val Arg Gln Ala Pro Gly Lys Gly Leu Glu Tyr Val
        35                  40                  45

Ser Tyr Ile Ser Ser Gly Ser Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Arg Gly Leu Leu Leu Asp Tyr Trp Gly Gln Gly Thr Leu Val
            100                 105                 110

Thr Val Ser Ser
            115

<210> SEQ ID NO 43
<211> LENGTH: 242
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 43

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Tyr Leu Glu Ser Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Trp Thr Phe Gly Gly Gly Thr Lys Val Glu Ile Lys Gly
            100                 105                 110

Gly Gly Gly Ser Gly Gly Gly Gly Ser Gly Gly Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ser Ala Ser Gly Phe Thr Phe Ser Asn Tyr Gly Met
145                 150                 155                 160

His Trp Val Arg Gln Ala Pro Gly Lys Gly Leu Glu Tyr Val Ser Tyr
                165                 170                 175

Ile Ser Ser Gly Ser Ser Thr Ile Tyr Tyr Ala Asp Thr Val Lys Gly
            180                 185                 190

Arg Phe Thr Ile Ser Arg Asp Asn Ser Lys Asn Thr Leu Tyr Leu Gln
        195                 200                 205

Met Ser Ser Leu Arg Ala Glu Asp Thr Ala Val Tyr Tyr Cys Val Lys
    210                 215                 220

Arg Gly Leu Leu Leu Asp Tyr Trp Gly Gln Gly Thr Leu Val Thr Val
225                 230                 235                 240

Ser Ser

<210> SEQ ID NO 44
<211> LENGTH: 883
<212> TYPE: PRT
<213> ORGANISM: Homo sapiens

<400> SEQUENCE: 44

Ala His Pro Gly Arg Pro Arg Ala Val Pro Thr Gln Cys Asp Val Pro
1               5                   10                  15

Pro Asn Ser Arg Phe Asp Cys Ala Pro Asp Lys Ala Ile Thr Gln Glu
            20                  25                  30

Gln Cys Glu Ala Arg Gly Cys Cys Tyr Ile Pro Ala Lys Gln Gly Leu
        35                  40                  45

Gln Gly Ala Gln Met Gly Gln Pro Trp Cys Phe Phe Pro Pro Ser Tyr
    50                  55                  60

Pro Ser Tyr Lys Leu Glu Asn Leu Ser Ser Ser Glu Met Gly Tyr Thr
65                  70                  75                  80

Ala Thr Leu Thr Arg Thr Thr Pro Thr Phe Phe Pro Lys Asp Ile Leu
                85                  90                  95
```

```
Thr Leu Arg Leu Asp Val Met Met Glu Thr Glu Asn Arg Leu His Phe
                100                 105                 110

Thr Ile Lys Asp Pro Ala Asn Arg Arg Tyr Glu Val Pro Leu Glu Thr
            115                 120                 125

Pro His Val His Ser Arg Ala Pro Ser Pro Leu Tyr Ser Val Glu Phe
130                 135                 140

Ser Glu Glu Pro Phe Gly Val Ile Val Arg Arg Gln Leu Asp Gly Arg
145                 150                 155                 160

Val Leu Leu Asn Thr Thr Val Ala Pro Leu Phe Phe Ala Asp Gln Phe
                165                 170                 175

Leu Gln Leu Ser Thr Ser Leu Pro Ser Gln Tyr Ile Thr Gly Leu Ala
            180                 185                 190

Glu His Leu Ser Pro Leu Met Leu Ser Thr Ser Trp Thr Arg Ile Thr
        195                 200                 205

Leu Trp Asn Arg Asp Leu Ala Pro Thr Pro Gly Ala Asn Leu Tyr Gly
210                 215                 220

Ser His Pro Phe Tyr Leu Ala Leu Glu Asp Gly Gly Ser Ala His Gly
225                 230                 235                 240

Val Phe Leu Leu Asn Ser Asn Ala Met Asp Val Val Leu Gln Pro Ser
                245                 250                 255

Pro Ala Leu Ser Trp Arg Ser Thr Gly Gly Ile Leu Asp Val Tyr Ile
            260                 265                 270

Phe Leu Gly Pro Glu Pro Lys Ser Val Val Gln Gln Tyr Leu Asp Val
        275                 280                 285

Val Gly Tyr Pro Phe Met Pro Pro Tyr Trp Gly Leu Gly Phe His Leu
290                 295                 300

Cys Arg Trp Gly Tyr Ser Ser Thr Ala Ile Thr Arg Gln Val Val Glu
305                 310                 315                 320

Asn Met Thr Arg Ala His Phe Pro Leu Asp Val Gln Trp Asn Asp Leu
                325                 330                 335

Asp Tyr Met Asp Ser Arg Arg Asp Phe Thr Phe Asn Lys Asp Gly Phe
            340                 345                 350

Arg Asp Phe Pro Ala Met Val Gln Glu Leu His Gln Gly Gly Arg Arg
        355                 360                 365

Tyr Met Met Ile Val Asp Pro Ala Ile Ser Ser Ser Gly Pro Ala Gly
370                 375                 380

Ser Tyr Arg Pro Tyr Asp Glu Gly Leu Arg Arg Gly Val Phe Ile Thr
385                 390                 395                 400

Asn Glu Thr Gly Gln Pro Leu Ile Gly Lys Val Trp Pro Gly Ser Thr
                405                 410                 415

Ala Phe Pro Asp Phe Thr Asn Pro Thr Ala Leu Ala Trp Trp Glu Asp
            420                 425                 430

Met Val Ala Glu Phe His Asp Gln Val Pro Phe Asp Gly Met Trp Ile
        435                 440                 445

Asp Met Asn Glu Pro Ser Asn Phe Ile Arg Gly Ser Glu Asp Gly Cys
450                 455                 460

Pro Asn Asn Glu Leu Glu Asn Pro Pro Tyr Val Pro Gly Val Val Gly
465                 470                 475                 480

Gly Thr Leu Gln Ala Ala Thr Ile Cys Ala Ser Ser His Gln Phe Leu
                485                 490                 495

Ser Thr His Tyr Asn Leu His Asn Leu Tyr Gly Leu Thr Glu Ala Ile
            500                 505                 510
```

Ala Ser His Arg Ala Leu Val Lys Ala Arg Gly Thr Arg Pro Phe Val
            515                 520                 525

Ile Ser Arg Ser Thr Phe Ala Gly His Gly Arg Tyr Ala Gly His Trp
        530                 535                 540

Thr Gly Asp Val Trp Ser Ser Trp Glu Gln Leu Ala Ser Ser Val Pro
545                 550                 555                 560

Glu Ile Leu Gln Phe Asn Leu Leu Gly Val Pro Leu Val Gly Ala Asp
                565                 570                 575

Val Cys Gly Phe Leu Gly Asn Thr Ser Glu Glu Leu Cys Val Arg Trp
            580                 585                 590

Thr Gln Leu Gly Ala Phe Tyr Pro Phe Met Arg Asn His Asn Ser Leu
        595                 600                 605

Leu Ser Leu Pro Gln Glu Pro Tyr Ser Phe Ser Glu Pro Ala Gln Gln
    610                 615                 620

Ala Met Arg Lys Ala Leu Thr Leu Arg Tyr Ala Leu Leu Pro His Leu
625                 630                 635                 640

Tyr Thr Leu Phe His Gln Ala His Val Ala Gly Glu Thr Val Ala Arg
                645                 650                 655

Pro Leu Phe Leu Glu Phe Pro Lys Asp Ser Ser Thr Trp Thr Val Asp
            660                 665                 670

His Gln Leu Leu Trp Gly Glu Ala Leu Leu Ile Thr Pro Val Leu Gln
        675                 680                 685

Ala Gly Lys Ala Glu Val Thr Gly Tyr Phe Pro Leu Gly Thr Trp Tyr
    690                 695                 700

Asp Leu Gln Thr Val Pro Val Glu Ala Leu Gly Ser Leu Pro Pro Pro
705                 710                 715                 720

Pro Ala Ala Pro Arg Glu Pro Ala Ile His Ser Glu Gly Gln Trp Val
                725                 730                 735

Thr Leu Pro Ala Pro Leu Asp Thr Ile Asn Val His Leu Arg Ala Gly
            740                 745                 750

Tyr Ile Ile Pro Leu Gln Gly Pro Gly Leu Thr Thr Thr Glu Ser Arg
        755                 760                 765

Gln Gln Pro Met Ala Leu Ala Val Ala Leu Thr Lys Gly Gly Glu Ala
    770                 775                 780

Arg Gly Glu Leu Phe Trp Asp Asp Gly Glu Ser Leu Glu Val Leu Glu
785                 790                 795                 800

Arg Gly Ala Tyr Thr Gln Val Ile Phe Leu Ala Arg Asn Asn Thr Ile
                805                 810                 815

Val Asn Glu Leu Val Arg Val Thr Ser Glu Gly Ala Gly Leu Gln Leu
            820                 825                 830

Gln Lys Val Thr Val Leu Gly Val Ala Thr Ala Pro Gln Gln Val Leu
        835                 840                 845

Ser Asn Gly Val Pro Val Ser Asn Phe Thr Tyr Ser Pro Asp Thr Lys
    850                 855                 860

Val Leu Asp Ile Cys Val Ser Leu Leu Met Gly Glu Gln Phe Leu Val
865                 870                 875                 880

Ser Trp Cys

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Gly Gly Ser Gly Gly Gly Ser Gly Gly Ser Gly Gly
1               5                   10

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Ile Leu Leu His Asp Phe Leu Leu Val Pro Arg Glu Leu Ser Gly
1               5                   10                  15

Ser Ser Pro Val Leu Glu Glu Thr His Pro Ala His
            20                  25

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Gln Lys Leu Ile Ser Glu Glu Asp Leu
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Ile Ser Ser Gly Ser Ser Thr Ile Tyr Tyr Ala Asp Ser Val Lys
1               5                   10                  15

Gly

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Lys Ser Val Ser Thr Ser Ser Tyr Ser Tyr Leu Ala
1               5                   10                  15
```

```
<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Ala Ser Tyr Leu Gln Ser
1               5

<210> SEQ ID NO 52
<211> LENGTH: 937
<212> TYPE: PRT
<213> ORGANISM: Bos taurus

<400> SEQUENCE: 52

Met Met Arg Trp Pro Pro Cys Ser Arg Pro Leu Leu Gly Val Cys Thr
1               5                   10                  15

Leu Leu Ser Leu Ala Leu Leu Gly His Ile Leu Leu His Asp Leu Glu
                20                  25                  30

Val Val Pro Arg Glu Leu Arg Gly Phe Ser Gln Asp Glu Ile His Gln
            35                  40                  45

Ala Cys Gln Pro Gly Ala Ser Ser Pro Glu Cys Arg Gly Ser Pro Arg
    50                  55                  60

Ala Ala Pro Thr Gln Cys Asp Leu Pro Pro Asn Ser Arg Phe Asp Cys
65                  70                  75                  80

Ala Pro Asp Lys Gly Ile Thr Pro Gln Gln Cys Glu Ala Arg Gly Cys
                85                  90                  95

Cys Tyr Met Pro Ala Glu Trp Pro Pro Asp Ala Gln Met Gly Gln Pro
            100                 105                 110

Trp Cys Phe Phe Pro Pro Ser Tyr Pro Ser Tyr Arg Leu Glu Asn Leu
        115                 120                 125

Thr Thr Thr Glu Thr Gly Tyr Thr Ala Thr Leu Thr Arg Ala Val Pro
130                 135                 140

Thr Phe Phe Pro Lys Asp Ile Met Thr Leu Arg Leu Asp Met Leu Met
145                 150                 155                 160

Glu Thr Glu Ser Arg Leu His Phe Thr Ile Lys Asp Pro Ala Asn Arg
                165                 170                 175

Arg Tyr Glu Val Pro Leu Glu Thr Pro Arg Val Tyr Ser Gln Ala Pro
            180                 185                 190

Phe Thr Leu Tyr Ser Val Glu Phe Ser Glu Glu Pro Phe Gly Val Val
        195                 200                 205

Val Arg Arg Lys Leu Asp Gly Arg Val Leu Leu Asn Thr Thr Val Ala
    210                 215                 220

Pro Leu Phe Phe Ala Asp Gln Phe Leu Gln Leu Ser Thr Ser Leu Pro
225                 230                 235                 240

Ser Gln His Ile Thr Gly Leu Ala Glu His Leu Gly Ser Leu Met Leu
                245                 250                 255

Ser Thr Asn Trp Thr Lys Ile Thr Leu Trp Asn Arg Asp Ile Ala Pro
            260                 265                 270

Glu Pro Asn Val Asn Leu Tyr Gly Ser His Pro Phe Tyr Leu Val Leu
        275                 280                 285

Glu Asp Gly Gly Leu Ala His Gly Val Phe Leu Leu Asn Ser Asn Ala
    290                 295                 300
```

-continued

```
Met Asp Val Val Leu Gln Pro Ser Pro Ala Leu Ser Trp Arg Ser Thr
305                 310                 315                 320

Gly Gly Ile Leu Asp Val Tyr Ile Phe Leu Gly Pro Glu Pro Lys Ser
            325                 330                 335

Val Val Gln Gln Tyr Leu Asp Val Val Gly Tyr Pro Phe Met Pro Pro
        340                 345                 350

Tyr Trp Gly Leu Gly Phe His Leu Cys Arg Trp Gly Tyr Ser Thr Ser
    355                 360                 365

Ala Ile Thr Arg Gln Val Val Glu Asn Met Thr Arg Ala Tyr Phe Pro
370                 375                 380

Leu Asp Val Gln Trp Asn Asp Leu Asp Tyr Met Asp Ala Arg Arg Asp
385                 390                 395                 400

Phe Thr Phe Asn Lys Asp His Phe Gly Asp Phe Pro Ala Met Val Gln
                405                 410                 415

Glu Leu His Gln Gly Gly Arg Arg Tyr Ile Met Ile Val Asp Pro Ala
            420                 425                 430

Ile Ser Ser Ser Gly Pro Ala Gly Thr Tyr Arg Pro Tyr Asp Glu Gly
        435                 440                 445

Leu Arg Arg Gly Val Phe Ile Thr Asn Glu Thr Gly Gln Pro Leu Ile
450                 455                 460

Gly Gln Val Trp Pro Gly Leu Thr Ala Phe Pro Asp Phe Thr Asn Pro
465                 470                 475                 480

Glu Thr Leu Asp Trp Trp Gln Asp Met Val Thr Glu Phe His Ala Gln
                485                 490                 495

Val Pro Phe Asp Gly Met Trp Ile Asp Met Asn Glu Pro Ser Asn Phe
            500                 505                 510

Val Arg Gly Ser Val Asp Gly Cys Pro Asp Asn Ser Leu Glu Asn Pro
        515                 520                 525

Pro Tyr Leu Pro Gly Val Val Gly Gly Thr Leu Arg Ala Ala Thr Ile
    530                 535                 540

Cys Ala Ser Ser His Gln Phe Leu Ser Thr His Tyr Asp Leu His Asn
545                 550                 555                 560

Leu Tyr Gly Leu Thr Glu Ala Leu Ala Ser His Arg Ala Leu Val Lys
                565                 570                 575

Ala Arg Gly Met Arg Pro Phe Val Ile Ser Arg Ser Thr Phe Ala Gly
            580                 585                 590

His Gly Arg Tyr Ser Gly His Trp Thr Gly Asp Val Trp Ser Asn Trp
        595                 600                 605

Glu Gln Leu Ser Tyr Ser Val Pro Glu Ile Leu Leu Phe Asn Leu Leu
    610                 615                 620

Gly Val Pro Leu Val Gly Ala Asp Ile Cys Gly Phe Leu Gly Asn Thr
625                 630                 635                 640

Ser Glu Glu Leu Cys Val Arg Trp Thr Gln Leu Gly Ala Phe Tyr Pro
                645                 650                 655

Phe Met Arg Asn His Asn Ala Leu Asn Ser Gln Pro Gln Glu Pro Tyr
            660                 665                 670

Arg Phe Ser Glu Thr Ala Gln Gln Ala Met Arg Lys Ala Phe Thr Leu
        675                 680                 685

Arg Tyr Val Leu Leu Pro Tyr Leu Tyr Thr Leu Phe His Arg Ala His
    690                 695                 700

Val Arg Gly Glu Thr Val Ala Arg Pro Leu Phe Leu Glu Phe Pro Glu
705                 710                 715                 720
```

```
Asp Pro Ser Thr Trp Thr Val Asp Arg Gln Leu Leu Trp Gly Glu Ala
                725                 730                 735

Leu Leu Ile Thr Pro Val Leu Glu Ala Glu Lys Val Glu Val Thr Gly
            740                 745                 750

Tyr Phe Pro Gln Gly Thr Trp Tyr Asp Leu Gln Thr Val Pro Met Glu
        755                 760                 765

Ala Phe Gly Ser Leu Pro Pro Ala Pro Leu Thr Ser Val Ile His
    770                 775                 780

Ser Lys Gly Gln Trp Val Thr Leu Ser Ala Pro Leu Asp Thr Ile Asn
785                 790                 795                 800

Val His Leu Arg Ala Gly His Ile Ile Pro Met Gln Gly Pro Ala Leu
                805                 810                 815

Thr Thr Thr Glu Ser Arg Lys Gln His Met Ala Leu Ala Val Ala Leu
            820                 825                 830

Thr Ala Ser Gly Glu Ala Gln Gly Glu Leu Phe Trp Asp Asp Gly Glu
        835                 840                 845

Ser Leu Gly Val Leu Asp Gly Gly Asp Tyr Thr Gln Leu Ile Phe Leu
    850                 855                 860

Ala Lys Asn Asn Thr Phe Val Asn Lys Leu Val His Val Ser Ser Glu
865                 870                 875                 880

Gly Ala Ser Leu Gln Leu Arg Asn Val Thr Val Leu Gly Val Ala Thr
                885                 890                 895

Ala Pro Gln Gln Val Leu Cys Asn Ser Val Pro Val Ser Asn Phe Thr
            900                 905                 910

Phe Ser Pro Asp Thr Glu Thr Leu Ala Ile Pro Val Ser Leu Thr Met
        915                 920                 925

Gly Glu Gln Phe Val Ile Ser Trp Ser
    930                 935

<210> SEQ ID NO 53
<211> LENGTH: 333
<212> TYPE: DNA
<213> ORGANISM: Mus sp.

<400> SEQUENCE: 53
gacattgtgc tgacacagtc tcctgcttcc ttagctgtat ctctggggca gagggccacc      60
atctcctgca gggccagcaa aagtgtcagt acatctagct atagttacat gcactggtac     120
caacagaaac caggacagcc acccaaactc ctcatcaagt atgcatccta cctagaatct     180
ggggttcctg ccaggttcag tggcagtggg tctgggacag actttcacct caacatccat     240
cctgtggagg aggaggatgc tgcaacatat tactgtcagc acagtaggga gtttccgtgg     300
acgttcggtg gaggcaccaa gctggagttg aaa                                  333

<210> SEQ ID NO 54
<211> LENGTH: 348
<212> TYPE: DNA
<213> ORGANISM: Mus sp.

<400> SEQUENCE: 54
gaggtgcagc tggtggagtc tgggggaggc ttagtgaagc ctggagggtc ccggaaactc      60
tcctgtgcag cctctggatt cactttcagt aactatggaa tgcactgggt ccgtcaggct     120
ccagagaagg ggctggagtg ggttgcatac attagtagtg gcagtagtac catctactat     180
gcagacacag tgaagggccg attcaccatc tccagagaca atgccaagaa caccctgttc     240
```

-continued

```
ctgcaaatga ccagtctaag gtctgaggac acagccatgt attactgtgc aaggcggggg    300
ttactacttg actactgggg ccaaggcacc actctcacag tctcctca                 348
```

<210> SEQ ID NO 55
<211> LENGTH: 367
<212> TYPE: PRT
<213> ORGANISM: Homo sapiens

<400> SEQUENCE: 55

```
Met Ala Leu Asn Val Ala Pro Val Arg Asp Thr Lys Trp Leu Thr Leu
1               5                   10                  15

Glu Val Cys Arg Gln Phe Gln Arg Gly Thr Cys Ser Arg Ser Asp Glu
            20                  25                  30

Glu Cys Lys Phe Ala His Pro Pro Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro Thr His Leu Lys Thr Gln Leu Glu
65                  70                  75                  80

Ile Asn Gly Arg Asn Asn Leu Ile Gln Gln Lys Thr Ala Ala Ala Met
                85                  90                  95

Leu Ala Gln Gln Met Gln Phe Met Phe Pro Gly Thr Pro Leu His Pro
            100                 105                 110

Val Pro Thr Phe Pro Val Gly Pro Ala Ile Gly Thr Asn Thr Ala Ile
        115                 120                 125

Ser Phe Ala Pro Tyr Leu Ala Pro Val Thr Pro Gly Val Gly Leu Val
    130                 135                 140

Pro Thr Glu Ile Leu Pro Thr Thr Pro Val Ile Val Pro Gly Ser Pro
145                 150                 155                 160

Pro Val Thr Val Pro Gly Ser Thr Ala Thr Gln Lys Leu Leu Arg Thr
                165                 170                 175

Asp Lys Leu Glu Val Cys Arg Glu Phe Gln Arg Gly Asn Cys Ala Arg
            180                 185                 190

Gly Glu Thr Asp Cys Arg Phe Ala His Pro Ala Asp Ser Thr Met Ile
        195                 200                 205

Asp Thr Ser Asp Asn Thr Val Thr Val Cys Met Asp Tyr Ile Lys Gly
    210                 215                 220

Arg Cys Met Arg Glu Lys Cys Lys Tyr Phe His Pro Pro Ala His Leu
225                 230                 235                 240

Gln Ala Lys Ile Lys Ala Ala Gln His Gln Ala Asn Gln Ala Ala Val
                245                 250                 255

Ala Ala Gln Ala Ala Ala Ala Ala Thr Val Met Ala Phe Pro Pro
            260                 265                 270

Gly Ala Leu His Pro Leu Pro Lys Arg Gln Ala Leu Glu Lys Ser Asn
        275                 280                 285

Gly Thr Ser Ala Val Phe Asn Pro Ser Val Leu His Tyr Gln Gln Ala
    290                 295                 300

Leu Thr Ser Ala Gln Leu Gln Gln His Ala Ala Phe Ile Pro Thr Gly
305                 310                 315                 320

Ser Val Leu Cys Met Thr Pro Ala Thr Ser Ile Val Pro Met Met His
                325                 330                 335
```

```
Ser Ala Thr Ser Ala Thr Val Ser Ala Ala Thr Thr Pro Ala Thr Ser
            340                 345                 350

Val Pro Phe Ala Ala Thr Ala Thr Ala Asn Gln Ile Ile Leu Lys
            355                 360                 365

<210> SEQ ID NO 56
<211> LENGTH: 361
<212> TYPE: PRT
<213> ORGANISM: Homo sapiens

<400> SEQUENCE: 56

Met Ala Leu Asn Val Ala Pro Val Arg Asp Thr Lys Trp Leu Thr Leu
1               5                   10                  15

Glu Val Cys Arg Gln Phe Gln Arg Gly Thr Cys Ser Arg Ser Asp Glu
            20                  25                  30

Glu Cys Lys Phe Ala His Pro Pro Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro Thr His Leu Lys Thr Gln Leu Glu
65                  70                  75                  80

Ile Asn Gly Arg Asn Asn Leu Ile Gln Gln Lys Thr Ala Ala Ala Met
                85                  90                  95

Leu Ala Gln Gln Met Gln Phe Met Phe Pro Gly Thr Pro Leu His Pro
            100                 105                 110

Val Pro Thr Phe Pro Val Gly Pro Ala Ile Gly Thr Asn Thr Ala Ile
        115                 120                 125

Ser Phe Ala Pro Tyr Leu Ala Pro Val Thr Pro Gly Val Gly Leu Val
    130                 135                 140

Pro Thr Glu Ile Leu Pro Thr Thr Pro Val Ile Val Pro Gly Ser Pro
145                 150                 155                 160

Pro Val Thr Val Pro Gly Ser Thr Ala Thr Gln Lys Leu Leu Arg Thr
                165                 170                 175

Asp Lys Leu Glu Val Cys Arg Glu Phe Gln Arg Gly Asn Cys Ala Arg
            180                 185                 190

Gly Glu Thr Asp Cys Arg Phe Ala His Pro Ala Asp Ser Thr Met Ile
        195                 200                 205

Asp Thr Ser Asp Asn Thr Val Thr Val Cys Met Asp Tyr Ile Lys Gly
    210                 215                 220

Arg Cys Met Arg Glu Lys Cys Lys Tyr Phe His Pro Pro Ala His Leu
225                 230                 235                 240

Gln Ala Lys Ile Lys Ala Ala Gln His Gln Ala Asn Gln Ala Ala Val
                245                 250                 255

Ala Ala Gln Ala Ala Ala Ala Ala Thr Val Met Ala Phe Pro Pro
            260                 265                 270

Gly Ala Leu His Pro Leu Pro Lys Arg Gln Ala Leu Glu Lys Ser Asn
        275                 280                 285

Gly Thr Ser Ala Val Phe Asn Pro Ser Val Leu His Tyr Gln Gln Ala
    290                 295                 300

Leu Thr Ser Ala Gln Leu Gln Gln His Ala Ala Phe Ile Pro Thr Asp
305                 310                 315                 320

Asn Ser Glu Ile Ile Ser Arg Asn Gly Met Glu Cys Gln Glu Ser Ala
                325                 330                 335
```

```
Leu Arg Ile Thr Lys His Cys Tyr Cys Thr Tyr Pro Val Ser Ser
                340                 345                 350

Ser Ile Glu Leu Pro Gln Thr Ala Cys
            355                 360

<210> SEQ ID NO 57
<211> LENGTH: 354
<212> TYPE: PRT
<213> ORGANISM: Homo sapiens

<400> SEQUENCE: 57

Met Thr Ala Val Asn Val Ala Leu Ile Arg Asp Thr Lys Trp Leu Thr
1               5                   10                  15

Leu Glu Val Cys Arg Glu Phe Gln Arg Gly Thr Cys Ser Arg Ala Asp
                20                  25                  30

Ala Asp Cys Lys Phe Ala His Pro Pro Arg Val Cys His Val Glu Asn
            35                  40                  45

Gly Arg Val Val Ala Cys Phe Asp Ser Leu Lys Gly Arg Cys Thr Arg
        50                  55                  60

Glu Asn Cys Lys Tyr Leu His Pro Pro His Leu Lys Thr Gln Leu
65                  70                  75                  80

Glu Ile Asn Gly Arg Asn Asn Leu Ile Gln Gln Lys Thr Ala Ala
                85                  90                  95

Met Phe Ala Gln Gln Met Gln Leu Met Leu Gln Asn Ala Gln Met Ser
            100                 105                 110

Ser Leu Gly Ser Phe Pro Met Thr Pro Ser Ile Pro Ala Asn Pro Pro
            115                 120                 125

Met Ala Phe Asn Pro Tyr Ile Pro His Pro Gly Met Gly Leu Val Pro
        130                 135                 140

Ala Glu Leu Val Pro Asn Thr Pro Val Leu Ile Pro Gly Asn Pro Pro
145                 150                 155                 160

Leu Ala Met Pro Gly Ala Val Gly Pro Lys Leu Met Arg Ser Asp Lys
                165                 170                 175

Leu Glu Val Cys Arg Glu Phe Gln Arg Gly Asn Cys Thr Arg Gly Glu
            180                 185                 190

Asn Asp Cys Arg Tyr Ala His Pro Thr Asp Ala Ser Met Ile Glu Ala
        195                 200                 205

Ser Asp Asn Thr Val Thr Ile Cys Met Asp Tyr Ile Lys Gly Arg Cys
210                 215                 220

Ser Arg Glu Lys Cys Lys Tyr Phe His Pro Ala His Leu Gln Ala
225                 230                 235                 240

Arg Leu Lys Ala Ala His His Gln Met Asn His Ser Ala Ala Ser Ala
                245                 250                 255

Met Ala Leu Gln Pro Gly Thr Leu Gln Leu Ile Pro Lys Arg Ser Ala
            260                 265                 270

Leu Glu Lys Pro Asn Gly Ala Thr Pro Val Phe Asn Pro Thr Val Phe
        275                 280                 285

His Cys Gln Gln Ala Leu Thr Asn Leu Gln Leu Pro Gln Pro Ala Phe
        290                 295                 300

Ile Pro Ala Gly Pro Ile Leu Cys Met Ala Pro Ala Ser Asn Ile Val
305                 310                 315                 320

Pro Met Met His Gly Ala Thr Pro Thr Thr Val Ser Ala Ala Thr Thr
                325                 330                 335
```

-continued

```
Pro Ala Thr Ser Val Pro Phe Ala Ala Pro Thr Thr Gly Asn Gln Leu
            340                 345                 350

Lys Phe

<210> SEQ ID NO 58
<211> LENGTH: 334
<212> TYPE: PRT
<213> ORGANISM: Homo sapiens

<400> SEQUENCE: 58

Met Thr Ala Val Asn Val Ala Leu Ile Arg Asp Thr Lys Trp Leu Thr
1               5                   10                  15

Leu Glu Val Cys Arg Glu Phe Gln Arg Gly Thr Cys Ser Arg Ala Asp
                20                  25                  30

Ala Asp Cys Lys Phe Ala His Pro Pro Arg Val Cys His Val Glu Asn
            35                  40                  45

Gly Arg Val Val Ala Cys Phe Asp Ser Leu Lys Gly Arg Cys Thr Arg
        50                  55                  60

Glu Asn Cys Lys Tyr Leu His Pro Pro His Leu Lys Thr Gln Leu
65                  70                  75                  80

Glu Ile Asn Gly Arg Asn Asn Leu Ile Gln Gln Lys Thr Ala Ala Ala
                85                  90                  95

Met Phe Ala Gln Gln Met Gln Leu Met Leu Gln Asn Ala Gln Met Ser
            100                 105                 110

Ser Leu Gly Ser Phe Pro Met Thr Pro Ser Ile Pro Ala Asn Pro Pro
        115                 120                 125

Met Ala Phe Asn Pro Tyr Ile Pro His Pro Gly Met Gly Leu Val Pro
    130                 135                 140

Ala Glu Leu Val Pro Asn Thr Pro Val Leu Ile Pro Gly Asn Pro Pro
145                 150                 155                 160

Leu Ala Met Pro Gly Ala Val Gly Pro Lys Leu Met Arg Ser Asp Lys
                165                 170                 175

Leu Glu Val Cys Arg Glu Phe Gln Arg Gly Asn Cys Thr Arg Gly Glu
            180                 185                 190

Asn Asp Cys Arg Tyr Ala His Pro Thr Asp Ala Ser Met Ile Glu Ala
        195                 200                 205

Ser Asp Asn Thr Val Thr Ile Cys Met Asp Tyr Ile Lys Gly Arg Cys
    210                 215                 220

Ser Arg Glu Lys Cys Lys Tyr Phe His Pro Ala His Leu Gln Ala
225                 230                 235                 240

Arg Leu Lys Ala Ala His His Gln Met Asn His Ser Ala Ala Ser Ala
                245                 250                 255

Met Ala Leu Thr Asn Leu Gln Leu Pro Gln Pro Ala Phe Ile Pro Ala
            260                 265                 270

Gly Pro Ile Leu Cys Met Ala Pro Ala Ser Asn Ile Val Pro Met Met
        275                 280                 285

His Gly Ala Thr Pro Thr Val Ser Ala Ala Thr Pro Ala Thr
    290                 295                 300

Ser Val Pro Phe Ala Ala Pro Thr Thr Gly Asn Gln Ile Pro Gln Leu
305                 310                 315                 320

Ser Ile Asp Glu Leu Asn Ser Ser Met Phe Val Ser Gln Met
                325                 330
```

```
<210> SEQ ID NO 59
<211> LENGTH: 116
<212> TYPE: PRT
<213> ORGANISM: Homo sapiens

<400> SEQUENCE: 59

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro
        115

<210> SEQ ID NO 60
<211> LENGTH: 107
<212> TYPE: PRT
<213> ORGANISM: Homo sapiens

<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 61
<211> LENGTH: 22
<212> TYPE: PRT
<213> ORGANISM: Homo sapiens

<400> SEQUENCE: 61

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 62
<211> LENGTH: 19
<212> TYPE: PRT
<213> ORGANISM: Homo sapiens
```

<400> SEQUENCE: 62

Met Glu Phe Gly Leu Ser Trp Leu Phe Leu Val Ala Ile Leu Lys Gly
1               5                   10                  15

Val Gln Cys

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggtgaacct gcaggtgggc aaagatgtcc                                    30

INTERNALIZING MOIETIES

RELATED APPLICATIONS

This application is a national stage filing under 35 U.S.C. § 371 of International Application No. PCT/US2015/011269, filed on Jan. 13, 2015, which claims the benefit of priority to U.S. provisional application Ser. No. 61/926,863, filed Jan. 13, 2014, U.S. provisional application Ser. No. 61/926,865, filed Jan. 13, 2014, U.S. provisional application Ser. No. 62/042,755, filed Aug. 27, 2014, U.S. provisional application Ser. No. 62/042,771, filed Aug. 27, 2014. The entire contents of each of the foregoing applications are hereby incorporated by reference in their entirety. International Application No. PCT/US2015/011269 was published under PCT Article 21(2) in English.

SEQUENCE LISTING

The instant application contains a Sequence Listing which has been submitted via EFS-Web and is hereby incorporated by reference in its entirety. Said ASCII copy, created on Jul. 11, 2016, is named 1061990029301_seq.txt, and is 157,360 bytes in size.

BACKGROUND OF THE DISCLOSURE

Monoclonal antibodies have been frequently used as powerful prophylactic, diagnostic, therapeutic, and research tools for scientists and physicians in their attempt to prevent, identify and treat diseases, as well as to understand biology and as reagents (Ducancel, 2012, Landes Bioscience, 4(4): 445-457). Many monoclonal antibodies are derived from rodent antibodies. However, the administration of purely rodent antibodies or antibody fragments has disadvantages that may, under some circumstances, limit their applicability in humans, particularly for chronic administration. Techniques exist to generate chimeric or humanize antibodies to decrease immunogenicity of entirely rodent antibodies and make them more suitable for use in human subjects. However, not all humanized or chimeric antibodies retain the properties of their rodent precursor. Moreover, even amongst humanized antibodies, not all share properties that make then suitable for manufacture and use as research, diagnostic, and/or therapeutic agents.

SUMMARY OF THE DISCLOSURE

The present disclosure provides antibodies and antigen-binding fragments based on a 3E10 parent antibody. In certain embodiments, the disclosure provides novel antibodies and antigen binding fragments having a novel combination of CDRs and, optionally, one or more improved characteristics, as described herein. Antibodies and antigen-binding fragments of the disclosure bind DNA and/or transit one or more cellular membranes (e.g., the plasma membrane). In certain embodiments, antibodies and antigen binding fragments of the disclosure can bind DNA and can transit one or more cellular membranes (e.g., the plasma membrane) via an ENT transporter (e.g., an ENT2 and/or ENT3 transporter), akin to a parent 3E10 antibody. In some cases, antibodies and antigen binding fragments of the disclosure have substantially the same or even improved DNA binding and/or cell penetration activity, relative to the 3E10 parent antibody described herein. In certain embodiments, antibodies and antigen-binding fragments of the disclosure comprise a humanized heavy chain (such as a humanized heavy chain variable domain—VH) and/or a humanized light chain (such as a humanized light chain variable domain—VL). When present as a full length antibody or a Fab, such humanized antibodies optionally comprise a human heavy chain constant domain and/or human light chain constant domain. However, it is appreciated that when antibodies of the disclosure are humanized, the heavy and/or light chain constant domain may be from human or from another species. Moreover, it is appreciated that a humanized antibody or antigen-binding fragment may include a humanized VH, a humanized VL, or both a humanized VH and VL. Finally, it is appreciated that, as described below, the term humanized does not require that all of the framework region residues of the murine parent antibody are replaced with sequences from a corresponding human antibody. Rather, the term includes embodiments in which one or more framework region residues corresponding to the murine sequence are retained, and thus, differ from a more frequent human sequence at that position. In other words, a humanized heavy or light chain variable domain may be humanized in whole or in part. The disclosure similarly contemplates that antibodies and antigen binding fragments of the disclosure may be chimeric antibodies or humanized antibodies. Throughout the disclosure, it is contemplated that functional and structural features, uses, or compositions that are described for humanized antibodies or antigen-binding fragments of the disclosure similarly apply to any antibody or antigen-binding fragment of the disclosure.

Throughout this application, the terms antibody or antigen-binding fragment of the disclosure and humanized antibody or antigen-binding fragment of the disclosure (or antibody and antigen binding fragment of the disclosure) are used to refer to any combination of antibody light chains and antibody heavy chains described herein, but not including an antibody comprising both the VH and VL of the murine, parent antibody used as the precursor and for comparison. In certain embodiments, one or both chains of an antibody or antigen binding fragment of the disclosure are humanized. In certain embodiments, the term antibody or antigen binding fragment of the disclosure specifically excludes a first generation humanized antibody set forth in Example 1. In certain embodiments, the disclosure provides novel antibodies and antigen binding fragments having a novel combination of CDRs and, optionally, one or more improved characteristics, as described herein. In certain embodiments, the combination of the 6 CDRs of an antibody or antigen binding fragment of the disclosure, according to Kabat, differ from that of the murine 3E10 parent antibody and from the humanized antibody set forth in Example 1.

In certain embodiments, the disclosure provides an antibody or antigen binding fragment comprising a heavy chain and a light chain, wherein the heavy chain comprises any of the heavy chain variable domains described herein. In certain embodiments, the disclosure provides an antibody or antigen binding fragment comprising a heavy chain and a light chain, wherein the light chain comprises any of the light chain variable domains described herein. In certain embodiments, the disclosure provides an antibody or antigen binding fragment comprising a heavy chain and a light chain, wherein the heavy chain comprises any of the heavy chain variable domains described herein and the light chain comprises any of the light chain variable domains described herein. By way of example, the disclosure provides an antibody or antigen binding fragment comprising a heavy chain and a light chain, wherein the heavy chain comprises a heavy chain variable domain comprising the amino acid sequence set forth in any of SEQ ID NOs: 10, 38 or 39. The disclosure also provides an antibody or antigen-binding fragment comprising a heavy chain and a light chain, wherein the light chain comprises light chain variable domain comprising the amino acid sequence set forth in either SEQ ID NO: 8 or 40. The disclosure also contemplates an antibody or antigen binding fragment comprising a heavy chain comprising a heavy chain variable domain comprising the amino acid sequence set forth in any of SEQ ID NOs: 10, 38 or 39 and a light chain comprising a light chain variable domain comprising an amino acid sequence set forth in either SEQ ID NO: 8 or 40. In certain embodiments, the antibody or antigen binding fragment comprises a light chain constant region (CL), such that the antibody or antigen binding fragment comprises a light chain comprising a VL and a CL, as described herein. In certain embodiments, the antibody or antigen binding fragment comprises a heavy chain constant region, comprising one or more of a CH1, hinge (such as an upper hinge), CH2, and CH3, such that the antibody or antigen binding fragment comprises a heavy chain comprising a VH and a portion of a heavy chain constant region (e.g., a portion of a Fc; one or more of a CH1, hinge (or upper hinge), CH2, and CH3 domain). Exemplary heavy chain and light chain constant regions are described herein. In certain embodiments, such as certain embodiments of any of the foregoing, the antibody or antigen binding fragment is an anti-DNA antibody or antigen binding fragment (e.g., can bind to DNA).

In certain embodiments, antibodies or antigen-binding fragments of the disclosure not only retain the advantageous properties of its rodent precursor (e.g., the parent antibody, such as the ability to bind DNA and penetrate into cells), but also have one or more improved properties in comparison to one or both of the parent murine precursor antibody and/or to certain one or more other antibodies (e.g., a different humanized antibody based on the same parent). Specifically, the disclosure provides antibodies and antibody fragments based on the cell-penetrating, murine 3E10 antibody (the parent antibody). Antibodies (and fragments thereof) of the disclosure, at least, substantially retain the DNA binding and cell penetrating activity of its murine precursor. However, in certain embodiments, an antibody or antigen binding fragment of the disclosure has at least one superior biological or physiological property as compared to its murine precursor. This antibody may also have, in certain embodiments, at least one superior biological or physiological property as compared to certain other humanized antibodies (e.g., other humanized antibodies based on the same parent antibody).

In certain embodiments, antibodies and antigen binding fragments of the disclosure differ in one or more CDRs, according to Kabat, in comparison to the murine 3E10 antibody (e.g., the combination of six CDRs is different from previously described antibodies). In certain embodiments, antibodies and antigen binding fragments of the disclosure differ in Kabat CDR2 of one or both of the VH and VL. In certain embodiments, antibodies and antigen binding fragments of the disclosure differ in Kabat CDR1 of the VL. In certain embodiments, antibodies and antigen binding fragments of the disclosure differ in Kabat VH CDR2, VL CDR2 and, optionally, VL CDR1, in comparison to the murine 3E10 antibody described herein.

Antibodies (and antigen-binding fragments thereof), including antibodies in accordance with the present disclosure, may be provided as a conjugate or fusion protein in association with a heterologous agent.

Such conjugates (e.g., chemical conjugates and/or fusions) are similarly contemplated. Any of the antibodies or antigen-binding fragments of the disclosure may further comprise a heterologous agent associated therewith (e.g., conjugated thereto; a conjugate comprising an antibody or antigen-binding fragment of the disclosure and a heterologous agent associated thereto).

The disclosure provides antibodies and antigen-binding fragments, as well as methods of making and using such antibodies or antigen-binding fragments thereof. Unless context clearly indicates otherwise, antibodies and antigen-binding fragments of the disclosure optionally comprise a heterologous agent.

In one aspect, the disclosure provides an antibody or antigen-binding fragment, wherein the antibody or antigen-binding fragment comprises a light chain variable (VL) domain and a heavy chain variable (VH) domain; wherein the VH domain is humanized and comprises:
a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3; which CDRs are defined using the IMGT system (e.g., the CDRs are according to the IMGT system);
and the VL domain is humanized
and comprises:
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6; which CDRs are defined using the IMGT system (e.g., the CDRs are according to the IMGT system), and wherein the antibody or antigen-binding fragment has increased DNA binding and/or cell penetration, relative to that of a murine 3E10 antibody comprising a light chain variable (VL) domain having the amino acid sequence of SEQ ID NO: 7 and a heavy chain variable (VH) domain having the amino acid sequence of SEQ ID NO: 9. Such a murine 3E10 comprises, when present, murine constant regions In certain embodiments of any of the foregoing, or of any of the aspects and embodiments disclosed herein, an antibody or antigen-binding fragment of the disclosure comprises a light chain variable (VL) domain and a heavy chain variable (VH) domain; wherein the VH domain comprises:
a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34,
as the CDRs are defined by the Kabat system (e.g., the CDRs are according to Kabat);
and the VL comprises:
a VL CDR1 having the amino acid sequence of SEQ ID NO: 35 or 50;
a VL CDR2 having the amino acid sequence of SEQ ID NO: 51; and
a VL CDR3 having the amino acid sequence of SEQ ID NO: 37,
as the CDRs are defined by the Kabat system (e.g., the CDRs are according to Kabat);
wherein the antibody or antigen-binding fragment binds DNA.

In some embodiments, the VL domain comprises a VL CDR1 having the amino acid sequence of SEQ ID NO: 35. In some embodiments the VL domain comprises a VL CDR1 having the amino acid sequence of SEQ ID NO: 50. In some embodiments, the VH domain is humanized. In some embodiments, the VL domain is humanized. In some embodiments both the VH domain and the VL domain are humanized. As noted above, humanization may be in whole or in part (e.g., all or a portion of one or more (or all) framework regions may be humanized).

In certain embodiments, an antibody or antigen binding fragment of the disclosure (e.g., a humanized antibody or antigen binding fragment of the disclosure) has DNA binding and cell penetration activity that is at least about comparable to that of the murine 3E10 parent antibody and, optionally, one or both of DNA binding and cell penetration activity is the same or even improved. In certain embodiments, an antibody or antigen binding fragment of the disclosure (e.g., humanized antibodies and antigen binding fragments of the disclosure) are capable of binding DNA and are capable of transiting one or more cell membrane (e.g., the plasma membrane). In certain embodiments, the antibodies or antigen binding fragments of the disclosure has DNA binding and cell penetration activity that is at least about comparable to that of the 3E10 parent antibody and, optionally, one or both of DNA binding and cell penetration activity is the same or even improved. In certain embodiments, antibodies and antigen binding fragments of the disclosure are capable of binding DNA and are capable of transiting one or more cell membrane (e.g., the plasma membrane; e.g., to facilitate delivery into the cytoplasm). In certain embodiments, comparisons to a parent antibody are to an antibody having the VH and VL domains of the 3E10 parent and murine constant regions.

In certain embodiments of any of the foregoing, or of any of the aspects and embodiments disclosed herein, the antibodies and antigen-binding fragments of the disclosure comprise a $V_L$ domain that comprises the amino acid sequence set forth in SEQ ID NO: 40, or an amino acid sequence that differs from SEQ ID NO: 40 by the presence of a total of 1, 2, 3, 4, 5, or 6 amino acid substitutions in the framework regions, as defined by the IMGT system, relative to SEQ ID NO: 40. In other embodiments, the $V_L$ domain comprises the amino acid sequence set forth in SEQ ID NO: 8, or an amino acid sequence that differs from SEQ ID NO: 8 by the presence of a total of 1, 2, 3, 4, 5, or 6 amino acid substitutions in the framework regions, as defined by the IMGT system, relative to SEQ ID NO: 8. In some embodiments, the VL domain comprises the amino acid sequence set forth in SEQ ID NO: 40. In some embodiments, the VL domain comprises the amino acid sequence set forth in SEQ ID NO: 8.

In certain embodiments, the disclosure provides an antibody or antigen binding fragment comprising a heavy chain and a light chain, wherein the light chain comprises a VL domain comprising the amino acid sequence set forth in SEQ ID NO: 40, or an amino acid sequence that differs from SEQ ID NO: 40 by the presence of a total of 1, 2, 3, 4, 5, or 6 amino acid substitutions in the framework regions, as defined by the IMGT system, relative to SEQ ID NO: 40. In certain embodiments, the disclosure provides an antibody or antigen binding fragment comprising a heavy chain and a light chain, wherein the light chain comprises a VL domain comprising the amino acid sequence set forth in SEQ ID NO: 8, or an amino acid sequence that differs from SEQ ID NO: 8 by the presence of a total of 1, 2, 3, 4, 5, or 6 amino acid substitutions in the framework regions, as defined by the IMGT system, relative to SEQ ID NO: 8. In some embodiments, the VL domain comprises the amino acid sequence set forth in SEQ ID NO: 40. In some embodiments, the VL domain comprises the amino acid sequence set forth in SEQ ID NO: 8.

In certain embodiments of any of the foregoing, or of any of the aspects and embodiments disclosed herein, the antibodies and antigen-binding fragments of the disclosure comprise a $V_H$ domain that comprises the amino acid sequence set forth in SEQ ID NO: 38, or an amino acid sequence that differs from SEQ ID NO: 38 by the presence of a total of 1, 2, 3, 4, 5, or 6 amino acid substitutions in the framework regions, as defined by the IMGT system, relative to SEQ ID NO: 38. In some embodiments, the $V_H$ domain comprises the amino acid sequence set forth in SEQ ID NO: 39, or an amino acid sequence that differs from SEQ ID NO: 39 by the presence of a total of 1, 2, 3, 4, 5, or 6 amino acid substitutions in the framework regions, as defined by the IMGT system, relative to SEQ ID NO: 39. In some embodiments, the $V_H$ domain comprises the amino acid sequence set forth in SEQ ID NO: 10, or an amino acid sequence that differs from SEQ ID NO: 10 by the presence of a total of 1, 2, 3, 4, 5, or 6 amino acid substitutions in the framework regions, as defined by the IMGT system, relative to SEQ ID NO: 10. In some embodiments, the VH domain comprises the amino acid sequence set forth in SEQ ID NO: 38. In some embodiments, the VH domain comprises the amino acid sequence set forth in SEQ ID NO: 39. In some embodiments, the VH domain comprises the amino acid sequence set forth in SEQ ID NO: 10.

In certain embodiments, the disclosure provides an antibody or antigen binding fragment comprising a heavy chain and a light chain, wherein the heavy chain comprises a $V_H$ domain that comprises the amino acid sequence set forth in SEQ ID NO: 38, or an amino acid sequence that differs from SEQ ID NO: 38 by the presence of a total of 1, 2, 3, 4, 5, or 6 amino acid substitutions in the framework regions, as defined by the IMGT system, relative to SEQ ID NO: 38. In some embodiments, the $V_H$ domain comprises the amino acid sequence that differs from SEQ ID NO: 39, or an amino acid sequence that differs from SEQ ID NO: 39 by the presence of a total of 1, 2, 3, 4, 5, or 6 amino acid substitutions in the framework regions, as defined by the IMGT system, relative to SEQ ID NO: 39. In some embodiments, the $V_H$ domain comprises the amino acid sequence set forth in SEQ ID NO: 10, or an amino acid sequence that differs from SEQ ID NO: 10 by the presence of a total of 1, 2, 3, 4, 5, or 6 amino acid substitutions in the framework regions, as defined by the IMGT system, relative to SEQ ID NO: 10. In some embodiments, the VH domain comprises the amino acid sequence set forth in SEQ ID NO: 38. In some embodiments, the VH domain comprises the amino acid sequence set forth in SEQ ID NO: 39. In some embodiments, the VH domain comprises the amino acid sequence set forth in SEQ ID NO: 10.

In certain embodiments of any of the foregoing, or of any of the aspects and embodiments disclosed herein, antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 8; and the $V_H$ domain comprises three CDRs of the amino acid sequence set forth in SEQ ID NO: 9, wherein the antibody or antigen-binding fragment binds DNA and penetrates cells. In certain embodiments, the $V_H$ domain comprises three CDRs of the amino acid sequence set forth in SEQ ID NO: 9, as defined by the IMGT system.

In certain embodiments of any of the foregoing, or of any of the aspects and embodiments disclosed herein, the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells. In certain embodiments, the $V_H$ domain comprises three CDRs of the amino acid sequence set forth in SEQ ID NO: 9, as defined by the IMGT system.

In certain embodiments of any of the foregoing, or of any of the aspects and embodiments disclosed herein, the antibodies or antigen-binding fragments described herein comprise a light chain variable ($V_L$) domain and a heavy chain variable ($V_H$) domain; wherein the $V_H$ domain is humanized and comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells. In certain embodiments, the $V_L$ domain comprises three CDRs of the amino acid sequence set forth in SEQ ID NO: 7, as defined by the IMGT system.

In certain embodiments of any of the foregoing, or of any of the aspects and embodiments disclosed herein, the antibodies or antigen-binding fragments described herein comprise a light chain variable ($V_L$) domain and a heavy chain variable ($V_H$) domain; wherein the $V_H$ domain is humanized and comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells. In certain embodiments, the $V_L$ domain comprises three CDRs of the amino acid sequence set forth in SEQ ID NO: 7, as defined by the IMGT system.

In certain embodiments of any of the foregoing, or of any of the aspects and embodiments disclosed herein, the antibodies or antigen-binding fragments described herein comprise a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells. In certain embodiments, the $V_L$ domain comprises three CDRs of the amino acid sequence set forth in SEQ ID NO: 7, as defined by the IMGT system.

In certain embodiments of any of the foregoing, or of any of the aspects and embodiments disclosed herein, the $V_H$ domain of the antibodies or antigen-binding fragments described herein comprise:

a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3.

In certain embodiments of any of the foregoing, or of any of the aspects and embodiments disclosed herein, the $V_L$ domain of the antibodies or antigen-binding fragments described herein comprise:

a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6.

In certain embodiments of any of the foregoing, or of any of the aspects and embodiments disclosed herein, the $V_H$ domain of any of the antibodies or antigen-binding fragments described herein comprise one or more of the following amino acid alterations: V5Q, E6Q, L11V, V12I, K13Q, R18L, K19R, V37I, E42G, A49S, T63S, A75S, F80Y, T84N, S88A, M93V, T111L or L112V, as compared with and numbered with respect to the linear amino acid sequence of SEQ ID NO: 9 (e.g., the VH domain comprises one or more of the amino acid alterations at the corresponding position, relative to the amino acid sequence of SEQ ID NO: 9). Exemplary alterations are in one or more framework regions. In certain embodiments, the antibody or antigen binding fragment comprises a VH domain comprising one or more: a Q at a position corresponding to position 5 of SEQ ID NO: 9, a Q at a position corresponding to position 6 of SEQ ID NO: 9, a V at a position corresponding to position 11 of SEQ ID NO: 9, an I at a position corresponding to position 12 of SEQ ID NO: 9, a Q at a position corresponding to position 13 of SEQ ID NO: 9, an L at a position corresponding to position 18 of SEQ ID NO: 9, an R at a position corresponding to position 19 of SEQ ID NO: 9, an I at a position corresponding to position 37 of SEQ ID NO: 9, a G at a position corresponding to position 42 of SEQ ID NO: 9, a S at a position corresponding to position 49 of SEQ ID NO: 9, a S at a position corresponding to position 63 of SEQ ID NO: 9, a S at a position corresponding to residue 75 of SEQ ID NO: 9, a Y at a position corresponding to position 80 of SEQ ID NO: 9, an N at a position corresponding to position 84 of SEQ ID NO: 9, an A at a position corresponding to position 88 of SEQ ID NO: 9, a valine at a position corresponding to position 93 of SEQ ID NO: 9, a L at a position corresponding to position 111 of SEQ ID NO: 9 or a V at a position corresponding to position 112 of SEQ ID NO: 9. In certain embodiments, the $V_H$ domain comprises one or more of the following amino acid alterations: V5Q, L11V, K13Q, R18L, K19R, V37I, E42G, A49S, T63S, A75S, F80Y, T84N, M93V, T111L or L112V, as compared with and numbered with respect to the linear amino acid sequence of SEQ ID NO: 9 (e.g., the VH domain comprises one or more of the amino acid alterations at the corresponding position, relative to the amino acid sequence of SEQ ID NO: 9). Exemplary alterations are in one or more framework regions. In certain embodiments, the $V_H$ domain comprises at least 5, at least 6, at least 7, at least 8, at least 9, or at least 10 amino acid of said alterations, as compared with and numbered with respect to the linear amino acid sequence of SEQ ID NO: 9. In certain embodiments, at least one of the alterations in the $V_H$ domain is a V5Q alteration, as compared with and numbered with respect to linear the amino acid sequence of SEQ ID NO: 9. In certain embodiments, at least one of the alterations in the $V_H$ domain is a E6Q alteration, as compared with and numbered with respect to the linear amino acid sequence of SEQ ID NO: 9. In certain embodiments, at least one of the alterations in the $V_H$ domain is a L11V alteration, as compared with and numbered with respect to the amino acid sequence of SEQ ID NO: 9. In certain embodiments, at least one of the alterations in the $V_H$ domain is a V37I alteration, as compared with and numbered with respect to the amino acid sequence of SEQ ID NO: 9. In certain embodiments, the $V_H$ domain retains a serine at the amino acid position corresponding to amino acid position 88 of SEQ ID NO: 9. In certain embodiments, the $V_H$ domain retains a valine at the amino acid position corresponding to amino acid position 12 of SEQ ID NO: 9. In certain embodiments, the $V_H$ domain retains a tryptophan at the amino acid position corresponding to amino acid position 47 of SEQ ID NO: 9. In certain embodiments, the VH domain comprises a serine at the amino acid position corresponding to amino acid position 88 of SEQ ID NO: 9. In certain embodiments, the VH domain comprises a valine at the amino acid position corresponding to amino acid position 12 of SEQ ID NO: 9. In certain embodiments, the VH domain comprises a tryptophan at the amino acid position corresponding to amino acid position 47 of SEQ ID NO: 9.

In certain embodiments of any of the foregoing, or of any of the aspects and embodiments disclosed herein, the $V_L$ domain of any of the antibodies or antigen-binding fragments described herein comprise one or more of the following amino acid alterations: V3Q, L4M, A9S, A12S, V13A, L15V, Q17D, A19V, S22T, M37L, H38A, G45E, Q46K, P47A, E59Q, A64S, H76T, N78T, H80S, P81S, V82L, E83Q, E84P, A87V, A87F, or G104A, as compared with and numbered with respect to the linear amino acid sequence of SEQ ID NO: 7 (e.g., the VL domain comprises one or more of the amino acid alterations at the corresponding position, relative to the amino acid sequence of SEQ ID NO: 7). Exemplary alterations are in one or more framework regions. In certain embodiments, the antibody or antigen binding fragment comprises a VL domain comprising one or more: a Q at a position corresponding to position 3 of SEQ ID NO: 7, a M at a position corresponding to position 4 of SEQ ID NO: 7, a S at a position corresponding to position 9 of SEQ ID NO: 7, an S at a position corresponding to position 12 of SEQ ID NO: 7, a A at a position corresponding to position 13 of SEQ ID NO: 7, an V at a position corresponding to position 15 of SEQ ID NO: 7, an D at a position corresponding to position 17 of SEQ ID NO: 7, an V at a position corresponding to position 19 of SEQ ID NO: 7, a T at a position corresponding to position 22 of SEQ ID NO: 7, a L at a position corresponding to position 37 of SEQ ID NO: 7, a A at a position corresponding to position 38 of SEQ ID NO: 7, a E at a position corresponding to position 45 of SEQ ID NO: 7, a K at a position corresponding to position 46 of SEQ ID NO: 7, an A at a position corresponding to position 47 of SEQ ID NO: 7, an Q at a position corresponding to position 59 of SEQ ID NO: 7, a S at a position corresponding to position 64 of SEQ ID NO: 7, a T at a position corresponding to position 76 of SEQ ID NO: 7, a T at a position corresponding to position 78 of SEQ ID NO: 7, a S at a position corresponding to position 80 of SEQ ID NO: 7, a S at a position corresponding to position 81 of SEQ ID NO: 7, a L at a position corresponding to position 82 of SEQ ID NO: 7, a Q at a position corresponding to position 83 of SEQ ID NO: 7, a P at a position corresponding to position 84 of SEQ ID NO: 7, a V at a position corresponding to position 87 of SEQ ID NO: 7, a F at a position corresponding to position 87 of SEQ ID NO: 7, or a A at a position corresponding to position 104 of SEQ ID NO: 7. In certain embodiments, the $V_L$ domain comprises one or more of the following amino acid alterations: V3Q, L4M, A9S, A12S, V13A, L15V, Q17D, A19V, G45E, Q46K, P47A, E59Q, A64S, H76T, N78T, H80S, P81S, V82L, E83Q, E84P, A87V, or G104A, as compared with and numbered with respect to the linear amino acid sequence of SEQ ID NO: 7 (e.g., the VL domain comprises one or more of the amino acid alterations at the corresponding position, relative to the amino acid sequence of SEQ ID NO: 7). Exemplary alterations are in one or more framework regions. In certain embodiments, the $V_L$ domain comprises at least 5, at least 6, at least 7, at least 8, at least 9, or at least 10, at least 11, at least 12, at least 13, at least 14, at least 15, at least 16, at least 17, or at least 18 of said amino acid alterations, as compared with and numbered with respect to the linear amino acid sequence of SEQ ID NO: 7. In certain embodiments, the $V_L$ domain comprises a serine at each of the amino acid positions corresponding to amino acid positions 80 and 81 of SEQ ID NO: 7. In certain embodiments, the $V_L$ domain retains a lysine at the amino acid position corresponding to amino acid position 53 of SEQ ID NO: 7. In certain embodiments, the $V_L$ domain does not have any one or more of the following amino acid combinations:

a) asparagine and serine at the amino acid positions corresponding to amino acid positions 80 and 81 of SEQ ID NO: 7, respectively; or b) asparagine and glycine at the amino acid positions corresponding to amino acid positions 80 and 81 of SEQ ID NO: 7, respectively; or c) asparagine and proline at the amino acid positions corresponding to amino acid positions 80 and 81 of SEQ ID NO: 7, respectively.

It should be understood that any of the foregoing variations at particular positions are referred to relative to the amino acid sequence set forth in SEQ ID No: 7 or 9. An antibody or antigen binding fragment of the disclosure may comprise one or more of such amino acid alterations at the corresponding position, relative to the amino acid sequence of SEQ ID NO: 7 or 9. By way of example, in certain embodiments, the VH domain comprises an L to V alteration at a position corresponding to position 11 of SEQ ID NO: 9 (e.g., an L11V alteration). This is exemplary of how all of the foregoing alterations can also be described, and such description is expressly contemplated. By way of another example, in certain embodiments, the VL domain comprises a V to Q alteration at a position corresponding to position 3 of SEQ ID NO: 7 (e.g., a V3Q alteration).

In certain embodiments of any of the foregoing, or of any of the aspects and embodiments disclosed herein, the antibody or antigen-binding fragment described herein is an scFv. In certain embodiments, the scFv includes a linker that interconnects the $V_H$ domain and the $V_L$ domain. In certain embodiments, the linker is a glycine-serine linker. In certain embodiments, the glycine-serine linker is a $(G_4S)_3$ linker. In certain embodiments, the $V_H$ domain of the scFv is N-terminal to the $V_L$ domain. In certain embodiments, the $V_H$ domain of the scFv is C-terminal to the $V_L$ domain.

In certain embodiments of any of the foregoing, or of any of the aspects and embodiments disclosed herein, the antibody or antigen-binding fragment described herein is a Fab or Fab'. In certain embodiments, the antibody or antigen-binding fragment described herein is a F(ab')2 fragment.

In certain embodiments of any of the foregoing, or of any of the aspects and embodiments disclosed herein, the antibody or antigen-binding fragment described herein is a full length antibody comprising a heavy chain constant domain and a light chain constant domain (e.g., a heavy chain constant domain comprising a Fc region comprising CH1, hinge, CH2 and CH3 domains). Less than full length antibodies are also contemplated.

In certain embodiments of any of the foregoing, or of any of the aspects and embodiments disclosed herein, the antibodies or antigen-binding fragments described herein are humanized and are associated with at least one superior biological or physiological property as compared to a murine antibody, which murine antibody comprises a $V_L$ domain comprising the amino acid sequence set forth in SEQ ID NO: 7 and a $V_H$ domain comprising the amino acid sequence set forth in SEQ ID NO: 9, and/or as compared to an alternative antibody or antigen-binding fragment thereof, wherein said alternative antibody or antigen-binding fragment comprises a $V_L$ domain comprising the CDRs of the amino acid sequence set forth in SEQ ID NO: 7 and a $V_H$ domain comprising the CDRs of the amino acid sequence set forth in SEQ ID NO: 9; and wherein said alternative antibody or fragment does not comprise a $V_L$ domain comprising the amino acid sequence of SEQ ID NO: 8 or 40, and/or wherein said alternative antibody or fragment does not comprise a $V_H$ domain comprising the amino acid sequence of any of SEQ ID NOs: 10, 38 or 39. In some embodiments, the antibody or antigen-binding fragment comprises a light chain variable ($V_L$) domain and a heavy chain variable ($V_H$) domain; wherein the $V_L$ domain comprises the amino acid sequence set forth in SEQ ID NO: 8; wherein the $V_H$ domain comprises three CDRs of the amino acid sequence set forth in SEQ ID NO: 9, wherein the antibody or antigen-binding fragment binds DNA and penetrates cells. In some embodiments, the antibody or antigen-binding fragment comprises a light chain variable ($V_L$) domain and a heavy chain variable ($V_H$) domain; wherein the $V_L$ domain comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells. In some embodiments, the antibody or antigen-binding fragment comprises a light chain variable ($V_L$) domain and a heavy chain variable ($V_H$) domain; wherein the $V_H$ domain comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells. In some embodiments, the antibody or antigen-binding fragment comprises a light chain variable ($V_L$) domain and a heavy chain variable ($V_H$) domain; wherein the $V_H$ domain comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells. In some embodiments, the antibody or antigen-binding fragment comprises a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells. In some embodiments, the alternative antibody or fragment thereof comprises:

a VH CDR1 having the amino acid sequence of SEQ ID NO: 1;
a VH CDR2 having the amino acid sequence of SEQ ID NO: 2;
a VH CDR3 having the amino acid sequence of SEQ ID NO: 3;
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are defined in accordance with the IMGT system. In some embodiments, the alternative antibody or fragment thereof comprises:

a VH CDR1 having the amino acid sequence of SEQ ID NO: 32;
a VH CDR2 having the amino acid sequence of SEQ ID NO: 33;
a VH CDR3 having the amino acid sequence of SEQ ID NO: 34;
a VL CDR1 having the amino acid sequence of SEQ ID NO: 35;
a VL CDR2 having the amino acid sequence of SEQ ID NO: 36; and
a VL CDR3 having the amino acid sequence of SEQ ID NO: 37, which CDRs are defined in accordance with Kabat.

In certain embodiments of any of the foregoing or following, the antibody or antigen binding fragment of the disclosure comprises a VH CDR1 having the amino acid sequence of SEQ ID NO: 1;
a VH CDR2 having the amino acid sequence of SEQ ID NO: 2;
a VH CDR3 having the amino acid sequence of SEQ ID NO: 3;
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are defined in accordance with the IMGT system; and/or a VH CDR1 having the amino acid sequence of SEQ ID NO: 32;
a VH CDR2 having the amino acid sequence of SEQ ID NO: 49;
a VH CDR3 having the amino acid sequence of SEQ ID NO: 34;
a VL CDR1 having the amino acid sequence of SEQ ID NO: 35 or 50;
a VL CDR2 having the amino acid sequence of SEQ ID NO: 51; and
a VL CDR3 having the amino acid sequence of SEQ ID NO: 37, which CDRs are defined in accordance with Kabat.

In certain embodiments of any of the foregoing, or of any of the aspects and embodiments disclosed herein, the superior biological or physiological property of the antibodies or antigen-binding fragments described herein as compared to a murine 3E10 antibody or to an alternative antibody is increased solubility of the antibody or fragment in a physiologically acceptable carrier. In certain embodiments, the superior biological or physiological property is a higher expression level of the antibody or fragment when made in a host cell. In certain embodiments, superior biological or physiological property is lower toxicity of the antibody or fragment in a cell. In certain embodiments, the superior biological or physiological property is reduced aggregation of the antibody or fragment in a physiologically acceptable carrier after a period of at least 24 hours. In certain embodiments, the superior biological or physiological property is increased stability of the antibody or fragment in a physiologically acceptable carrier after a period of at least 24 hours. In certain embodiments, the superior biological or physiological property is improved cell penetration by the antibody or fragment. In certain embodiments, the superior biological or physiological property is improved DNA binding by the antibody or fragment. In certain embodiments, the superior biological or physiological property is reduced glycosylation of the antibody or fragment following production in a cell type as compared to that of the murine antibody or alternative antibody following production in the same cell type. In certain embodiments, the superior biological or physiological property is increased glycosylation of the antibody or fragment following production in a cell type as compared to that of the murine antibody or alternative antibody following production in the same cell type. In certain embodiments, the superior biological or physiological property is reduced deamidation of the antibody or fragment in a physiologically acceptable carrier. In certain embodiments, the superior biological or physiological property is reduced oxidation of the antibody or fragment in a physiologically acceptable carrier. In certain embodiments, the superior biological or physiological property is reduced lipidation of the antibody or fragment following production in a cell type as compared to that of the murine antibody or alternative antibody following production in the same cell type. In certain embodiments, the superior biological or physiological property is increased internalization via an ENT transporter (e.g., an ENT2 and/or ENT3 transporter) of the antibody or fragment and/or higher affinity binding to DNA indicated by a lower $K_D$, as measured by SPR or QCM, or as measured by ELISA.

In certain embodiments of any of the foregoing, or of any of the aspects and embodiments disclosed herein, any of the antibodies or antigen-binding fragments described herein are conjugated (e.g., interconnected; linked or associated with) to a heterologous agent (e.g, the antibody or antigen-binding fragment further comprises a heterologous agent associated thereto). In certain embodiments, an antibody or antigen-binding fragment of the disclosure is not conjugated to a heterologous agent (e.g., the antibody or antigen-binding fragment does not further comprise a heterologous agent). In certain embodiments, the antibody or antigen-binding fragment is not conjugated to a therapeutic heterologous agent. In certain embodiments, the heterologous agent is a polypeptide or peptide, such as a therapeutic polypeptide or peptide. In certain embodiments, the heterologous agent is a nucleic acid or small organic molecule. In certain embodiments, the antibody or antigen-binding fragment is N-terminal to the heterologous agent. In certain embodiments, the antibody or antigen-binding fragment is C-terminal to the heterologous agent. In certain embodiments, the antibody or antigen-binding fragment and the heterologous agent are interconnected via a linker. In certain embodiments, the antibody or antigen-binding fragment and the heterologous agent are interconnected without a linker. In certain embodiments, the heterologous agent is not an epitope tag, such as an HA or myc tag. In certain embodiments, an epitope tag, such as an HA or myc tag is present, but an additional heterologous agent is also present (e.g., the antibody or antigen binding fragment is not conjugated solely to an epitope tag). In certain embodiments, the heterologous agent is not a radioactive or fluorescent moiety. For the avoidance of doubt, a signal sequence is not a heterologous agent. In certain embodiments, the heterologous agent is a therapeutic agent. In certain embodiments, the antibody or fragment and the heterologous agent are chemically conjugated. In certain embodiments, the antibody or antigen-binding fragment and the heterologous agent are a fusion protein (e.g., all or a portion of the interconnection is via a fusion protein between a portion of the antibody and a portion of the heterologous agent). As described in detail herein, conjugated refers to scenarios where any of the antibody or antigen binding portions of the disclosure are associated with or interconnected with the heterologous agent, regardless of the interconnection (e.g., the interconnection/association may comprise a chemical conjugation, covalent bond, di-sulfide bond, etc. or combinations thereof). In certain embodiments, at least a portion of the interconnection is via a covalent bond, such as the forming of a fusion protein between a heavy chain of the antibody of the disclosure and the heterologous agent (which may further associate with a light chain of the antibody of the disclosure). Accordingly, the disclosure provides such conjugates and pharmaceutical compositions comprising such conjugates. A conjugate is a molecule comprising an antibody or antigen binding portion of the disclosure associated with a heterologous agent. Similarly, antibodies or antigen binding fragments of the disclosure may further comprise a heterologous agent.

In certain embodiments of any of the foregoing, or of any of the aspects and embodiments disclosed herein, the heterologous agent conjugated to the antibodies or antigen-binding fragments disclosed herein is an agent suitable for treating a nucleotide repeat disorder or an exon splicing disorder. In certain embodiments, the disorder is myotonic dystrophy. In certain embodiments, the disorder is Huntington's Disease. In certain embodiments, the disorder is neurofibromatosis. In certain embodiments, the agent is an MBNL1 polypeptide or a fragment thereof capable of binding CUG repeats (e.g., binding CUG when present in the context of CUG repeats) and/or regulating exon splicing. In some embodiments, the agent is an MBNL1 polypeptide comprising an amino acid sequence that is at least 90% identical to the amino acid sequence set forth in any of SEQ ID NOs: 12-18 or a fragment thereof capable of binding CUG repeats, binding a YGCY motif, and/or regulating exon splicing. In some embodiments, the agent is an MBNL polypeptide comprising an amino acid sequence that is at least 90% (or at least 95%, 96%, 97%, 98%, 99% or 100%) identical to the amino acid sequence set forth in any of SEQ ID NOs: 12-18 or 55-59, or a fragment thereof capable of binding CUG repeats and/or regulating exon splicing. In certain embodiments, the fragment thereof is a fragment of MBNL comprising at least four zinc finger motifs. In certain embodiments, the fragment thereof is a fragment of MBNL comprising at least two zinc finger motifs.

In certain embodiments of any of the foregoing, or of any of the aspects and embodiments disclosed herein, the heterologous agent conjugated to the antibodies or antigen-binding fragments disclosed herein is an enzyme. In certain embodiments, the enzyme is suitable for use as an enzyme replacement therapy. In certain embodiments, the enzyme replacement therapy is for treating myotubular myopathy. In certain embodiments, the heterologous agent is an MTM1 protein, or functional fragment thereof. In certain embodiments, the MTM1 protein comprises an amino acid sequence that is at least 90% (or at least 95%, 96%, 97%, 98%, 99%, or 100%) identical to the amino acid sequence set forth in SEQ ID NO: 11, or a functional fragment thereof.

In certain embodiments of any of the foregoing, or of any of the aspects and embodiments disclosed herein, the heterologous agent conjugated to the antibodies or antigen-binding fragments disclosed herein is an agent suitable for treating a glycogen storage disorder. In certain embodiments, the glycogen storage disorder is Pompe Disease. In certain embodiments, the glycogen storage disorder is Forbes-Cori Disease. In some embodiments, the heterologous agent is an acid alpha-glucosidase (GAA) polypeptide comprising a mature GAA polypeptide. In some embodiments, the heterologous agent is a GAA polypeptide comprising a mature GAA, wherein the GAA polypeptide is not a GAA precursor polypeptide of approximately 110 kilodaltons. In some embodiments, the mature GAA polypeptide has a molecular weight of approximately 70-76 kilodaltons. In certain embodiments, the GAA polypeptide does not include amino acid residues 1-56 of SEQ ID NO: 22. In certain embodiments, the mature GAA polypeptide consists of an amino acid sequence selected from residues 122-782 of SEQ ID NO: 22 or residues 204-782 of SEQ ID NO: 22. In certain embodiments, the agent is an amyloglucosidase (AGL) polypeptide or functional fragment thereof, wherein the AGL polypeptide or fragment has amylo-1,6-glucosidase activity and 4-alpha-glucotransferase activity. In certain embodiments, the AGL polypeptide comprises an amino acid sequence at least 90% identical to any of SEQ ID NOs: 19-21, and wherein the conjugate has amylo-1,6-glucosidase activity and 4-alpha-glucotransferase activity.

In certain embodiments of any of the foregoing, or of any of the aspects and embodiments disclosed herein, the disclosure provides a nucleic acid encoding any of the antibodies or antigen-binding fragments disclosed herein. In other embodiments, the disclosure provides a nucleic acid encoding any of the conjugates (e.g., any of the conjugates comprising (i) an antibody or antigen binding fragment of the disclosure and (ii) a heterologous agent) disclosed herein. In certain embodiments, the nucleic acid is a pair of nucleic acids expressed on different vectors.

In certain embodiments of any of the foregoing, or of any of the aspects and embodiments disclosed herein, the disclosure provides a vector comprising any of the nucleic acids disclosed herein. In certain embodiments, the disclosure provides a pair of vectors, wherein a first vector comprises a nucleotide sequence encoding a heavy chain (or a portion of a heavy chain) of an antibody or antigen binding fragment of the disclosure and a second vector comprises a nucleotide sequence encoding a light chain (or a portion of a light chain) of an antibody or antigen binding fragment of the disclosure.

In certain embodiments of any of the foregoing, or of any of the aspects and embodiments disclosed herein, the disclosure provides a host cell comprising any of the vectors disclosed herein. In certain embodiments, the host cell is an immortalized cell or is stably transfected to express the vector. In certain embodiments of any of the foregoing, or of any of the aspects and embodiments disclosed herein, the disclosure provides a method of producing a polypeptide, comprising providing the host cell and culturing the host cells under suitable condition to produce the polypeptide.

In certain embodiments of any of the foregoing, or of any of the aspects and embodiments disclosed herein, the disclosure provides a method of treating a nucleotide repeat disorder in a subject in need thereof, comprising administering to the subject any of the antibodies or antigen-binding fragments disclosed herein conjugated to a heterologous agent, such as the MBNL1 polypeptide or fragment thereof capable of binding CUG repeats and/or regulating exon splicing. In some embodiments, the disorder is myotonic dystrophy. In certain embodiments, the disorder is Huntington's Disease.

In certain embodiments of any of the foregoing, or of any of the aspects and embodiments disclosed herein, the disclosure provides a method of providing an enzyme replacement treatment to a subject in need thereof, comprising administering to the subject any of the antibodies or antigen-binding fragments disclosed herein conjugated to a heterologous agent, such as an MTM1 protein, a GAA polypeptide, or an AGL polypeptide.

In certain embodiments of any of the foregoing, or of any of the aspects and embodiments disclosed herein, the disclosure provides a method of treating a glycogen storage disorder in a subject in need thereof, comprising administering to the subject any of the antibodies or antigen-binding fragments disclosed herein conjugated to a GAA polypeptide or an AGL polypeptide, such as any of the GAA polypeptides or AGL polypeptides disclosed herein.

In certain embodiments of any of the foregoing, or of any of the aspects and embodiments disclosed herein, the disclosure provides a method of treating myotubular myopathy in a subject in need thereof, comprising administering to the subject any of the antibodies or antigen-binding fragments disclosed herein conjugated to an MTM1 protein, such as any of the MTM proteins disclosed herein.

In certain embodiments of any of the foregoing, or of any of the aspects and embodiments disclosed herein, the disclosure provides a method of treating Pompe Disease in a subject in need thereof, comprising administering to the subject any of the antibodies or antigen-binding fragments disclosed herein conjugated to a GAA polypeptide, such as any of the GAA polypeptides disclosed herein.

In certain embodiments of any of the foregoing, or of any of the aspects and embodiments disclosed herein, the disclosure provides a method of treating Forbes-Cori Disease in a subject in need thereof, comprising administering to the subject any of the antibodies or antigen-binding fragments disclosed herein conjugated to a GAA polypeptide or an AGL polypeptide, such as any of the GAA polypeptides or AGL polypeptides disclosed herein.

In certain embodiments of any of the foregoing, or of any of the aspects and embodiments disclosed herein, the disclosure provides a method of treating Neurofibromatosis 1 in a subject in need thereof, comprising administering to the subject any of the antibodies or antigen-binding fragments disclosed herein conjugated to an MBNL polypeptide, or a fragment thereof, such as any of the MBNL polypeptides or fragments thereof disclosed herein.

In certain embodiments of any of the foregoing, or of any of the aspects and embodiments disclosed herein, the disclosure provides a method of inhibiting the growth of a tumor cell and/or treating cancer in a subject in need thereof, comprising administering to the subject any of the antibodies or antigen-binding fragments disclosed herein.

In certain embodiments of any of the foregoing, or of any of the aspects and embodiments disclosed herein, the disclosure provides a composition comprising any of the antibodies or antigen-binding fragments described herein formulated in a physiologically acceptable carrier. In certain embodiments, the composition is pyrogen free. In certain embodiments of any of the foregoing, or of any of the aspects and embodiments disclosed herein, the disclosure provides a method of delivering a heterologous agent into cells or tissue, such as in to cytoplasm, comprising contacting a cell with any of the antibodies or antigen binding fragments described herein. In certain embodiments, the cells or tissue are in a subject, and contacting comprises administering the antibody or antigen binding fragment to the subject. In certain embodiments, the cells or tissue are in vitro. In certain embodiments, the cells are skeletal muscle cells, and the tissue comprises skeletal muscle. In certain embodiments, the cells are cardiac muscle cells, and the tissue comprises cardiac muscle. In certain embodiments, the cells are hepatic cells, and the tissue comprises hepatic tissue. In certain embodiments, the cells are neurons, and the tissue comprises nervous tissue. In certain embodiments, the cells are kidney cells, and the tissue comprises kidney tissue. In certain embodiments, the subject is a subject having a nucleotide repeat disorder or an exon splicing disorder. In certain embodiments, the subject is a subject having an enzyme deficiency disorder and in need of enzyme replacement therapy. In certain embodiments, the subject is a subject is a subject having a glycogen storage disorder. In certain embodiments, the antibody or antigen-binding fragment is delivered into cells of the subject. In certain embodiments, the antibody or antigen binding fragment is delivered into cytoplasm.

The disclosure contemplates all combinations of any of the foregoing aspects and embodiments, as well as combinations with any of the embodiments set forth in the detailed description and examples.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 provides a sequence alignment of each of the second generation, humanized heavy chain variable domains (HH1, HH2, and HH3) as compared to each other and the murine, parent 3E10 heavy chain variable domain (MH1) (See top half of FIG. 1), and also provides a sequence alignment of each of the second generation, humanized light chain variable domains (HL1 and HL2) as compared to each other and the murine, parent 3E10 light chain variable domain (ML1). The CDRs, as determined in accordance with the Kabat Sequences of Proteins of Immunological Interest (1987 and 1991, National Institutes of Health, Bethesda, Md.) or in accordance with the IMGT system (LeFranc et al., 2003, Development and Comparative Immunology, 27: 55-77 and IMGT/V-QUEST database), are underlined by a black bar (Kabat) or highlighted in dark gray (IMGT; shown in blue in the color figure), while changes in the humanized heavy or light chain variable domain sequences, as compared to the respective murine 3E10 parent chain are highlighted in light gray (shown in yellow in the color figure). Amino acid changes introduced to improve folding of a humanized heavy chain are in bold and in lowercase (shown in green in the color figure). The sequence identifiers for the amino acid sequence of each of the different antibody chains indicated are as follows: ML1=SEQ ID NO: 7; MH1=SEQ ID NO: 9; HH1=SEQ ID NO: 38; HH2=SEQ ID NO: 39; HH3=SEQ ID NO: 10; HL1=SEQ ID NO: 40; HL2=SEQ ID NO: 8.

FIG. 4 provides a summary of the results of the experiments analyzing the properties of the pre- and post-concentration antibody samples comprising the indicated combinations of heavy and light chain variable domains. The following abbreviations are used: Opal=opalescent; VP=Visible Particles; NC=No change; NBTG.

DETAILED DESCRIPTION OF THE DISCLOSURE

Figure 2A:
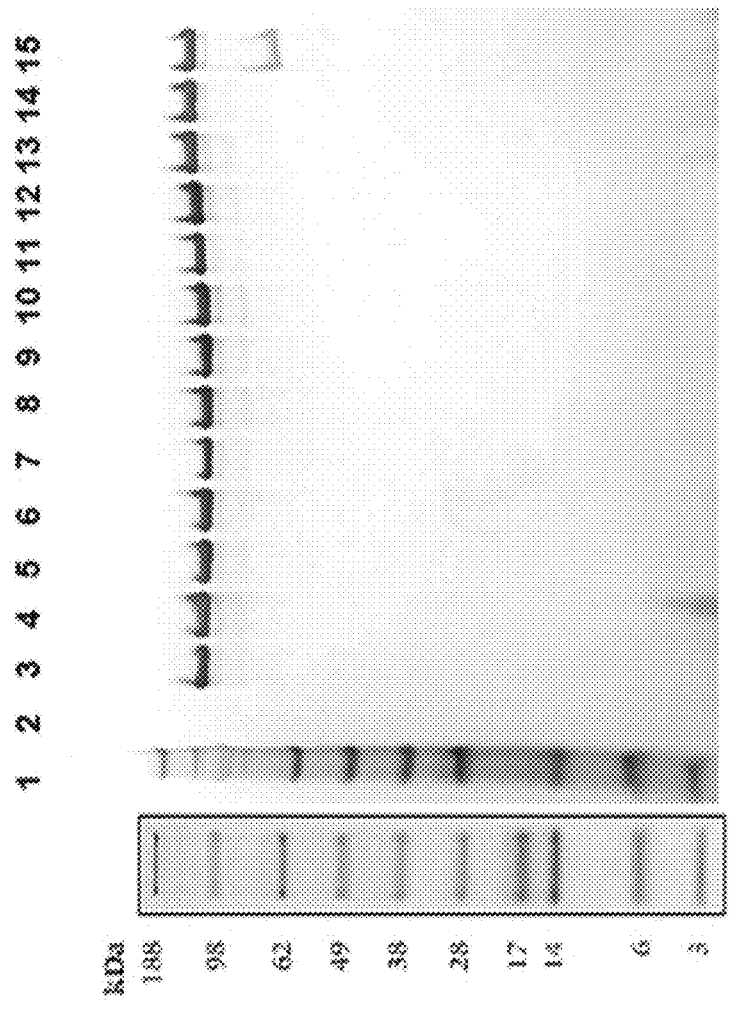
FIGS. 2A and 2B show representative gels resulting from SDS-PAGE analysis of full length antibodies comprising the indicated heavy and light chain variable domains. For FIG. 2A, samples were prepared under non-reducing conditions, and one microgram of sample was loaded per well. A single predominant band of the expected antibody size was observed for each sample, and no obvious aggregate bands were observed at the top of the gel for any of the samples tested. For FIG. 2B, samples were prepared under reducing conditions, and one microgram of sample was loaded per well. Two bands of the expected heavy and light chains were observed for each sample, and no obvious aggregate bands were observed at the top of the gel for any of the samples tested. For FIGS. 2A and 2B, no bands indicating any obvious signs of proteolytic breakdown were observed for any of the antibodies tested.

The disclosure provides antibodies and antigen-binding fragments. In certain embodiments, these antibodies and antigen-binding fragments are humanized (e.g., comprise at least a humanized VH or a humanized VL). In certain embodiments, these antibodies and antigen-binding fragments bind DNA and/or transit cellular membranes, such as via an ENT transporter (e.g., an ENT2 and/or ENT3 transporter). In other words, in some embodiments, the antibodies and antigen-binding fragments of the disclosure have properties consistent with the 3E10 parent antibody described herein. In certain embodiments, antibodies and antigen-binding fragments of the disclosure bind DNA (e.g., single stranded DNA or double stranded DNA) with a $K_D$ of less 100 nM, less than 75 nM, less than 50 nM, or less than 30 nM, as measured by SPR or QCM using currently standard protocols. In certain embodiments, antibodies and antigen-binding fragments of the disclosure bind DNA with a $K_D$ of less 20 nM, less than 10 nM, or less than 1 nM, as measured by SPR or QCM using currently standard protocols. In certain embodiments, the antibodies or antigen binding fragments of the disclosure compete for binding to DNA with 3E10, as produced by the hybridoma having ATCC accession No. PTA-2439 and as disclosed in U.S. Pat. No. 7,189,396. In certain embodiments, antibodies and antigen binding fragments of the disclosure comprise Kabat CDRs that differ in comparison to murine 3E10 (e.g., comprise one or more changes in the CDRs, relative to murine 3E10, such as differing at one or more of VH CDR2, VL CDR1 and/or VL CDR2).

I. Internalizing Moiety

As used herein, the term "internalizing moiety" refers to a polypeptide moiety capable of interacting with a target tissue or a cell type such that the moiety is internalized into the target tissue or the cell type. In preferred embodiments, the internalizing moieties for use in the present disclosure are antibodies and antigen-binding fragments of the disclosure, such as antibodies and antigen-binding fragments comprising a humanized VH and/or a humanized VL (e.g., a humanized $V_H$ domain and/or a humanized $V_L$ domain).

As used herein, "antibodies or antigen binding fragments of the disclosure" refer to any one or more of the antibodies and antigen binding fragments provided herein (e.g., antibodies and antigen binding fragments based on a parent, 3E10 antibody and, in certain embodiments, comprising at least one humanized $V_H$ and/or $V_L$ domain). The term "antibodies of the disclosure" is not intended to include the parent, murine antibody that comprises both a murine heavy chain and a murine light chain. Antibodies and antigen binding fragments of the disclosure comprise a heavy chain comprising a heavy chain variable domain and a light chain comprising a light chain variable domain. A $V_H$ domain comprises three CDRs, such as any of the CDRs provided herein and as defined or identified by the Kabat or IMGT systems. These CDRs are typically interspersed with framework regions (FR), and together comprise the $V_H$ domain. Similarly, a VL comprises three CDRs, such as any of the CDRs provided herein and as defined by the Kabat or IMGT systems. These CDRs are typically interspersed with framework regions (FR), and together comprise the $V_L$ domain. The FR regions, such as FR1, FR2, FR3, and/or FR4 can similarly be defined or identified by the Kabat or IMGT systems. Throughout the application, when CDRs are indicated as being, as identified or defined by the Kabat or IMGT systems, what is meant is that the CDRs are in accordance with that system (e.g., the Kabat CDRs or the IMGT CDRs). Any of these terms can be used to indicate whether the Kabat or IMGT CDRs are being referred to.

The disclosure contemplates that an antibody or antigen binding fragment may comprise any combination of a $V_H$ domain, as provided herein, and a $V_L$ domain, as provided herein. In certain embodiments, at least one of the $V_H$ and/or $V_L$ domains are humanized (collectively, antibodies or antigen binding fragments of the disclosure). Chimeric antibodies are also included. Any antibody or antigen binding fragment of the disclosure may be provided alone or, optionally, as a conjugate associated with a heterologous agent. Non-limiting examples of heterologous agents, which may include polypeptides, peptides, small molecules (e.g., a chemotherapeutic agent small molecule), or polynucleotides, are provided herein. Conjugates may refer to an antibody or antigen binding fragment associated with a heterologous agent.

In some embodiments, the antibody or antigen-binding fragment is isolated and/or purified. Any of the antibodies or antigen-binding fragments described herein, including those provided in an isolated or purified form, may be provided as a composition, such as a composition comprising an antibody or antigen-binding fragment formulated with one or more pharmaceutical and/or physiological acceptable carriers and/or excipients. Any of the antibodies or antigen-binding fragments described herein, including compositions (e.g., pharmaceutical compositions) may be used in any of the methods described herein and may be optionally provided conjugated (e.g., interconnected; associated) with a heterologous agent. Such conjugates may similarly be provided as a composition and may be used in any of the methods described herein.

In one embodiment, the disclosure provides an antibody or antigen-binding fragment comprising a humanized antibody or antigen-binding fragment, wherein the humanized antibody or antigen-binding fragment comprises a light chain variable (VL) domain and a heavy chain variable (VH) domain; wherein the $V_H$ domain is humanized and comprises:

a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3;
and the VL is humanized and comprises:
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6;

which CDRs are in accordance with the IMGT system, and wherein the humanized antibody or antigen-binding fragment has increased DNA binding and/or cell penetration, relative to that of a murine 3E10 antibody comprising a light chain variable (VL) domain having the amino acid sequence of SEQ ID NO: 7 and a heavy chain variable (VH) domain having the amino acid sequence of SEQ ID NO: 9. In certain embodiments, when comparing an antibody or antigen-binding fragment of the disclosure to a murine antibody or to another humanized antibody, the suitable comparison is between two proteins of the same structure (e.g., comparing a full length antibody to another full length antibody or comparing an Fab to another Fab).

In some embodiments, an asparagine is mutated to another amino acid residue in the VH or VL domains in order to reduce N-linked glycosylation of the humanized antibody or antibody fragment. This humanized antibody or antibody fragment is based on a murine parent antibody—specifically a murine 3E10 antibody comprising a heavy chain and a light chain, wherein the light chain comprises a VL comprising the amino acid sequence of SEQ ID NO: 7 and the heavy chain comprises a VH comprising the amino acid sequence of SEQ ID NO: 9. In preferred embodiments, the internalizing moieties and fragments are associated with at least the cell-penetration properties associated with the murine 3E10 antibody (e.g., retain at least 75%, 80%, 85%, 90%, 95%, or greater than 95%) of the cell penetration properties. In certain embodiments, the humanized antibody or antibody fragment has one or more preferable cell penetration characteristics, such as improved penetration efficiency.

As used herein, the term "fragment" or "antigen-binding fragment" of a humanized antibody moiety or "antigen binding fragment" includes any fragment of a humanized internalizing moiety that retains at least the cell-penetration and/or DNA binding properties associated with the murine 3E10 antibody. In this application, the terms "fragment" and "antigen binding fragment" are used interchangeably. Exemplary antibody fragments include scFv fragments, Fab fragments (e.g., Fab' or F(ab')2), and the like.

In some embodiments, the humanized internalizing moiety (e.g., the humanized antibody and antigen binding fragments of the disclosure) is not directly fused to any heterologous agent. However, in such embodiments, and as described in greater detail below, the internalizing moiety may still be post-translationally modified (e.g., glycosylated or) and/or provided as part of a composition.

In other embodiments, the humanized internalizing moiety (e.g., the antibodies or antigen binding fragments of the disclosure, such as humanized antibodies or antibody binding fragments) is fused to a heterologous agent. In some embodiments, the internalizing moiety effects delivery of a heterologous agent into a cell (i.e., penetrate desired cell; transport across a cellular membrane; deliver across cellular membranes to, at least, the cytoplasm). In certain embodiments, this disclosure relates to an internalizing moiety which promotes delivery of a heterologous agent into muscle cells (e.g., skeletal muscle), as well as certain other cell types. This portion promotes entry of the conjugate into cells. Like the murine, parental antibody, the humanized antibody and antigen binding fragments of the disclosure promote entry into cells via an ENT transporter, such as an ENT2 transporter and/or an ENT3 transporter. Without being bound by theory, ENT2 is expressed preferentially in certain cell types, including muscle (skeletal and cardiac), neuronal, liver and/or tumor cells. Accordingly, conjugates (e.g., conjugates in which a humanized antibody or antigen binding fragment of the disclosure is conjugated to a heterologous agent) are delivered into cells, but generally not ubiquitously. Rather, the conjugates may be delivered with some level of enrichment for particular tissues, including skeletal muscle, cardiac muscle, diaphragm, and ENT2 and/or ENT3 expressing cancer cells.

In certain embodiments, the internalizing moiety is capable of binding polynucleotides (e.g., a target/antigen for an antibody of the disclosure is DNA). This is consistent with the properties of the 3E10 antibody which is known to bind DNA (e.g., to specifically bind DNA). In certain embodiments, the internalizing moiety is capable of binding DNA. In certain embodiments, the internalizing moiety is capable of binding DNA with a $K_D$ of less than 100 nM. In certain embodiments, the internalizing moiety is capable of binding DNA (e.g., single stranded DNA or blunt double stranded DNA) with a $K_D$ of less than 500 nM, less than 100 nM, less than 75 nM, less than 50 nM, or even less than 30 nM, less than 20 nM, less than 10 nM, or even less than 1 nM. $K_D$ can be measured using Surface Plasmon Resonance (SPR) or Quartz Crystal Microbalance (QCM), or by ELISA, in accordance with currently standard methods. By way of example, an antibody or antibody fragment comprising a VH having the amino acid sequence set forth in SEQ ID NO: 10 and a VL having an amino acid sequence set forth in SEQ ID NO: 8 specifically binds DNA with a $K_D$ of less than 100 nM, and is an example of an anti-DNA antibody. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed.3004385), such as by ELISA, QCM, or Biacore. In certain embodiments, the foregoing $K_D$ of the antibody or antibody fragment (such as an antibody fragment comprising an antigen-binding fragment) is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3' (SEQ ID NO: 63)). In certain embodiments, the internalizing moiety is an anti-DNA antibody. Thus, in certain embodiments, an internalizing moiety (e.g., an antibody or antigen binding fragment) for use alone or associated with a heterologous agent comprises an antibody or antibody fragment that can transit cellular membranes into the cytoplasm and/or the nucleus and is capable of binding to DNA. In certain embodiments, the antibody and antigen binding fragments of the disclosure, such as humanized antibodies and antigen binding fragments, are based upon a murine, parental 3E10 antibody having VH and VL domains, as described above.

Preferably, the humanized antibody has the same, substantially the same, or even improved cell penetration and/or DNA binding characteristics in comparison to the murine, parental antibody, including a murine parental antibody comprising, when present, a murine constant domain.

In certain embodiments, the antibodies and antigen binding fragments of the disclosure have the same CDRs, as defined using the IMGT system, as the murine, parent antibody (e.g., the antibody comprising a heavy chain comprising a VH comprising the amino acid sequence set forth in SEQ ID NO: 9 and a light chain comprising a VL comprising the amino acid sequence set forth in SEQ ID NO: 7). In certain embodiments, the antibodies and antigen binding fragments of the disclosure have at least one CDR of the heavy chain and/or the light chain that differs from that of the murine, parent antibody (e.g., differ at VH CDR2 and/or VL CDR2 and/or VL CDR1, according to Kabat). In some embodiments, a humanized antibody or antigen binding fragment of the disclosure comprises a $V_H$ domain and a $V_L$ domain comprising:

a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3;
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are in accordance with the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 32;
a VH CDR2 having the amino acid sequence of SEQ ID NO: 33; and
a VH CDR3 having the amino acid sequence of SEQ ID NO: 34, which CDRs are according to Kabat; and
a VL CDR1 having the amino acid sequence of SEQ ID NO: 4;
a VL CDR2 having the amino acid sequence of SEQ ID NO: 5; and
a VL CDR3 having the amino acid sequence of SEQ ID NO: 6, which CDRs are according to the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3, which CDRs are according to the IMGT system, and
a VL CDR1 having the amino acid sequence of SEQ ID NO: 35;
a VL CDR2 having the amino acid sequence of SEQ ID NO: 36; and
a VL CDR3 having the amino acid sequence of SEQ ID NO: 37, which CDRs are according to Kabat.

In certain embodiments, an antibody or antigen binding fragment of the disclosure comprises a $V_H$ domain comprising:

a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34, which CDRs are according to the Kabat system, and
a $V_L$ domain comprising
a VL CDR1 having the amino acid sequence of SEQ ID NO: 35 or 50;
a VL CDR2 having the amino acid sequence of SEQ ID NO: 51; and
a VL CDR3 having the amino acid sequence of SEQ ID NO: 37, which CDRs are according to Kabat.

As detailed throughout the application, the antibody or antigen-binding fragments of the disclosure, such as humanized antibody or antigen binding fragments, can be compared to the murine, parent antibody. Additionally or alternatively, antibodies of the disclosure (or antigen binding fragments thereof) can be compared to alternate antibodies and fragments (e.g., other humanized antibodies based on the same murine parent). In such scenarios, the comparison would be to an alternate antibody or antigen binding fragment have the foregoing 6 IMGT or Kabat CDRs, but have one or more changes in the framework regions relative to the humanized antibody or antigen-binding fragment of the disclosure. When comparing activity, the ability and efficiency to penetrate cells, such as skeletal muscle cells, via ENT2 and/or ENT3 may be assessed. Activity will be considered comparable or substantially the same if it is approximately 70%, 75%, 80%, 85%, 90%, 95%, or greater than about 95% the activity of the murine, parental antibody. Activity is considered improved, relative to the murine, parental antibody, if a characteristic is at least about 5%, preferably at least about 10% better (e.g., approximately 105%, 110%, 115%, 120%, 125%, 130%, 150%, or greater than 150% the activity of the murine, parental antibody or an alternate humanized antibody). In certain embodiments, an activity is considered improved, relative to another antibody, if a characteristic is at least 2-fold better. In other embodiments, an activity is considered improved if a characteristic is at least 3-, 4-, 5-, 6-, 8, or 10-fold better.

Without being bound by theory, the internalizing moieties described herein are, in certain embodiments, capable of any one or more of the following: a) targeting (e.g., delivering) an agent conjugated to the internalizing moiety (e.g., any of the heterologous agents described herein) to muscle cells (e.g., cardiac or skeletal muscle), liver cells, neurons, glial cells and/or tumor or cancerous cells, b) killing and/or decreasing the growth, proliferation, size, survival or migration of a targeted tumor or cancer cell, c) sensitizing a tumor or cancer cell to the effects of any agent conjugated to the internalizing moiety (e.g., any of the MBNL polypeptides described herein or a chemotherapeutic attached thereto), and/or d) sensitizing a tumor or cancer cell to the effects of any separately administered agent or therapy (e.g., a chemotherapeutic agent or radiation therapy). In certain embodiments, the internalizing moiety is administered/delivered to cells in the absence of a heterologous agent (e.g., not interconnected to a heterologous agent; not interconnected to a therapeutic agent). For example, in certain embodiments, an internalizing moiety is administered to cells in the absence of a therapeutic heterologous agent for delivery into a tumor (e.g., to treat cancer).

In some embodiments, antibodies or humanized antibodies may comprise antibody fragments, derivatives or analogs thereof, including without limitation: antibody fragments comprising an antigen binding fragments (e.g., Fv fragments, single chain Fv (scFv) fragments, Fab fragments, Fab' fragments, F(ab')2 fragments, single domain antibodies, and multivalent versions of the foregoing; multivalent internalizing moieties including without limitation: Fv fragments, single chain Fv (scFv) fragments, Fab fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antigen-binding fragment is an scFv and a peptide linker interconnects the VH domain and the VL domain. In some embodiments, the antibodies or variants thereof may comprise a constant region that is a hybrid of several different antibody subclass constant domains (e.g., any combination of IgG1, IgG2a, IgG2b, IgG3 and IgG4).

In certain embodiments, the internalizing moiety is an antibody fragment comprising an antigen binding fragment. In other words, in certain embodiments, the internalizing moiety is not a full length antibody but is a fragment thereof comprising an antigen binding fragment. In certain embodiments, the internalizing moiety is an scFv, Fab, Fab', or Fab2'. In certain embodiments, the internalizing moiety is a full length antibody comprising a heavy chain comprising a CH1, hinge, CH2, and CH3 domains, optionally substituted to reduce effector function, such as in the hinge and/or CH2 domains, as described herein. In certain embodiments, the heavy chain comprises a VH domain, and a constant domain comprising a CH1, hinge, CH2, and CH3 domain. In certain embodiments, a heavy chain comprises a VH domain, and a constant domain comprising a CH1 domain and, optionally the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In certain embodiments, an antibody or antigen binding fragment as disclosed herein is a full length antibody comprising CH1, hinge, CH2, and CH3 of a heavy chain constant domain and a light chain constant domain. In certain embodiments the heavy chain constant region comprises one or more of a CH1, CH2, and CH3 domains, optionally with a hinge.

Monoclonal antibody 3E10 can be produced by hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used also herein to refer to a murine antibody (or antigen binding fragment) comprising the a VL domain comprising the amino acid sequence of SEQ ID NO: 7 and a VH domain comprising the amino acid sequence of SEQ ID NO: 9, regardless of the method used to produce the antibody. Thus, in the context of the present application, 3E10 antibody will refer, unless otherwise specified, to an antibody having the sequence of the hybridoma or comprising a variable heavy chain domain comprising the amino acid sequence set forth in SEQ ID NO: 9 (which has a one amino acid substitution relative to that of the 3E10 antibody deposited with the ATCC, as described herein and previously demonstrated as retaining cell penetration and DNA binding activity) and the variable light chain domain comprising the amino acid sequence set forth in SEQ ID NO: 7. However, in the context of the present disclosure, the parent murine antibody used as the basis for humanization was an antibody comprising the VL domain comprising the amino acid sequence of SEQ ID NO: 7 and a VH domain comprising the amino acid sequence of SEQ ID NO: 9. The disclosure provides, in certain embodiments, humanized antibodies based on murine 3E10.

Similarly, when referring to variants or antigen-binding fragments of 3E10, such terms are used without reference to the manner in which the antibody was produced. At this point, 3E10 is generally produced recombinantly.

The humanized internalizing moiety may also be derived from variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. In some embodiments, the light chain or heavy chain may be modified at the N-terminus or C-terminus. Moreover, the antibody or antibody fragment may be modified to facilitate conjugation to a heterologous agent. Similarly, the foregoing description of variants applies to antigen binding fragments. Any of these antibodies, variants, or fragments may be made recombinantly by expression of the nucleotide sequence(s) in a host cell. Such internalizing moieties can transit cells via an ENT transporter, such as ENT2 and/or ENT3 and/or bind the same epitope (e.g., target, such as DNA) as 3E10.

Monoclonal antibody 3E10 has been shown to penetrate cells to deliver proteins and nucleic acids into the cytoplasmic or nuclear spaces of target tissues (Weisbart R H et al., J Autoimmun. 1998 October; 11(5):539-46; Weisbart R H, et al. Mol Immunol. 2003 March; 39(13):783-9; Zack D J et al., J Immunol. 1996 Sep. 1; 157(5):2082-8.). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 Jun. 10; 195(2):211-9; Weisbart R H et al., J Drug Target. 2005 February; 13(2):81-7; Weisbart R H et al., J Immunol. 2000 Jun. 1; 164(11):6020-6; Hansen J E et al., J Biol Chem. 2007 Jul. 20; 282(29):20790-3). Moreover, as noted above, the one amino acid substitution in the VH used as part of the 3E10 parent antibody herein, has likewise previously been shown to bind DNA and penetrate cells. The 3E10 is built on the antibody scaffold present in all mammals; a mouse variable heavy chain and variable kappa light chain. 3E10 gains entry to cells via the ENT2 nucleotide transporter that is particularly enriched in skeletal muscle and cancer cells, and in vitro studies have shown that 3E10 is nontoxic. (Weisbart R H et al., Mol Immunol. 2003 March; 39(13):783-9; Pennycooke M et al., Biochem Biophys Res Commun. 2001 Jan. 26; 280(3):951-9). 3E10 may also be capable of transiting membranes via ENT3.

The humanized internalizing moiety may also be derived from mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like).

Such mutants include variants wherein one or more conservative substitutions are introduced into the heavy chain or the light chain. Numerous variants of mAb 3E10 have been characterized in, e.g., U.S. Pat. No. 7,189,396 and WO 2008/091911, the teachings of which are incorporated by reference herein in their entirety. In the examples provided herein, the parent, murine 3E10 comprises a VH comprising the amino acid sequence set forth in SEQ ID NO: 9 and a VL comprising the amino acid sequence set forth in SEQ ID NO: 7.

In certain embodiments, the internalizing moiety is an antigen binding fragment, such as a humanized single chain Fv (scFv). In other embodiments, the humanized antibody is a Fab' fragment.

In some embodiments, the internalizing moiety is an antibody or antibody fragment comprising an immunoglobulin heavy chain constant region or fragment thereof. As is known, each immunoglobulin heavy chain constant region comprises four or five domains. The domains are named sequentially as follows: $C_H1$-hinge-$C_H2$-$C_H3$(-$C_H4$). The DNA sequences of the heavy chain domains have cross-homology among the immunoglobulin classes, e.g., the $C_H2$ domain of IgG is homologous to the $C_H2$ domain of IgA and IgD, and to the $C_H3$ domain of IgM and IgE. As used herein, the term, "immunoglobulin Fc region" is understood to mean the carboxyl-terminal portion of an immunoglobulin heavy chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In one embodiment, the immunoglobulin Fc region comprises at least an immunoglobulin hinge region a CH2 domain and a CH3 domain, and lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region may comprise at least a portion of a hinge domain, and preferably at least a portion of a CH3 domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. In certain embodiments, the constant region domains are human.

In some embodiments, the antibody or antigen binding fragment comprises hybrid heavy chain constant regions, i.e., the antibody or antigen binding fragment comprise multiple heavy chain constant region domains selected from: a CH1 domain, a CH2 domain, a CH3 domain, and a CH4 domain; wherein at least one of the constant region domains in the antibody or antigen binding fragment is of a class or subclass of immunoglobulin distinct from the class or subclass of another domain in the antibody or antigen binding fragment. In some embodiments, at least one of the constant region domains in the antibody or antigen binding fragment is an IgG constant region domain, and at least one of the constant region domains in the antibody or antigen binding fragment is of a different immunoglobulin class, i.e., an IgA, IgD, IgE, or IgM constant region domain. In some embodiments, at least one of the constant region domains in the antibody or antigen binding fragment is an IgG1 constant region domain, and at least one of the constant region domains in the antibody or antigen binding fragment is of a different IgG subclass, i.e., an IgG2A, IgG2B, IgG3 or IgG4. Suitable constant regions may be human or from another species (e.g., murine). Humanized antibodies and antigen binding fragments of the disclosure are consider humanized regardless of whether and constant region sequence (heavy or light chain), if present, corresponds to that of a human immunoglobulin or corresponds to that of another species.

The cell penetrating ability of the humanized internalizing moieties or fragments or variants may be utilized to promote delivery of a heterologous agent. Humanized moieties derived from 3E10 are particularly well suited for this because of their demonstrated ability to effectively promote delivery to muscle cells, including skeletal and cardiac muscle, as well as diaphragm. Thus, humanized internalizing moieties are especially useful for promoting effective delivery into cells in subjects, such as human patients or model organisms. In certain embodiments, antibodies and antigen binding fragments of the disclosure are useful as intermediates for further conjugation to a heterologous agent, such as a heterologous protein, peptide, polynucleotide, or small molecule.

Preparation of antibodies or fragments thereof (e.g., a single chain Fv fragment encoded by $V_H$-linker-$V_L$ or $V_L$-linker-$V_H$) is well known in the art. In particular, methods of recombinant production of mAb 3E10 antibody fragments have been described in WO 2008/091911. Further, methods of generating scFv fragments of antibodies are well known in the art. When recombinantly producing an antibody or antibody fragment, a linker may be used. For example, typical surface amino acids in flexible protein regions include Gly, Asn and Ser. One exemplary linker is provided in SEQ ID NO: 30 or 31. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4. Other near neutral amino acids, such as Thr and Ala, can also be used in the linker sequence.

In addition to linkers interconnecting portions of, for example, an scFv, the disclosure contemplates the use of additional linkers to, for example, interconnect the heterologous agent to the antibody portion of a conjugate or to interconnect the heterologous agent portion to the antibody portion of conjugate.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the humanized internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising an peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

A "Fab fragment" is comprised of one light chain and the $C_H1$ and variable regions of one heavy chain. Generally, the heavy chain of a Fab molecule cannot form a disulfide bond with another heavy chain molecule. A Fab may optionally include a portion of the hinge, such as the upper hinge.

A "Fab' fragment" contains one light chain and one heavy chain that contains more of the constant region, between the $C_H1$ and $C_H2$ domains, such that an interchain disulfide bond can be formed between two heavy chains to form a F(ab')$_2$ molecule.

A "F(ab')$_2$ fragment" contains two light chains and two heavy chains containing a portion of the constant region between the CH1 and CH2 domains, such that an interchain disulfide bond is formed between two heavy chains.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the disclosure include full length or intact antibody, antibody fragments, native sequence antibody or amino acid variants, human, humanized (a form of chimeric antibodies), post-translationally modified, chimeric antibodies, immunoconjugates, and functional fragments thereof. The antibodies can be modified in the Fc region to provide desired effector functions or serum half-life.

Preparation of Antibodies

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. See, e.g., Fundamental Immunology, Ch. 7, 2.sup.nd ed., (Paul, W., ed.), 1989, Raven Press, N.Y. (incorporated by reference in its entirety for all purposes). The combination of the variable regions of each light chain/heavy chain pair typically forms the antigen-binding site. In some embodiments, antibodies or antigen binding fragments of the disclosure comprise the following constant domain scheme: IgG2a CH1-IgG1 hinge-IgG1 CH2-CH3. Other suitable combinations are also contemplated. In other embodiments, the antibody comprises a full length antibody and the CH1, hinge, CH2, and CH3 is from the same constant domain subclass (e.g., IgG1). In some embodiments, the antibodies or antigen binding fragment comprises an antigen binding fragment comprising a portion of the constant domain of an immunoglobulin, for example, the following constant domain scheme: IgG2a CH1-IgG1 upper hinge. In some embodiments, the antibodies or antigen binding fragments of the disclosure comprise a kappa constant domain (e.g., SEQ ID NO: 60).

The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific target (e.g., antigen, DNA in the context of the present disclosure). From N-terminal to C-terminal, both light and heavy chain variable regions typically comprise the domains FR1, CDR1, FR2, CDR2, FR3, CDR3 and FR4. The assignment of amino acids to each domain (FR or CDR) is typically in accordance with the definitions of Kabat Sequences of Proteins of Immunological Interest (1987 and 1991, National Institutes of Health, Bethesda, Md.). In certain embodiments, the CDRs of a particular antibody, such as an antibody provided herein, are CDRs, as defined by this Kabat system (e.g., the CDRs being referred to for an antibody or antigen binding fragment are identified using the Kabat system). Similarly, in certain embodiments, particularly when the CDRs are defined or identified as by the Kabat system, the FR regions are also defined and/or identified using the Kabat system. However, alternative systems for identifying CDR and FR regions are also available, including the IMGT system (described herein). In certain embodiments, the CDRs of a particular antibody, such as an antibody provided herein, are CDRs as defined by the IMGT system (e.g., CDRs for an antibody or antigen binding fragment are identified using the IMGT system).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63). In many cases, hybridomas are used to generate an initial antibody of murine or rodent origin. That initial antibody may then be modified, such as using recombinant techniques to produce rodent variants, chimeric antibodies, humanized antibodies and the like. Other methods exist to produce an initial antibody, and such methods are known in the art. However, regardless of the method used to generate an initial antibody or even a variant of that initial antibody, any given antibody of non-human origin can then be modified to increase its humanness.

It can be advantageous to increase the humanness of a non-human antibody to make it more suitable for use in human subject and cells, whether for diagnostic, therapeutic, or research purposes. Antibodies may be modified for use as therapeutics. Examples of such antibodies (including antibody fragments) include chimeric, humanized, and fully human antibodies. Numerous methods exist in the art for the generation of chimeric, humanized and human antibodies. In the context of the present disclosure, an antibody is considered humanized if at least one of the VH domain or VL domain is humanized. Moreover, an VH or VL domain is humanized if the amino acid sequence of at least a portion of at least one FR regions has been modified, relative to a parent murine antibody, such that the amino acid sequence of that portion corresponds to that of a human antibody or a human consensus sequence. In certain embodiments, at least one, two, three, or four FR regions of the VH domain and/or at least one, two, three, or four FR regions of the VL domain have been modified (in whole or in part) so that their sequence is more closely related to a human sequence. For any of the foregoing in certain embodiments, a humanized antibody fragment may be provided in the context of a human or non-human light chain and/or heavy chain constant region (e.g., comprising a CL and one or more of a CH1, hinge, CH2, and/or CH3 domains). In certain embodiments, a humanized antibody or antigen binding fragment of the disclosure is provided in the context of human light and/or heavy chain constant domains, when present. Numerous examples of humanized light and heavy chain variable domains based on a 3E10 parent antibody are provided herein. Antibodies and antibody binding fragments combining any of the humanized light chain variable domains and/or heavy chain variable domains described herein are exemplary of antibodies and antigen binding fragments of the disclosure.

Once the nucleotide sequences encoding such antibodies have been determined, chimeric or humanized antibodies may be produced by recombinant methods. Nucleic acids encoding the antibodies are introduced into host cells and expressed using materials and procedures generally known in the art.

In certain embodiments, the antibodies or antigen binding fragments of the disclosure are of the IgG1, IgG2, or IgG4 isotype. In certain embodiments of the disclosure, the antibodies comprise a human kappa light chain and a human IgG1, IgG2, or IgG4 heavy chain. In certain embodiments, the antibodies of the disclosure have been cloned for expression in mammalian cells.

Regardless of when an antibody of the disclosure is a full length antibody or an antigen binding fragment, antibodies and antigen binding fragments of the disclosure can be recombinantly expressed in cell lines. In these embodiments, sequences encoding particular antibodies can be used for transformation of a suitable host cell, such as a mammalian host cell or yeast host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the disclosure, a nucleic acid molecule encoding the amino acid sequence of a heavy chain constant region (all or a portion), a heavy chain variable region of the disclosure, a light chain constant region, or a light chain variable region of the disclosure is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, Meth. Enzymol. Vol. 185, Academic Press. N.Y. In the context of antibody expression, both the heavy and light chain may be expressed from the same vector (e.g., from the same or different promoters present on the same vector) or the heavy and light chains may be expressed from different vectors. In certain embodiments, the heavy and light chains are expressed from different vectors which are transfected into the same host cell and co-expressed. Regardless of when the heavy and light chains are expressed in the same host cell from the same or a different vector, the chains can then associate to form an antibody (or antibody fragment, depending on the portions of the heavy and light chain being expressed).

In certain embodiments, an antibody or antigen binding fragment of the disclosure is conjugated to a heterologous agent. In certain embodiments, the heterologous agent is a protein or peptide. That protein or peptide may be expressed as an inframe, co-translation fusion protein with, for example, the heavy chain, and expressed as described herein. Chemical conjugation is also possible. Conjugated as described in detail herein and unless otherwise specified, refers to scenarios where any of the antibody or antigen binding portions of the disclosure are associated with or interconnected with the heterologous agent, regardless of the interconnection (e.g., the interconnection/association may comprise a chemical conjugation, covalent bond, di-sulfide bond, etc. or combinations thereof). In certain embodiments, at least a portion of the interconnection is via a covalent bond, such as the forming of a fusion protein between a heavy chain of the antibody of the disclosure and the heterologous agent (which may further associate with a light chain of the antibody of the disclosure). Accordingly, the disclosure provides such conjugates and pharmaceutical compositions comprising such conjugates. A conjugate is a molecule comprising an antibody or antigen binding portion of the disclosure associate with a heterologous agent. Similarly, antibodies or antigen binding fragments of the disclosure may further comprise a heterologous agent. Conjugates along molecules where the two portions are associated or interconnected (e.g., the interconnection may comprise a chemical conjugation, covalent bond, di-sulfide bond, etc. or combinations thereof). In certain embodiments, at least a portion of the interconnection is via a covalent bond, such as the forming of a fusion protein between a heavy chain of an antibody of the disclosure and the heterologous agent (which may further associate with a light chain of the antibody or antibody fragment of the disclosure).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These portions of vectors are well known, and there are numerous generally available vectors that can be selected and used for the expression of proteins. One can readily selected vectors based on the desired host cell and application.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

The expression and cloning vectors of the disclosure will typically contain a promoter that is recognized by the host organism and operably linked to the molecule encoding heavy and/or light chain. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the heavy chain or light chain comprising an antibody or antigen binding fragment of the disclosure. In certain embodiments, the same promoter is used for both the heavy and light chain. In other embodiments, different promoters (present on the same or different vectors) are used for each.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, Nature 290:304-10); the CMV promoter; the promoter contained in the 3' long terminal repeat of Rous sarcoma virus (Yamamoto et al., 1980, Cell 22:787-97); the herpes thymidine kinase promoter (Wagner et al., 1981, Proc. Natl. Acad. Sci. USA 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. USA 75:3727-31); or the tac promoter (DeBoer et al., 1983, Proc. Natl. Acad. Sci. USA 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol. 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol. 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:338-40; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

The vector may also include an enhancer sequence to increase transcription of DNA encoding light chain or heavy chain.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an antibody or antigen binding fragment of the disclosure has been inserted into the proper site of the vector, the completed vector may be inserted into a suitable host cell for amplification and/or polypeptide expression. The transformation of an expression vector into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes the antibody or antigen binding fragment of the disclosure that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, one may select a cell line from the B cell lineage that does not make its own antibody but has a capacity to make and secrete a heterologous antibody (e.g., mouse myeloma cell lines NS0 and SP2/0). In other embodiments, a cell other than a mammalian cell is used, such as a yeast cell line (e.g., *Pichia*).

In certain embodiments, the cell line stably expresses an antibody or antigen binding fragment of the disclosure. In other embodiments, the cells transiently express an antibody or antigen binding fragment of the disclosure.

In certain embodiments is provided antibodies of the disclosure (including antigen binding fragments) that are substantially purified/isolated. Numerous methods, filters, and devices for substantially purifying antibodies grown in recombinant cell culture are available.

Antibody fragments can also be made by enzymatic digestion of a full length antibody.

In certain embodiments, the antibodies or antigen binding fragments of the disclosure, whether provided alone or as conjugates with a heterologous agent, are detectably labeled. In certain embodiments, the detectable label is itself an example of a heterologous agent. Methods for conjugation to a substance, such as a detectable label, are well known in the art. In one embodiment, the attached substance is a detectable label (also referred to herein as a reporter molecule). Suitable substances for attachment to include, but are not limited to, a fluorophore, a chromophore, a dye, a radioisotope, and combinations thereof. Methods for conjugation or covalently attaching another substance to an antibody are well known in the art.

The terms "label" or "labeled" refers to incorporation of a detectable marker, e.g., by incorporation of a radiolabeled amino acid or attachment to a polypeptide of biotin moieties that can be detected by marked avidin (e.g., streptavidin preferably comprising a detectable marker such as a fluorescent marker, a chemiluminescent marker or an enzymatic activity that can be detected by optical or colorimetric methods). Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}$H, $^{14}$C, $^{15}$N, $^{35}$S, $^{90}$Y, $^{99}$mTc, $^{111}$In, $^{125}$I, $^{131}$I). In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$SM, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh and $^{97}$Ru.).

Further examples of labels include fluorescent labels (e.g., fluoroscein isothiocyanate (FITC), rhodamine, or lanthanide phosphors), enzymatic labels (e.g., horseradish peroxidase, .beta.-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

When present, regardless of the particular label, one of skill can select an appropriate label to facilitate purification, diagnostic, or research use. In other embodiments, the heterologous agent is a therapeutic molecule and either does not include a detectable label and/or epitope tag, or includes a therapeutic molecule in addition to the detectable label and/or epitope tag.

"Humanized" refers to an immunoglobulin such as an antibody, wherein the amino acids directly involved in antigen binding, the so-called complementary determining regions (CDR), of the heavy and light chains are not necessarily of human origin, while at least a portion of the rest of the variable domain (e.g., one or more of FR1, FR2, FR3, FR4) of one or both chains of the immunoglobulin molecule, the so-called framework regions of the variable heavy and/or light chains, and, if present, optionally the constant regions of the heavy and light chains are modified so that their amino acid sequence more closely correspond to human sequences.

A "humanized antibody" as used herein in the case of a two or greater chain antibody is one where at least one chain is humanized. A humanized antibody chain has a variable region where one or more of the framework regions are human or contain alterations, relative to a murine parent, so that one or more framework regions are more human than a murine parent. A humanized antibody which is a single chain is one where the chain has a variable region where one or more of the framework regions are human or contain alterations, relative to a murine parent, so that one or more framework regions are more human. The non-human portions of the variable region of the humanized antibody chain or antigen-binding fragment is derived from a non-human source, particularly a non-human antibody, typically of rodent origin. The non-human contribution to the humanized antibody is typically provided in the form of at least one CDR region which is interspersed among framework regions derived from one (or more) human immunoglobulin(s). In addition, framework support residues may be altered to preserve binding affinity. Thus, as is understood in the art, an entire framework region or all of the framework regions on a particular chain need not contain residues corresponding to a human antibody in order for the antibody to be considered humanized.

A "humanized antibody" may further comprise constant regions (e.g., at least one constant region or portion thereof, in the case of a light chain, and in some embodiments three constant regions in the case of a heavy chain). The constant regions of a humanized antibody, if present, typically are human in origin.

In some embodiments, a humanized antibody is generated by first subjecting a murine 3E10 light or heavy chain antibody sequence (e.g., the murine 3E10 antibody light and heavy chain amino acid sequences of SEQ ID NO: 7 and 9, respectively) to a sequence database search (e.g., BLAST) in order to identify the top closest human immunoglobulin kappa or heavy chain homologues in sequence similarity (e.g., the top 1, 2, 3, 4, 5, 6, 7, 8, 9 or 10 closest immunoglobulin kappa or heavy chain homologues). The top closest human immunoglobulin kappa or heavy chain homologues are considered candidates for kappa or heavy chain CDR grafting. In some embodiments, sequence alignment tools, such as Vector NTi sequence alignment tools, are then used to analyze the chimeric amino acid sequences consisting of the CDRs from the 3E10 kappa or heavy chain and the framework regions of any one of the top human immunoglobulin kappa or heavy chain homologues.

In general, as used herein, humanized antibodies comprise one or two variable domains in which all or part of the CDR regions correspond to parts derived from the non-human parent sequence and in which all or part of the FR regions are derived from a human immunoglobulin sequence. The humanized antibody can then, optionally, comprise at least one portion of a constant region of immunoglobulin (Fc), in particular that of a selected reference human immunoglobulin.

In some embodiments, the antibodies and antigen binding fragments of the disclosure (e.g., an antibody or antigen binding fragment, such as a humanized antibody or antigen binding fragment) comprises one or more of the CDRs of the 3E10 antibody. In certain embodiments, the antibodies and antigen binding fragments comprise one or more of the CDRs of a 3E10 antibody comprising a $V_H$ domain comprising the amino acid sequence set forth in SEQ ID NO: 9 and a $V_L$ domain comprising the amino acid sequence set forth in SEQ ID NO: 7. Either or both of the Kabat or IMGT CDRs may be used to refer to or describe an antibody. CDRs of the 3E10 antibody or an antibody of the disclosure may be determined using any of the CDR identification schemes available in the art, and such scheme may be used to describe the antibody. For example, in some embodiments, the CDRs are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs are defined according to Chothia et al., 1987, J Mol Biol. 196: 901-917 and Chothia et al., 1989, Nature. 342: 877-883. In other embodiments, the CDRs are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs are defined according to any of the CDR identification schemes discussed in Kunik et al., 2012, PLoS Comput Biol. 8(2): e1002388. In certain embodiments, antibodies and antigen binding fragments of the disclosure comprise one or more differences in the Kabat CDRs as compared to the murine, parent antibody. For example, in certain embodiments, the antibodies and antigen binding fragments of the disclosure differ at VH CDR2 and/or VL CDR2 and, optionally, at VL CDR1 in comparison to the murine, parent antibody. However, in certain embodiments, such antibodies share the IMGT CDRs of the murine, parent antibody.

Herein, the amino acid positions of residues in the VH and VL domains are referred to by linear sequence relative to, for example, SEQ ID NO: 7 or 9. Thus, the sequence of the VH and/or VL of an antibody or antigen binding fragment of the disclosure can be described relative to the corresponding amino acid position(s) of SEQ ID NO: 7 or 9. For example, an VH or VL domain may include an alteration at a particular amino acid position, and that position may correspond to a particular position in SEQ ID NO: 7 or 9.

However, the CDR identification scheme also provide numbering systems that may be used to facilitate comparisons between antibodies. Although not specifically used herein, one of skill in the art can readily use the available numbering scheme to refer to the CDRs described herein using a uniform numbering system, rather than by referring to the linear sequence. In certain embodiments, to number residues of an antibody for the purpose of identifying CDRs according to any of the CDR identification schemes known in the art, one may align the antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence. These uniform schemes for numbering residues are not expressly used herein, but can be readily used based on the disclosed sequences and identified CDRs.

In certain embodiments, the antibodies and antigen binding fragments of the disclosure (e.g., a humanized antibody or antigen binding fragment of the disclosure) comprises Kabat CDRs. In some embodiments, the antibodies and antigen binding fragments comprise a $V_H$ CDR1 that corresponds to amino acid residues 31-35 of SEQ ID NO: 9, a $V_H$ CDR2 that corresponds to amino acid residues 50-66 of SEQ ID NO: 9, and/or a $V_H$ CDR3 that corresponds to amino acid residues 99-105 of SEQ ID NO: 9. We note that this numbering of amino acid residues is with reference to the linear amino acid sequence of SEQ ID NO: 9. One of skill in the art can readily use the Kabat system to identify these residues using Kabat numbering. In certain embodiments, the antibodies and antigen binding fragments comprise a $V_L$ CDR1 that corresponds to amino acid residues 24-38 of SEQ ID NO: 7, a $V_L$ CDR2 that corresponds to amino acid residues 54-60 of SEQ ID NO: 7, and/or a $V_L$ CDR3 that corresponds to amino acid residues 93-101 of SEQ ID NO: 7. We note that this numbering of amino acid residues is with reference to the linear amino acid sequence of SEQ ID NO: 7. One of skill in the art can readily use the Kabat system to identify these residues using Kabat numbering.

In certain embodiments, the antibodies and antigen binding fragments of the disclosure comprise CDRs that are defined using the IMGT system. In some embodiments, the antibodies and antigen binding fragments comprise $V_H$ CDR1 that corresponds to amino acid residues 26-33 of SEQ ID NO: 9, a $V_H$ CDR2 that corresponds to amino acid residues 51-58 of SEQ ID NO: 9, and/or a $V_H$ CDR3 that corresponds to amino acid residues 97-105 of SEQ ID NO: 9. We note that this numbering of amino acid residues is with reference to the linear amino acid sequence of SEQ ID NO: 9. In certain embodiments, the antibodies and antigen binding fragments comprise a $V_L$ CDR1 that corresponds to amino acid residues 27-36 of SEQ ID NO: 7, a $V_L$ CDR2 that corresponds to amino acid residues 54-56 of SEQ ID NO: 7, and/or a $V_L$ CDR3 that corresponds to amino acid residues 93-101 of SEQ ID NO: 7. We note that this numbering of amino acid residues is with reference to the linear amino acid sequence of SEQ ID NO: 7. In certain embodiments, an antibody or antigen binding fragment of the disclosure comprises all 6 of the foregoing CDRs. In certain embodiments, the antibody or antigen binding fragment comprises 4 of the foregoing CDRs, and a VH CDR2 as set forth in SEQ ID NO: 49 and a VL CDR 2 as set forth in SEQ ID NO: 51.

In certain embodiments, the antibodies and antigen binding fragments of the disclosure comprise at least 1, 2, 3, 4, or 5 of the CDRs of 3E10 as determined using the Kabat CDR identification scheme (e.g., the CDRs set forth in SEQ ID NOs: 32-37). In certain embodiments, the antibody or antigen binding fragment further comprises a VH CDR2 as set forth in SEQ ID NO: 49 and/or a VL CDR2 as set forth in SEQ ID NO: 51 and/or a VL CDR1 as set forth in SEQ ID NO: 50. In certain embodiments, the antibodies and antigen binding fragments comprise at least 1, 2, 3, 4 or 5 of the CDRS of 3E10 as determined using the IMGT identification scheme (e.g., the CDRs set forth in SEQ ID NOs: 1-6). In certain embodiments, the antibodies and antigen binding fragments comprise all six CDRs of 3E10 as determined using the Kabat CDR identification scheme (e.g., comprises SEQ ID NOs 32-37). In other embodiments, the antibodies and antigen binding fragments comprise all six CDRS of 3E10 as determined using the IMGT identification scheme (e.g., which are set forth as SEQ ID NOs: 1-6). For any of the foregoing, in certain embodiments, the antibodies and antigen binding fragments is an antibody that binds the same epitope (e.g., the same target, such as DNA) as 3E10 and/or the internalizing moiety competes with 3E10 for binding to antigen (e.g., DNA). Exemplary antibodies and antigen binding fragments can transit cells via ENT2 and/or ENT3.

In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using IMGT numbering (e.g., in one or more CDRs having the amino acid sequence of any one of SEQ ID NOs: 1-6, such as having 1-2, 1-3, 1-4, or 1-5 alternations) or Kabat numbering (e.g., in one or more CDRs having the amino acid sequence of any one of SEQ ID NOs: 32-37, such as having 1-2, 1-3, 1-4, or 1-5 alterations). In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using Kabat numbering (e.g., in one or more CDRs having the amino acid sequence of any one of SEQ ID NOs: 32-37, such as have 2, 3, 4, or 5 alterations) In some embodiments, antibodies or antigen binding fragments of the disclosure comprise a $V_L$ domain comprising one or more of the following amino acid alterations: M37L, H38A or E59Q, as compared with and numbered with respect to the linear amino acid sequence of SEQ ID NO: 7. In some embodiments, any of the antibodies or antigen binding fragments disclosed herein comprise a $V_H$ domain comprising a T63S alteration, as compared with and numbered with respect to the linear amino acid sequence of SEQ ID NO: 9. In some embodiments, antibodies or antigen binding fragments of the disclosure comprise a $V_L$ domain comprising an E59Q alteration as compared with and numbered with respect to the linear amino acid sequence of SEQ ID NO: 7, and a $V_H$ domain comprising a T63S alteration as compared with and numbered with respect to the linear amino acid sequence of SEQ ID NO: 9.

Without wishing to be bound by theory, one of the surprising findings of the present disclosure is the ability to generate antibodies and antigen-binding fragments that— have improved DNA binding activity versus murine 3E10, and further include an amino acid alteration (here, a substitution) in certain Kabat CDRs. Moreover, in certain embodiments, these improved antibodies having CDR substitutions are, in certain embodiments, also humanized.

In certain embodiments, the antibodies and antigen binding fragments of the disclosure comprise a variable heavy chain domain comprising at least one CDR different from the corresponding CDR set forth in SEQ ID NO: 9, as determined using the Kabat CDR identification scheme. In some embodiments, the at least one different CDR is $V_H$ CDR2 as set forth in SEQ ID NO: 49.

In certain embodiments, the antibodies and antigen binding fragments of the disclosure comprise a variable light chain domain comprising at least one CDR different from the corresponding CDR set forth in SEQ ID NO: 7, as determined using the Kabat CDR identification scheme. In some embodiments, the at least one different CDR is a $V_L$ CDR1 as set forth in SEQ ID NO: 50. In some embodiments, the at least one different CDR is a $V_L$ CDR2 as set forth in SEQ ID NO: 51.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in public databases. Regardless of the specific methodologies used to generate a humanized antibody or antibody fragment, the antibody must be evaluated to make sure that it (i) retains the desired function of the parent, murine antibody (or optionally has enhanced function); (ii) does not have deleterious properties that make it difficult to make or use; and preferably (iii) possesses one or more advantageous properties in comparison to the murine, parent antibody. Whether and to what extent any or all of these occur for any specific humanized antibody is unpredictable and uncertain. This is particularly true where substitutions are also introduced into the CDRs. Moreover, amongst a panel of humanized antibodies or antibody fragments, some may not have the required activity and one or more antibodies that do have the required activity may have advantageous properties in comparison to other humanized antibodies. This too is unpredictable and uncertain.

In certain embodiments, the antibodies or antigen-binding fragments of the disclosure comprise a light chain variable (VL) domain and a heavy chain variable (VH) domain; wherein the VL domain is humanized and comprises:

a VH CDR1 having the amino acid sequence of SEQ ID NO: 1;

a VH CDR2 having the amino acid sequence of SEQ ID NO: 2; and a VH CDR3 having the amino acid sequence of SEQ ID NO: 3; which CDRs are in accordance with the IMGT system and the VH domain is humanized and comprises:

a VL CDR1 having the amino acid sequence of SEQ ID NO: 4;

a VL CDR2 having the amino acid sequence of SEQ ID NO: 5; and a VL CDR3 having the amino acid sequence of SEQ ID NO: 6; which CDRs are in accordance with the IMGT system, and wherein the antibody or antigen-binding fragment has increased DNA binding and/or cell penetration, relative to that of a murine 3E10 antibody comprising a light chain variable (VL) domain having the amino acid sequence of SEQ ID NO: 7 and a heavy chain variable (VH) domain having the amino acid sequence of SEQ ID NO: 9.

In certain embodiments the antibodies or antigen-binding fragments of the disclosure comprise a light chain variable (VL) domain and a heavy chain variable (VH) domain; wherein the VH domain comprises:

a VH CDR1 having the amino acid sequence of SEQ ID NO: 32;

a VH CDR2 having the amino acid sequence of SEQ ID NO: 49; and a VH CDR3 having the amino acid sequence of SEQ ID NO: 34,
which CDRs are according to the Kabat system;
and the VL comprises:
a VL CDR1 having the amino acid sequence of SEQ ID NO: 50;
a VL CDR2 having the amino acid sequence of SEQ ID NO: 51; and
a VL CDR3 having the amino acid sequence of SEQ ID NO: 37,
which CDRs are according to the Kabat system;
wherein the antibody or antigen-binding fragment binds DNA.

In certain embodiments the antibodies or antigen-binding fragments of the disclosure comprise a light chain variable (VL) domain and a heavy chain variable (VH) domain; wherein the VH domain comprises:
a VH CDR1 having the amino acid sequence of SEQ ID NO: 32;
a VH CDR2 having the amino acid sequence of SEQ ID NO: 49; and
a VH CDR3 having the amino acid sequence of SEQ ID NO: 34,
which CDRs are according to Kabat;
and the VL comprises:
a VL CDR1 having the amino acid sequence of SEQ ID NO: 35;
a VL CDR2 having the amino acid sequence of SEQ ID NO: 51; and
a VL CDR3 having the amino acid sequence of SEQ ID NO: 37,
which CDRs are according to Kabat;
wherein the antibody or antigen-binding fragment binds DNA.

In certain embodiments, antibodies or antigen binding fragments of the disclosure penetrate cells (e.g., can transit the plasma membrane and enter into cells, such as cells expressing ENT2).

In some embodiments, the VH domain is humanized. In some embodiments, the VL domain is humanized.

In certain embodiments the antibodies or antigen-binding fragments of the disclosure comprise a $V_L$ domain that comprises the amino acid sequence set forth in SEQ ID NO: 40, or an amino acid sequence that differs from SEQ ID NO: 40 by the presence of a total of 1, 2, 3, 4, 5, or 6 amino acid substitutions, insertions and/or deletions in the framework regions, as defined by the IMGT system, relative to SEQ ID NO: 40. In other embodiments, the $V_L$ domain comprises the amino acid sequence set forth in SEQ ID NO: 8, or an amino acid sequence that differs from SEQ ID NO: 8 by the presence of a total of 1, 2, 3, 4, 5, or 6 amino acid substitutions, insertions and/or deletions in the framework regions, as defined by the IMGT system, relative to SEQ ID NO: 8. In some embodiments, the VL domain comprises the amino acid sequence set forth in SEQ ID NO: 40. In some embodiments, the VL domain comprises the amino acid sequence set forth in SEQ ID NO: 8.

In certain embodiments the antibodies or antigen-binding fragments of the disclosure comprise a $V_H$ domain that comprises the amino acid sequence set forth in SEQ ID NO: 38, or an amino acid sequence that differs from SEQ ID NO: 38 by the presence of a total of 1, 2, 3, 4, 5, or 6 amino acid substitutions, insertions and/or deletions in the framework regions, as defined by the IMGT system, relative to SEQ ID NO: 38. In some embodiments, the $V_H$ domain comprises the amino acid sequence set forth in SEQ ID NO: 39, or an amino acid sequence that differs from SEQ ID NO: 39 by the presence of a total of 1, 2, 3, 4, 5, or 6 amino acid substitutions, insertions and/or deletions in the framework regions, as defined by the IMGT system, relative to SEQ ID NO: 39. In some embodiments, the $V_H$ domain comprises the amino acid sequence set forth in SEQ ID NO: 10, or an amino acid sequence that differs from SEQ ID NO: 10 by the presence of a total of 1, 2, 3, 4, 5, or 6 amino acid substitutions, insertions and/or deletions in the framework regions, as defined by the IMGT system, relative to SEQ ID NO: 10. In some embodiments, the VH domain comprises the amino acid sequence set forth in SEQ ID NO: 38. In some embodiments, the VH domain comprises the amino acid sequence set forth in SEQ ID NO: 39. In some embodiments, the VH domain comprises the amino acid sequence set forth in SEQ ID NO: 10.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 8; wherein the $V_H$ domain comprises three CDRs of the amino acid sequence set forth in SEQ ID NO: 9, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells.

In certain embodiments, the $V_H$ domain of the antibodies or antigen-binding fragments described herein comprise:
a VH CDR1 having the amino acid sequence of SEQ ID NO: 1;
a VH CDR2 having the amino acid sequence of SEQ ID NO: 2; and
a VH CDR3 having the amino acid sequence of SEQ ID NO: 3.

In certain embodiments, the $V_L$ domain of the antibodies or antigen-binding fragments described herein comprise:

a VL CDR1 having the amino acid sequence of SEQ ID NO: 4;

a VL CDR2 having the amino acid sequence of SEQ ID NO: 5; and a VL CDR3 having the amino acid sequence of SEQ ID NO: 6.

In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 8; wherein the $V_H$ domain comprises three CDRs of the amino acid sequence set forth in SEQ ID NO: 9, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 40; wherein the $V_H$ domain comprises three CDRs of the amino acid sequence set forth in SEQ ID NO: 9, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 10; wherein the $V_L$ domain comprises three CDRs of the amino acid sequence set forth in SEQ ID NO: 7, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 38; wherein the $V_L$ domain comprises three CDRs of the amino acid sequence set forth in SEQ ID NO: 7, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 39; wherein the $V_L$ domain comprises three CDRs of the amino acid sequence set forth in SEQ ID NO: 7, wherein the antibody or antigen-binding fragment binds DNA and penetrates cells.

In some embodiments, an antibody or antigen-binding fragment of the disclosure comprises: a) a humanized $V_H$ domain that comprises the amino acid sequence of SEQ ID NO: 10, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 10, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 10, and b) a humanized $V_L$ domain that comprises the amino acid sequence of SEQ ID NO: 40. In some embodiments, an antibody or antigen-binding fragment of the disclosure comprises: a) a humanized $V_H$ domain that comprises the amino acid sequence of SEQ ID NO: 38, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 38, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 38, and b) a humanized $V_L$ domain that comprises the amino acid sequence of SEQ ID NO: 40. In some embodiments, an antibody or antigen-binding fragment of the disclosure comprises: a) a humanized $V_H$ domain that comprises the amino acid sequence of SEQ ID NO: 39, and b) a $V_L$ domain that comprises the amino acid sequence of SEQ ID NO: 7. In some embodiments, an antibody or antigen-binding fragment of the disclosure comprises: a) a humanized $V_H$ domain that comprises the amino acid sequence of SEQ ID NO: 39, and b) a humanized $V_L$ domain that comprises the amino acid sequence of SEQ ID NO: 8. In some embodiments, an antibody or antigen-binding fragment of the disclosure comprises: a) a humanized $V_H$ domain that comprises the amino acid sequence of SEQ ID NO: 39, and b) a humanized $V_L$ domain that comprises the amino acid sequence of SEQ ID NO: 40. In some embodiments, an antibody or antigen-binding fragment of the disclosure comprises: a) a $V_H$ domain that comprises the amino acid sequence of SEQ ID NO: 9, and b) a humanized $V_L$ domain that comprises the amino acid sequence of SEQ ID NO: 8. In some embodiments, an antibody or antigen-binding fragment of the disclosure comprises: a) a $V_H$ domain that comprises the amino acid sequence of SEQ ID NO: 9, and b) a humanized $V_L$ domain that comprises the amino acid sequence of SEQ ID NO: 40.

In some embodiments, an antibody or antigen-binding fragment of the disclosure includes a signal sequence. In some embodiments, the signal sequence is conjugated to the N-terminal portion of any of the $V_L$ sequences disclosed herein (e.g., SEQ ID NO: 8). In some embodiments, the signal sequence conjugated to the light chain is SEQ ID NO: 61. In some embodiments, the signal sequence is conjugated to the N-terminal portion of any of the $V_H$ sequences disclosed herein (e.g., SEQ ID NO: 10). In some embodiments, the signal sequence conjugated to the heavy chain is SEQ ID NO: 62. It is understood that, when a signal sequence is included for expression of an antibody or antibody fragment, that signal sequence is generally cleaved and not present in the finished polypeptide (e.g., the signal sequence is generally cleaved and present only transiently during protein production).

In some embodiments, the $V_H$ domain of any of the antibodies or antigen-binding fragments of the disclosure described herein comprise one or more of the following amino acid alterations: V5Q, E6Q, L11V, V12I, K13Q, R18L, K19R, V37I, E42G, A49S, T63S, A75S, F80Y, T84N, S88A, M93V, T111L or L112V, as compared with an numbered with reference to the amino acid sequence of SEQ ID NO: 9. In other words, in certain embodiments, an antibody or antigen-binding fragment comprises one or more amino acid alteration at a position corresponding to the foregoing, where the corresponding position is compared with SEQ ID NO: 9. In certain embodiments, the $V_H$ domain comprises one or more of the following amino acid alterations: V5Q, L11V, K13Q, R18L, K19R, V37I, E42G, A49S, T63S, A75S, F80Y, T84N, M93V, T111L or L112V, as compared with and numbered with reference to the amino acid sequence of SEQ ID NO: 9. In certain embodiments, the $V_H$ domain comprises at least 5, at least 6, at least 7, at least 8, at least 9, at least 10, at least 11, at least 12, at least 13, at least 14, at least 15, at least 16, or at least 17 of said alterations, as compared with and numbered with reference to the amino acid sequence of SEQ ID NO: 9. In certain embodiments, at least one of the alterations in the $V_H$ domain is a V5Q alteration, as compared with and numbered with reference to the amino acid sequence of SEQ ID NO: 9. In certain embodiments, at least one of the alterations in the $V_H$ domain is a E6Q alteration, as compared with and numbered with reference to the amino acid sequence of SEQ ID NO: 9. In certain embodiments, at least one of the alterations in the $V_H$ domain is a L11V alteration, as compared with and numbered with reference to the amino acid sequence of SEQ ID NO: 9. In certain embodiments, at least one of the alterations in the $V_H$ domain is a V37I alteration, as compared with and numbered with reference to the amino acid sequence of SEQ ID NO: 9. In certain embodiments, the $V_H$ domain retains a serine at the amino acid position corresponding to amino acid position 88 of SEQ ID NO: 9. In certain embodiments, the $V_H$ domain retains a valine at the amino acid position corresponding to amino acid position 12 of SEQ ID NO: 9. In certain embodiments, the $V_H$ domain retains a tryptophan at the amino acid position corresponding to amino acid position 47 of SEQ ID NO: 9. All operable combinations of the foregoing are contemplated, as are combinations with any of the aspect and embodiments provided herein for the VL. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In certain embodiments of any of the foregoing, or of any of the aspects and embodiments disclosed herein, the $V_L$ domain of any of the humanized antibodies or antigen-binding fragments described herein comprise one or more of the following amino acid alterations: V3Q, L4M, A9S, A12S, V13A, L15V, Q17D, A19V, S22T, M37L, H38A, G45E, Q46K, P47A, E59Q, A64S, H76T, N78T, H80S, P81S, V82L, E83Q, E84P, A87V, A87F, or G104A, as compared with and numbered with reference to the amino acid sequence of SEQ ID NO: 7. In certain embodiments, the $V_L$ domain comprises one or more of the following amino acid alterations: V3Q, L4M, A9S, A12S, V13A, L15V, Q17D, A19V, G45E, Q46K, P47A, E59Q, A64S, H76T, N78T, H80S, P81S, V82L, E83Q, E84P, A87V, or G104A, as compared with and numbered with reference to the amino acid sequence of SEQ ID NO: 7. In certain embodiments, the $V_L$ domain comprises at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 of said amino acid alterations, as compared with and numbered with reference to the amino acid sequence of SEQ ID NO: 7.

It should be understood that any of the foregoing variations at particular positions are referred to relative to the amino acid sequence set forth in SEQ ID No: 7 or 9. An antibody or antigen binding fragment of the disclosure may comprise one or more of such amino acid alterations at the corresponding position, relative to the amino acid sequence of SEQ ID NO: 7 or 9. By way of example, in certain embodiments, the VH domain comprises an L to V alteration at a position corresponding to position 11 of SEQ ID NO: 9 (e.g., an L11V alteration). This is exemplary of how all of the foregoing alterations can also be described, and such description is expressly contemplated. By way of another example, in certain embodiments, the VL domain comprises a V to Q alteration at a position corresponding to position 3 of SEQ ID NO: 7 (e.g., a V3Q alteration).

In certain embodiments, the $V_L$ domain comprises a serine at each of the amino acid positions corresponding to amino acid positions 80 and 81 of SEQ ID NO: 7. In certain embodiments, the $V_L$ domain retains a lysine at the amino acid position corresponding to amino acid position 53 of SEQ ID NO: 7. In certain embodiments, the $V_L$ domain does not have any one or more of the following amino acid combinations:

a) asparagine and serine at the amino acid positions corresponding to amino acid positions 80 and 81 of SEQ ID NO: 7, respectively; or b) asparagine and glycine at the amino acid positions corresponding to amino acid positions 80 and 81 of SEQ ID NO: 7, respectively; or c) asparagine and proline at the amino acid positions corresponding to amino acid positions 80 and 81 of SEQ ID NO: 7, respectively. All operable combinations of the foregoing are contemplated, as are combinations with any of the aspect and embodiments provided herein for the VH. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In some embodiments, the humanized internalizing moiety (e.g., a humanized antibody or antigen-binding fragment comprising a light chain variable ($V_L$) domain comprising the amino acid sequence set forth in SEQ ID NO: 8 and a heavy chain variable ($V_H$) domain comprising the amino acid sequence set forth in SEQ ID NO: 10) is associated with at least one superior physiological or biological property as compared to a reference non-humanized internalizing moiety (e.g., the murine, parent 3E10 antibody). In other embodiments, the humanized internalizing moiety is associated with at least two superior physiological or biological properties as compared to a reference non-humanized internalizing moiety. In other embodiments, the humanized internalizing moiety is associated with at least three superior physiological or biological properties as compared to a reference non-humanized internalizing moiety (e.g., the murine, parent 3E10 antibody). In some embodiments, the reference non-humanized internalizing moiety comprises the murine parent antibody comprising a VH comprising the amino acid sequence of SEQ ID NO: 9 and a VL comprising the amino acid sequence of SEQ ID NO: 7. In some embodiments, the reference humanized internalizing moiety is an antibody comprising the amino acid sequence of SEQ ID NO: 43. In some embodiments, the reference internalizing moiety is a humanized antibody or antigen binding fragment comprising the $V_H$ amino acid sequence of SEQ ID NO: 42 and the $V_L$ amino acid sequence of SEQ ID NO: 41.

In certain embodiments, the antibodies or antigen-binding fragments described herein are humanized and are associated with at least one superior biological or physiological property as compared to a murine antibody, which murine antibody comprises a $V_L$ domain comprising the amino acid sequence set forth in SEQ ID NO: 7 and a $V_H$ domain comprising the amino acid sequence set forth in SEQ ID NO: 9, and/or as compared to an alternative antibody or antigen-binding fragment thereof, wherein said alternative antibody or antigen-binding fragment comprises a $V_L$ domain comprising the CDRs of the amino acid sequence set forth in SEQ ID NO: 7 and a $V_H$ domain comprising the CDRs of the amino acid sequence set forth in SEQ ID NO:

9; and wherein said alternative antibody or fragment does not comprise a V$_L$ domain comprising the amino acid sequence of SEQ ID NO: 8 or 40, and/or wherein said alternative antibody or fragment does not comprise a V$_H$ domain comprising the amino acid sequence of any of SEQ ID NOs: 10, 38 or 39; or, in some embodiments, wherein said alternative antibody or fragment does not comprise a V$_L$ domain comprising the amino acid sequence of SEQ ID NO: 8, and/or wherein said alternative antibody or fragment does not comprise a V$_H$ domain comprising the amino acid sequence of any of SEQ ID NOs: 10.

In some embodiments, a humanized internalizing moiety of the disclosure (e.g., a humanized antibody or antigen-binding fragment thereof comprises a light chain variable (V$_L$) domain comprising the amino acid sequence set forth in SEQ ID NO: 8 and a heavy chain variable (V$_H$) domain comprising the amino acid sequence set forth in SEQ ID NO: 10) is associated with at least one superior physiological or biological property as compared to an alternative internalizing moiety or fragment thereof (e.g., a different humanized antibody based on the same parent, murine antibody and, optionally, having the same CDRs). In other embodiments, a humanized internalizing moiety of the disclosure is associated with at least two superior physiological or biological properties as compared to the alternative internalizing moiety (e.g., a different humanized antibody based on the same parent, murine antibody and, optionally, having the same CDRs). In other embodiments, the humanized internalizing moiety of the disclosure is associated with at least three superior physiological or biological properties as compared to the alternative internalizing moiety (e.g., a different humanized antibody based on the same parent, murine antibody and, optionally, having the same CDRs). In some embodiments, the alternative antibody is the parent antibody from which the humanized antibody was derived (e.g., the parent, murine antibody). In some embodiments, the alternative antibody is another humanized antibody that is derived from the 3E10 antibody but that has a different amino acid sequence than the humanized internalizing moieties or antigen-binding fragments thereof of the present disclosure. In some embodiments, an antibody or antigen binding fragment of the disclosure has one or more improved characteristics in comparison to the murine parent antibody and/or an alternative humanized antibody. In some embodiments, the alternative humanized antibody has one, two, or three amino acid substitutions in the Kabat CDRs, as compared to an antibody of the disclosure. In some embodiments, the alternative internalizing moiety or fragment thereof comprises:

a VH CDR1 having the amino acid sequence of SEQ ID NO: 32;
a VH CDR2 having the amino acid sequence of SEQ ID NO:33;
a VH CDR3 having the amino acid sequence of SEQ ID NO: 34;
a VL CDR1 having the amino acid sequence of SEQ ID NO: 35;
a VL CDR2 having the amino acid sequence of SEQ ID NO: 36; and
a VL CDR3 having the amino acid sequence of SEQ ID NO: 37, which CDRs are defined in accordance with Kabat, but does not comprise the same scaffold amino acid sequence present in the humanized internalizing moieties or fragments thereof of the present disclosure (e.g. a humanized internalizing moiety or fragment thereof comprising the amino acid sequence of any of SEQ ID NOs: 8, 10, or 38-40).

In some embodiments, the superior biological or physiological property associated with the humanized internalizing moieties or fragments of the disclosure described herein is that the humanized internalizing moiety or antigen-binding fragment is associated with reduced immunogenicity in a human patient as compared to the immunogenicity of the non-humanized or to the alternative antibody or antigen-binding fragment in a human patient. The skilled worker is familiar with numerous assays for determining the immunogenicity of the antibodies. In preferred embodiments, the humanized antibodies of the disclosure are associated with reduced immunogenicity in a human patient, but retain the cell penetration properties associated with the murine 3E10 antibody.

In some embodiments, the superior biological or physiological property associated with the humanized internalizing moieties or fragments of the disclosure described herein is that the humanized internalizing moiety or antigen-binding fragment is associated with increased solubility in a physiologically acceptable carrier as compared to the solubility of the non-humanized or to the alternative antibody or antigen-binding fragment in the same type of physiologically acceptable carrier. As used herein, a physiologically acceptable carrier includes include water, ethanol, polyols (such as glycerol, propylene glycol, polyethylene glycol, and the like), and suitable mixtures thereof, vegetable oils, such as olive oil, and injectable organic esters, such as ethyl oleate. In some embodiments, the humanized internalizing moiety or fragment is associated with at least 5%, 10%, 25%, 50%, 75%, 100%, 150%, 200% or 300% greater solubility in a physiologically acceptable carrier as compared to a non-humanized or alternative internalizing moiety or antigen-binding fragment in the same type of physiologically acceptable carrier. The skilled worker is aware of routine experiments that may be utilized for testing the solubility of the humanized internalizing moieties or fragments thereof. Examples of solubility assays include standard turbidity or light-scattering assays, commercial solubility assays, such as the OptiSol™ solubility assay kit (DiLyx, Seattle, Wash.), or the protein solubility assay screen described in Bondos et al., 2003, Analytical Biochemistry, 316:223-231 may be utilized.

In some embodiments, the superior biological or physiological property associated with the humanized internalizing moieties or fragments of the disclosure described herein is that the humanized internalizing moiety or antigen-binding fragment is associated with a higher expression level in a type of cell as compared to the expression level of the non-humanized or alternative antibody or antigen-binding fragment in the same type of cell. In some embodiments, the humanized internalizing moiety or fragment is associated with at least 5%, 10%, 25%, 50%, 75%, 100%, 150%, 200% or 300% higher expression level in a cell as compared to the expression level of a non-humanized or alternative internalizing moiety or antigen-binding fragment in the same type of cell. The skilled worker is aware of routine experiments that may be utilized for testing the expression level of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with lower toxicity (e.g., cytotoxicity and/or genotoxicity) in a cell type as compared to the toxicity in the same type of cell that is associated with the non-humanized or alternative antibody or antigen-binding fragment. In some embodiments, the humanized internalizing moiety or fragment is associated with at least 5%, 10%, 25%, 50%, 75%, 100%, 150%, 200% or 300% lower toxicity as compared to the toxicity of a non-humanized or alternative internalizing moiety or antigen-binding fragment in the same type of cell. In some embodiments the cell is a mammalian cell. In some embodiments the cell is a human cell. In some embodiments, the cell is in an organism, such as a mammal. In some embodiments, the cell is a human cell in a human organism. The skilled worker is aware of routine experiments that may be utilized for testing the toxicity of the humanized internalizing moieties or fragments thereof. For example, the toxicity of the humanized internalizing moieties or fragments of the disclosure and of the non-humanized or alternative internalizing moieties or fragments thereof may be tested in an in vitro cell or cell culture, such as in a cell or cell culture derived from human cells, or may be tested in an in vitro animal model such as a mouse or rat.

In some embodiments, the superior biological or physiological property associated with the humanized internalizing moieties or fragments of the disclosure described herein is that the humanized internalizing moiety or antigen-binding fragment is associated with reduced aggregation in a physiologically acceptable carrier as compared to aggregation of the non-humanized or alternative antibody or anti-gen-binding fragment in the same type of physiologically acceptable carrier. In some embodiments, the humanized internalizing moiety or fragment is associated with at least 5%, 10%, 25%, 50%, 75%, 100%, 150%, 200% or 300% less aggregation in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with reduced aggregation after a period of at least 1 hour, 6 hours, 12 hours, 18 hours, 24 hours, 36 hours, 2 days, 5 days, one week, two weeks, four weeks, one month, two months, three months, six months or one year. The skilled worker is aware of routine experiments that may be utilized for testing the aggregation of the humanized internalizing moieties or fragments thereof. Examples of aggregation assays include standard turbidity or light-scattering assays (e.g., A600 nm assay), visual inspection, SDS-PAGE, commercial aggregation assays, such as the OptiSol™ aggregation assay kit (DiLyx, Seattle, Wash.), HP-SEC analysis, or the protein aggregation assay screen described in Bondos et al., 2003, Analytical Biochemistry, 316:223-231 may be utilized.

In some embodiments, the superior biological or physiological property associated with the humanized internalizing moieties or antigen-binding fragments of the disclosure described herein is that the humanized internalizing moiety or antigen-binding fragment is associated with increased stability in a physiologically acceptable carrier as compared to the stability of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% greater stability in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with increased stability after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the stability of the humanized internalizing moieties or fragments thereof. For example, the skilled worker could test the stability of the humanized and non-humanized or alternative internalizing moieties or fragments thereof after various intervals of being stored in a physiologically acceptable carrier. Commercial assays such as the ProteoStat™ Thermal shift stability assay (Enzo, Farmingdale, N.Y.) may be utilized in assessing the stability of the moieties or fragments thereof. Alternatively, the stability of the moieties or fragments thereof may be determined by HP-SEC or by SDS-PAGE analysis.

In some embodiments, the superior biological or physiological property associated with the humanized internalizing moieties or antigen-binding fragments of the disclosure described herein is that the humanized internalizing moiety or antigen-binding fragment is associated with improved cell penetration as compared to the cell penetration of the non-humanized or alternative antibody or antigen-binding fragment. In some embodiments, the improved penetration is due to the increased efficiency of the humanized internalizing moiety or antigen-binding fragment to be internalized by an ENT transporter (e.g., an ENT2 and/or ENT3 transporter). In some embodiments, the humanized internalizing moiety or fragment is associated with at least 5%, 10%, 25%, 50%, 75%, 100%, 150%, 200% or 300% greater cell penetration as compared to a non-humanized or alternative internalizing moiety or antigen-binding fragment in the same type of physiologically acceptable carrier. The skilled worker is aware of routine experiments that may be utilized for testing the cell penetration of the humanized internalizing moieties or fragments thereof. For example, the humanized internalizing moieties or fragments thereof may be labeled (e.g. fluorescently or radiolabeled) and administered to a cell or cell culture in order to determine the cell penetration of the humanized internalizing moieties or fragments thereof. Alternatively, the humanized internalizing moieties or fragments may be administered to a cell or cell culture and then detected with a secondary agent, e.g., a fluorescently labeled or radiolabeled secondary antibody, in order to determine the cell penetration of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with reduced glycosylation in a cell type as compared to the glycosylation of the non-humanized or alternative antibody or antigen-binding fragment in the same cell type. In some embodiments, an asparagine is mutated to another amino acid residue in the VH or VL domains in order to reduce N-linked glycosylation of the humanized antibody or antibody fragment. In other embodiments, the superior biological or physiological property associated with the humanized internalizing moieties or fragments described herein is that the humanized internalizing moiety or antigen-binding fragment is associated with increased glycosylation in a cell type as compared to the glycosylation of the non-humanized or alternative antibody or antigen-binding fragment in the same cell type. In some embodiments, the superior biological or physiological property associated with the humanized internalizing moieties or fragments described herein is that the humanized internalizing moiety or antigen-binding fragment is associated with a specific pattern of glycosylation in a cell type that differs from the glycosylation pattern of the non-humanized or alternative internalizing moiety or antigen-binding fragment in the same type of cell. For example, the humanized internalizing moiety or antigen-binding fragment may be hemi-glycosylated in a cell type while the non-humanized or alternative internalizing moiety or antigen-binding fragment is not hemi-glycosylated in the same type of cell. In some embodiments, the superior biological or physiological property associated with the humanized internalizing moieties or fragments described herein is that the humanized internalizing moiety or antigen-binding fragment is post-translationally modified with a specific glycosylation group in a cell type that differs from the post-translational modification of the non-humanized or alternative internalizing moiety or antigen-binding fragment in the same type of cell. The skilled worker is aware of routine experiments that may be utilized for testing the glycosylation patterns of the humanized internalizing moieties or fragments thereof. Examples of experiments for testing the glycosylation levels and patterns of the internalizing moieties and fragments thereof include protocols described in Mohammad, 2002, Protein Protocols Handbook, pages 795-802; standard procedures involving mass spectrometry and/or HPLC; GLYCO-PRO™ (Sigma-Aldrich); and Qproteome Total Glycoprotein Kit™ (Qiagen, Valencia, Calif.). In order to identify the exact sites of glycosylation in a protein sequence, standard endoproteinase cleavage may be performed (e.g. tryptic digest) followed by analysis by LC/MS or HILIC-MS/MS, similar to the protocols described in Zauner G et al., 2010, J Sep Sci., 33:903-10.

In some embodiments, the superior biological or physiological property associated with the humanized internalizing moieties or fragments of the disclosure described herein is that the humanized internalizing moiety or antigen-binding fragment is associated with reduced deamidation in a physiologically acceptable carrier as compared to deamidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less deamidation in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with reduced deamidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the deamidation of the humanized internalizing moieties or fragments thereof. Examples of assays for testing protein deamidation include commercially available deamidation assays such as the ISOQUANT® Isoaspartate Detection Kit (Promega, Madison Wis.) or Dionex UltiMate 3000 Titanium System (Dionex, Sunnyvale, Calif.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced oxidation in a physiologically acceptable carrier as compared to oxidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less oxidation in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with reduced oxidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the oxidation of the humanized internalizing moieties or fragments thereof. For example, oxidation levels may be assessed by using any one of several commercially available oxidation assays, such as the Methionine Sulfoxide Immunoblotting Kit (Cayman Chemical, Ann Arbor, Mich.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced lipidation when produced in a cell type as compared to the lipidation of the non-humanized or alternative antibody or fragment when produced in the same type of cell. In other embodiments, the superior biological or physiological property associated with the humanized internalizing moieties or fragments described herein is that the humanized internalizing moiety or antigen-binding fragment is associated with increased lipidation when produced in a cell type as compared to the lipidation of the non-humanized or alternative antibody or antigen-binding fragment when produced in the same type of cell. In some embodiments, the superior biological or physiological property associated with the humanized internalizing moieties or fragments described herein is that the humanized internalizing moiety or antigen-binding fragment is associated with a specific pattern of lipidation when produced in a cell type that differs from the lipidation pattern of the non-humanized or alternative internalizing moiety or antigen-binding fragment when produced in the same type of cell. In some embodiments, the superior biological or physiological property associated with the humanized internalizing moieties or fragments described herein is that the humanized internalizing moiety or antigen-binding fragment is post-translationally modified with a specific lipidation group when produced in a cell type that differs from the post-translational modification of the non-humanized or alternative internalizing moiety or antigen-binding fragment when produced in the same type of cell. The skilled worker is aware of routine experiments that may be utilized for testing the lipidation patterns of the humanized internalizing moieties or fragments thereof. For example, the internalizing moieties or fragments thereof may be assessed by the protocols described in Gelb et al., 1999, Protein Lipidation Protocols, Humana Press, pages 1-256.

In some embodiments, the superior biological or physiological property associated with the humanized internalizing moieties or fragments of the disclosure described herein is that the humanized internalizing moiety or antigen-binding fragment is capable of binding a polynucleotide (e.g., DNA) with higher affinity (lower $K_D$) as compared to the binding affinity of the non-humanized, parent antibody or an alternative antibody or fragment, such as a different humanized antibody. In some embodiments, the humanized internalizing moiety or fragment is associated with at least 5%, 10%, 25%, 50%, 75%, 100%, 150%, 200% or 300% stronger binding affinity for a polynucleotide (e.g., DNA; double stranded blunt DNA) as compared to a non-humanized or alternative internalizing moiety or antigen-binding fragment in the same type of physiologically acceptable carrier. The skilled worker is aware of routine experiments that may be utilized for testing the binding affinity ($K_D$) of the humanized internalizing moieties or fragments thereof. Binding affinity can be measured using Surface Plasmon Resonance (SPR) or Quartz Crystal Microbalance (QCM), in accordance with currently standard methods and the manufacturer's protocols.

III. Heterologous Agents

In some embodiments, an antibody or antigen-binding fragment, as described herein (e.g., a humanized antibody or antigen-binding fragment thereof of the present disclosure) may be conjugated to a heterologous agent. Accordingly, the disclosure provides conjugates comprising an antibody or antigen-binding fragment of the disclosure associated with a heterologous agent. By heterologous, it is meant that the agent is not itself a portion of the antibody or antigen binding fragment and/or is not a natural, endogenous target of the antibody or antigen binding fragment. In certain embodiments, the heterologous agent is conjugated to the antibody or antigen binding fragment (e.g., the two portions are joined by a covalent bond, such as via co-translational fusion or chemical conjugation).

In some embodiments, the heterologous agent is a polypeptide or peptide. In other embodiments, the heterologous agent is a polynucleotide (e.g., comprises a nucleic acid, such as DNA or RNA, including antisense DNA or RNA). In other embodiments, the heterologous agent is a small organic molecule. In certain embodiments, the polypeptide, peptide, or polynucleotide is a therapeutic agent. In certain embodiments, the small organic molecule is a therapeutic agent. In other embodiments, the heterologous agent is a toxin. In other embodiments, the heterologous agent is a radionucleide or other detectable label. Exemplary radionucleides and detectable labels facilitate visualization or localization of a conjugate in vivo or in vitro, and thus, facilitate diagnostic use as well as in vitro studies using conjugates of the disclosure.

In some embodiments, the heterologous agent is a polynucleotide. In some embodiments, the polynucleotide is administered to a cell as a form of gene therapy. In some embodiments, the polynucleotide increases the expression of a gene already expressed in the cell. In some embodiments, the polynucleotide is a wildtype copy of a gene, and the cell expresses a mutant copy of the gene. In some embodiments, the polynucleotide is a mutant copy of a gene. In some embodiments, the polynucleotide is a mutant copy of a gene, and the cell expresses a wildtype copy of the gene. In some embodiments, the polynucleotide is a mutant copy of a gene, and the cell expresses a mutant copy of the gene. In some embodiments, the polynucleotide is an antisense molecule.

In some embodiments, the polynucleotide is an RNAi molecule. In particular embodiments, the polynucleotide is an siRNA molecule. In some embodiments, the polynucleotide is one or both of trRNA and/or crRNA for use in CRISPR technology. In some embodiments, the polynucleotide is a synthetic single guide RNA (sgRNA). See, e.g., Jinek, M., et al. (2012) Science, 337, 816-821. In some embodiments, the trRNA, crRNA and/or sgRNA are administered in combination with a Cas9 protein or a polynucleotide encoding a Cas9 protein. In some embodiments, the Cas9 protein or polynucleotide encoding the Cas9 protein is administered to a cell by means of any of the internalizing moieties described herein. In some embodiments, the Cas9 protein has a D10A and/or an H840A mutation. In some embodiments, the polynucleotide encodes for a Cas9 protein having a D10A and/or an H840A mutation. See, e.g., Cong L., et al. (2013) Science, 339, 819-823; Jinek, M., et al. (2012) Science, 337, 816-821; Gasiunas, G., et al. (2012) Proc. Natl. Acad. Sci. USA, 109, E2579-2586; and Mali, P., et al. (2013) Science, 339, 823-826; each of which is incorporated by reference herein in its entirety. In some embodiments, any of the internalizing moieties described herein is conjugated to a Cas9 protein having both a D10A and H840A mutation, and in some embodiments, this mutant Cas9 protein may be used to target protein domains for transcriptional regulation (Perez-Pinera, P., et al. (2013) Nat. Methods, 10, 239-242, Mali, P., et al. (2013) Nat. Biotechnol. 31, 833-838; Cheng, A. W., et al. (2013) Cell Res. 23, 1163-1171), epigenetic modification (Hu, J., et al. (2014) Nucleic Acids Res. doi:10.1093/nar/gku109), and microscopic visualization of specific genome loci (Chen, B., et al. (2013) Cell, 155, 1479-1491).

In some embodiments, conjugation between the antibody or antigen-binding fragment (e.g., a humanized antibody or antigen-binding fragment thereof of the disclosure) and the heterologous agent is accomplished by generating a fusion protein containing a heterologous agent polypeptide and an internalizing moiety, expressed as one contiguous polypeptide chain. It is recognized that, in the case of conjugation of a full length antibody or Fab, the final product comprises more than one polypeptide chain, but the heterologous agent may be covalently associated (e.g., produced as an inframe, co-translational fusion) to one of the chains, such as the heavy chain. In either case, such polypeptides are referred to herein as being recombinantly conjugated or as comprising a fusion protein. This is one example of conjugation (e.g., interconnection; association) between an antibody or antigen-binding fragment and a heterologous agent. In preparing such fusion proteins, a fusion gene is constructed comprising nucleic acids which encode a heterologous agent polypeptide and an internalizing moiety, and optionally, a peptide linker sequence to span the heterologous agent polypeptide and the internalizing moiety. The disclosure contemplates that suitable complexes, such as fusion proteins, may be in either orientation. In other words, the humanized antibody or antigen-binding fragment thereof portion may be N-terminal or C-terminal to the heterologous agent. When the final product comprises one that one polypeptide chain that, for example, an antibody where the heavy and light chains associate following expression in host cells, the disclosure contemplates that the heavy and light chains (optionally with heterologous agent expressed as a fusion protein with, for example the heavy chain) may be expressed from a single vector or from a set of vectors expressed in the same host cell.

In certain specific embodiments, conjugates for use in the methods of the present disclosure can be produced by using a universal carrier system. For example, a heterologous agent polypeptide can be conjugated to a common carrier such as protein A, poly-L-lysine, hex-histidine, and the like. The conjugated carrier will then form a complex with an antibody which acts as an internalizing moiety, e.g., the humanized antibody or antigen-binding fragment thereof of the present disclosure. A small portion of the carrier molecule that is responsible for binding immunoglobulin could be used as the carrier.

In some embodiments, a humanized antibody or antigen-binding fragment of the disclosure is chemically conjugated to the heterologous agent. In certain embodiments, the humanized antibody or antigen-binding fragment thereof is chemically conjugated using well-known cross-linking reagents and protocols. For example, there are a large number of chemical cross-linking agents that are known to those skilled in the art and useful for cross-linking the heterologous agent with the humanized antibody or antigen-binding fragment thereof. For example, the cross-linking agents may be heterobifunctional cross-linkers, which can be used to link molecules in a stepwise manner. Examples of representative cross-linking agents, including representative heterobifunctional cross-linkers, are provided herein.

The foregoing is exemplary. Numerous methods exist to conjugate or otherwise join an antibody or antigen binding fragment of the disclosure to a heterologous agent, regardless of whether that heterologous agent is a protein, peptide, polynucleotide, or small molecule (e.g., a chemotherapeutic agent small molecule). One of skill in the art can select the appropriate scheme to associate an antibody or antigen binding fragment of the disclosure with a heterologous agent, including doing so directly or via a linker (e.g., a polypeptide or other linker).

As described above, the disclosure contemplates that a heterologous agent suitable for conjugation to an antibody or antigen binding fragment of the disclosure may be a polypeptide, peptide, small molecule (e.g., small organic or inorganic molecules) (e.g., a chemotherapeutic agent small molecule), or polynucleotide (e.g., nucleic acid, such as DNA or RNA). Moreover, the following categories of heterologous agents are contemplated. Examples of each are provided. Exemplary heterologous agents are briefly described below. These are merely exemplary of categories of heterologous agents and specific agents that may be delivered into cells using the instant technology. However, conjugates comprising and methods of delivering peptides, polypeptides (including enzymes), polynucleotides, and small molecules are contemplated and provided.

A. Nucleotide Repeat Disorders or Exon Splicing Disorders

One category of heterologous agents is agents suitable for treating or studying a nucleotide repeat disorder or an exon splicing disorder. Suitable heterologous agents include polypeptides, peptides, polynucleotides, and small molecules. There are numerous examples in the art of nucleotide repeat disorders and exon splicing disorders, such as myotonic dystrophy, Huntington's disease, and neurofibromatosis. For many nucleotide repeat disorders and exon splicing disorders, one or more proteins involved in disease pathology are known and represent heterologous agents that may be conjugated to an antibody or antigen binding fragment of the disclosure for delivery in vitro or in vivo—either to study disease in cells or animals or for therapeutic purposes. In certain embodiments, conjugates are suitable to identify targets that the heterologous agent can bind to in an in vitro or in vivo system. A few specific examples of heterologous agents suitable for treating or studying a nucleotide repeat disorder or an exon splicing disorder are provided below. These are merely exemplary of heterologous agents and of this category of heterologous agents.

In some embodiments, the heterologous agent is an MBNL polypeptide, or a fragment, mutant or variant thereof. Accordingly the disclosure provides conjugates comprising (i) an antibody or antigen binding fragment of the disclosure and (ii) an MBNL polypeptide (e.g., an antibody of the disclosure conjugated or otherwise associated with a MBNL polypeptide). A detailed description of the MBNL polypeptides, and fragments, mutants and variants thereof, that may be used as heterologous agents may be found in PCT application, WO 2010/044894, which is incorporated herein by reference in its entirety. In some embodiments, the MBNL polypeptides are conjugated to an antibody or antigen-binding fragment of the disclosure as a fusion protein, in a universal carrier system or by means of chemical conjugation.

As used herein, the term "MBNL polypeptides" or "MBNL proteins" include various splicing isoforms, fragments, variants, fusion proteins, and modified forms of the wildtype MBNL polypeptide (e.g., MBNL1, MBNL2, or MBNL3), unless explicitly stated otherwise. Such isoforms, fragments, variants, fusion proteins, and modified forms of the MBNL polypeptides have at least a portion of the amino acid sequence of substantial sequence identity to the native MBNL protein, and retain at least two zinc finger motifs. In certain embodiments, a fragment, variant, or fusion protein of an MBNL polypeptide comprises an amino acid sequence that is at least 80%, 85%, 90%, 91%, 92%, 93%, 94%, 95%, 96%, 97%, 98%, 99% or 100% identical to any of MBNL1 polypeptides (e.g., SEQ ID NOs: 12-18), MBNL2 polypeptides (e.g., SEQ ID NOs: 55-56), or MBNL3 polypeptides, (e.g., SEQ ID NOs: 57-58), or fragments thereof (e.g., SEQ ID NO: 59). In certain embodiments of any of the foregoing, the MBNL polypeptide or fragment thereof lacks an N-terminal methionine.

In certain embodiments, an MBNL polypeptide, such as a fragment of MBNL, comprises at least two zinc finger motifs but comprising less than four zinc finger motifs. In certain embodiments, the MBNL polypeptide has reduced activity of at least one native function of a full length MBNL polypeptide, and that reduced activity is evaluated by comparison (in the same assay) to, for example, the full length MBNL polypeptide most closely related to the MBNL fragment. For example, if the MBNL polypeptide is a fragment of an MBNL1 polypeptide, the comparison can be made to a full length MBNL1 polypeptide, such as the full length MBNL polypeptide most closely related to the fragment.

Here and elsewhere in the specification, sequence identity refers to the percentage of residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. In certain embodiments, neither N- or C-terminal extensions nor insertions shall be construed as reducing identity or homology.

Methods and computer programs for the alignment of sequences and the calculation of percent identity are well known in the art and readily available. Sequence identity may be measured using sequence analysis software. For example, alignment and analysis tools available through the ExPasy bioinformatics resource portal, such as ClustalW algorithm, set to default parameters. Suitable sequence alignments and comparisons based on pairwise or global alignment can be readily selected. One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (www.ncbi.nlm.nih.gov/). In certain embodiments, the now current default settings for a particular program are used for aligning sequences and calculating percent identity.

The structure and various motifs of MBNL polypeptides are known in the art (see, e.g., Kino et al., 2004, Human Molecular Genetics, 13:495-507). In certain embodiments, the polypeptides described herein comprise a fragment of an MBNL polypeptide. In certain specific embodiments, a fragment of an MBNL polypeptide lacks a portion of the C-terminus. Optionally, a fragment of an MBNL polypeptide comprises all four zinc finger motifs. In other embodiments, a fragment of an MBNL polypeptide comprises less than four of the zinc finger motifs. In some embodiments, a fragment of an MBNL1 polypeptide comprises 1, 2 or 3 of the zinc finger motifs, and, optionally, does not comprise four zinc finger motifs. In particular embodiments, a fragment of an MBNL polypeptide comprises two of the zinc finger motifs. In some embodiments, a fragment of an MBNL polypeptide lacks at least a portion of the amino acid sequence between the second zinc finger motif and the third zinc finger motif. In particular embodiments, a fragment of an MBNL polypeptide lacks at least a portion of the amino acids corresponding to amino acids 73-178 of SEQ ID NO: 12. In certain embodiments, the fragment of an MBNL polypeptide comprises at least two zinc finger motifs but comprises less than all four zinc finger motifs. In certain embodiments, the fragment of the MBNL polypeptide has reduction in at least one functional activity when compared to and relative to the full length MBNL polypeptide and/or relative to an MBNL polypeptide comprising all four zinc finger motifs. Such comparison of functional activity would be made in the same assay. In certain embodiments, the fragment of MBNL functions, with respect to that functional activity, as a dominant negative.

In certain embodiments, a fragment of an MBNL polypeptide comprises a truncation of a naturally occurring MBNL polypeptide. In certain embodiments, a fragment of an MBNL polypeptide comprises any of the MBNL fragments described in Edge et al., 2013, BMC Molecular Biology, 14(29):1-16 and Grammatikakis, et al., 2011, Nucleic Acids Research, 39(7): 2769-2780 (e.g., a fragment of an MBNL polypeptide that comprises any of amino acid residues 41-382, 81-382, 121-382, 161-382, 201-382, 241-382, 1-342, 1-302, 1-262, 1-222, 1-182, 1-142, 1-102, 2-183, 2-116, 2-102, 2-91, 2-72, 73-183, 73-253, 116-253, or 184-253 of SEQ ID NO: 12), each of which is incorporated by reference herein. In certain embodiments, a fragment of an MBNL polypeptide comprises (or does not comprise) residues 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, or 1-240 of any of SEQ ID NOs: 12-18 or 55-58, or a variant thereof having at least 80%, 85%, 90%, 91%, 92%, 93%, 94%, 95%, 96%, 97%, 98%, 99% or 100% identity to any of the foregoing fragments. In certain embodiments, a fragment of an MBNL polypeptide comprises residues 1-116 of SEQ ID NO: 12 or 13. In certain embodiments, a fragment of an MBNL polypeptide comprises the amino acid sequence of SEQ ID NO: 59, or an amino acid sequence comprising one, two, three, or four amino acid substitutions in a corresponding position relative to the amino acid sequence set forth in SEQ ID NO: 59. In certain embodiments, a fragment of an MBNL polypeptide comprises residues 75-240, 80-240, 90-240, 100-240, 110-240, 120-240, 130-240, 140-240, or 150-240 of any of SEQ ID NOs: 12-18 or 55-58, or a variant thereof having at least 80%, 85%, 90%, 91%, 92%, 93%, 94%, 95%, 96%, 97%, 98%, 99% or 100% identity to any of the foregoing fragments. In some embodiments, any of the MBNL fragments described herein lack at least 1, 2, 3, 4, or 5 amino acid residues at the N- or C-terminal ends of any of the fragments described herein. For example, in some embodiments, the MBNL fragments comprise an amino acid sequence corresponding to residues 2-116, 3-116, 4-116, 5-116, 1-115, 1-114, 1-113, 1-112, 1-111, 2-115, 3-115, 2-114, or 3-114 of SEQ ID NO: 12 or 13, or a variant thereof having at least 80%, 85%, 90%, 91%, 92%, 93%, 94%, 95%, 96%, 97%, 98%, 99% or 100% identity to any of the foregoing fragments.

In certain embodiments, the MBNL polypeptide or fragment binds CUG repeats (e.g., is capable of binding CUG repeats; can bind CUG repeats; can bind CUG when CUG is presented as CUG repeats). In certain embodiments, an MBNL polypeptide or fragment thereof binds CUG repeats. In certain embodiments, a polypeptide of the disclosure comprising an MBNL polypeptide or fragment thereof regulates exon splicing and/or rescues aberrant splicing.

In some embodiments, a fragment of an MBNL polypeptide comprises all four zinc finger motifs. In some embodiments, the fragment of an MBNL polypeptide comprises residues 1-250, 1-260, 1-270, 1-280, 1-290, 1-300, 1-310, 1-320, 1-330, 1-340, 1-350, or 1-360 of any of SEQ ID NOs: 12-18 or 55-58. In particular embodiments, the fragment of an MBNL polypeptide comprises residues 1-252 or 1-253 of SEQ ID NO: 12 or 13. In particular embodiments, the fragment of an MBNL polypeptide comprises residues 1-253 of SEQ ID NO: 13. In some embodiments, any of the MBNL fragments described herein lack at least 1, 2, 3, 4, or 5 amino acids at the N- and/or C-terminal ends of any of the fragments described herein. In certain embodiments, similar functional fragments from other MBNL polypeptides (e.g., MBNL2 or 3) can be used. In certain embodiments, similar functional fragments from other MBNL polypeptides whose molecular weight is about 40 kD can be used. In some embodiments, the molecular weight of the MBNL peptide or fragment thereof may be determined using any of the methods routinely used in the art, e.g., SDS PAGE.

In certain embodiments, a fragment of an MBNL polypeptide comprises at least two zinc finger motifs but comprises less than all four zinc finger motifs. In certain embodiments, the fragment of the MBNL polypeptide has reduction in at least one functional activity when compared to and relative to the full length MBNL polypeptide and/or relative to an MBNL polypeptide comprising all four zinc finger motifs. Such comparison of functional activity would be made in the same assay. In certain embodiments, the fragment of MBNL functions, with respect to that functional activity, as a dominant negative. In certain embodiments, the functional activity is splicing activity, and the fragment of MBNL has reduction in the native splicing activity of full length MBNL polypeptide. The comparison is made, in certain embodiments, to a full length MBNL polypeptide most closely related to the fragment present in the conjugate (e.g., a native full length MBNL1polypeptide is used when the MBNL polypeptide is a fragment of an MBNL1 polypeptide).

In certain embodiments, the fragment of an MBNL polypeptide, such as any of the fragments set forth herein, comprises one, two, three, four, or five amino acid alterations (substitutions, deletions, additions) relative to the corresponding portion of the MBNL polypeptides set forth in any of SEQ ID NO: 12-18 or 55-58. In certain embodiments, the fragment of an MBNL polypeptide, such as any of the fragments set forth herein, comprises one, two, three, four, or five amino acid substitutions (independently conservative or non-conservative substitutions) relative to the corresponding portion of the MBNL polypeptides set forth in any of SEQ ID NO: 12-18 or 55-58. In certain embodiments, the fragment of an MBNL polypeptide, such as any of the fragments set forth herein, comprises one, two, three, four, or five amino acid substitutions (independently conservative or non-conservative substitutions), wherein at least one of the substitutions is a conservative substitution relative to the corresponding portion of the MBNL polypeptides set forth in any of SEQ ID NO: 12-18 or 55-58. In certain embodiments, the fragment of an MBNL polypeptide comprises one substitution, such as a conservative substitution relative to the corresponding portion of the MBNL polypeptides set forth in any of SEQ ID NO: 12-18 or 55-58.

In some embodiments, the MBNL polypeptide or fragment thereof has at least one of the same biological activities of a wildtype MBNL polypeptide (e.g., an MBNL polypeptide having any of the amino acid sequences of SEQ ID NOs: 12-18 or 55-58, such as an MBNL1 polypeptide, such as a full length MBNL polypeptide having the amino acid sequence of any of SEQ ID NO: 12-18, such as having the amino acid sequence of SEQ ID NO: 13). By the terms "biological activity", "bioactivity" or "functional" is meant the ability of the MBNL polypeptide or fragment thereof to carry out at least one of the functions associated with wildtype MBNL proteins, for example, the regulation of exon splicing in a cell, and/or the ability to bind a YGCY motif in a polynucleotide (e.g., DNA or RNA) sequence. In certain embodiments, the MBNL polypeptide or fragment binds CUG repeats (e.g., is capable of binding CUG repeats; can bind CUG repeats). In certain embodiments, an MBNL polypeptide or fragment thereof binds CUG repeats. The terms "biological activity", "bioactivity", and "functional" are used interchangeably herein.

By the terms "has the ability" or "is capable of" is meant the recited polypeptide will carry out the stated bioactivity under suitable conditions (e.g., physiological conditions or standard laboratory conditions). In certain embodiments, the term "can" may be used to describe this ability (e.g., "can bind" or "binds" to a given sequence). For example, if an MBNL polypeptide has the ability or is capable of binding a CUG motif, the MBNL polypeptide will bind to a CUG motif in the presence of a polynucleotide having a CUG motif and under normal physiological conditions. One of ordinary skill in the art would understand what conditions would be needed to test whether a polypeptide has the ability or is capable of carrying out a recited bioactivity.

In certain embodiments, and as described herein, an MBNL protein or fragment thereof having biological activity has the ability to bind a consensus binding site in a polynucleotide (e.g, DNA or RNA). In some embodiments, the consensus binding site in a polynucleotide is a CUG motif (Warf, 2007, RNA, 12: 2238-51) and/or a YGCY motif (e.g., a UGCU motif) in a polynucleotide (e.g., DNA or RNA) sequence. In other embodiments, an MBNL protein or fragment thereof having biological activity has the ability to bind a CAG motif (Ho, 2005, J. Cell Science, 118: 2923-2933). In other embodiments, an MBNL protein or fragment thereof having biological activity has the ability to bind one or more of CUG, CAG, CCUG, CCG, CGG and/or UGCUGU motifs. As used herein, "fragments" are understood to include bioactive fragments (also referred to as functional fragments) or bioactive variants that exhibit "bioactivity" as described herein. That is, bioactive fragments or variants of MBNL exhibit bioactivity that can be measured and tested. In some embodiments, bioactive fragments/functional fragments or variants exhibit the same or substantially the same bioactivity as native (i.e., wild-type, or normal) MBNL protein, and such bioactivity can be assessed by the ability of the fragment or variant to bind to a YGCY motif (e.g., a UGCU motif) in a polynucleotide (e.g., DNA or RNA) sequence (as evaluated in vitro or in vivo). As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the MBNL polypeptide retains at least 50%, 60%, 70%, 80%, 85%, 90%, 95% or 100% of at least one of the MBNL biological activities associated with the native MBNL polypeptide.

In certain embodiments, any of the fragments or variants of any of the MBNL polypeptides described herein may retain one biological activity of a full-length native (i.e., a wildtype or normal) MBNL polypeptide (e.g., an MBNL polypeptide having an amino acid sequence of any of SEQ ID NOs: 12-18 or 55-58), but lack or have reduced levels of another biological activity as compared to a wildtype or normal MBNL polypeptide (e.g., an MBNL polypeptide having an amino acid sequence of any of SEQ ID NOs: 12-18 or 55-58). In certain embodiments, the comparison is versus a full length MBNL1 polypeptide, such as a full length MBNL polypeptide having the amino acid sequence of any of SEQ ID NO: 12-18, such as having the amino acid sequence of SEQ ID NO: 13. In some embodiments, the MBNL polypeptides or fragments thereof described herein are capable of binding a polynucleotide such as DNA or RNA (e.g., by binding to a YGCY motif), but are less efficient (e.g., reduced activity) in regulating pre-mRNA splicing as compared to a full-length native (i.e., a wildtype or normal) MBNL polypeptide (e.g., an MBNL polypeptide having an amino acid sequence of any of SEQ ID NOs: 12-18 or 55-58). In certain embodiments, the comparison is versus a full length MBNL1 polypeptide, such as a full length MBNL polypeptide having the amino acid sequence of any of SEQ ID NO: 12-18, such as having the amino acid sequence of SEQ ID NO: 13. In some embodiments, the MBNL polypeptides or fragments thereof are 10%, 20%, 30%, 40%, 50%, 60%, 70%, 80%, 90% or 100% less efficient in regulating pre-mRNA splicing as compared to a wildtype or normal MBNL polypeptide. In some embodiments, the MBNL polypeptides or fragments thereof are incapable of regulating pre-mRNA splicing, as compared to a full length MBNL polypeptide. In some embodiments, any of the MBNL polypeptides described herein may act as a "dominant negative" MBNL polypeptide, e.g., the MBNL polypeptides are capable of competing with a wildtype or normal MBNL polypeptide (e.g., an MBNL polypeptide having an amino acid sequence of any of SEQ ID NOs: 12-18 or 55-58) for binding to an RNA binding site (e.g., a YGCY motif), but are incapable of, or less efficient at, regulating pre-mRNA splicing as compared to a wildtype or normal MBNL polypeptide. In certain embodiments, the comparison is versus a full length MBNL1 polypeptide, such as a full length MBNL polypeptide having the amino acid sequence of any of SEQ ID NO: 12-18, such as having the amino acid sequence of SEQ ID NO: 13.

In certain embodiments, fragments or variants of any of the MBNL polypeptides described herein have a half-life ($t_{1/2}$) which is enhanced relative to the half-life of the native protein. Preferably, the half-life of MBNL fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native MBNL protein. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native MBNL protein.

The described methods based on administering any of the polypeptides described herein or contacting cells with any of the polypeptides described herein can be performed in vitro (e.g., in cells or culture) or in vivo (e.g., in a patient or animal model). In certain embodiments, the method is an in vitro method. In certain embodiments, the method is an in vivo method.

In certain embodiments, fragments or variants of the MBNL polypeptides can be obtained by screening polypeptides recombinantly produced from the corresponding fragment of the nucleic acid encoding an MBNL polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that have the desired function. Decrease in a functional activity can be measured in a given assay in comparison to a full length, native MBNL polypeptide, such as the polypeptide set forth in any of SEQ ID NO: 12-18 or 55-58. In certain embodiments, if a fragment of an MBNL1 polypeptide is being evaluated, its function is evaluated versus a full length, native MBNL1 polypeptide (e.g., rather than versus an MBNL3 polypeptide). In certain embodiments, the comparison is versus a full length MBNL1 polypeptide, such as a full length MBNL polypeptide having the amino acid sequence of any of SEQ ID NO: 12-18, such as having the amino acid sequence of SEQ ID NO: 13.

In certain embodiments, the present disclosure contemplates modifying the structure of an MBNL polypeptide for such purposes as enhancing therapeutic or prophylactic efficacy, or stability (e.g., ex vivo shelf life and resistance to proteolytic degradation in vivo). Such modified MBNL polypeptides are considered functional equivalents of the naturally-occurring MBNL polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the MBNL biological activity of the resulting molecule. Conservative replacements are those that take place within a family of amino acids that are related in their side chains.

In certain embodiments, the MBNL polypeptide or fragment (e.g., any of the polypeptides or fragments described above) is a variant of a wildtype or normal MBNL polypeptide, or fragment thereof, wherein the MBNL polypeptide variant has at least one amino acid alteration (e.g., deletion, insertion, substitution) in the amino acid residues corresponding to amino acid residues 73-178 of SEQ ID NO: 12 or SEQ ID NO: 13. In certain embodiments, the variant has one, two, three, four or five, amino acid alternations (e.g., deletion, insertion, substitutions) in the amino acid residues corresponding to amino acid residues 73-178 of SEQ ID NO: 12 or SEQ ID NO: 13. In certain embodiments, the variant has one amino acid substitution in the amino acid residues corresponding to amino acid residues 73-178 of SEQ ID NO: 12 or SEQ ID NO: 13. In another embodiment, the variant has one, two, three, or four amino acid substitutions in the amino acid residues corresponding to amino acid residues 73-178 of SEQ ID NO: 12 or SEQ ID NO: 13. In certain embodiments, the variant has an amino substitution in the amino acid residue corresponding to residue 127 of SEQ ID NO: 12 or SEQ ID NO: 13. In certain embodiments, the alteration is a substitution. In certain embodiments, the substitution(s) are independently selected from a conservative and non-conservative substitution. In certain embodiments, at least one substitution is a conservative substitution. In certain embodiments, all of the substitutions are conservative substitutions. In certain embodiments, the substitution at position 127 is a conservative substitution. In certain embodiments, the MBNL polypeptide or fragment comprises an N to Serine substitution at a position corresponding to position 127 of SEQ ID NO: 12 or 13. In certain embodiments, the MBNL polypeptide or fragment comprises a serine at a position corresponding to position 127 of SEQ ID NO: 12 or 13.

In some embodiments, the MBNL polypeptide or variant MBNL polypeptide is capable of binding RNA (e.g., by binding to a YGCY motif), but is less efficient in regulating pre-mRNA splicing as compared to a wildtype or normal MBNL polypeptide (e.g., an MBNL polypeptide having an amino acid sequence of any of SEQ ID NOs: 12-18 or 55-58). In some embodiments, the MBNL polypeptide rescues aberrant splicing.

In some embodiments, the MBNL polypeptide (e.g., fragment) can replace or restore or augment decreased, missing, or inadequate neurofibromin activity.

This disclosure further contemplates generating sets of combinatorial mutants of an MBNL polypeptide, as well as truncation mutants, and is especially useful for identifying functional variant sequences. Combinatorially-derived variants can be generated which have a selective potency relative to a naturally occurring MBNL polypeptide. For example, in some embodiments, the MBNL polypeptide can be mutated to bind a YGCY in a polynucleotide (e.g., DNA or RNA) sequence with greater affinity than an MBNL polypeptide having any of the amino acid sequences of SEQ ID NOs: 12-18 or 55-58. Likewise, mutagenesis can give rise to variants which have intracellular half-lives dramatically different than the corresponding wild-type MBNL polypeptide. For example, the altered protein can be rendered either more stable or less stable to proteolytic degradation or other cellular process which result in destruction of, or otherwise inactivation of the protein of interest (e.g., MBNL1, MBNL2, or MBNL3, or the fragments thereof). Such variants can be utilized to alter the MBNL polypeptide level by modulating their half-life. There are many ways by which the library of potential MBNL variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, MBNL polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated forms of the MBNL polypeptide (e.g., MBNL1, MBNL2, or MBNL3). Examples of specific mutagenesis experiments of the MBNL polypeptide can be found in Edge et al., 2013, BMC Molecular Biology, 14(29):1-16 and Grammatikakis, et al., 2011, Nucleic Acids Research, 39(7): 2769-2780, each of which is incorporated by reference herein.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the MBNL polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an MBNL polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the MBNL polypeptides.

In certain embodiments, an MBNL polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified MBNL polypeptides may contain non-amino acid elements, such as lipids, poly- or mono-saccharide, and phosphates. Effects of such non-amino acid elements on the functionality of an MBNL polypeptide may be tested for its biological activity. In certain embodiments, the MBNL polypeptide may further comprise one or more polypeptide portions that enhance one or more of in vivo stability, in vivo half life, uptake/administration, and/or purification. In other embodiments, the targeting moiety comprises an antibody or an antigen-binding fragment thereof.

In one specific embodiment of the present disclosure, an MBNL polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

In some aspects, the present disclosure also provides a method of producing any of the foregoing polypeptides (e.g., any of the MBNL polypeptides or MBNL conjugates described herein) as described herein. Further, the present disclosure contemplates any number of combinations of the foregoing methods and compositions.

In certain aspects, an MBNL polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. An exemplary His tag has the sequence HHH-HHH (SEQ ID NO: 47), and an exemplary c-myc tag has the sequence EQKLISEEDL (SEQ ID NO: 48). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the MBNL polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In certain embodiments, an MBNL polypeptide may include or not include an N-terminal methionine.

Any of the MBNL polypeptides and fragments thereof described herein may be used in a conjugate of the disclosure. Any of the MBNL polypeptides and fragments described herein may be described using any of the structural and/or functional features described above or below. For example, the disclosure contemplates that any of the MBNL polypeptides and fragments thereof described above or herein may be conjugated (interconnected; associated; whether by chemical conjugation or as part of a fusion protein) with an internalizing moiety, as described herein. Any such conjugate may be used in any of the methods described herein and may be formulated as a composition, such as a pharmaceutical composition. In certain embodiments, the conjugate of the disclosure may also be described based on a functional feature of one or both of the MBNL portion or the internalizing moiety portion, and any of the functional features described above may be so used.

The disclosure contemplates that suitable complexes or fusion proteins may be in either orientation. In other words, the internalizing moiety portion may be N-terminal or C-terminal to the MBNL polypeptide or bioactive fragment. Specific, non-limiting examples are provided herein.

B. Protein Deficiencies or Disorders Suitable for Protein Replacement Therapy

A second category of heterologous agents is agents suitable for treating or studying a protein deficiency, such as agents suitable for providing a protein replacement therapy. In some embodiments, the protein is an enzyme. Generally, the heterologous agents, in this category, are proteins to replace the deficient protein (e.g., enzyme). There are numerous examples in the art of protein (e.g., enzyme) deficiencies, including Pompe disease, Gaucher's disease, and myotubular myopathy. In the case of protein (e.g., enzyme) deficiencies, the missing or insufficiently active protein (e.g., enzyme) is typically known, and the primary barrier is being able to effectively replace it. This has proven difficult in many instances because it is difficult to deliver effective amount of proteins into the appropriate cell types. These proteins (e.g., enzymes) represent heterologous agents that may be conjugated to an antibody or antigen binding fragment of the disclosure for delivery in vitro or in vivo—either to study disease in cells or animals or for therapeutic purposes. A few specific examples of heterologous agents suitable for treating or studying protein (e.g., enzyme) deficiency are provided below. These are merely exemplary and other proteins, such as enzymes, may similarly be provided. Further exemplary enzymes include kinases, phosphatases, recombinases and the like.

In some embodiments, the heterologous agent is an MTM1 polypeptide, or functional fragment thereof. A detailed description of the MTM1 polypeptides, and fragments, mutants and variants thereof, that may be used as heterologous agents may be found in PCT application, WO 2010/148010, which is incorporated herein by reference in its entirety. In some embodiments, the MTM polypeptides are conjugated to a humanized antibody or antigen-binding fragment of the disclosure as a fusion protein, in a universal carrier system or by means of chemical conjugation.

As used herein, the MTM1 polypeptides for use in the methods and compositions described herein include various splicing isoforms, fusion proteins, and modified forms of the wildtype MTM1 polypeptide. In certain embodiments, a bioactive fragment, variant, or fusion protein of an MTM1 polypeptide comprises an amino acid sequence that is at least 80%, 85%, 90%, 95%, 97%, 98%, 99% or 100% identical to an MTM1 polypeptide (such as the MTM1 polypeptide set forth as SEQ ID NO: 11). As used herein, "fragments" are understood to include bioactive fragments or bioactive variants that exhibit "bioactivity" as described herein. That is, bioactive fragments or variants of MTM1 exhibit bioactivity that can be measured and tested. For example, bioactive fragments or variants exhibit the same or substantially the same bioactivity as native (i.e., wild-type, or normal) MTM1 protein, and such bioactivity can be assessed by the ability of the fragment or variant to, e.g., cleave or hydrolyze an endogenous phosphoinositide substrate known in the art, or an artificial phosphoinositide substrate for in vitro assays (i.e., a phosphoinositide phosphatase activity), recruit and/or associate with other proteins such as, for example, the GTPase Rab5, the PI 3-kinase Vps34 or Vps15 (i.e., proper localization), or treat myotubular myopathy. Methods in which to assess any of these criteria are described herein.

The structure and various motifs of the MTM1 polypeptide have been well characterized in the art (see, e.g., Laporte et al., 2003, Human Molecular Genetics, 12(2): R285-R292; Laporte et al., 2002, Journal of Cell Science 15:3105-3117; Lorenzo et al., 2006, 119:2953-2959). As such, in certain embodiments, various bioactive fragments or variants of the MTM1 polypeptides can be designed and identified by screening polypeptides made, for example, recombinantly from the corresponding fragment of the nucleic acid encoding an MTM1 polypeptide. For example, several domains of MTM1 have been shown to be important for its phosphatase activity or localization. To illustrate, these domains include: Glucosyltransferase, Rab-like GTPase Activator and Myotubularins (GRAM; amino acid positions 29-97 or up to 160 of SEQ ID NO: 11), Rac-Induced recruitment Domain (RID; amino acid positions 161-272 of SEQ ID NO: 11), PTP/DSP homology (amino acid positions 273-471 of SEQ ID NO: 11; catalytic cysteine is amino acid 375 of SEQ ID NO: 11), and SET-interacting domain (SID; amino acid positions 435-486 of SEQ ID NO: 11). Accordingly, any combination of such domains may be constructed to identify fragments or variants of MTM1 that exhibit the same or substantially the same bioactivity as native MTM1. Suitable bioactive fragments can be used to make conjugates, and such conjugates can be used in any of the methods described herein and/or may be conjugated to an antibody or antigen binding fragment of the disclosure.

Exemplary fragments that may be used as part of a conjugate (e.g., a conjugate comprising (i) an antibody or antigen binding fragment of the disclosure associated with (ii) a heterologous agent include, for example: about residues 29-486 of SEQ ID NO: 11. Thus, in certain embodiments, the conjugates comprise residues 29-486 of SEQ ID NO: 11 (e.g., an antibody or antigen binding fragment of the disclosure is associated with a polypeptide comprising or consisting of residues 29-486 of SEQ ID NO: 11).

In certain embodiments, the MTM1 portion of the conjugate corresponds to the sequence of human MTM1. For example, the MTM1 portion of the conjugate comprises an amino acid sequence at least 90%, 92%, 95%, 96%, 97%, 98%, 99%, or 100% identical to SEQ ID NO: 11.

In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native MTM1 protein, for example, by testing their ability to cleave or hydrolyze a endogenous phosphoinositide substrate or a synthetic phosphoinositide substrate (i.e., phosphoinositide phosphatase activity), recruit and/or associate with other proteins such as, for example, GTPase Rab5, PI 3-kinase hVps34 or hVps15 (i.e., proper localization), or treat myotubular myopathy.

In certain embodiments, an MTM1 polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified MTM1 polypeptides may contain non-amino acid elements, such as lipids, poly- or mono-saccharide, and phosphates. Effects of such non-amino acid elements on the functionality of an MTM1 polypeptide may be tested for its biological activity, for example, its ability to treat myotubular myopathy or ability to cleave phosphoinositides (e.g., PIP3). Given that the native MTM1 polypeptide is glycosylated, in certain embodiments an MTM1 polypeptide used in a conjugate according to the present disclosure is glycosylated. In certain embodiments, the level and pattern of glycosylation is the same as or substantially the same as that of the native MTM1 polypeptide. In other embodiments, the level and/or pattern of glycosylation differs from that of the native MTM1 polypeptide (e.g., underglycosylated, overglycosylated, not glycosylated).

In one specific embodiment of the present disclosure, an MTM1 polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

In certain embodiments, fragments or variants of the MTM1 polypeptide will preferably retain at least 50%, 60%, 70%, 80%, 85%, 90%, 95% or 100% of the biological activity associated with the native MTM1 polypeptide. In certain embodiments, fragments or variants of the MTM1 polypeptide have a half-life (t½) which is enhanced relative to the half-life of the native protein. For embodiments in which the half-life is enhanced, the half-life of MTM1 fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native MTM1 protein. In some embodiments, the protein half-life is determined in vitro, such as in a buffered saline solution or in serum. In other embodiments, the protein half-life is an in vivo half life, such as the half-life of the protein in the serum or other bodily fluid of an animal. Similarly, any of the foregoing characteristics may be evaluated for MTM1 in the context of a conjugate and compared to that of native MTM1.

In certain embodiments, the MTM1 polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

The disclosure contemplates conjugates comprising (i) an antibody or antigen binding fragment of the disclosure and (ii) an MTM1 portion, wherein the MTM1 portion comprises any of the MTM1 polypeptides, fragments, or variants described herein or known in the art. Exemplary MBNL1 polypeptides are set forth in SEQ ID NO: 11, and the disclosure contemplates that the heterologous agent for use herein is, in certain embodiments a polypeptide comprising the amino acid sequence set forth in SEQ ID NO: 11, or any of the fragments or variants described above. Moreover, in certain embodiments, the MTM1 portion of any of the foregoing conjugates may, in certain embodiments, be a fusion protein. Any of the MTM1 polypeptides disclosed herein may be used as a heterologous agent and associated with an antibody or antigen binding fragment of the disclosure, such as chemically conjugated or fused via a co-translational fusion.

It should be noted that any portion of a conjugate of the disclosure may be similarly modified, such as with an epitope tag, a PEG moiety or moieties, and the like. In other words, an epitope tag may be to MTM1 and/or the internalizing moiety. Moreover, the conjugates may comprise more than one epitope tags, such as 2 epitope tags, or may include 0 epitope tags.

In certain aspects, an MTM1 polypeptide may be a fusion protein which further comprises one or more fusion domains, wherein the one or more fusion domains facilitate purification of the MTM1 polypeptide. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

In some embodiments, an MTM1 protein may be a fusion protein with all or a portion of an Fc region of an immunoglobulin for purposes of purifying the MTM1 protein.

In certain embodiments, the MTM1 polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

The disclosure contemplates that suitable complexes, such as fusion proteins, may be in either orientation. In other words, the internalizing moiety portion may be N-terminal or C-terminal to the MTM polypeptide.

Here and elsewhere in the specification, sequence identity refers to the percentage of residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology.

Methods and computer programs for the alignment of sequences and the calculation of percent identity are well known in the art and readily available. Sequence identity may be measured using sequence analysis software. For example, alignment and analysis tools available through the ExPasy bioinformatics resource portal, such as ClustalW algorithm, set to default parameters. Suitable sequence alignments and comparisons based on pairwise or global alignment can be readily selected. One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (www.ncbi.nlm.nih.gov/). In certain embodiments, the now current default settings for a particular program are used for aligning sequences and calculating percent identity.

C. Glycogen Storage Disorder

A third category of heterologous agents is agents suitable for treating or studying a glycogen storage disorder. Suitable heterologous agents include polypeptides, peptides, polynucleotides, and small molecules. There are numerous examples in the art of glycogen storage disorders. For many of these disorders, the missing or defective enzyme or other source of disease pathology is known and represent heterologous agents that may be conjugated to an antibody or antigen binding fragment of the disclosure for delivery in vitro or in vivo—either to study disease in cells or animals or for therapeutic purposes. A few specific examples of heterologous agents suitable for treating or studying a glycogen storage disorder are provided below.

1. AGL Polypeptides

In some embodiments, the heterologous agent is an AGL polypeptide, or a functional fragment thereof. As used herein, AGL polypeptides include various functional fragments and variants, fusion proteins, and modified forms of the wildtype AGL polypeptide. Such functional fragments or variants, fusion proteins, and modified forms of the AGL polypeptides have at least a portion of the amino acid sequence of substantial sequence identity to the native AGL protein, and retain the function of the native AGL protein (e.g., retain the two enzymatic activities of native AGL). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

In certain embodiments, a functional fragment, variant, or fusion protein of an AGL polypeptide comprises an amino acid sequence that is at least 80%, 85%, 90%, 95%, 97%, 98%, 99% or 100% identical to an AGL polypeptide (e.g., at least 80%, 85%, 90%, 95%, 97%, 98%, 99% or 100% identical to SEQ ID NOs: 19-21).

In certain embodiments, the AGL polypeptide for use in the conjugates and methods of the disclosure is a full length or substantially full length AGL polypeptide. In certain embodiments, the AGL polypeptide for use in the conjugate and methods of the disclosure is a functional fragment that has amylo-1,6-glucosidase activity and 4-alpha-glucotransferase activity.

In certain embodiments, fragments or variants of the AGL polypeptides can be obtained by screening polypeptides recombinantly produced from the corresponding fragment of the nucleic acid encoding an AGL polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native AGL protein, for example, by testing their ability to treat Forbes-Cori Disease in vivo and/or by confirming in vitro (e.g., in a cell free or cell based assay) that the fragment or variant has amylo-1,6-glucosidase activity and 4-alpha-glucotransferase activity. An example of an in vitro assay for testing for activity of the AGL polypeptides disclosed herein would be to treat Forbes-Cori cells with or without the AGL-containing conjugates and then, after a period of incubation, stain the cells for the presence of glycogen, e.g., by using a periodic acid Schiff (PAS) stain.

In certain embodiments, the present disclosure contemplates modifying the structure of an AGL polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the AGL biological activity of the resulting molecule. Conservative replacements are those that take place within a family of amino acids that are related in their side chains.

This disclosure further contemplates generating sets of combinatorial mutants of an AGL polypeptide, as well as truncation mutants, and is especially useful for identifying functional variant sequences. Combinatorially-derived variants can be generated which have a selective potency relative to a naturally occurring AGL polypeptide. Likewise, mutagenesis can give rise to variants which have intracellular half-lives dramatically different than the corresponding wild-type AGL polypeptide. For example, the altered protein can be rendered either more stable or less stable to proteolytic degradation or other cellular process which result in destruction of, or otherwise inactivation of AGL. Such variants can be utilized to alter the AGL polypeptide level by modulating their half-life. There are many ways by which the library of potential AGL variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, AGL polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the AGL polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the AGL polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an AGL polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the AGL polypeptides.

In certain embodiments, an AGL polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified AGL polypeptides may contain non-amino acid elements, such as lipids, poly- or mono-saccharides, and phosphates. Effects of such non-amino acid elements on the functionality of an AGL polypeptide may be tested for its biological activity, for example, its ability to hydrolyze glycogen or treat Forbes-Cori Disease. In certain embodiments, the AGL polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, an AGL polypeptide is not N-glycosylated or lacks one or more of the N-glycosylation groups present in a wildtype AGL polypeptide. For example, the AGL polypeptide for use in the present disclosure may lack all N-glycosylation sites, relative to native AGL, or the AGL polypeptide for use in the present disclosure may be under-glycosylated, relative to native AGL. In some embodiments, the AGL polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the AGL polypeptide is substituted by another amino acid. Examples of Asn-Xaa-Ser sequence stretches in the AGL amino acid sequence include amino acids corresponding to amino acid positions 813-815, 839-841, 927-929, and 1032-1034 of SEQ ID NO: 19. Examples of Asn-Xaa-Thr sequence stretches in the AGL amino acid sequence include amino acids corresponding to amino acid positions 69-71, 219-221, 797-799, 1236-1238 and 1380-1382 of SEQ ID NO: 19. In some embodiments, the asparagine at any one, or combination, of amino acid positions corresponding to amino acid positions 69, 219, 797, 813, 839, 927, 1032, 1236 and 1380 of SEQ ID NO: 19 is substituted or deleted. In some embodiments, the serine at any one, or combination of, amino acid positions corresponding to amino acid positions 815, 841, 929 and 1034 of SEQ ID NO: 19 is substituted or deleted. In some embodiments, the threonine at any one, or combination of, amino acid positions corresponding to amino acid positions 71, 221, 799, 1238 and 1382 of SEQ ID NO: 19 is substituted or deleted. In some embodiments, the Xaa amino acid corresponding to any one of, or combination of, amino acid positions 220, 798, 814, 840, 928, 1033, 1237 and 1381 of SEQ ID NO: 19 is deleted or replaced with a proline. The disclosure contemplates that any one or more of the foregoing examples can be combined so that an AGL polypeptide of the present disclosure lacks one or more N-glycosylation sites, and thus is either not glycosylated or is under glycosylated relative to native AGL.

In some embodiments, an AGL polypeptide is not O-glycosylated or lacks one or more of the O-glycosylation groups present in a wildtype AGL polypeptide. In some embodiments, the AGL polypeptide comprises a modified amino acid sequence that is unable to be O-glycosylated at one or more O-glycosylation sites. In some embodiments, serine or threonine at any one or more predicted O-glycosylation site in the AGL polypeptide sequence is substituted or deleted. The disclosure contemplates that any one or more of the foregoing examples can be combined so that an AGL polypeptide of the present disclosure lacks one or more N-glycosylation and/or O-glycosylation sites, and thus is either not glycosylated or is under glycosylated relative to native AGL.

In one specific embodiment of the present disclosure, an AGL polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the AGL protein to carry out the functions associated with wildtype AGL proteins, for example, having oligo-1,4-1,4-glucotransferase activity and/or amylo-1,6-glucosidase activity. The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of AGL exhibit bioactivity that can be measured and tested. For example, bioactive fragments/functional fragments or variants exhibit the same or substantially the same bioactivity as native (i.e., wild-type, or normal) AGL protein, and such bioactivity can be assessed by the ability of the fragment or variant to, e.g., debranch glycogen via the AGL fragment's or variant's 4-alpha-glucotransferase activity and/or amylo-1,6-glucosidase activity. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the AGL polypeptide will preferably retain at least 50%, 60%, 70%, 80%, 85%, 90%, 95% or 100% of the AGL biological activity associated with the native AGL polypeptide, when assessed under the same or substantially the same conditions.

In certain embodiments, fragments or variants of the AGL polypeptide have a half-life ($t_{1/2}$) which is enhanced relative to the half-life of the native protein. Preferably, the half-life of AGL fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native AGL protein. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native AGL protein.

With respect to methods of increasing AGL bioactivity in cells, the disclosure contemplates all combinations of any of the foregoing aspects and embodiments, as well as combinations with any of the embodiments set forth in the detailed description and examples. The described methods based on administering conjugates or contacting cells with conjugates can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing conjugates as described herein. Further, the present disclosure contemplates any number of combinations of the foregoing methods and compositions.

In certain aspects, an AGL polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 47), and an exemplary c-myc tag has the sequence EQKLISEEDL (SEQ ID NO: 48). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the AGL polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

In some embodiments, an AGL protein may be a fusion protein with an Fc region of an immunoglobulin.

In certain embodiments of any of the foregoing, the AGL portion of the conjugate of the disclosure comprises an AGL polypeptide, which in certain embodiments may be a functional fragment of an AGL polypeptide or may be a substantially full length AGL polypeptide. In some embodiments, the AGL polypeptide lacks the methionine at the N-terminal-most amino acid position (i.e., lacks the methionine at the first amino acid of any one of SEQ ID NOs: 19-21). Suitable AGL polypeptides for use in the conjugates and methods of the disclosure have oligo-1,4-1,4-glucotransferase activity and amylo-1,6-glucosidase activity, as evaluated in vitro or in vivo. Exemplary functional fragments comprise, at least 500, at least 525, at least 550, at least 575, at least 600, at least 625, at least 650, at least 675, at least 700, at least 725, at least 750, at least 775, at least 800, at least 825, at least 850, at least 875, at least 900, at least 925, at least 925, at least 950, at least 975, at least 1000, at least 1025, at least 1050, at least 1075, at least 1100, at least 1125, at least 1150, at least 1175, at least 1200, at least 1225, at least 1250, at least 1275, at least 1300, at least 1325, at least 1350, at least 1375, at least 1400, at least 1425, at least 1450, at least 1475, at least 1500, at least 1525 or at least 1532 amino consecutive amino acid residues of a full length AGL polypeptide (e.g., SEQ ID NOs: 19-21). In some embodiments, the functional fragment comprises 500-750, 500-1000, 500-1200, 500-1300, 500-1500, 1000-1100, 1000-1200, 1000-1300, 1000-1400, 1000-1500, 1000-1532 consecutive amino acids of a full-length AGL polypeptide (e.g., SEQ ID NOs: 19-21). Similarly, in certain embodiments, the disclosure contemplates conjugates where the AGL portion is a variant of any of the foregoing AGL polypeptides or bioactive fragments. Exemplary variants have an amino acid sequence at least 90%, 92%, 95%, 96%, 97%, 98%, or at least 99% identical to the amino acid sequence of a native AGL polypeptide or functional fragment thereof, and such variants retain the ability to debranch glycogen via the AGL variant's oligo-1,4-1,4-glucotransferase activity and amylo-1,6-glucosidase activity. The disclosure contemplates conjugates and the use of such polypeptides wherein the AGL portion comprises any of the AGL polypeptides, fragments, or variants described herein in combination with any internalizing moiety described herein. Moreover, in certain embodiments, the AGL portion of any of the foregoing conjugates may, in certain embodiments, by a fusion protein. Any such conjugates comprising any combination of AGL portions and internalizing moiety portions, and optionally including one or more linkers, one or more tags, etc., may be used in any of the methods of the disclosure.

2. GAA Polypeptides

In some embodiments, the heterologous agent is a GAA polypeptide, for example a GAA polypeptide comprising mature GAA. It has been demonstrated that mature GAA polypeptides have enhanced glycogen clearance as compared to the full length, precursor GAA (Bijvoet, et al., 1998, Hum Mol Genet, 7(11): 1815-24), whether at low pH (i.e., the pH of the lysosome or autophagic vacuole) or neutral pH (i.e., the pH of the cytoplasm) conditions. In addition, while mature GAA is a lysosomal protein that has optimal activity at lower pHs, mature GAA retains approximately 40% activity at neutral pH (i.e., the pH of the cytoplasm) (Martin-Touaux et al., 2002, Hum Mol Genet, 11(14): 1637-45). Accordingly, a GAA polypeptide comprising mature GAA is suitable for cytoplasmic delivery, and thus, suitable to address an unaddressed issue of Pompe disease: cytoplasmic glycogen accumulation.

As used herein, the mature GAA polypeptides include variants, and in particular the mature, active forms of the protein (the active about 76 kDa or about 70 kDa forms or similar forms having an alternative starting and/or ending residue, collectively termed "mature GAA"). The term "mature GAA" refers to a polypeptide having an amino acid sequence corresponding to that portion of the immature GAA protein that, when processed endogenously, has an apparent molecular weight by SDS-PAGE of about 70 kDa to about 76 kDa, as well as similar polypeptides having alternative starting and/or ending residues. Conjugates of the disclosure comprise a GAA polypeptide comprising mature GAA and, in certain embodiments, the GAA polypeptide lacks the signal sequence (amino acids 1-27 of SEQ ID NOs: 22 or 23 or the sequence designated by amino acids 1-56 of SEQ ID NO: 22 or 23). Exemplary mature GAA polypeptides include polypeptides having residues 122-782 of SEQ ID NOs: 22 or 23; residues 123-782 of SEQ ID NOs: 22 or 23; or residues 204-782 of SEQ ID NOs: 22 or 23. The term "mature GAA" includes polypeptides that are glycosylated in the same or substantially the same way as the endogenous, mature proteins, and thus have a molecular weight that is the same or similar to the predicted molecular weight. The term also includes polypeptides that are not glycosylated or are hyper-glycosylated, such that their apparent molecular weight differ despite including the same primary amino acid sequence. Any such variants or isoforms, functional fragments or variants, fusion proteins, and modified forms of the mature GAA polypeptides have at least a portion of the amino acid sequence of substantial sequence identity to the native mature GAA protein, and retain enzymatic activity. In certain embodiments, a functional fragment, variant, or fusion protein of a mature GAA polypeptide comprises an amino acid sequence that is at least 80%, 85%, 90%, 95%, 97%, 98%, 99% or 100% identical to mature GAA polypeptides set forth in one or both of SEQ ID NOs: 24 and 25, or is at least 80%, 85%, 90%, 95%, 97%, 98%, 99% or 100% identical to mature GAA polypeptides corresponding to one or more of: residues 122-782 of SEQ ID NOs: 22 or 23; residues 123-782 of SEQ ID NOs: 22 or 23; or residues 204-782 of SEQ ID NOs: 22 or 23. In certain embodiments, a functional fragment, variant, or fusion protein of a GAA polypeptide comprises an amino acid sequence that is at least 80%, 85%, 90%, 95%, 97%, 98%, 99% or 100% identical to GAA polypeptides set forth in any one of SEQ ID NOs: 26, 27 and 44. In some embodiments, the GAA polypeptide is a GAA polypeptide from a non-human species, e.g., mouse, rat, dog, zebrafish, pig, goat, cow, horse, monkey or ape. In some embodiments, the GAA protein comprises the mature form, but not the full-length form, of a bovine GAA protein having the amino acid sequence of SEQ ID NO: 52.

In certain specific embodiments, the conjugate comprises a GAA polypeptide comprising mature GAA (e.g., the heterologous agent is a GAA polypeptide comprising mature GAA). The mature GAA polypeptide may be the 76 kDa or the 70 kDa form of GAA, or similar forms that use alternative starting and/or ending residues. As noted in Moreland et al. (Lysosomal Acid α-Glucosidase Consists of Four Different Peptides Processed from a Single Chain Precursor, Journal of Biological Chemistry, 280(8): 6780-6791, 2005), the nomenclature used for the processed forms of GAA is based on an apparent molecular mass as determined by SDS-PAGE. In some embodiments, mature GAA may lack the N-terminal sites that are normally glycosylated in the endoplasmic reticulum. An exemplary mature GAA polypeptide comprises SEQ ID NO: 24 or SEQ ID NO: 25. Further exemplary mature GAA polypeptide may comprise or consist of an amino acid sequence corresponding to about: residues 122-782 of SEQ ID NOs: 22 or 23; residues 123-782 of SEQ ID NOs: 22 or 23, such as shown in SEQ ID NO: 24; residues 204-782 of SEQ ID NOs: 22 or 23; residues 206-782 of SEQ ID NOs: 22 or 23; residues 288-782 of SEQ ID NOs: 22 or 23, as shown in SEQ ID NO: 25. Mature GAA polypeptides may also have the N-terminal and or C-terminal residues described above.

In certain embodiments, the conjugate does not comprise a full-length GAA polypeptide, but comprises a mature GAA polypeptide and at least a portion of the full-length GAA polypeptide. In certain embodiments, the conjugate comprises a GAA polypeptide but does not include residues 1-56 of SEQ ID NO: 22 or 23. In certain embodiments, the conjugate comprises a GAA polypeptide but does not include residues 1-56 of SEQ ID NO: 22 or 23. In certain embodiments the GAA polypeptide does not comprise the 110 kilodalton GAA precursor. All of these are examples of the heterologous agents of the disclosure, specifically examples of embodiments wherein the heterologous agent is a GAA polypeptide comprising mature GAA.

In certain embodiments, the GAA polypeptide portion of the conjugates described herein comprise a mature form of GAA that does not comprise a GAA translation product set forth in SEQ ID NO: 22. In some embodiments, neither the GAA polypeptide nor the conjugate comprise a contiguous amino acid sequence corresponding to the amino acids 1-27 or 1-56 of SEQ ID NO: 22 or 23. In some embodiments, the GAA polypeptide lacks at least a portion of the GAA full linker region (SEQ ID NO: 46), wherein the full linker region corresponds to amino acids 57-78 of SEQ ID NOs: 22 or 23. In particular embodiments, the GAA polypeptide does not comprise a contiguous amino acid sequence corresponding to the amino acids 1-60 of SEQ ID NOs: 22 or 23 (e.g., the GAA polypeptide comprises the amino acid sequence of SEQ ID NO: 26). In other embodiments, the GAA portion does not comprise a contiguous amino acid sequence corresponding to the amino acids 1-66 of SEQ ID NO: 22 or 23 (e.g., the GAA polypeptide comprises the amino acid sequence of SEQ ID NO: 27). In some embodiments, the GAA portion does not comprise a contiguous amino acid sequence corresponding to the amino acids 1-69 of SEQ ID NO: 22 or 23 (e.g., the GAA polypeptide comprises the amino acid sequence of SEQ ID NO: 44). In other embodiments, the mature GAA polypeptides may be glycosylated, or may be not glycosylated. For those GAA polypeptides that are glycosylated, the glycosylation pattern may be the same as that of naturally-occurring human GAA or may be different. One or more of the glycosylation sites on the precursor GAA protein may be removed in the final mature GAA construct. Further exemplary GAA polypeptides may comprise or consist of an amino acid sequence corresponding to any one of SEQ ID NOs: 26, 27 and 44.

In certain embodiments, a GAA polypeptide comprising mature GAA is human.

By the terms "biological activity", "bioactivity" or "functional" is meant the ability of a conjugate comprising a GAA polypeptide to carry out the functions associated with wild-type GAA proteins, for example, the hydrolysis of α-1,4- and α-1,6-glycosidic linkages of glycogen, for example lysosomal glycogen. The terms "biological activity", "bioactivity", and "functional" are used interchangeably herein. In certain embodiments, the biological activity comprises the ability to hydrolyze glycogen. In other embodiments, the biological activity is the ability to lower the concentration of lysosomal and/or cytoplasmic glycogen. In still other embodiments, the conjugate has the ability to treat symptoms associated with Pompe disease. As used herein, "fragments" are understood to include bioactive fragments (also referred to as functional fragments) or bioactive variants that exhibit "bioactivity" as described herein. That is, bioactive fragments or variants of mature GAA exhibit bioactivity that can be measured and tested. For example, bioactive fragments/functional fragments or variants exhibit the same or substantially the same bioactivity as native (i.e., wild-type, or normal) GAA protein, and such bioactivity can be assessed by the ability of the fragment or variant to, e.g., hydrolyze glycogen in vitro or in vivo. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured, when assessed under the same or substantially the same conditions. In certain embodiments, fragments or variants of the mature GAA polypeptide will preferably retain at least 50%, 60%, 70%, 80%, 85%, 90%, 95% or 100% of the GAA biological activity associated with the native GAA polypeptide, when assessed under the same or substantially the same conditions. In certain embodiments, fragments or variants of the mature GAA polypeptide have a half-life ($t_{1/2}$) which is enhanced relative to the half-life of the native protein. Preferably, the half-life of mature GAA fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native GAA protein, when assessed under the same or substantially the same conditions. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native GAA protein.

In certain embodiments, a conjugate comprising a GAA polypeptide and an internalizing moiety can enter into a cell, such as into the cytoplasm, in the presence of an agent that blocks mannose-6-phosphate receptors (MPRs).

With respect to methods of increasing GAA bioactivity in cells, the disclosure contemplates all combinations of any of the foregoing aspects and embodiments, as well as combinations with any of the embodiments set forth in the detailed description and examples. The described methods based on administering conjugates or contacting cells with conjugates can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing conjugates as described herein. Further, the present disclosure contemplates any number of combinations of the foregoing methods and compositions.

In certain aspects, a mature GAA polypeptide may be a fusion protein which further comprises one or more fusion domains. Well-known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His, and c-myc tags. An exemplary His tag has the sequence HHHHHH (SEQ ID NO: 47), and an exemplary c-myc tag has the sequence EQKLISEEDL (SEQ ID NO: 48). It is recognized that any such tags or fusions may be appended to the mature GAA portion of the conjugate or may be appended to the internalizing moiety portion of the conjugate, or both. In certain embodiments, the conjugates comprise a "AGIH" portion (SEQ ID NO: 28) on the N-terminus (or within 10 amino acid residues of the N-terminus) of the conjugate, and such conjugates may be provided in the presence or absence of one or more epitope tags. In further embodiments, the conjugate comprises a serine at the N-terminal most position of the polypeptide. In some embodiments, the conjugates comprise an "SAGIH" (SEQ ID NO: 29) portion at the N-terminus (or within 10 amino acid residues of the N-terminus) of the polypeptide, and such conjugates may be provided in the presence or absence of one or more epitope tags.

In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the mature GAA polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In some embodiments, a GAA polypeptide may be a fusion protein with an Fc region of an immunoglobulin.

In certain embodiments of any of the foregoing, the GAA portion of the conjugate comprises one of the mature forms of GAA, e.g., the 76 kDa fragment, the 70 kDa fragment, similar forms that use an alternative start and/or stop site, or a functional fragment thereof. In certain embodiments, such mature GAA polypeptide or functional fragment thereof retains the ability of to hydrolyze glycogen, as evaluated in vitro or in vivo. Further, in certain embodiments, the conjugate that comprises such a mature GAA polypeptide or functional fragment thereof can hydrolyze glycogen. Exemplary bioactive fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length mature GAA polypeptide.

In certain embodiments, the GAA polypeptide portion of the conjugates described herein comprise a mature form of GAA that does not comprise a GAA polypeptide set forth in SEQ ID NO: 22. In some embodiments, the GAA polypeptide lacks at least a portion of the GAA full linker region (SEQ ID NO: 46), wherein the full linker region corresponds to amino acids 57-78 of SEQ ID NOs: 22 or 23. In particular embodiments, the GAA polypeptide does not comprise a contiguous amino acid sequence corresponding to the amino acids 1-60 of SEQ ID NOs: 22 or 23. In other embodiments, the GAA portion does not comprise a contiguous amino acid sequence corresponding to the amino acids 1-66 of SEQ ID NO: 22 or 23. In some embodiments, the GAA portion does not comprise a contiguous amino acid sequence corresponding to the amino acids 1-69 of SEQ ID NO: 22 or 23.

In particular embodiments, the GAA polypeptide does not comprise a contiguous amino acid sequence corresponding to the amino acids 1-60 of SEQ ID NOs: 22 or 23 (e.g., the conjugate does not comprise amino acids 1-60 of SEQ ID NO: 22 or 23). In other embodiments, the GAA portion does not comprise a contiguous amino acid sequence corresponding to the amino acids 1-66 of SEQ ID NO: 22 or 23 (e.g., the conjugate does not comprise a contiguous amino acid sequence corresponding to amino acids 1-60 or 1-66 of SEQ ID NO: 22 or 23). In some embodiments, the GAA portion does not comprise a contiguous amino acid sequence corresponding to the amino acids 1-69 of SEQ ID NO: 22 or 23 (e.g., the conjugate does not comprise a contiguous amino acid sequence corresponding to amino acids 1-60 or 1-66 or 1-69 of SEQ ID NO: 22 or 23). Suitable combinations, as set forth herein, are specifically contemplated.

In certain embodiments, the GAA polypeptide comprises an amino acid sequence corresponding to amino acids 61-952 of SEQ ID NO: 22. In some embodiments, the conjugate comprises amino acids 61-952 of SEQ ID NO: 22 and does not include a contiguous amino acid sequence corresponding to amino acids 1-60 of SEQ ID NO: 22. In certain embodiments, the GAA polypeptide comprises an amino acid sequence corresponding to amino acids 67-952 of SEQ ID NO: 22. In some embodiments, the conjugate comprises amino acids 67-952 of SEQ ID NO: 22 and does not include a contiguous amino acid sequence corresponding to amino acids 1-60 or, in certain embodiments, 1-66, of SEQ ID No: 22). In certain embodiments, the GAA polypeptide comprises an amino acid sequence corresponding to amino acids 70-952 of SEQ ID NO: 22. In some embodiments, the conjugate comprises amino acids 70-952 of SEQ ID NO: 22 and does not include a contiguous amino acid sequence corresponding to amino acids 1-60 or, in certain embodiments, 1-66 or, in certain embodiments, 1-70, of SEQ ID NO: 22. Conjugates comprising any such GAA polypeptides comprising mature GAA may be used to deliver GAA activity into cells.

In certain embodiments, the disclosure contemplates conjugates where the mature GAA portion is a variant of any of the foregoing mature GAA polypeptides or functional fragments. Exemplary variants have an amino acid sequence at least 90%, 92%, 95%, 96%, 97%, 98%, or at least 99% identical to the amino acid sequence of a native GAA polypeptide or bioactive fragment thereof, and such variants retain the ability of native GAA to hydrolyze glycogen, as evaluated in vitro or in vivo. The disclosure contemplates conjugates and the use of such proteins wherein the GAA portion comprises any of the mature GAA polypeptides, forms, or variants described herein in combination with any internalizing moiety described herein. Moreover, in certain embodiments, the mature GAA portion of any of the foregoing conjugates may, in certain embodiments, be a fusion protein. Any such conjugates comprising any combination of GAA portions and internalizing moiety portions, and optionally including one or more linkers, one or more tags, etc., may be used in any of the methods of the disclosure.

IV. Conjugates

In certain embodiments, the disclosure provides conjugates of the disclosure.

Conjugates of the disclosure comprise (i) an antibody or antigen binding fragment of the disclosure associated with (fused or otherwise conjugated to) (ii) a heterologous agent. Conjugates of the disclosure and for use in the present disclosure can be made in various manners. In certain embodiments, the heterologous agent is a polypeptide, and the C-terminus of a heterologous agent can be linked to the N-terminus of a humanized internalizing moiety. Alternatively, the C-terminus of a humanized internalizing moiety can be linked to the N-terminus of the heterologous agent. For example, conjugates can be designed to place the heterologous agent at the amino or carboxy terminus of either the antibody (or antibody fragment) heavy or light chain. In certain embodiments, potential configurations include the use of truncated portions of an antibody's heavy and light chain sequences (e.g., 3E10) as needed to maintain the functional integrity of the attached heterologous agent. Further still, the humanized internalizing moiety can be linked to an exposed internal (non-terminus) residue of the heterologous agent. In further embodiments, any combination of the heterologous agent-internalizing moiety configurations can be employed, thereby resulting in an heterologous agent:internalizing moiety ratio that is greater than 1:1 (e.g., two heterologous agent molecules to one internalizing moiety).

In certain embodiments, the conjugates comprise a "AGIH" portion (SEQ ID NO: 28) on the N-terminus of the polypeptide, and such conjugates may be provided in the presence or absence of one or more epitope tags. In further embodiments, the chimeric polypeptide comprises a serine at the N-terminal most position of the polypeptide. In some embodiments, the conjugates comprise an "SAGIH" (SEQ ID NO: 29) portion at the N-terminus of the polypeptide, and such conjugates may be provided in the presence or absence of one or more epitope tags.

The heterologous agent and the internalizing moiety may be conjugated directly to each other. Alternatively, they may be linked to each other via a linker sequence, which separates the heterologous agent and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the heterologous agent polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 15 amino acids can be used to provide a suitable separation of functional protein domains, although longer or shorter linker sequences may also be used. The length of the linker sequence separating the heterologous agent and the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the heterologous agent to an internalizing moiety can be a constant domain of an antibody (e.g., constant domain of Ab 3E10 or all or a portion of an Fc region of another antibody). By way of example, the linker that joins heterologous agent with an internalizing moiety may be GSTSGSGKSSEGKG (see, e.g., SEQ ID NO: 31). In certain embodiments, the linker is a cleavable linker. As noted above, the conjugate may include more than one linker, such as a linker joining the internalizing moiety to the heterologous agent and a linker joining portions of the internalizing moiety to each other (e.g., a linker joining a VH and VL domain of a single chain Fv fragment). When the conjugate includes more than one linker, such as two linkers, the linkers are independently selected and may be the same or different.

In certain embodiments, the conjugates for use in the methods of the present disclosure can be generated using well-known cross-linking reagents and protocols. For example, there are a large number of chemical cross-linking agents that are known to those skilled in the art and useful for cross-linking the heterologous agent with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino) hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, conjugates for use in the methods of the present disclosure can be produced by using a universal carrier system. For example, a heterologous agent polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, conjugates for use in the methods of the present disclosure can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of a heterologous agent to an internalizing moiety, a cleavable domain or cleavable linker can be used. Cleavage will allow separation of the internalizing moiety and the heterologous agent. For example, following penetration of a cell by a conjugate, cleavage of the cleavable linker would allow separation of the heterologous agent from the internalizing moiety.

In certain embodiments, the conjugates for use in the methods of the present disclosure are generated as a fusion protein containing a heterologous agent polypeptide and an internalizing moiety, expressed as one contiguous polypeptide chain. Such conjugates are referred to herein as recombinantly conjugated. In preparing such fusion proteins, a fusion gene is constructed comprising nucleic acids which encode a heterologous agent polypeptide and an internalizing moiety, and optionally, a peptide linker sequence to span the heterologous agent polypeptide and the internalizing moiety. Alternatively, one or more portions of the conjugate may be recombinantly produced separately, and the portions may be later combined chemically or recombinantly. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or staggered termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The conjugates encoded by the fusion gene may be recombinantly produced using various expression systems as is well known in the art (also see below).

Recombinantly conjugated conjugates include embodiments in which the heterologous agent polypeptide is conjugated to the N-terminus or C-terminus of the internalizing moiety.

In some embodiments, the immunogenicity of the conjugate may be reduced by identifying a candidate T-cell epitope within a junction region spanning the conjugate and changing an amino acid within the junction region as described in U.S. Patent Publication No. 2003/0166877.

V. Nucleic Acids and Expression

In certain embodiments, the present disclosure makes use of nucleic acids for producing any of the antibodies or antigen-binding fragments of the disclosure (e.g., humanized internalizing moieties or fragments thereof), or any of the conjugates disclosed herein.

The nucleic acids may be single-stranded or double-stranded, DNA or RNA molecules. In further embodiments, the humanized internalizing moiety or fragment thereof nucleic acid sequences can be isolated, recombinant, and/or fused with a heterologous nucleotide sequence, or in a DNA library.

In certain embodiments, humanized internalizing moieties or fragments thereof nucleic acids also include nucleotide sequences that hybridize under highly stringent conditions to a polynucleotide encoding any of the above-mentioned humanized internalizing moieties or fragments thereof nucleotide sequence, or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0× SSC at 50° C. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6× SSC at room temperature followed by a wash at 2× SSC at room temperature.

Isolated nucleic acids which differ from the humanized internalizing moieties or fragment thereof nucleic acids due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant humanized internalizing moieties or fragments thereof and/or conjugate encoding nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a humanized internalizing moieties or fragments thereof and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This disclosure also pertains to a host cell transfected with a recombinant gene which encodes a humanized internalizing moieties or fragment thereof or a conjugate for use in the methods of the disclosure. The host cell may be any prokaryotic or eukaryotic cell. For example, a humanized internalizing moiety or fragment thereof or a conjugate may be expressed in bacterial cells such as *E. coli*, insect cells (e.g., using a baculovirus expression system), yeast, or mammalian cells. Other suitable host cells are known to those skilled in the art. In some embodiments, the host cell is immortalized or is stably transfected to express a vector. The present disclosure also provides for a method of producing a polypeptide (e.g., any of the antibodies or antigen binding fragments described herein), comprising providing the host cell and culturing the host cells under suitable condition to produce the polypeptide.

The present disclosure further pertains to methods of producing a humanized internalizing moiety or fragment thereof, an internalizing moiety, and/or a conjugate for use in the methods of the disclosure. For example, a host cell transfected with an expression vector encoding a humanized internalizing moiety or fragment thereof or a conjugate can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an MTM1 polypeptide). In a preferred embodiment, the polypeptide is a fusion protein, and may optionally contain a domain which facilitates its purification.

A recombinant humanized internalizing moiety or fragment thereof (or other antibody or antigen-binding fragment of the disclosure) nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2$^{nd}$ Ed., ed. By Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

It should be understood that conjugates can be made in numerous ways. For example, a humanized internalizing moiety (or fragment thereof) and a heterologous agent can be made separately, such as recombinantly produced in two separate cell cultures from nucleic acid constructs encoding their respective proteins. Once made, the proteins can be chemically conjugated directly or via a linker. By way of another example, the conjugate can be made as an inframe fusion in which the entire conjugate, optionally including one or more linkers, and optionally including one or more epitope tags, is made from a nucleic acid construct that includes nucleotide sequence encoding both the heterologous agent and the internalizing moiety. By way of another example, the conjugate comprises: a) a humanized internalizing moiety (or fragment thereof) that comprises a light chain variable ($V_L$) domain (e.g., SEQ ID NO: 8) that is fused to a heavy chain variable ($V_H$) domain (e.g., SEQ ID NO: 10) by means of an inframe fusion; and b) a heterologous agent; wherein the humanized internalizing moiety and the heterologous agent are conjugated together by means of a universal carrier system or by means of chemical conjugation.

Antibodies of the disclosure, provided alone or as a conjugate with a heterologous agent, have numerous uses, including in vitro and in vivo uses. In vivo uses include not only therapeutic uses but also diagnostic and research uses in, for example, animal models of a particular disease. By way of example, conjugates of the disclosure may be used as research reagents and delivered to animals to understand bioactivity, localization and trafficking, protein-protein interactions, enzymatic activity, and impacts of the heterologous agent on animal physiology in healthy or diseases animals.

Conjugates may also be used in vitro to evaluate, for example, bioactivity, localization and trafficking, protein-protein interactions, and enzymatic activity of the heterologous agent in cells in culture, including healthy and diseased cells (e.g., cells lacking MTM, GAA, and/or AGL) in culture. The disclosure contemplates that conjugates comprising (i) an antibody or antigen binding fragment of the disclosure and (ii) a heterologous agent (e.g., such as conjugates comprising an antibody or antigen binding fragment of the disclosure and a heterologous protein or peptide) may be used to deliver the heterologous agent to cytoplasm, lysosome, and/or autophagic vesicles of cells, including cells in culture.

VI. Methods of Administration

Various delivery systems are known and can be used to administer the antibodies or antigen-binding fragments of the disclosure (whether provided alone or as a conjugate with another agent) (any one or more of which may be referred to as "compositions of the disclosure" or "humanized compositions of the disclosure"), e.g., various formulations, encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, and oral routes. In particular embodiments, parenteral introduction includes intramuscular, subcutaneous, intravenous, intravascular, and intrapericardial administration.

The present disclosure provides systemic delivery of one or more doses of a antibodies or antigen-binding fragments of the disclosure (whether provided alone or as a conjugate with another agent) (any one or more of which may be referred to as "compositions of the disclosure" or "humanized compositions of the disclosure"). Systemic delivery includes, for example, subcutaneous, intravenous, or intramuscular. In fact, the results described in published PCT application WO 2013/177428 demonstrate that, following intramuscular delivery of a 3E10 internalizing antibody or fragment thereof or conjugate, therapeutic efficacy is observed in other muscles (e.g., not limited to the injected muscle). This is not the case following intramuscular delivery of all agents and indicates that the humanized internalizing antibody or fragment thereof or conjugate is available systemically following intramuscular administration.

The antibodies or antigen binding fragments of the disclosure, including those internalizing moieties or fragments thereof conjugated to heterologous agents, may be administered by any convenient route, for example, by infusion or bolus injection.

In certain embodiments, antibodies or antigen binding fragments of the disclosure, including those conjugated to heterologous agents, are administered by intravenous infusion. In certain embodiments, the conjugates are infused over a period of at least 10, at least 15, at least 20, or at least 30 minutes. In other embodiments, antibodies or antigen binding fragments of the disclosure (provided alone or as a conjugate with heterologous agent) are infused over a period of at least 60, 90, or 120 minutes. Regardless of the infusion period, the disclosure contemplates that each infusion is part of an overall treatment plan where a composition of the disclosure is administered according to a regular schedule (e.g., weekly, monthly, etc.).

The composition and route of administration is chosen depending on the particular use of the technology. For example, a different composition and/or route of administration may be appropriate when using the compositions of the disclosure for research purposes, such as in vitro or in an animal model, versus when using for diagnostic or therapeutic purposes in human patients. One of skill in the art can select the appropriate route of administration depending on the particular application of the technology.

VII. Pharmaceutical Compositions

In certain embodiments of the present disclosure, antibodies or antigen-binding fragments of the disclosure (whether provided alone or as a conjugate with another agent) (any one or more of which is referred to as "compositions of the disclosure" or "humanized compositions of the disclosure") are formulated with a pharmaceutically acceptable carrier. For example, the disclosure provides a composition comprising an antibody or antigen-binding fragment of the disclosure (optionally conjugated to another agent) formulated with one or more pharmaceutically acceptable carriers and/or excipients. One or more such compositions of the disclosure (whether provided alone or as a conjugate with another agent) can be administered alone or as a component of a pharmaceutical formulation (composition). The compositions of the disclosure (whether provided alone or as a conjugate with another agent) may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the disclosure include those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining the therapeutic agent and a carrier and, optionally, one or more accessory ingredients. In general, the formulations can be prepared with a liquid carrier, or a finely divided solid carrier, or both, and then, if necessary, shaping the product.

Pharmaceutical compositions suitable for parenteral administration may comprise one or more compositions of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers (e.g., HEPES buffer), bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the present disclosure, the compositions of the disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compositions of the disclosure for use in the methods of the present disclosure can be determined by standard clinical techniques and may vary depending on the particular indication or use. Effective doses may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The foregoing applies to any of the compositions and methods described herein. The disclosure specifically contemplates any combination of the features of compositions of the present disclosure (alone or in combination) with the features described for the various pharmaceutical compositions and route of administration described in this section.

VII. Methods of Treatment

For any of the methods described herein, the disclosure contemplates the use of any of the compositions of the disclosure (whether provided alone or conjugated to a heterologous agent described throughout the application). In addition, for any of the methods described herein, the disclosure contemplates the combination of any step or steps of one method with any step or steps from another method. In certain embodiments, the antibodies or antigen-binding fragments conjugated to a heterologous agent can be used in methods of treatment and/or in methods of delivering a heterologous agent into cells in vitro or in vivo (e.g., such as to a human subject). These methods involve administering to an individual in need thereof an effective amount of a compound of the disclosure appropriate for the particular disease or condition. In specific embodiments, these methods involve delivering any of the antibodies or antigen binding fragments disclosed herein to the cells of a subject in need thereof.

The terms "treatment", "treating", and the like are used herein to generally mean obtaining a desired pharmacologic and/or physiologic effect. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

In certain embodiments, the present disclosure provides methods of treating a nucleotide repeat disorder or an exon splicing disorder. In other embodiments, the present disclosure provides a method of delivering to a subject in need thereof a conjugate comprising an antibody or antigen binding fragment of the disclosure associated with a heterologous agent, wherein the subject in need thereof has a nucleotide repeat disorder or an exon splicing disorder. In certain embodiments, the conjugate is delivered into cells of the subject. In certain embodiments, the heterologous agent is an agent suitable for treating, diagnosing or evaluating the nucleotide repeat disorder or exon splicing disorder.

In certain embodiments, the present disclosure provides methods of treating a disorder associated with aberrant microsatellite expansion, such as myotonic dystrophy. In other embodiments, the disclosure provides a method of delivering to a subject in need thereof a conjugate comprising an antibody or antigen binding fragment of the disclosure associated with a heterologous agent, wherein the subject in need thereof has a disorder associated with aberrant microsatellite expansion, such as myotonic dystrophy. In certain embodiments, the conjugate is delivered into cells of the subject.

Myotonic dystrophy type 1 (DM1) is caused by a trinucleotide $(CTG)_n$ expansion (n=50 to >3000) in the 3'-untranslated region (3'UTR) of the Dystrophia myotonica-protein kinase (DMPK) gene. Myotonic dystrophy type 2 (DM2) is caused by a tetranucleotide $(CCTG)_n$ expansion (n=75 to about 11,000) in the first intron of zinc finger protein 9 (ZNF9) gene (Ranum, et al., 2002, Curr. Opin. in Genet. and Dev. 12:266-271). Pathogenesis in DM1 and DM2 is believed to be due, in part, to loss of function of MBNL1 in skeletal muscle cells because of MBNL1 sequestration on RNA having microsattelite expansions (Miller et al., 2000, EMBO J 19: 4439-4448). An internalizing moiety that targets skeletal muscle cells, e.g., the humanized antibodies and antibody fragments thereof disclosed herein, would be useful in delivering the MBNL1 proteins or an antisense oligonucleotides disclosed herein to skeletal muscle cells in DM1 and DM2 patients. "Treatment" of DM1 and DM2 includes an improvement in any of the following effects associated with DM1, DM2 or combination thereof: muscle weakness, muscle wasting, grip strength, cataracts, difficulty relaxing grasp, irregularities in heartbeat, constipation and other digestive problems, retinal degeneration, low IQ, cognitive defects, frontal balding, skin disorders, atrophy of the testicles, insulin resistance and sleep apnea. Improvements in any of these conditions can be readily assessed according to standard methods and techniques known in the art. For example, for the treatment of myotonic dystrophy, a subject in need thereof may be administered an antibody or antigen binding fragment of the disclosure conjugated to a polypeptide comprising the amino acid sequence of SEQ ID NO: 13, or a functional fragment thereof. In certain embodiments, these methods are aimed at therapeutic and prophylactic treatments of animals, and more particularly, humans. With respect to methods for treating myotonic dystrophy, the disclosure contemplates all combinations of any of the foregoing aspects and embodiments, as well as combinations with any of the embodiments set forth in the detailed description and examples. Suitable animal models for testing the efficacy of any of the humanized internalizing moieties/fragments conjugated to any of the heterologous agents described herein in treating myotonic dystrophy are well known by the skilled worker and include the $MBNL1^{-/-}$ mouse, the $MBNL2^{-/-}$ mouse, the DMPK-CTG mouse and the has1r41. See, e.g., published PCT application WO 2010/044894.

In certain embodiments, the present disclosure provides methods of treating a disorder associated with aberrant splicing of the neurofibramotosis type 1 (NF1) gene RNA transcript. This is exemplary of an exon splicing disorder or a disorder characterized by aberrant exon splicing. It has recently been demonstrated that MBNL protein is involved in proper splicing of the NF1 gene RNA transcript. See, Fleming, 2012, BMC, Mol. Biol., 13:35. As such, any of the antibodies or antigen-binding fragments of the disclosure described herein conjugated to any of the MBNL polypeptides or fragments thereof (e.g., SEQ ID NO: 59) described herein may be therapeutically useful for treating a subject having a disorder associated with aberrant exon splicing. In some embodiments, the disorder is neurofibramotosis.

In certain embodiments, the present disclosure provides methods of treating a disorder associated with aberrant microsatellite expansion, such as Huntington's Disease. Huntington's Disease is a neurodegenerative genetic disorder that affects muscle coordination and leads to cognitive decline and psychiatric problems. This disease typically becomes noticeable in mid-adult life and is associated with abnormal involuntary writhing movements called chorea. The Huntingtin gene encodes the "huntingtin" protein. Expansion of a CAG triplet repeat stretch within the Huntingtin gene results in a different (mutant) form of the protein, which gradually damages cells in the brain. In some embodiments, the disclosure provides for a method of treating Huntington's Disease by administering to a subject in need thereof any of the humanized internalized moieties described herein, or fragments thereof, conjugated to any of the MBNL polypeptides described herein, or functional fragments thereof "Treatment" of Huntington's Disease includes an improvement in cognitive and/or psychiatric defects and/or chorea symptoms, or a delay or halt in further progression of Huntington's Disease. These methods are particularly aimed at therapeutic and prophylactic treatments of animals, and more particularly, humans. With respect to methods for treating Huntington's Disease, the disclosure contemplates all combinations of any of the foregoing aspects and embodiments, as well as combinations with any of the embodiments set forth in the detailed description and examples. Suitable animal models for testing the efficacy of any of the humanized internalizing moieties/fragments conjugated to any of the heterologous agents described herein (e.g., an MBNL polypeptide or functional fragment thereof) in treating Huntington's Disease are well known by the skilled worker and include, for example, any of the animal models discussed in Pouladi et al., 2013, Nature Review Neuroscience, 14: 708-721.

In certain embodiments of any of the foregoing, the disclosure provides a method of increasing MBNL activity in a cell in vitro or in a subject by administering a conjugate comprising (i) an antibody or antigen binding fragment of the disclosure and (ii) an MBNL polypeptide.

In certain embodiments, the present disclosure provides methods of providing an enzyme suitable for use as an enzyme replacement therapy (e.g., treating or studying an enzyme deficiency). Similarly, the present disclosure provides methods of providing a protein suitable for use as a protein replacement therapy (e.g., treating or studying a protein deficiency). Any suitable enzyme or other protein may be used as a heterologous agent and antibodies and antigen binding fragments of the disclosure are useful for delivering such proteins and enzymes into cells.

In some embodiments, the enzyme is MTM1, GAA or AGL. Other suitable enzymes and other proteins are similarly contemplated. In other embodiments, the present disclosure provides a method of delivering to a subject in need thereof a conjugate comprising an antibody or antigen binding fragment of the disclosure associated with a heterologous agent, wherein the subject in need thereof has an enzyme deficiency and/or is in need of enzyme replacement therapy. In certain embodiments, the conjugate is delivered into cells of the subject. In certain embodiments, the heterologous agent is an agent suitable for treating, diagnosing or evaluating the enzyme deficiency. In certain embodiments, the disclosure provides a method of increasing enzyme activity in a cell in vitro or in a subject by administering a conjugate comprising (i) an antibody or antigen binding fragment of the disclosure and (ii) an enzyme, such as an enzyme suitable for use as an enzyme replacement therapy.

In some embodiments, the present disclosure provides methods for treating conditions associated with myotubular myopathy. Myotubular myopathy (MTM) is caused by a deficiency of the myotubularin 1 (MTM1) protein, a phosphoinositide phosphatase (Bello A B et al., Human Molecular Genetics, 2008, Vol. 17, No. 14). MTM1 is ubiquitously expressed yet the absence of MTM1 in skeletal muscle solely accounts for the pathophysiology of MTM (Taylor G S et al., Proc Natl Acad Sci USA. 2000 Aug. 1; 97(16):8910-5; Bello A B et al., Proc Natl Acad Sci USA. 2002 Nov. 12; 99(23):15060-5), and suggests that the phosphoinositide phosphatase activity of MTM1 possesses a unique subcellular function that is particularly crucial to normal skeletal muscle function. An internalizing moiety that targets skeletal muscle cells, e.g., the humanized antibodies and antibody fragments thereof disclosed herein, would be useful in delivering MTM1 protein to skeletal muscle cells in myotubular myopathy patients. "Treatment" of MTM includes an improvement in any of the following effects associated with MTM or combination thereof: short life expectancy, respiratory insufficiency (partially or completely), poor muscle tone, drooping eyelids, poor strength in proximal muscles, poor strength in distal muscles, facial weakness with or without eye muscle weakness, abnormal curvature of the spine, joint deformities, and weakness in the muscles that control eye movement (ophthalmoplegia). Improvements in any of these conditions can be readily assessed according to standard methods and techniques known in the art. These methods involve administering to an individual in need thereof a therapeutically effective amount of a composition of the disclosure appropriate to treating myotublar myopathy. These methods are particularly aimed at therapeutic and prophylactic treatments of animals, and more particularly, humans. With respect to methods for treating myotubular myopathy, the disclosure contemplates all combinations of any of the foregoing aspects and embodiments, as well as combinations with any of the embodiments set forth in the detailed description and examples. Suitable animal models for testing efficacy in treating myotubular myopathy are well known by the skilled worker and include the MTM$^{-/-}$ mouse, the Mtm1p.R69C mouse, and the zebrafish model of myotubular myopathy. See, e.g., WO 2010/148010; Piersen et al., 2012, Hum Mol Genet, 21: 811-825; Dowling et al., 2009, PLoS Genetics, 5(2): e1000372.

In certain embodiments, the present disclosure provides methods for treating a glycogen storage disorder. In other embodiments, the present disclosure provides a method of delivering to a subject in need thereof a conjugate comprising an antibody or antigen binding fragment of the disclosure associated with a heterologous agent, wherein the subject in need thereof has a glycogen storage disorder. In certain embodiments, the conjugate is delivered into cells of the subject. In certain embodiments, the heterologous agent is an agent suitable for treating, diagnosing or evaluating the glycogen storage disorder.

In certain embodiments, the present disclosure provides methods for treating Pompe Disease. Pompe Disease is an autosomal recessive metabolic disorder characterized by a deficiency in the lysosomal enzyme acid α-glucosidase (GAA). Patients suffering from the disorder are unable to convert lysosomal stores of glycogen into glucose, which leads initially to accumulation of glycogen in the lysosome, and later to accumulation of glycogen in the cytoplasm and autophagic vesicles of cells. Eventually, the buildup of toxic levels of glycogen damages the cells and impairs proper function. The lysosomal enzyme acid α-glucosidase (GAA) is one of the enzymes that mediates glycogen hydrolysis. These methods involve administering to an individual in need thereof a therapeutically effective amount of a composition of the disclosure appropriate to treating Pompe Disease. In certain aspects, it may be beneficial to either (i) deliver a mature form of GAA, (ii) deliver a GAA polypeptide that, although longer than the mature form is shorter than the 110 kDa precursor form, and/or (iii) to deliver a GAA polypeptide with activity of any size as a conjugate connected to an internalizing moiety to facilitate delivery of polypeptide into cells, and even into the appropriate subcellular compartment. Without being bound by theory, even if a polypeptide of the disclosure has substantially the same activity as a precursor GAA polypeptide, delivery to the proper cellular location, optionally facilitated by an internalizing moiety that promotes delivery to the cytoplasm, would increase the effective GAA activity delivered to cells.

"Treatment" of Pompe disease includes an improvement in any of the following effects associated with dysfunction of GAA (or combination thereof): decreased GAA activity (e.g., treatment increases GAA activity), glycogen accumulation in cells (e.g., treatment decreases glycogen accumulation), increased creatine kinase levels, elevation of urinary glucose tetrasaccharide, reduction in heart size, hypertrophic cardiomyopathy, respiratory complications, dependence on a ventilator, muscle dysfunction and/or weakening, loss of motor function, dependence on a wheelchair or other form of mobility assistance, dependence on neck or abdominal support for sitting upright, ultrastructural damage of muscle fibers, loss of muscle tone and function. Improvements in any of these symptoms can be readily assessed according to standard methods and techniques known in the art. Other symptoms not listed above may also be monitored in order to determine the effectiveness of treating Pompe Disease. These methods are particularly aimed at therapeutic and prophylactic treatments of animals, and more particularly, humans. With respect to methods for treating Pompe Disease, the disclosure contemplates all combinations of any of the foregoing aspects and embodiments, as well as combinations with any of the embodiments set forth in the detailed description and examples. Suitable animal models for testing efficacy in treating Pompe Disease are well known by the skilled worker and include animals such as Brahman and Shorthorn cattle, Lapland dog, cats, sheep, and a strain of Japanese quail (Kikuchi et al., Clinical and Metabolic Correction of Pompe Disease by Enzyme Therapy in Acid Maltase-deficient Quail, J. Clin. Invest., 101(4): 827-833, 1998). In addition, mouse models have been developed by targeted disruption of the GAA gene (summarized in Geel et al., Pompe disease: Current state of treatment modalities and animal models, *Molecular Genetics and Metabolism*, 92:299-307, 2007).

In certain embodiments, the present disclosure provides methods for treating Forbes-Cori Disease. Forbes-Cori Disease, also known as Glycogen Storage Disease Type III or glycogen debrancher deficiency, is an autosomal recessive neuromuscular/hepatic disease with an estimated incidence of 1 in 100,000 births. The clinical picture in Forbes-Cori Disease is reasonably well established but exceptionally variable. Although generally considered a disease of the liver, with hepatomegaly and cirrhosis, Forbes-Cori Disease also is characterized by abnormalities in a variety of other systems. Muscle weakness, muscle wasting, hypoglycemia, dyslipidemia, and occasionally mental retardation also may be observed in this disease. Some patients possess facial abnormalities. Some patients also may be at an increased risk of osteoporosis. Forbes-Cori Disease is caused by mutations in the AGL gene. The AGL gene encodes the amylo-1,6-glucosidase (AGL) protein, which is a cytoplasmic enzyme responsible for catalyzing the cleavage of terminal α-1,6-glucoside linkages in glycogen and similar molecules. The AGL protein has two separate enzymatic activities: 4-alpha-glucotransferase activity and amylo-1,6-glucosidase activity. Both catalytic activities are required for normal glycogen debranching activity. The methods and compositions provided herein can be used to replace functional AGL and/or to otherwise decrease deleterious glycogen build-up in the cytoplasm of cells, such as cells of the liver and muscle. These methods involve administering to an individual in need thereof a therapeutically effective amount of a composition of the disclosure (e.g., a composition comprising any of the humanized internalizing moieties described herein, or fragments thereof, conjugated to a GAA or AGL polypeptide) appropriate to treat Forbes-Cori Disease. "treatment" of Forbes-Cori Disease includes an improvement in any of the following effects associated with Forbes-Cori Disease or combination thereof: skeletal myopathy, cardiomyopathy, cirrhosis of the liver, hepatomegaly, hypoglycemia, short stature, dyslipidemia, failure to thrive, mental retardation, facial abnormalities, osteoporosis, muscle weakness, fatigue and muscle atrophy. Treatment may also include one or more of reduction of abnormal levels of cytoplasmic glycogen, decrease in elevated levels of one or more of alanine transaminase, aspartate transaminase, alkaline phosphatase, or creatine phosphokinase, such as decrease in such levels in serum. Improvements in any of these conditions can be readily assessed according to standard methods and techniques known in the art. Other symptoms not listed above may also be monitored in order to determine the effectiveness of treating Forbes-Cori Disease. Suitable animal models for testing efficacy in treating myotubular myopathy are well known by the skilled worker and include curly-coated retriever dogs having a frame-shift mutation in their AGL gene display a disease similar to Forbes-Cori Disease in humans (Yi, et al., 2012, Disease Models and Mechanisms, 5: 804-811) and a mouse model of Forbes-Cori in which mice possess a single ENU-induced base pair mutation within the AGL gene. Anstee, et al., 2011, J. Hepatology, 54(Supp 1-Abstract 887): S353.

In certain embodiments of any of the foregoing, the disclosure provides a method of increasing GAA activity in a cell in vitro or in a subject by administering a conjugate comprising (i) an antibody or antigen binding fragment of the disclosure and (ii) a GAA polypeptide comprising mature GAA. In certain embodiments of any of the foregoing, the disclosure provides a method of increasing AGL activity in a cell in vitro or in a subject by administering a conjugate comprising (i) an antibody or antigen binding fragment of the disclosure and (ii) an AGL polypeptide.

In certain embodiments of any of the foregoing, the disclosure provides a method of treating a tumor or cancer cell with any of the internalizing moieties described herein. Without being bound by theory, the internalizing moieties described herein are, in certain embodiments, capable of any one or more of the following: a) targeting (e.g., delivering) an agent conjugated to the internalizing moiety (e.g., any of the heterologous agents described herein) to tumor or cancerous cells, b) killing and/or decreasing the growth, proliferation, size, survival or migration of a targeted tumor or cancer cell, c) sensitizing a tumor or cancer cell to the effects of any agent conjugated to the internalizing moiety (e.g., a chemotherapeutic agent), and/or d) sensitizing a tumor or cancer cell to the effects of any separately administered agent or therapy (e.g., a chemotherapeutic agent or radiation therapy). In certain embodiments, the internalizing moiety is administered/delivered to cells in the absence of a heterologous agent (e.g., not interconnected to a heterologous agent) or in the absence of a therapeutic heterologous agent. For example, in certain embodiments, an internalizing moiety is administered to cells in the absence of a heterologous agent for delivery into a tumor.

VIII. Other Uses

The compositions of the disclosure have numerous uses. For example, the humanized antibodies and antigen binding fragments, either alone or conjugated to a heterologous agent, are useful for studying preferential cell and tissue distribution in cells and in tissues in vitro and/or in vivo. Similarly, the humanized antibodies and antigen binding fragments, either alone or conjugated to a heterologous agent are useful as imaging agents, such as for ex vivo or in vivo diagnostic applications. For example, the humanized antibodies or antigen binding fragments conjugated to a radioactive moiety are useful for ex vivo or in vivo imaging studies. Such studies are particularly useful for imaging cancer and defects or injuries of skeletal and cardiac muscle—due to localization of the antibody portion to such tissues. See, WO 2012/145125. Similarly, any of the antibodies or antigen binding fragments of the disclosure are similarly useful.

Moreover, the antibodies and antigen binding fragments of the disclosure, such as humanized antibodies and antigen binding fragments are useful for delivering heterologous agents into cells and tissues, either in vitro or in vivo. By way of example, the disclosure provides methods of delivering a conjugate or other conjugate comprising a heterologous agent into cells. When used in vitro, conjugates of the disclosure are suitable for identifying binding partners for the heterologous agent being delivered (e.g., identifying proteins or peptides that bind the heterologous agent), and for evaluating localization and trafficking. Similarly, when used in vivo, conjugates of the disclosure are suitable for identifying binding partners for the heterologous agent being delivered (e.g., identifying proteins or peptides that bind the heterologous agent), for evaluating localization and trafficking, for evaluating biodistribution and half-life, and for evaluating immunogenicity.

Moreover, antibodies and antigen binding fragments of the disclosure, such as humanized antibodies or antigen binding fragment of the disclosure are useful as diagnostic agents in vitro or in vivo, such as in human subjects. For example, an antibody or antigen binding fragment of the disclosure can be labeled, such as with a detectable label suitable for imaging. The labeled antibody or antigen binding fragment can be administered to cells, ex vivo, or to subjects and use to evaluate localization of the antibody in cells and tissues and/or to evaluate clearance. Given that 3E10 antibodies localize to ENT2 expressing cancers, in certain embodiments, labeled antibodies are useful as diagnostic reagents for imaging and/or diagnosing ENT2 expressing cancers.

In certain embodiments, the humanized antibodies and antigen binding fragments have decreased immunogenicity, in comparison to a murine antibody, and thus are preferred for use in human subjects. Finally, the humanized antibodies and antigen binding fragments, either alone or conjugated to a heterologous agent, are useful for elucidating the comparative properties of this humanized antibody in comparison to the murine parent antibody, as well as other humanized antibodies. Such comparisons are useful for optimizing delivery agents, both from an efficacy perspective, as well as for characteristics that improve manufacturability. Similarly, any of the antibodies or antigen binding fragments of the disclosure are similarly useful.

EXEMPLIFICATION

The disclosure now being generally described, it will be more readily understood by reference to the following examples, which are included merely for purposes of illustration of certain aspects and embodiments of the present disclosure, and are not intended to limit the disclosure.

Example 1

Preparation of First Generation Humanized 3E10 Antibodies

First generation humanized 3E10 antibodies were generated using a humanized antibody framework selection and design protocol. The parent, murine antibody was a murine 3E10 antibody comprising a light chain variable ($V_L$) domain comprising the amino acid sequence set forth in SEQ ID NO: 7 and a heavy chain variable ($V_H$) domain comprising the amino acid sequence set forth in SEQ ID NO: 9. We note that this heavy chain variable domain is not that of the original 3E10 antibody deposited with the ATCC, but rather, contains a single amino acid substitution (e.g., a D to N in the $V_H$). However, this variant $V_H$ was previously generated and has been shown to retain cell penetrating and DNA binding activity. A murine antibody comprising the foregoing $V_L$ and $V_H$ was used as the parent, murine 3E10 antibody.

The nucleotide sequence encoding the murine antibody $V_L$ amino acid sequence (SEQ ID NO: 53) was subjected to a BLAST database search and the top five closest human immunoglobulin light chain homologues were identified and considered candidates for light chain CDR grafting. Similarly, the nucleotide sequence encoding the murine antibody $V_H$ amino acid sequence (SEQ ID NO: 54) was subjected to a BLAST database search and the top five closest human immunoglobulin heavy chain homologues were identified and considered candidates for heavy chain CDR grafting. In this analysis, the CDRs determined according to Kabat were identified and considered as the relevant CDRs. The Kabat CDRs are set forth in SEQ ID NOs: 32-37.

Utilizing Vector NTi sequence alignment tools, the chimeric amino acid sequences consisting of the Kabat CDRs from the foregoing murine 3E10 light and heavy chains and the framework regions (FR) of any one of the five human immunoglobulin light and heavy chain homologues were then analyzed. Based on the Vector NTi analyses, the amino acid sequences of the top three candidates of humanized light chain amino acid sequences and the amino acid sequences of the top three candidates of humanized heavy chain amino acid sequences were then combined in various combinations in order to generate a panel of humanized scFv amino acid sequences. Based on analysis of this panel of humanized scFvs, a humanized scFv comprising a $V_L$ domain comprising the amino acid sequence of SEQ ID NO: 41 and a $V_H$ domain comprising the amino acid sequence of SEQ ID NO: 42 was selected as the first generation lead humanized antibody fragment. Thus, based on this approach, the lead candidate humanized antibody (or fragment) comprises a $V_H$ domain comprising the amino acid sequence of SEQ ID NO: 42 and a $V_L$ domain comprising the amino acid sequence of SEQ ID NO: 41. As noted above, generation of the first generation humanized antibody was done using the CDRs, as defined by the Kabat scheme (Kabat et al. Sequences of Proteins of Immunological Interest, 5th Ed. Public Health Service, National Institutes of Health, Bethesda, Md. (1991)). In this example, the Kabat CDRs of the parent antibody are maintained in this humanized antibody (e.g., the VH and VL of this first generation humanized antibody comprise the six CDRs set forth in SEQ ID NO: 32-37).

The first generation lead humanized antibody was initially produced as a fragment (an scFv) in mammalian cells. Specifically, 1×200 ml of CHO-K1 cells were transiently transfected with a DNA vector comprising a polynucleotide sequence encoding a His-tagged humanized scFv antibody fragment. SEQ ID NO: 43 provides the sequence of the scFv produced by that vector (signal sequence not shown). Transfected cell cultures were incubated at 37° C., 10% $CO_2$ with shaking. Six days after transfection, the observed cell viability upon harvest was 97%, and culture supernatant was harvested and clarified by centrifugation (2000 rpm, 10 minutes). The clarified supernatant was purified using a 5 ml HisTrap FF Nickel-affinity column (GE Healthcare) and a linear elution gradient to 500 mM imidazole in 50 mM Tris, pH 7.6. One major peak was observed during elution, and three of the 3 ml fractions of the peak were taken and analyzed via SDS-PAGE, anti-$His_6$ Western Blots and SE-HPLC.

All three elution peak fractions showed positive results for anti-His-tag detection, confirming the presence of His-tagged scFv product. Fraction samples run in the anti-$His_6$ Western Blots under non-reducing conditions indicated the presence of monomeric, dimeric and larger oligomeric bands, suggesting that the scFv product dimerize or oligomerize.

Example 2

Generation of Second Generation Antibodies

Due to the difficulties in purifying the antigen binding fragments described in Example 1, and in order to develop superior humanized antibodies, we sought to develop an alternative humanized antibody. When designing the second generation humanized light and heavy chain variable domains, once again the murine 3E10 variable domains described in Example 1 were used as the parent VH and VL. For this approach, while the CDRs in accordance with the IMGT scheme were held constant, such that potential FR changes were evaluated relative to the IMGT scheme, (LeFranc et al., 2003, Development and Comparative Immunology, 27: 55-77), several substitutions were introduced in the CDRs in accordance with the Kabat scheme. Using this approach, the second generation humanized light and heavy chain variable domains produced have a number of sequence differences as compared to the first generation humanized antibody and the murine, parent antibody. The CDRs as determined using the IMGT scheme are set forth in SEQ ID NOs: 1-6, and the CDRs as determined using the Kabat scheme are set forth as follows: a VH CDR1 having the amino acid sequence of SEQ ID NO: 32; a VH CDR2 having the amino acid sequence of SEQ ID NO: 49; a VH CDR3 having the amino acid sequence of SEQ ID NO: 34; a VL CDR1 having the amino acid sequence of SEQ ID NO: 35 or 50; a VL CDR2 having the amino acid sequence of SEQ ID NO: 51; and a VL CDR3 having the amino acid sequence of SEQ ID NO: 37.

Alternative second generation light and heavy chain variable domains were designed such that they included a number of amino acid sequence alterations as compared to the first generation lead VL amino acid sequence of SEQ ID NO: 41 and to the first generation lead VH amino acid sequence of SEQ ID NO: 42. In addition, several specific amino acid residues of the murine 3E10 VL amino acid sequence of SEQ ID NO: 7 and of the murine 3E10 VH amino acid sequence of SEQ ID NO: 9 that had been modified in the first generation humanized antibody (comprising SEQ ID NOs: 41 and 42, respectively) were specifically retained in each of the second generation humanized light and heavy chain sequences. For example, the tryptophan at amino acid position 47 of SEQ ID NO: 9 was not altered in any of the second generation humanized heavy chains, as this position was later appreciated as likely involved in proper heavy chain folding. Also, the lysine at position 53 of SEQ ID NO: 7 was not altered in any of the second generation humanized light chains, as this position was thought to be involved in proper DNA target binding. In addition, while the first generation lead light chain variable domain of SEQ ID NO: 41 described in Example 1 had an asparagine and proline at amino acid positions 80 and 81, respectively, these two amino acids could lead to non-enzymatic self-cleavage during a large-scale production. As such, none of the second generation humanized light chain sequences included an asparagine and proline combination at the amino acid positions corresponding to amino acid positions 80 and 81, respectively, of SEQ ID NO: 41 (which also corresponds to position 80 and 81 of SEQ ID NO: 7). Also, while all of the humanized light chain sequences generated in Example 1 were derived from a V-light 7-3 light chain sequence, the second generation humanized light chain sequences were derived from the V-light 1 family of light chains. We note that here we have described the alterations introduced into the VH or VL by amino acid position relative to the linear sequences set forth in SEQ ID NO: 7 or 9 (murine) or SEQ ID NO: 41 or 42 (first generation humanized) (e.g., changes are described with reference to a linear amino acid sequence, and changes in other molecules are understood at being at a position corresponding to the recited position in a linear sequence). To make comparisons to other molecules, such as molecules that differ in length from SEQ ID NOs 7, 9, 41, or 42, the alternations can be understood as being at a position corresponding to a recited position in SEQ ID NO: 7, 9, 41, 42. A corresponding position can readily be determined by aligning sequences, such as using readily available sequence alignment tools and default parameters. Moreover, amino acid positions described relative to the linear amino acid sequences of SEQ ID NOs: 7, 9, 41, or 42 can also be described using the numbering scheme of Kabat or the numbering scheme of IMGT. Either system provides a scheme for identifying corresponding amino acids in a CDR or FR region when comparing different variable domains. One of skill in the art can readily identify amino acid residues in the variable domains disclosed herein by reference to the Kabat (see, e.g., http://www.biocomputing.it/digit/index.php) or IMGT (see http://www.imgt.org/IMGT_vquest/vquest?livret=0&Option=mouseIg) numbering schemes, and can use that numbering scheme to compare the disclosed VH and VL domains to other antibodies.

Two second generation humanized light chain variable domains derived from the murine sequence of SEQ ID NO: 7 (e.g., SEQ ID NO: 7 was the parent $V_L$), and three second generation humanized heavy chain variable domains derived from the murine sequence of SEQ ID NO: 9 (e.g., SEQ ID NO: 9 was the parent $V_H$) were designed. We refer to the three second generation humanized $V_H$ domains as HH1, HH2, and HH3. We refer to the two second generation humanized $V_L$ domains as HL1 and HL2.

A sequence alignment for each of the designed, second generation humanized sequences as compared to the murine SEQ ID NO: 7 or SEQ ID NO: 9 parent sequences is illustrated in FIG. 1. A description of the murine parent VH and VL and each of the different second generation heavy and light chain variable domains made and tested is provided in Table 1. The murine, parent VH comprises the IMGT CDRs set forth in SEQ ID NOs: 1-3, and each of the humanized VH also comprise these IMGT CDRs. Additionally, the murine, parent VL comprises the IMGT CDRs set forth in SEQ ID NOs: 4-6, and each of the humanized VL also comprise these IMGT CDRs. However, the Kabat CDRs differ between the humanized and murine VH and VL.

TABLE 1

| Chain Description | Abbreviation | Sequence Identifier Number |
| --- | --- | --- |
| Murine 3E10 Light Chain Variable Domain | ML1 | SEQ ID NO: 7 |
| Murine 3E10 Heavy Chain Variable Domain | MH1 | SEQ ID NO: 9 |
| Humanized 3E10 Light Chain Variable Domain-1 | HL1 | SEQ ID NO: 40 |
| Humanized 3E10 Light Chain Variable Domain-2 | HL2 | SEQ ID NO: 8 |
| Humanized 3E10 Heavy Chain Variable Domain-1 | HH1 | SEQ ID NO: 38 |
| Humanized 3E10 Heavy Chain Variable Domain-2 | HH2 | SEQ ID NO: 39 |
| Humanized 3E10 Heavy Chain Variable Domain-3 | HH3 | SEQ ID NO: 10 |

The heavy chain variable domain of murine 3E10 (MH1—SEQ ID NO: 9) and each of the HH1, HH2 and HH3 heavy chain variable domains were expressed in various pairwise combinations with a light chain variable domain selected from: (i) the murine 3E10 (ML1—SEQ ID NO: 7), (ii) the HL1, and (iii) the HL2. For simplicity, each pairwise combination will be referred to in these examples in terms of the heavy and light chain variable domains present in the respective antibodies (e.g., HH1/HL1 is an antibody comprising the HH1 heavy chain variable domain and the HL1 light chain variable domain). Note that, for these experiments, full length antibodies were made and tested with each pairwise combination of VHs and VLs expressed recombinantly on a human IgG1 Fc. Antibody fragments, such as Fabs or scFvs comprising combinations of heavy and light chain variable domains are similarly contemplated and can be made and evaluated as described herein. Moreover, antibodies can readily be made on other immunoglobulin backbones, including non-human backbones, but preferably, on other human immunoglobulin heavy and light chain constant backbones, such as an IgG2a, IgG3, or IgG4 backbone.

DNA encoding for each pairwise heavy/light combination (total of 12-see Table 2) was inserted into a single vector using the GS Xceed Gene Expression System (Lonza), and the resulting vector was stably transfected and expressed in CHOK1SV GS-KO cells.

TABLE 2

| Antibody Construct Designation | Description |
| --- | --- |
| MH1/ML1 | Comprises: a heavy chain comprising the murine, parent VH; and a light chain comprising the murine, parent VL |
| MH1/HL1 | Comprises: a heavy chain comprising the murine, parent VH; and a light chain comprising the HL1 light chain variable domain |
| MH1/HL2 | Comprises: a heavy chain comprising the murine, parent VH; and a light chain comprising the HL2 light chain variable domain |
| HH1/ML1 | Comprises: a heavy chain comprising the HH1 heavy chain variable domain; and a light chain comprising the murine, parent VL |
| HH1/HL1 | Comprises: a heavy chain comprising the HH1 heavy chain variable domain; and a light chain comprising the HL1 light chain variable domain |

TABLE 2-continued

| Antibody Construct Designation | Description |
| --- | --- |
| HH1/HL2 | Comprises: a heavy chain comprising the HH1 heavy chain variable domain; and a light chain comprising the HL2 light chain variable domain |
| HH2/ML1 | Comprises: a heavy chain comprising the HH2 heavy chain variable domain; and a light chain comprising the murine, parent VL |
| HH2/HL1 | Comprises: a heavy chain comprising the HH2 heavy chain variable domain; and a light chain comprising the HL1 light chain variable domain |
| HH2/HL2 | Comprises: a heavy chain comprising the HH2 heavy chain variable domain; and a light chain comprising the HL2 light chain variable domain |
| HH3/ML1 | Comprises: a heavy chain comprising the HH3 heavy chain variable domain; and a light chain comprising the murine, parent VL |
| HH3/HL1 | Comprises: a heavy chain comprising the HH3 heavy chain variable domain; and a light chain comprising the HL1 light chain variable domain |
| HH3/HL2 | Comprises: a heavy chain comprising the HH3 heavy chain variable domain; and a light chain comprising the HL2 light chain variable domain |

One transfection for each of the twelve constructs was set up in a 125 mL Erlenmeyer flask. The cultures were passaged to 100 mL culture when their viable cell density was higher than $0.6 \times 10^6$ cells/mL. Cells were further passaged to produce 2×400 mL cultures (800 mL total) in 1 L vented Erlenmeyer flasks for each variant. Good viability and antibody expression was observed in the stably-transfected cultures for all of the above antibodies made after 4-6 days in culture. The cells were harvested following six days in culture, and the clarified supernatants were pooled and purified on 5 mL HiTrap MabSelect SuRe Protein A columns. The eluted products were neutralized with 1 M Tris (1:40 volume ratio) and filtered through 0.22 μm filters. The final pH values for all products ranged from 7.2 to 7.6.

Figure 2B:
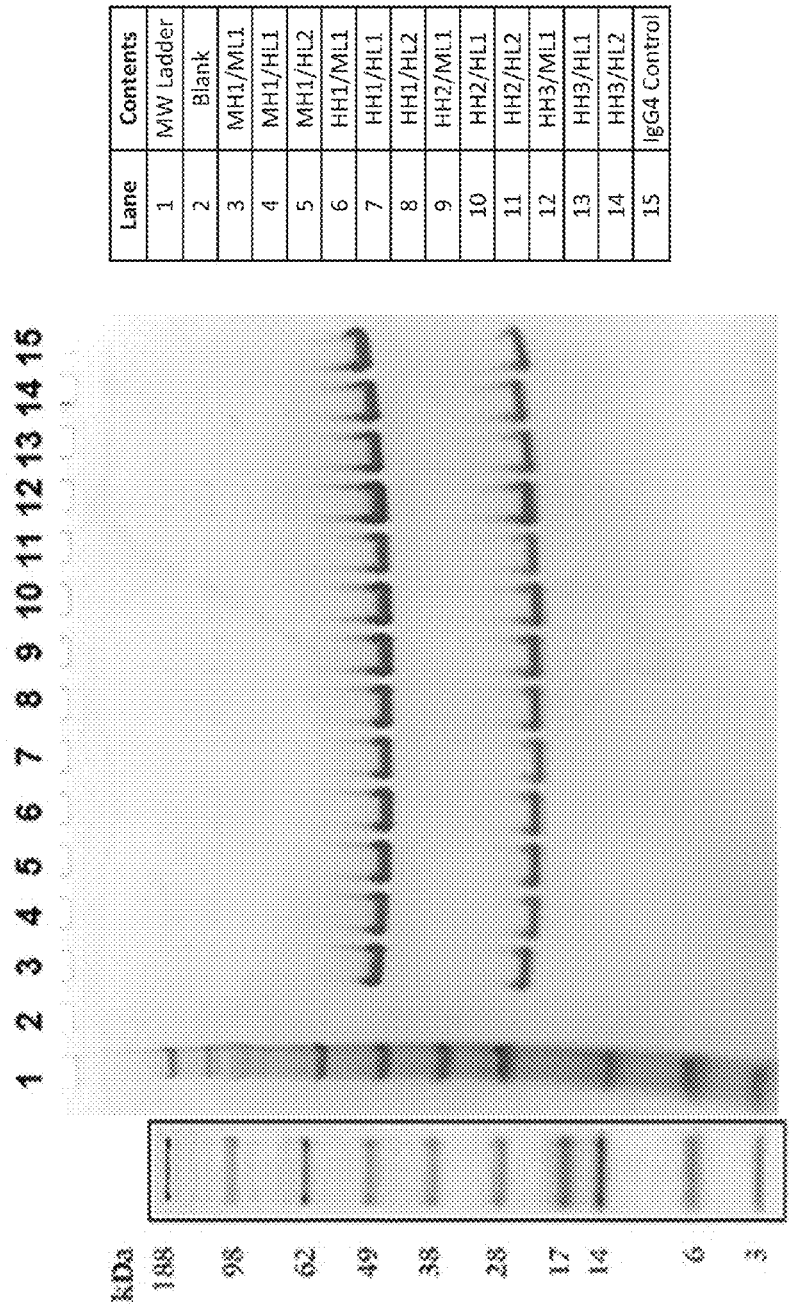

As illustrated in FIG. 2A, a single predominant band of the expected antibody size (150 kDa), and with no obvious aggregates, was observed for all antibodies made and tested under non-reducing conditions using SDS-PAGE. Similarly, as illustrated in FIG. 2B, two bands of expected antibody heavy and light chain sizes (50 and 28 kDa, respectively), with no obvious proteolytic breakdown, were observed for all antibodies made and tested under reducing conditions.

Figure 3A:
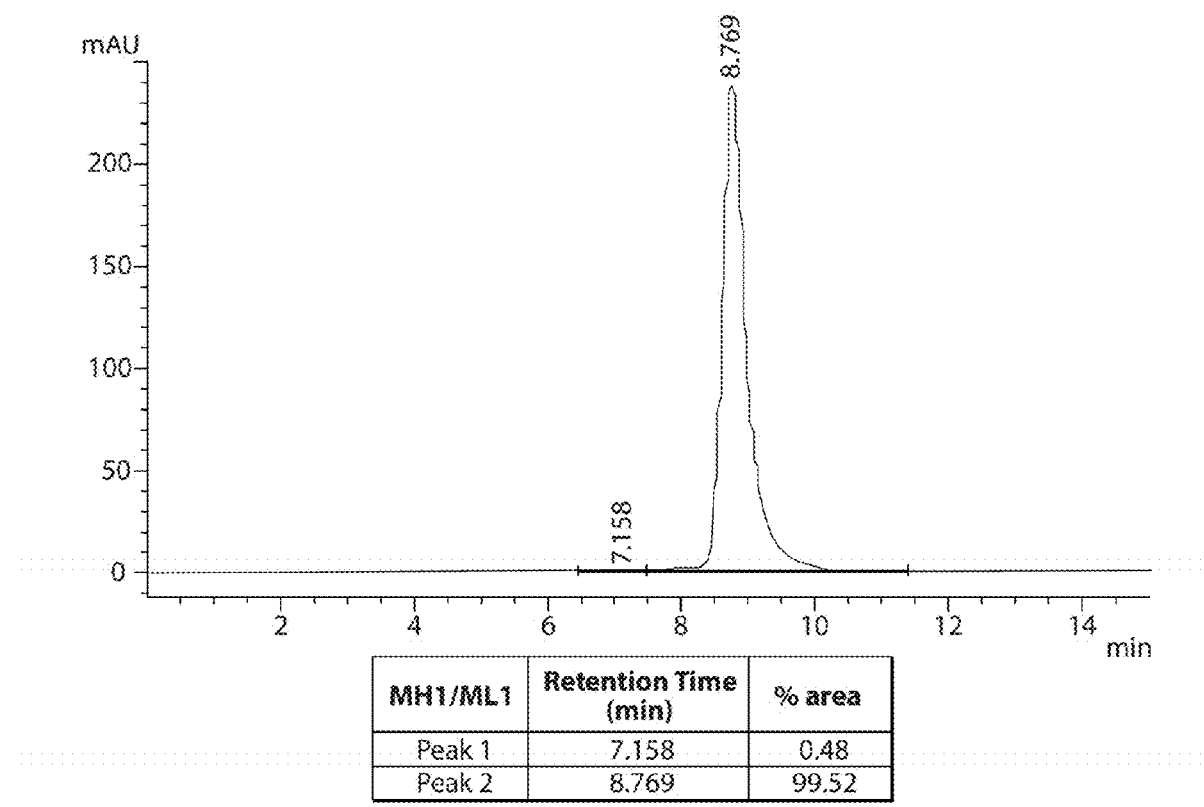
FIGS. 3A and 3B depict representative SE-HPLC charts of full length antibodies comprising the murine, parent heavy and light chain variable domains (MH1/ML1—FIG. 3A) or humanized heavy and light chain variable domains (HH1/HL1—FIG. 3B).
Figure 3B:
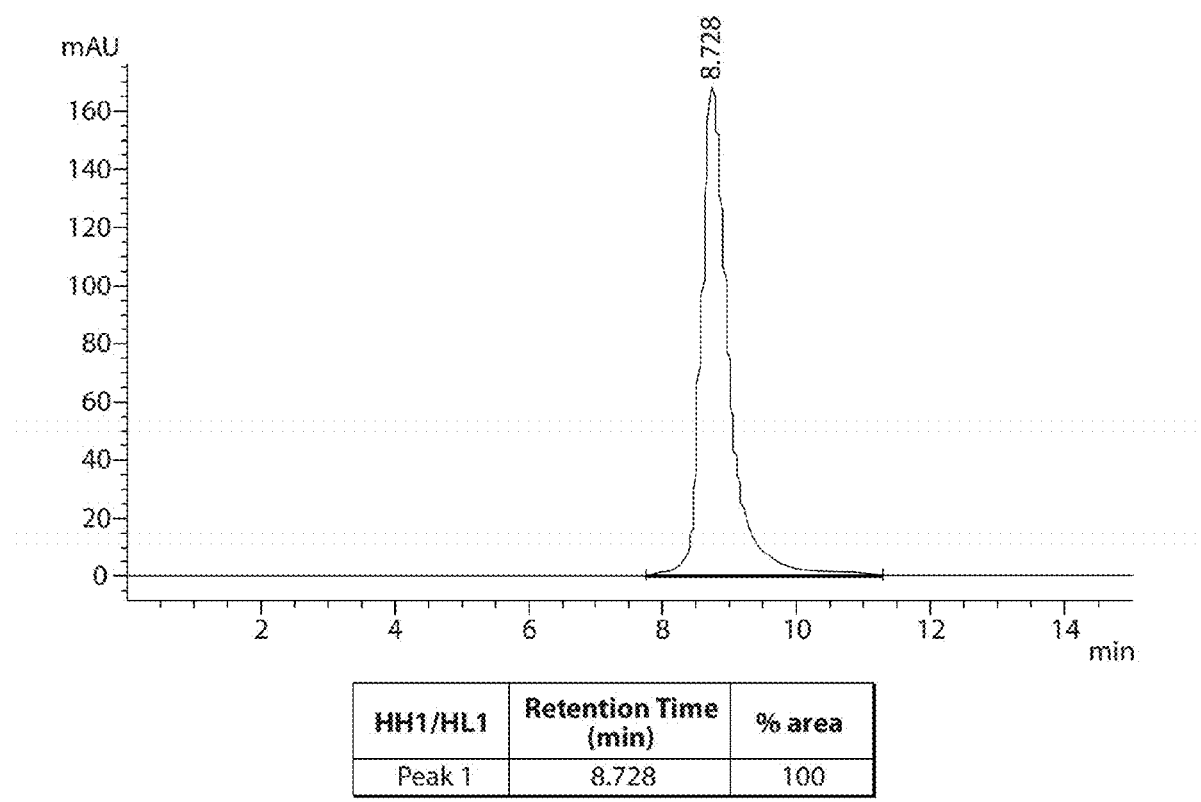

SEC-HPLC analysis on a Zorbax GF-250 9.4 mm ID×25 cm column (Agilent) show a high level of purity after purification for all the second generation humanized antibodies. As illustrated for representative antibodies in FIGS. 3A and 3B, SE-HPLC demonstrated a high level of purity for all antibody products tested, consistent with the SDS-PAGE analysis. A main peak was detected at retention time of about 8.7 min for the tested antibodies suggesting that most of the antibody produced is present as monomer (>99%). However, the SE-HPLC analysis indicated the presence of low levels of higher molecular weight impurities (<0.5%), consistent with low levels of soluble aggregates, in purified compositions of the MH1/ML1 and the HH3/ML1 antibodies.

Example 3

QCM Binding Assay

Murine 3E10, including the specific 3E10 comprising the VL set forth in SEQ ID NO: 7 and the VH set forth in SEQ ID NO: 9, is known for its ability to bind DNA (e.g., DNA is an antigen/epitope (e.g., target) recognized by 3E10). Thus, binding properties for each of the different antibodies generated in Example 2 versus DNA were assessed using QCM. The DNA substrate used was a short blunt DNA where one strand consisted of the nucleotide sequence set forth in SEQ ID NO: 63. All of the antibodies set forth in Example 2 as having any combination of one or more humanized VH and/or VL domains were tested and had DNA binding activity. As a negative control, an antibody comprising the murine, parent heavy and light chain variable domains but having a R92N mutation in the VL (a mutation known to disrupt DNA binding activity) was generated and used.

In addition, a previously generated sample of a MH1/ML1 antibody on a human Fc backbone (3E10 HuIgG1) was utilized in these experiments as a control to monitor the sensitivity of the QCM assay over time, i.e., from the start of the QCM experiment to its end. A significant increase in $K_D$ from the start of the experiment to the end for 3E10 HuIgG1 was observed and indicates degradation of the assay over the course of an experiment. This indicates that data obtained later during a particular experiment may underestimate affinity (e.g., may show $K_D$ as being higher than it actually is). Thus, a humanized antibody evaluated later during the experiment may underestimate the improvement in $K_D$ achieved with our humanized antibodies (e.g., suggests that a humanized antibody sample tested towards the end of the experiment would actually be associated with an even lower $K_D$ (more improved affinity) had that humanized antibody sample been tested earlier during a particular QCM experiment. This sample of a chimeric antibody (murine variable domains on human constant regions) was not made and purified at the same time as the humanized antibodies, and thus, is not being used herein for specific comparison to the second generation humanized antibodies. Rather, the comparison is with respect to MH1/ML1.

Results from the QCM binding assay are illustrated in Table 3.

TABLE 3

| mAb | $K_D$ nM |
|---|---|
| 3E10 HuIgG1-start | 12.6 |
| 3E10 R92N | 1100 |
| IgG4 | 0 |
| MH1/ML1 | 21.4 |
| MH1/HL1 | 6.7 |
| MH1/HL2 | 5.8 |
| HH1/ML1 | 30.7 |
| HH1/HL1 | 12.6 |
| HH1/HL2 | 6.3 |
| HH2/ML1 | 39.7 |
| HH2/HL1 | 8.0 |
| HH2/HL2 | 7.7 |
| HH3/ML1 | 42.5 |
| HH3/HL1 | 8.8 |
| HH3/HL2 | 8.6 |
| 3E10 HuIgG1-End | 28.2 |

Example 4

Humanized Antibody Concentration Study

Each respective antibody heavy/light chain combination was concentrated using a 30K MWCO centrifugal filter, 5 mL (Millipore). The stability of each of the humanized antibodies was assessed in formulations in which the antibody was concentrated up to ~30 mg/mL. The stability and properties of each pre- and post-concentration antibody sample was assessed by means of numerous assays, including: visual inspection, A280, A600-turbidity, pH, HP-SEC and SDS-PAGE (under reducing and non-reducing conditions).

For visual inspection analysis, the respective starting and concentrated antibody material were placed in Type-I glass vials in a light box (non-USP) to determine clarity, opalescence, and the presence of any visible particles.

In order to determine the percent recovery of each antibody following the antibody concentration process, A280 nm analysis was performed. For A280 nm analysis, concentrated material was diluted 1:40 and analyzed by A280 nm analysis. Percent recovery of the concentrated sample was determined by comparison of total protein recovered pre-concentration (8 mg load) and that recovered after concentration (volume times A280 concentration).

For A600 nm turbidity analysis, turbidity was determined by measuring the difference between pre-concentration A600 nm and concentrated A600 nm levels in each of the antibody compositions.

For pH analysis, pre- and post-concentration antibody samples were analyzed neat with a microprobe.

For HP-SEC analysis, ~60 μg starting and concentrated antibody samples were loaded neat onto HP-SEC and monitored at 280 nm. The column used was a Sepax Zenix-C 300 with the following conditions: MP=0.2M $KPO_4$, 0.25M KCl, pH 6.0. HPLC profiles were normalized for comparison pre- and post-concentration. For SDS-PAGE analysis, pre- and post-concentration antibody samples were analyzed under non-reducing and reducing conditions.

Results from the humanized antibody concentration study are provided in FIG. 4.

Example 5

Biacore Binding Assay

To further assess the binding characteristics of each of the different antibodies prepared in Example 2, Biacore binding assays were performed (binding affinity by SPR). Binding studies were performed at 25° C. using three Biacore 2000 optical biosensors equipped with Xantec CMD500m sensor chips and equilibrated with running buffer (PBS, 0.01% Tween-20, pH 7.4). At the end of each DNA binding cycle, the antibody surfaces were regenerated with a 14-second injection of 3M NaCl, 1% Tween-20. For immobilization, the antibodies were each diluted 1/50 in 10 mM sodium acetate pH 5.0 and immobilized to densities of ~15,000-27,000 RU using standard amine coupling chemistry. Short blunt DNA comprising two strands, wherein one of the strands consisted of the sequence of SEQ ID NO: 63, was tested in duplicate for binding in a three-fold dilution series starting at 67 nM.

All of the antibodies set forth in Example 2 as having any combination of one or more humanized VH and/or VL domains were tested and had DNA binding activity.

Example 6

Cell Penetration Assay

The murine 3E10 antibody is capable of penetrating both cytoplasmic and nuclear membranes. A cell penetration assay was performed to evaluate cell penetration activity of the humanized antibodies generated. COS7 cells were plated in a 96-well plate at 10,000 cells/well/100 μl, and 100 μl of each of the Example 2 antibodies in 10% PBS was added/per well. The final antibody concentration per well was 50 µg/ml. The antibodies were incubated with the cells in an incubator for 1 hour, followed by aspiration and two washes with 100 µl PBS. Cells were then permeabilized with EtOH for 10 minutes and rehydrated with 2 washes of PBS. The wells were then blocked in 100 µl 2% serum in PBST (PBS plus 0.1% Tween-20). Samples were then incubated with a diluted secondary antibody. Following this incubation, cells were washed twice with PBS and incubated with an alkaline phosphatase chromogen (BCIP/NBT). The absorbance was measured at 595 nm, and each well was then viewed microscopically and the precipitate intensity score was recorded. This experiment was performed twice: In Study A the evaluator was not blinded and intensity of the precipitate was scored on a scale from 1 (least intense) to 5 (most intense); and in Study B, the evaluator was blinded and precipitate intensity was scored on a scale from 1 (least intense) to 10 (most intense). The higher the intensity score, the higher the observed level of cell penetration.

All of the antibodies set forth in Example 2 as having any combination of one or more humanized VH and/or VL domains were tested and were capable of penetrating the cytoplasmic and nuclear membrane. In other words, these antibodies penetrated COS cells.

Example 7

Assessment of Genotoxicity and Cytotoxicity

The genotoxicity (i.e., the ability of an agent to cause damage to nucleic acids) and cytotoxicity of one of the humanized antibodies was assessed in a GreenScreen HC assay. In performing this test, a dilution series of the humanized antibody was generated in a 96-well, black microplate with an optically clear base. A standard genotoxic compound (methyl methanesulfonate, MMS) was also added as an intra-plate quality control check. Two strains of cultured human lymphoblastoid TK6 cells were used, the test strain (GenM-T01) and the non-fluorescent control strain (GenM-C01), the latter used to allow correction for any autofluorescence from the test compounds. Incorporated in the test strain was a green fluorescent protein (GFP) reporter system that exploits the proper regulation of the GADD45a gene, which mediates the adaptive response to genotoxic stress. Exposure to a genotoxic compound increases expression of GFP and hence the induction of cellular fluorescence in the test strain. Each dilution of the antibody was combined with an equal volume of a specialized growth medium containing GreenScreen HC cells. The micro-plates were covered with a breathable membrane and incubated at 37° C. with 5% $CO_2$ and 95% humidity for 48 hours. The plates were analyzed at 24 hour and 48 hour time points using a microplate reader that provides measurements of light absorbance and fluorescence for cells and solutions in the micro-plate wells. Absorbance is proportional to cell proliferation, which was lowered by toxic analytes, and fluorescence is proportional to the activity of the cell's DNA repair system, which is increased by genotoxic analytes. Fluorescence was normalized to the absorbance signal to correct for variation in cell yield caused by cytotoxicity. The GreenScreen HC assay has automatic compensation for a test compound's auto-fluorescence by the use of the non-fluorescent control strain, fluorescence data (per cell) from which are subtracted from those of the test strain. In cases of more intense test article auto-fluorescence (automatically flagged in the data analysis template) a fluorescence polarization (FP) data collection protocol is then employed. Essentially, this exploits the high fluorescence anisotropy of GFP to discriminate GFP fluorescence from test compound auto-fluorescence. FP data were collected by illuminating each microplate well with parallel polarised light and measuring fluorescence intensity both parallel (Ipara) and perpendicular (Iperp) to the excitation light. The fluorescence intensity used for data analysis is the difference between these measurements (Ipara−Iperp), which is large for GFP and disproportionately small for auto-fluorescent test molecules that are commonly much smaller in size and with a low fluorescence anisotropy. There was no observed genotoxicity or cytotoxicity associated with the humanized antibody in healthy human cells as determined by a Cyprotex GreenScreen assay.

Example 8

Assessment of Stability, Deamidation and Oxidation of Humanized Antibody

Additional properties of any of the humanized antibodies of Example 2 (any one or more of which may be improved relative to the parent, murine antibody) are stability, deamidation, and oxidation. Additionally or alternatively, any one or more of these properties may, independently, also be better for any of the humanized antibodies relative to other humanized antibodies generated from this same murine parent, such as the humanized antibody of Example 1. Note that although a humanized antibody suitable for research, diagnostic, or therapeutic use may have one or more improved properties, relative to its murine parent antibody and/or relative to another humanized antibody, it may not. For example, a suitable humanized antibody may simply be comparable or show only minimal or a non-significant reduction in a particular parameter versus the murine parent. Moreover, some properties may be improved while others are merely comparable or not reduced in a way that meaningfully impairs the use of the antibody.

To address the question of whether any of the humanized antibodies of Example 2 are associated with improved stability, deamidation characteristics, and/or oxidation characteristics as compared to either or both of the murine, parent, 3E10 antibody and one or more other humanized antibodies (such as the humanized antibody of Example 1), the following assays may be performed. These assays are exemplary, and other available assays may also be utilized. We also note that, in addition to full length antibodies, antibody fragments comprising these various combinations of humanized heavy and light chain variable domains are also contemplated and taught herein. Such antibody fragments, although not provided on a human Ig backbone, can also be referred to a humanized. Suitable fragments include, for example, an scFv comprising a VH and VL interconnected via a linker or an Fab. The properties of antibodies and antibody fragments can be readily evaluated using any of the methods described herein or other available methods.

Following a period of incubation (e.g., 6 hours, 24 hours, 1 week) at a given temperature (e.g., 0° C., 4° C., 25° C.) in a given solution (e.g., a saline solution), the stability, the deamidation levels and the oxidation levels of any one or more of the humanized antibodies of Example 2 or antibody fragments thereof, the murine, parental antibody, and optionally, one or more additional humanized antibodies generated from the same murine parental antibody (such as the humanized antibodies of Example 1) may be assessed.

In order to test the stability of humanized and murine antibodies, the commercially available ProteoStat™ Thermal shift stability assay (Enzo, Farmingdale, N.Y.) may be utilized. Other commercially available or routinely performed assays for assessing whether the humanized or murine 3E10 antibodies are properly folded or are degrading in a given solution over time are well known to the skilled worker. If any of the humanized antibodies of Example 2 displays reduced degradation or unfolding as compared to the murine antibody and/or as compared to one or more other humanized antibodies generated from this same parent (such as the humanized antibody of Example 1), this indicates that the humanized antibody of Example 2 is associated with increased stability. In certain embodiments, a humanized antibody may not have increased stability but may have comparable stability, even if slightly reduced.

Deamidation is a chemical reaction in which an amide functional group is removed from an organic molecule, and amino acid deamidation is known to affect the stability and activity of proteins. Examples of amino acids that may be deamidated include asparagine and glutamine. Means to test glutamine deamidation levels of the humanized and murine chimeric control antibodies of Example 2 may include the assays described in Liu, et al., 2008, Rapid Commun Mass Spectrom. (24):4081-8. Means to test the asparagine deamidation levels of the humanized and murine chimeric control antibodies of Example 2 may include any one of several commercially available deamidation assays, such as the ISOQUANT® Isoaspartate Detection Kit (Promega, Madison Wis.) or Dionex UltiMate 3000 Titanium System (Dionex, Sunnyvale, Calif.). Other commercially available or routinely performed assays for assessing whether the humanized or murine chimeric control 3E10 antibodies are deamidated in a given solution over a period of time are well known to the skilled worker. If the humanized antibody displays lower levels of deamidation than the murine control antibody and/or one or more other humanized antibodies generated from this parent (such as the humanized antibody of Example 1), this indicates that the humanized antibody is associated with reduced deamidation as compared to the murine antibody.

Amino acid oxidation is known to affect the structure, activity, and rate of degradation of proteins. Examples of amino acids that may be oxidized include methionine, cysteine, and tryptophan. Means to test the tryptophan oxidation levels of any of the humanized and murine chimeric antibodies of Example 2 may include the assays discussed in Hensel et al., 2011, PLoS One, 6(3): e17708. Means to test the methionine oxidation levels of the humanized and murine antibodies of Example 2 may include any one of several commercially available oxidation assays, such as the Methionine Sulfoxide Immunoblotting Kit (Cayman Chemical, Ann Arbor, Mich.). Other commercially available or routinely performed assays for assessing whether the humanized or murine chimeric 3E10 antibodies are oxidized in a given solution over a period of time are well known to the skilled worker. If the humanized antibody displays lower levels of oxidation than the murine chimeric control antibody, this indicates that the humanized antibody is associated with reduced oxidation as compared to the murine chimeric control antibody and/or one or more other humanized antibodies.

Amino acid oxidation, deamidation and other possible chemical changes also may be monitored by peptide mapping. Specifically, the humanized and murine antibodies are digested with an endoprotease, such as Endoproteinase Lys-C (Wako Pure Chemicals), in the presence of dithiothreitol and the resulting peptide fragments are separated by reverse-phase HPLC. See generally, Kalgahtgi, K., & Horvath, C. "Rapid Peptide Mapping by High Performance Liquid Chromatography", J. Chromatography 443, 343-354 (1988).

Example 9

Assessment of Glycosylation and Lipidation of the Humanized Antibody

Different proteins are often subject to different post-translational modifications in a cell, depending on a protein's primary amino acid sequence and its corresponding structure. The presence or absence of particular post-translational modifications may result in any of the humanized antibodies of Example 2 having one or more improved properties in comparison to the parental, murine antibody and/or in comparison to one or more other humanized antibodies generated from the same murine, parental antibody (such as the humanized antibody of Example 1). Additional properties of the humanized antibody, any one or more of which may be improved relative to the parent, murine antibody are glycosylation state and lipidation state. Additionally or alternatively, any one or more of these properties may, independently, also be better for this humanized antibody relative to other humanized antibodies based on this same murine parent (such as the humanized antibody of Example 1). To address the question of whether any of the humanized antibodies of Example 2 are associated with different glycosylation or lipidation patterns as compared to the murine, parental 3E10 antibody and/or in comparison to one or more other humanized antibodies based on this same parent (such as the humanized antibody of Example 1), several standard assays may be employed. These assays are exemplary, and other available assays may also be utilized.

Glycosylation patterns and glycosylation levels can affect antibody clearance and activity in a patient (Wright et al., 1997, Trends in Biotechnology, 15(1): 26-32). Indeed, antibodies with reduced glycosylation have been shown to be associated with reduced half-life and bioactivity (Naoko, 2009, MAbs. 2009, 1(3): 230-236). In addition, glycosylation also can significantly affect the in vivo safety and efficacy profiles of monoclonal antibodies. For assessing glycosylation levels or patterns, the humanized and murine antibodies may be produced in a given cell line (e.g., CHO cells) in a manner similar to that described in Example 2. For experimental control purposes, the humanized and murine antibodies are produced in the same type of cell. After purifying the humanized and murine antibodies produced by the cells, the antibodies are subjected to any one of the routinely used or commercially available glycosylation analysis protocols, such as the protocols of Mohammad, 2002, Protein Protocols Handbook, pages 795-802; standard procedures involving mass spectrometry and/or the protocols of the HPLC; GLYCO-PRO™ (Sigma-Aldrich); Qproteome Total Glycoprotein Kit™ (Qiagen, Valencia, Calif.). In order to identify the exact sites of glycosylation in a protein sequence, standard endoproteinase cleavage may be performed (e.g. tryptic digest) followed by analysis by LC/MS or HILIC-MS/MS, similar to the protocols described in Zauner G et al., 2010, J Sep Sci., 33:903-10. Other commercially available assays for assessing the glycosylation patterns are well known to the skilled worker.

If any of the humanized antibodies of Example 2 displays fewer instances of glycosylation than the murine, parent antibody and/or other humanized antibodies generated from this parent (such as the humanized antibody of Example 1), this indicates that the humanized antibody is associated with reduced glycosylation. If the humanized antibody displays a greater number of instances of glycosylation than the murine, parent antibody and/or other humanized antibodies generated from this parent, this indicates that the humanized antibody is associated with increased glycosylation. The assays discussed above may also be used to determine whether the humanized antibody is glycosylated with different glycosylation groups or in a different pattern as compared to the glycosylation patterns observed in the murine antibody. Note that the glycosylation pattern and characteristics may vary depending on the cell line in which the protein is produced. Accordingly, this assessment can be made in one cell line (e.g., a cell type in which one intends to manufacture the protein) or across multiple different cell types to provide information about glycosylation characteristics following production in different cell types. Lipidation levels of a protein may affect the half-life and/or bioactivity of that protein. As such, it may be advantageous to have specific lipidation groups conjugated to the humanized antibodies (or fragments). For assessing lipidation levels or patterns, the humanized and murine antibodies may be produced in a given cell line (e.g., CHO cells) in a manner similar to that described in Example 2. For experimental control purposes, the humanized and murine antibodies are produced in the same type of cell. After purifying the humanized and murine 3E10 antibodies produced by the cells, the antibodies are subjected to any one of a number of commercially available lipidation analysis protocols, such as those described in Gelb et al., 1999, Protein Lipidation Protocols, Humana Press, pages 1-256. Other commercially available assays for assessing the lipidation patterns of the humanized or murine antibodies are well known to the skilled worker. If the lead humanized antibody displays fewer instances of lipidation than the murine, parent antibody and/or than one or more other humanized antibodies generated from the same parent, this indicates that the humanized antibody of Example 2 is associated with reduced lipidation. If the humanized antibody displays a greater number of instances of lipidation than the murine, parent antibody and/or other humanized antibodies, this indicates that the humanized antibody is associated with increased lipidation. The assays discussed above may also be used to determine whether the humanized antibody is lipidated with different lipidation groups or in a different pattern as compared to the lipidation patterns observed in the murine, parent or other humanized antibodies. Note that lipidation and the lipidation pattern and characteristics may vary depending on the cell line in which the protein is produced. Accordingly, this assessment can be made in one cell line (e.g., a cell type in which one intends to manufacture the protein) or across multiple different cell types to provide information about lipidation characteristics following production in different cell types.

Example 10

An Antibody of the Disclosure Conjugated to an MBNL Polypeptide

Conjugates comprising an antibody of the disclosure interconnected (e.g., associated; interconnected) to two different fragments of an MBNL polypeptide were generated. Specifically, the C-terminus of a humanized heavy chain (comprising the amino acid sequence of one of SEQ ID NO: 38, SEQ ID NO: 39 or SEQ ID NO: 10; associated with an IgG1 constant domain) was linked recombinantly (e.g., genetically linked so as to generate a fusion) to the N-terminus of an MBNL fragment (comprising either amino acids 1-253 or amino acids 1-116 of SEQ ID NO: 12) via a linker (SEQ ID NO: 45). A vector comprising a nucleotide sequence encoding this humanized heavy chain-MBNL fusion and a vector comprising a nucleotide sequence encoding a humanized light chain (comprising one of SEQ ID NO: 8 or SEQ ID NO: 40) were expressed together in HEK293 cells and the resulting conjugate produced by the transiently transfected cells was purified from the cell pellet fraction of the cultured cells using a MabSelect SuRe column. Humanized mAb-MBNL polypeptides (comprising either MBNL 1-253 or MBNL 1-116) were detected in the purified samples by means of SDS PAGE. Briefly, HEK293 cells were transiently transfected with each of the foregoing vectors using fectin293 and cultured until harvest. Chimeric polypeptide was recovered from cell pellets which were lysed with either M-PER or 0.1 M $K_2HPO4$+20% glycerol+ 0.1 mM $ZnSO_4$+nuclease+either (i) 1 M arginine, (ii) 1 M arginine+0.8% CHAPS, or (iii) 1 M arginine+0.5 M NaCl. Following solubilization, cell pellet from 50 mL cell culture was purified on a 0.5 mL MabSelect SuRe column. Elution from the column was using a pH gradient with 0.1 M acetic acid+20% glycerol+1 M arginine+0.8% CHAPS (pH 3.6). Dialysis and concentration of the pooled fractions was with 0.1 M $K_2HPO_4$+20% glycerol+1 M arginine+0.8% CHAPS (pH 7.4).

Similarly, a conjugate comprising an Fab of the disclosure conjugated (e.g., associated; interconnected) to an MBNL polypeptide was generated. Specifically, the C-terminus of a humanized heavy chain (comprising the amino acid sequence of one of SEQ SEQ ID NO: 38, SEQ ID NO: 39 or SEQ ID NO: 10 and constant domain comprising IgG2a CH1-IgG1 upper hinge domains) was linked recombinantly (e.g., genetically linked so as to generate a fusion) to the N-terminus of an MBNL fragment (comprising either amino acids 1-253 or amino acids 1-116 of SEQ ID NO: 12) via a linker (SEQ ID NO: 45). A vector comprising a nucleotide sequence encoding this humanized heavy chain-MBNL fusion and a vector comprising a nucleotide sequence encoding a humanized 3E10 light chain (comprising one of SEQ ID NO: 8 or SEQ ID NO: 40) were expressed together in HEK293 cells.

Example 11

An Antibody Fragment of the Disclosure Conjugated to a GAA Polypeptide

A conjugate comprising an antibody fragment of the disclosure associated with (e.g., conjugated to; interconnected) a GAA polypeptide was generated. Specifically, the C-terminus of a humanized heavy chain (comprising the amino acid sequence of one of SEQ ID NO: 38, SEQ ID NO: 39 or SEQ ID NO: 10 and the IgG1 constant domain of the G1m17 allotype) was linked recombinantly to the N-terminus of a GAA polypeptide via a linker (SEQ ID NO: 45). The humanized heavy chain-GAA fusion and humanized light chain (comprising a VL comprising one of SEQ ID NO: 8 or SEQ ID NO: 40) were expressed together in cells and the resulting chimeric polypeptides produced by the transgenic cells were purified by means of Sephadex G100 Purification. Humanized Fab-GAA polypeptides were detected in the purified samples by means of SDS PAGE. Signal sequences were present at the N-terminal portion of the light chain (signal sequence=SEQ ID NO: 61) or the humanized heavy chain-GAA fusion (signal sequence=SEQ ID NO: 62), but these signal sequences are not present in the final chimeric polypeptide products.

Activity of this conjugate comprising an antigen binding fragment of the disclosure and a GAA polypeptide was tested utilizing a fluorometric plate-based assay which measures the catalysis of a 4-methylumbelliferyl α-D-glucosidase (MU-α-Glu) substrate. Using this assay, it was determined that this antigen binding fragment of the disclosure conjugated to a GAA polypeptide possessed enzymatic activity.

In an additional assay, the ability of this Fab-GAA polypeptide to hydrolyze glycogen was tested in a colorimetric assay. For this assay, the Fab-GAA was diluted to 1 mg/mL, 0.5 mg/mL, or 0.25 mg/mL with pH 4.3 buffer. Five microliters of each of the foregoing diluted Fab-GAA was then added to 30 µL of 0.2 mg/mL glycogen (i.e., 5 µg, 2.5 µg, and 1.25 µg Fab-GAA was added in serial samples) and samples were incubated at 37° C. for 2 hours. Ten microliters of sample was quenched with 10 µL of 0.3M Tris pH 8.0. Glycogen standard from the Abcam assay kit (Abcam Cat# ab65620) was used as a positive control and was diluted to 0.2 mg/mL with 0.1M Na Acetate pH 4.3 buffer, and then further diluted in water to prepare standards having glucose concentrations ranging from 1 mM to 0.031 mM. Twenty microliters of each sample or standard was then added to a 96-well plate. Eighty microliters of glucose assay reagent (from the Glucose assay kit; Sigma Cat# GAGO20-1KT) was added to each well with a multi-channel pipet and the plate was covered and incubated at 37° C. for 30 minutes. Reactions were then quenched with 100 µL of 12N sulfuric acid and samples were read at 540 nm. The intensity of the pink color measured at 540 nm is proportional to the glucose concentration. Given that a function of GAA is hydrolyzing glycogen to glucose, measuring glucose concention is indicative of GAA functional activity (when present as a Fab-GAA conjugate). The Fab-GAA conjugate polypeptide was capable of hydrolyzing glycogen to glucose at all concentrations of Fab-GAA tested. Moreover, its calculated specific activity in this experiment was approximately 330 micromolar/min/mg (e.g., ranging from 306 micromolar/min/mg when FabGAA was present in the reaction mixture at 5 ug; 328 micromolar/min/mg when Fab-GAA was present in the reaction mixture at 2.5 ug; 360 micromolar/min/mg when FabGAA was present in the reaction mixture at 1.25 ug.

Sequence Information

SEQ ID NO: 1—heavy chain variable ($V_H$) domain CDR1 of exemplary 3E10 molecule, in accordance with CDRs as defined by the IMGT system

GFTFSNYG

SEQ ID NO: 2—heavy chain variable ($V_H$) domain CDR2 of exemplary 3E10 molecule, in accordance with CDRs as defined by the IMGT system

ISSGSSTI

SEQ ID NO: 3—heavy chain variable ($V_H$) domain CDR3 of exemplary 3E10 molecule, in accordance with CDRs as defined by the IMGT system

ARRGLLLDY

SEQ ID NO: 4—light chain variable ($V_L$) domain CDR1 of exemplary 3E10 molecule, in accordance with CDRs as defined by the IMGT system

KSVSTSSYSY

SEQ ID NO: 5—light chain variable ($V_L$) domain CDR2 of exemplary 3E10 molecule, in accordance with CDRs as defined by the IMGT system

YAS

SEQ ID NO: 6—light chain variable ($V_L$) domain CDR3 of exemplary 3E10 molecule, in accordance with CDRs as defined by the IMGT system

QHSREFPWT

SEQ ID NO: 7—amino acid sequence of murine 3E10 light chain variable domain ($V_L$) used as parent VL

DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELK

SEQ ID NO: 8—amino acid sequence of humanized 3E10 light chain variable domain (hVL2)

DIQMTQSPSSLSASVGDRVTISCRASKSVSTSSYSYMHWYQQKPEKAPKL

LIKYASYLQSGVPSRFSGSGSGTDFTLTISSLQPEDVATYYCQHSREFPW

TFGAGTKLELK

SEQ ID NO: 9—amino acid sequence of murine 3E10 heavy chain variable domain ($V_H$) used as parent VH

EVQLVESGGGLVKPGGSRKLSCAASGFTFSNYGMHWVRQAPEKGLEWVAY

ISSGSSTIYYADTVKGRFTISRDNAKNTLFLQMTSLRSEDTAMYYCARRG

LLLDYWGQGTTLTVSS

SEQ ID NO: 10—amino acid sequence of humanized 3E10 heavy chain variable domain (hVH3)

EVQLQESGGGVVQPGGSLRLSCAASGFTFSNYGMHWIRQAPGKGLEWVSY

ISSGSSTIYYADSVKGRFTISRDNSKNTLYLQMNSLRSEDTAVYYCARRG

LLLDYWGQGTLVTVSS

SEQ ID NO: 11—amino acid sequence of the human MTM1 protein (NP_000243.1)

ASASTSKYNSHSLENESIKRTSRDGVNRDLTEAVPRLPGETLITDKEVIY

ICPFNGPIKGRVYITNYRLYLRSLETDSSLILDVPLGVISRIEKMGGATS

RGENSYGLDITCKDMRNLRFALKQEGHSRRDMFEILTRYAFPLAHSLPLF

AFLNEEKFNVDGWTVYNPVEEYRRQGLPNHHWRITFINKCYELCDTYPAL

LVVPYRASDDDLRRVATFRSRNRIPVLSWIHPENKTVIVRCSQPLVGMSG

```
KRNKDDEKYLDVIRETNKQISKLTIYDARPSVNAVANKATGGGYESDDAY

HNAELFFLDIHNIHVMRESLKKVKDIVYPNVEESHWLSSLESTHWLEHIK

LVLTGAIQVADKVSSGKSSVLVHCSDGWDRTAQLTSLAMLMLDSFYRSIE

GFEILVQKEWISFGHKFASRIGHGDKNHTDADRSPIFLQFIDCVWQMSKQ

FPTAFEFNEQFLIIILDHLYSCRFGTFLFNCESARERQKVTERTVSLWSL

INSNKEKFKNPFYTKEINRVLYPVASMRHLELWVNYYIRWNPRIKQQQPN

PVEQRYMELLALRDEYIKRLEELQLANSAKLSDPPTSPSSPSQMMPHVQT

HF
```

SEQ ID NO: 12—The amino acid sequence of the human MBNL1 protein, isoform a (GenBank Accession No. NP_066368.2).

```
AVSVTPIRDTKWLTLEVCREFQRGTCSRPDTECKFAHPSKSCQVENGRVI

ACFDSLKGRCSRENCKYLHPPPHLKTQLEINGRNNLIQQKNMAMLAQQMQ

LANAMMPGAPLQPVPMFSVAPSLATNASAAAFNPYLGPVSPSLVPAEILP

TAPMLVTGNPGVPVPAAAAAAAQKLMRTDRLEVCREYQRGNCNRGENDCR

FAHPADSTMIDTNDNTVTVCMDYIKGRCSREKCKYFHPPAHLQAKIKAAQ

YQVNQAAAAQAAATAAAMGIPQAVLPPLPKRPALEKTNGATAVFNTGIFQ

YQQALANMQLQQHTAFLPPGSILCMTPATSVVPMVHGATPATVSAATTSA

TSVPFAATATANQIPIISAEHLTSHKYVTQM
```

SEQ ID NO: 13—The amino acid sequence of the human MBNL1 protein, isoform b (GenBank Accession No. NP_997175.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMGIPQAVLPPLPKRPALEKTNGATAVFNTGIF

QYQQALANMQLQQHTAFLPPVPMVHGATPATVSAATTSATSVPFAATATA

NQIPIISAEHLTSHKYVTQM
```

SEQ ID NO: 14—The amino acid sequence of the human MBNL1 protein, isoform c (GenBank Accession No. NP_997176.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMTQSAVKSLKRPLEATFDLGIPQAVLPPLPKR

PALEKTNGATAVFNTGIFQYQQALANMQLQQHTAFLPPVPMVHGATPATV

SAATTSATSVPFAATATANQIPIISAEHLTSHKYVTQM
```

SEQ ID NO: 15—The amino acid sequence of the human MBNL1 protein, isoform d (GenBank Accession No. NP_997177.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVVCREYQRGNCNRGENDCRFAHPADSTMIDTNDNTV

TVCMDYIKGRCSREKCKYFHPPAHLQAKIKAAQYQVNQAAAAQAAATAAA

MGIPQAVLPPLPKRPALEKTNGATAVFNTGIFQYQQALANMQLQQHTAFL

PPVPMVHGATPATVSAATTSATSVPFAATATANQIPIISAEHLTSHKYVT

QM
```

SEQ ID NO: 16—The amino acid sequence of the human MBNL1 protein, isoform e (GenBank Accession No. NP_997178.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVVCREYQRGNCNRGENDCRFAHPADSTMIDTNDNTV

TVCMDYIKGRCSREKCKYFHPPAHLQAKIKAAQYQVNQAAAAQAAATAAA

MGIPQAVLPPLPKRPALEKTNGATAVFNTGIFQYQQALANMQLQQHTAFL

PPGSILCMTPATSVVPMVHGATPATVSAATTSATSVPFAATATANQIPII

SAEHLTSHKYVTQM
```

SEQ ID NO: 17—The amino acid sequence of the human MBNL1 protein, isoform f (GenBank Accession No. NP_997179.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMFPWCTVLRQPLCPQQQHLPQVFPSLQQPQPT

SPILDASTLLGATSCPAAAGKMIPIISAEHLTSHKYVTQM
```

SEQ ID NO: 18—The amino acid sequence of the human MBNL1 protein, isoform g (GenBank Accession No. NP_997180.1).

```
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMGIPQAVLPPLPKRPALEKTNGATAVFNTGIF

QYQQALANMQLQQHTAFLPPGSILCMTPATSVDTHNICRTSD
```

SEQ ID NO: 19—The amino acid sequence of the human AGL protein, isoform 1 (GenBank Accession No. NP_000019.2)

MGHSKQIRILLLNEMEKLEKTLFRLEQGYELQFRLGPTLQGKAVTVYTNY
PFPGETFNREKFRSLDWENPTEREDDSDKYCKLNLQQSGSFQYYFLQGNE
KSGGGYIVVDPILRVGADNHVLPLDCVTLQTFLAKCLGPFDEWESRLRVA
KESGYNMIHFTPLQTLGLSRSCYSLANQLELNPDFSRPNRKYTWNDVGQL
VEKLKKEWNVICITDVVYNHTAANSKWIQEHPECAYNLVNSPHLKPAWVL
DRALWRFSCDVAEGKYKEKGIPALIENDHHMNSIRKIIWEDIFPKLKLWE
FFQVDVNKAVEQFRRLLTQENRRVTKSDPNQHLTIIQDPEYRRFGCTVDM
NIALTTFIPHDKGPAAIEECCNWFHKRMEELNSEKHRLINYHQEQAVNCL
LGNVFYERLAGHGPKLGPVTRKHPLVTRYFTFPFEEIDFSMEESMIHLPN
KACFLMAHNGWVMGDDPLRNFAEPGSEVYLRRELICWGDSVKLRYGNKPE
DCPYLWAHMKKYTEITATYFQGVRLDNCHSTPLHVAEYMLDAARNLQPNL
YVVAELFTGSEDLDNVFVTRLGISSLIREAMSAYNSHEEGRLVYRYGGEP
VGSFVQPCLRPLMPAIAHALFMDITHDNECPIVHRSAYDALPSTTIVSMA
CCASGSTRGYDELVPHQISVVSEERFYTKWNPEALPSNTGEVNFQSGIIA
ARCAISKLHQELGAKGFIQVYVDQVDEDIVAVTRHSPSIHQSVVAVSRTA
FRNPKTSFYSKEVPQMCIPGKIEEVVLEARTIERNTKPYRKDENSINGTP
DITVEIREHIQLNESKIVKQAGVATKGPNEYIQEIEFENLSPGSVIIFRV
SLDPHAQVAVGILRNHLTQFSPHFKSGSLAVDNADPILKIPFASLASRLT
LAELNQILYRCESEEKEDGGGCYDIPNWSALKYAGLQGLMSVLAEIRPKN
DLGHPFCNNLRSGDWMIDYVSNRLISRSGTIAEVGKWLQAMFFYLKQIPR
YLIPCYFDAILIGAYTTLLDTAWKQMSSFVQNGSTFVKHLSLGSVQLCGV
GKFPSLPILSPALMDVPYRLNEITKEKEQCCVSLAAGLPHFSSGIFRCWG
RDTFIALRGILLITGRYVEARNIILAFAGTLRHGLIPNLLGEGIYARYNC
RDAVWWWLQCIQDYCKMVPNGLDILKCPVSRMYPTDDSAPLPAGTLDQPL
FEVIQEAMQKHMQGIQFRERNAGPQIDRNMKDEGFNITAGVDEETGFVYG
GNRFNCGTWMDKMGESDRARNRGIPATPRDGSAVEIVGLSKSAVRWLLEL
SKKNIFPYHEVTVKRHGKAIKVSYDEWNRKIQDNFEKLFHVSEDPSDLNE
KHPNLVHKRGIYKDSYGASSPWCDYQLRPNFTIAMVVAPELFTTEKAWKA
LEIAEKKLLGPLGMKTLDPDDMVYCGIYDNALDNDNYNLAKGFNYHQGPE
WLWPIGYFLRAKLYFSRLMGPETTAKTIVLVKNVLSRHYVHLERSPWKGL
PELTNENAQYCPFSCETQAWSIATILETLYDL

SEQ ID NO: 20—The amino acid sequence of the human AGL protein, isoform 2 (GenBank Accession No. NM_000645.2)

MSLLTCAFYLGYELQFRLGPTLQGKAVTVYTNYPFPGETFNREKFRSLDW
ENPTEREDDSDKYCKLNLQQSGSFQYYFLQGNEKSGGGYIVVDPILRVGA
DNHVLPLDCVTLQTFLAKCLGPFDEWESRLRVAKESGYNMIHFTPLQTLG
LSRSCYSLANQLELNPDFSRPNRKYTWNDVGQLVEKLKKEWNVICITDVV
YNHTAANSKWIQEHPECAYNLVNSPHLKPAWVLDRALWRFSCDVAEGKYK
EKGIPALIENDHHMNSIRKIIWEDIFPKLKLWEFFQVDVNKAVEQFRRLL
TQENRRVTKSDPNQHLTIIQDPEYRRFGCTVDMNIALTTFIPHDKGPAAI
EECCNWFHKRMEELNSEKHRLINYHQEQAVNCLLGNVFYERLAGHGPKLG
PVTRKHPLVTRYFTFPFEEIDFSMEESMIHLPNKACFLMAHNGWVMGDDP
LRNFAEPGSEVYLRRELICWGDSVKLRYGNKPEDCPYLWAHMKKYTEITA
TYFQGVRLDNCHSTPLHVAEYMLDAARNLQPNLYVVAELFTGSEDLDNVF
VTRLGISSLIREAMSAYNSHEEGRLVYRYGGEPVGSFVQPCLRPLMPAIA
HALFMDITHDNECPIVHRSAYDALPSTTIVSMACCASGSTRGYDELVPHQ
ISVVSEERFYTKWNPEALPSNTGEVNFQSGIIAARCAISKLHQELGAKGF
IQVYVDQVDEDIVAVTRHSPSIHQSVVAVSRTAFRNPKTSFYSKEVPQMC
IPGKIEEVVLEARTIERNTKPYRKDENSINGTPDITVEIREHIQLNESKI
VKQAGVATKGPNEYIQEIEFENLSPGSVIIFRVSLDPHAQVAVGILRNHL
TQFSPHFKSGSLAVDNADPILKIPFASLASRLTLAELNQILYRCESEEKE
DGGGCYDIPNWSALKYAGLQGLMSVLAEIRPKNDLGHPFCNNLRSGDWMI
DYVSNRLISRSGTIAEVGKWLQAMFFYLKQIPRYLIPCYFDAILIGAYTT
LLDTAWKQMSSFVQNGSTFVKHLSLGSVQLCGVGKFPSLPILSPALMDVP
YRLNEITKEKEQCCVSLAAGLPHFSSGIFRCWGRDTFIALRGILLITGRY
VEARNIILAFAGTLRHGLIPNLLGEGIYARYNCRDAVWWWLQCIQDYCKM
VPNGLDILKCPVSRMYPTDDSAPLPAGTLDQPLFEVIQEAMQKHMQGIQF
RERNAGPQIDRNMKDEGFNITAGVDEETGFVYGGNRFNCGTWMDKMGESD
RARNRGIPATPRDGSAVEIVGLSKSAVRWLLELSKKNIFPYHEVTVKRHG
KAIKVSYDEWNRKIQDNFEKLFHVSEDPSDLNEKHPNLVHKRGIYKDSYG
ASSPWCDYQLRPNFTIAMVVAPELFTTEKAWKALEIAEKKLLGPLGMKTL
DPDDMVYCGIYDNALDNDNYNLAKGFNYHQGPEWLWPIGYFLRAKLYFSR
LMGPETTAKTIVLVKNVLSRHYVHLERSPWKGLPELTNENAQYCPFSCET
QAWSIATILETLYDL

SEQ ID NO: 21—The amino acid sequence of the human AGL protein, isoform 3 (GenBank Accession No. NM_000646.2)

MAPILSINLFIGYELQFRLGPTLQGKAVTVYTNYPFPGETFNREKFRSLD
WENPTEREDDSDKYCKLNLQQSGSFQYYFLQGNEKSGGGYIVVDPILRVG
ADNHVLPLDCVTLQTFLAKCLGPFDEWESRLRVAKESGYNMIHFTPLQTL
GLSRSCYSLANQLELNPDFSRPNRKYTWNDVGQLVEKLKKEWNVICITDV
VYNHTAANSKWIQEHPECAYNLVNSPHLKPAWVLDRALWRFSCDVAEGKY
KEKGIPALIENDHHMNSIRKIIWEDIFPKLKLWEFFQVDVNKAVEQFRRL
LTQENRRVTKSDPNQHLTIIQDPEYRRFGCTVDMNIALTTFIPHDKGPAA
IEECCNWFHKRMEELNSEKHRLINYHQEQAVNCLLGNVFYERLAGHGPKL
GPVTRKHPLVTRYFTFPFEEIDFSMEESMIHLPNKACFLMAHNGWVMGDD
PLRNFAEPGSEVYLRRELICWGDSVKLRYGNKPEDCPYLWAHMKKYTEIT
ATYFQGVRLDNCHSTPLHVAEYMLDAARNLQPNLYVVAELFTGSEDLDNV

FVTRLGISSLIREAMSAYNSHEEGRLVYRYGGEPVGSFVQPCLRPLMPAI

AHALFMDITHDNECPIVHRSAYDALPSTTIVSMACCASGSTRGYDELVPH

QISVVSEERFYTKWNPEALPSNTGEVNFQSGIIAARCAISKLHQELGAKG

FIQVYVDQVDEDIVAVTRHSPSIHQSVVAVSRTAFRNPKTSFYSKEVPQM

CIPGKIEEVVLEARTIERNTKPYRKDENSINGTPDITVEIREHIQLNESK

IVKQAGVATKGPNEYIQEIEFENLSPGSVIIFRVSLDPHAQVAVGILRNH

LTQFSPHFKSGSLAVDNADPILKIPFASLASRLTLAELNQILYRCESEEK

EDGGGCYDIPNWSALKYAGLQGLMSVLAEIRPKNDLGHPFCNNLRSGDWM

IDYVSNRLISRSGTIAEVGKWLQAMFFYLKQIPRYLIPCYFDAILIGAYT

TLLDTAWKQMSSFVQNGSTFVKHLSLGSVQLCGVGKFPSLPILSPALMDV

PYRLNEITKEKEQCCVSLAAGLPHFSSGIFRCWGRDTFIALRGILLITGR

YVEARNIILAFAGTLRHGLIPNLLGEGIYARYNCRDAVWWWLQCIQDYCK

MVPNGLDILKCPVSRMYPTDDSAPLPAGTLDQPLFEVIQEAMQKHMQGIQ

FRERNAGPQIDRNMKDEGFNITAGVDEETGFVYGGNRFNCGTWMDKMGES

DRARNRGIPATPRDGSAVEIVGLSKSAVRWLLELSKKNIFPYHEVTVKRH

GKAIKVSYDEWNRKIQDNFEKLFHVSEDPSDLNEKHPNLVHKRGIYKDSY

GASSPWCDYQLRPNFTIAMVVAPELFTTEKAWKALEIAEKKLLGPLGMKT

LDPDDMVYCGIYDNALDNDNYNLAKGFNYHQGPEWLWPIGYFLRAKLYFS

RLMGPETTAKTIVLVKNVLSRHYVHLERSPWKGLPELTNENAQYCPFSCE

TQAWSIATILETLYDL

SEQ ID NO: 22=full-length, immature GAA amino acid sequence (952 amino acids; signal sequence indicated in bold/underline)

<u>MGVRHPPCSHRLLAVCALVSLATAALLGHILLHDFLLVPRELSGSSPVLE</u>

<u>ETHPAH</u>QQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPVEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKVLDICVSLLMGEQFLVS

WC

SEQ ID NO: 23=full-length, immature GAA amino acid sequence (957 amino acids; signal sequence indicated in bold/underline)

(GenBank Accession No. EAW89583.1)

<u>MGVRHPPCSHRLLAVCALVSLATAALLGHILLHDFLLVPRELSGSSPVLE</u>

<u>ETHPAH</u>QQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPIEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKARGPRVLDICVSLLMGE

QFLVSWC

SEQ ID NO: 24=exemplary mature GAA amino acid sequence (corresponding to residues 123-782 of SEQ ID NO: 22; one embodiment of a mature GAA polypeptide)

GQPWCFFPPSYPSYKLENLSSSEMGYTATLTRTTPTFFPKDILTLRLDVM

METENRLHFTIKDPANRRYEVPLETPHVHSRAPSPLYSVEFSEEPFGVIV

RRQLDGRVLLNTTVAPLFFADQFLQLSTSLPSQYITGLAEHLSPLMLSTS

WTRITLWNRDLAPTPGANLYGSHPFYLALEDGGSAHGVFLLNSNAMDVVL

QPSPALSWRSTGGILDVYIFLGPEPKSVVQQYLDVVGYPFMPPYWGLGFH

LCRWGYSSTAITRQVVENMTRAHFPLDVQWNDLDYMDSRRDFTFNKDGFR

DFPAMVQELHQGGRRYMMIVDPAISSSGPAGSYRPYDEGLRRGVFITNET

GQPLIGKVWPGSTAFPDFTNPTALAWWEDMVAEFHDQVPFDGMWIDMNEP

SNFIRGSEDGCPNNELENPPYVPGVVGGTLQAATICASSHQFLSTHYNLH

NLYGLTEAIASHRALVKARGTRPFVISRSTFAGHGRYAGHWTGDVWSSWE

QLASSVPEILQFNLLGVPLVGADVCGFLGNTSEELCVRWTQLGAFYPFMR

NHNSLLSLPQEPYSFSEPAQQAMRKALTLRYALLPHLYTLFHQAHVAGET

-continued
VARPLFLEFPKDSSTWTVDHQLLWGEALLITPVLQAGKAEVTGYFPLGTW

YDLQTVPVEA

SEQ ID NO: 25=exemplary mature GAA amino acid sequence (corresponding to residues 288-782 of SEQ ID NO: 22; one embodiment of a mature GAA polypeptide)

GANLYGSHPFYLALEDGGSAHGVFLLNSNAMDVVLQPSPALSWRSTGGIL

DVYIFLGPEPKSVVQQYLDVVGYPFMPPYWGLGFHLCRWGYSSTAITRQV

VENMTRAHFPLDVQWNDLDYMDSRRDFTFNKDGFRDFPAMVQELHQGGRR

YMMIVDPAISSSGPAGSYRPYDEGLRRGVFITNETGQPLIGKVWPGSTAF

PDFTNPTALAWWEDMVAEFHDQVPFDGMWIDMNEPSNFIRGSEDGCPNNE

LENPPYVPGVVGGTLQAATICASSHQFLSTHYNLHNLYGLTEAIASHRAL

VKARGTRPFVISRSTFAGHGRYAGHWTGDVWSSWEQLASSVPEILQFNLL

GVPLVGADVCGFLGNTSEELCVRWTQLGAFYPFMRNHNSLLSLPQEPYSF

SEPAQQAMRKALTLRYALLPHLYTLFHQAHVAGETVARPLFLEFPKDSST

WTVDHQLLWGEALLITPVLQAGKAEVTGYFPLGTWYDLQTVPVEA

SEQ ID NO: 26—Exemplary GAA polypeptide comprising mature GAA (residues 61-952; one embodiment of a GAA polypeptide)

SRPGPRDAQAHPGRPRAVPTQCDVPPNSRFDCAPDKAITQEQCEARGCCY

IPAKQGLQGAQMGQPWCFFPPSYPSYKLENLSSSEMGYTATLTRTTPTFF

PKDILTLRLDVMMETENRLHFTIKDPANRRYEVPLETPHVHSRAPSPLYS

VEFSEEPFGVIVRRQLDGRVLLNTTVAPLFFADQFLQLSTSLPSQYITGL

AEHLSPLMLSTSWTRITLWNRDLAPTPGANLYGSHPFYLALEDGGSAHGV

FLLNSNAMDVVLQPSPALSWRSTGGILDVYIFLGPEPKSVVQQYLDVVGY

PFMPPYWGLGFHLCRWGYSSTAITRQVVENMTRAHFPLDVQWNDLDYMDS

RRDFTFNKDGFRDFPAMVQELHQGGRRYMMIVDPAISSSGPAGSYRPYDE

GLRRGVFITNETGQPLIGKVWPGSTAFPDFTNPTALAWWEDMVAEFHDQV

PFDGMWIDMNEPSNFIRGSEDGCPNNELENPPYVPGVVGGTLQAATICAS

SHQFLSTHYNLHNLYGLTEAIASHRALVKARGTRPFVISRSTFAGHGRYA

GHWTGDVWSSWEQLASSVPEILQFNLLGVPLVGADVCGFLGNTSEELCVR

WTQLGAFYPFMRNHNSLLSLPQEPYSFSEPAQQAMRKALTLRYALLPHLY

TLFHQAHVAGETVARPLFLEFPKDSSTWTVDHQLLWGEALLITPVLQAGK

AEVTGYFPLGTWYDLQTVPVEALGSLPPPPAAPREPAIHSEGQWVTLPAP

LDTINVHLRAGYIIPLQGPGLTTTESRQQPMALAVALTKGGEARGELFWD

DGESLEVLERGAYTQVIFLARNNTIVNELVRVTSEGAGLQLQKVTVLGVA

TAPQQVLSNGVPVSNFTYSPDTKVLDICVSLLMGEQFLVSWC

SEQ ID NO: 27—Exemplary GAA polypeptide comprising mature GAA (residues 67-952; one embodiment of a GAA polypeptide)

DAQAHPGRPRAVPTQCDVPPNSRFDCAPDKAITQEQCEARGCCYIPAKQG

LQGAQMGQPWCFFPPSYPSYKLENLSSSEMGYTATLTRTTPTFFPKDILT

-continued
LRLDVMMETENRLHFTIKDPANRRYEVPLETPHVHSRAPSPLYSVEFSEE

PFGVIVRRQLDGRVLLNTTVAPLFFADQFLQLSTSLPSQYITGLAEHLSP

LMLSTSWTRITLWNRDLAPTPGANLYGSHPFYLALEDGGSAHGVFLLNSN

AMDVVLQPSPALSWRSTGGILDVYIFLGPEPKSVVQQYLDVVGYPFMPPY

WGLGFHLCRWGYSSTAITRQVVENMTRAHFPLDVQWNDLDYMDSRRDFTF

NKDGFRDFPAMVQELHQGGRRYMMIVDPAISSSGPAGSYRPYDEGLRRGV

FITNETGQPLIGKVWPGSTAFPDFTNPTALAWWEDMVAEFHDQVPFDGMW

IDMNEPSNFIRGSEDGCPNNELENPPYVPGVVGGTLQAATICASSHQFLS

THYNLHNLYGLTEAIASHRALVKARGTRPFVISRSTFAGHGRYAGHWTGD

VWSSWEQLASSVPEILQFNLLGVPLVGADVCGFLGNTSEELCVRWTQLGA

FYPFMRNHNSLLSLPQEPYSFSEPAQQAMRKALTLRYALLPHLYTLFHQA

HVAGETVARPLFLEFPKDSSTWTVDHQLLWGEALLITPVLQAGKAEVTGY

FPLGTWYDLQTVPVEALGSLPPPPAAPREPAIHSEGQWVTLPAPLDTINV

HLRAGYIIPLQGPGLTTTESRQQPMALAVALTKGGEARGELFWDDGESLE

VLERGAYTQVIFLARNNTIVNELVRVTSEGAGLQLQKVTVLGVATAPQQV

LSNGVPVSNFTYSPDTKVLDICVSLLMGEQFLVSWC

SEQ ID NO: 28—"AGIH"

AGIH

SEQ ID NO: 29—"SAGIH"

SAGIH

SEQ ID NO: 30—linker sequence "GS3"

GGGGSGGGGSGGGGS

SEQ ID NO: 31—linker sequence "GSTS"

GSTSGSGKSSEGKG

SEQ ID NO: 32—heavy chain variable domain CDR1 of VH (as that VH is defined with reference to SEQ ID NO: 9), in accordance with CDRs as defined by Kabat

NYGMH

SEQ ID NO: 33—heavy chain variable domain CDR2 of VH (as that VH is defined with reference to SEQ ID NO: 9), in accordance with CDRs as defined by Kabat

YISSGSSTIYYADTVKG

SEQ ID NO: 34—heavy chain variable domain CDR3 of VH (as that VH is defined with reference to SEQ ID NO: 9), in accordance with CDRs as defined by Kabat

RGLLLDY

SEQ ID NO: 35—light chain variable domain CDR1 of VL (as that VL is defined with reference to SEQ ID NO: 7), in accordance with CDRs as defined by Kabat

RASKSVSTSSYSYMH

SEQ ID NO: 36—light chain variable domain CDR2 of VL (as that VL is defined with reference to SEQ ID NO: 7), in accordance with CDRs as defined by Kabat

YASYLES

SEQ ID NO: 37—light chain variable domain CDR3 of VL (as that VL is defined with reference to SEQ ID NO: 7), in accordance with CDRs as defined by Kabat

QHSREFPWT

SEQ ID NO: 38—amino acid sequence of humanized 3E10 heavy chain (hVH1)

EVQLVQSGGGLIQPGGSLRLSCAASGFTFSNYGMHWVRQAPGKGLEWVSY
ISSGSSTIYYADSVKGRFTISRDNSKNTLYLQMNSLRAEDTAVYYCARRG
LLLDYWGQGTTVTVSS

SEQ ID NO: 39—amino acid sequence of humanized 3E10 heavy chain (hVH2)

EVQLVESGGGLIQPGGSLRLSCAASGFTFSNYGMHWVRQAPGKGLEWVSY
ISSGSSTIYYADSVKGRFTISRDNSKNTLYLQMTSLRAEDTAVYYCARRG
LLLDYWGQGTTLTVSS

SEQ ID NO: 40—amino acid sequence of humanized 3E10 light chain (hVL1)

DIQMTQSPSSLSASVGDRVTITCRASKSVSTSSYSYLAWYQQKPEKAPKL
LIKYASYLQSGVPSRFSGSGSGTDFTLTISSLQPEDFATYYCQHSREFPW
TFGAGTKLELK

SEQ ID NO: 41—amino acid sequence of humanized 3E10 light chain

DIVLTQSPASLAVSPGQRATITCRASKSVSTSSYSYMHWYQQKPGQPPKL
LIYYASYLESGVPARFSGSGSGTDFTLTINPVEANDTANYYCQHSREFPW
TFGQGTKVEIK

SEQ ID NO: 42—amino acid sequence of humanized 3E10 heavy chain

EVQLVESGGGLVQPGGSLRLSCSASGFTFSNYGMHWVRQAPGKGLEYVSY
ISSGSSTIYYADTVKGRFTISRDNSKNTLYLQMSSLRAEDTAVYYCVKRG
LLLDYWGQGTLVTVSS

SEQ ID NO: 43—Humanized Fv3E10

DIVLTQSPASLAVSPGQRATITCRASKSVSTSSYSYMHWYQQKPGQPPKL
LIYYASYLESGVPARFSGSGSGTDFTLTINPVEANDTANYYCQHSREFPW
TFGQGTKVEIKGGGGSGGGGSGGGGSEVQLVESGGGLVQPGGSLRLSCSA
SGFTFSNYGMHWVRQAPGKGLEYVSYISSGSSTIYYADTVKGRFTISRDN
SKNTLYLQMSSLRAEDTAVYYCVKRGLLLDYWGQGTLVTVSS

SEQ ID NO: 44—Exemplary GAA polypeptide comprising mature GAA (residues 70-952; one embodiment of a GAA polypeptide)

AHPGRPRAVPTQCDVPPNSRFDCAPDKAITQEQCEARGCCYIPAKQGLQG
AQMGQPWCFFPPSYPSYKLENLSSSEMGYTATLTRTTPTFFPKDILTLRL
DVMMETENRLHFTIKDPANRRYEVPLETPHVHSRAPSPLYSVEFSEEPFG
VIVRRQLDGRVLLNTTVAPLFFADQFLQLSTSLPSQYITGLAEHLSPLML
STSWTRITLWNRDLAPTPGANLYGSHPFYLALEDGGSAHGVFLLNSNAMD
VVLQPSPALSWRSTGGILDVYIFLGPEPKSVVQQYLDVVGYPFMPPYWGL
GFHLCRWGYSSTAITRQVVENMTRAHFPLDVQWNDLDYMDSRRDFTFNKD
GFRDFPAMVQELHQGGRRYMMIVDPAISSSGPAGSYRPYDEGLRRGVFIT
NETGQPLIGKVWPGSTAFPDFTNPTALAWWEDMVAEFHDQVPFDGMWIDM
NEPSNFIRGSEDGCPNNELENPPYVPGVVGGTLQAATICASSHQFLSTHY
NLHNLYGLTEAIASHRALVKARGTRPFVISRSTFAGHGRYAGHWTGDVWS
SWEQLASSVPEILQFNLLGVPLVGADVCGFLGNTSEELCVRWTQLGAFYP
FMRNHNSLLSLPQEPYSFSEPAQQAMRKALTLRYALLPHLYTLFHQAHVA
GETVARPLFLEFPKDSSTWTVDHQLLWGEALLITPVLQAGKAEVTGYFPL
GTWYDLQTVPVEALGSLPPPPAAPREPAIHSEGQWVTLPAPLDTINVHLR
AGYIIPLQGPGLTTTESRQQPMALAVALTKGGEARGELFWDDGESLEVLE
RGAYTQVIFLARNNTIVNELVRVTSEGAGLQLQKVTVLGVATAPQQVLSN
GVPVSNFTYSPDTKVLDICVSLLMGEQFLVSWC

SEQ ID NO: 45—linker sequence

GGSGGGSGGGSGG

SEQ ID NO: 46—full linker region (residues 57-78 of GAA)

HILLLHDFLLVPRELSGSSPVLEETHPAH

SEQ ID NO: 47—His Tag

HHHHHH

SEQ ID NO: 48—Exemplary c-myc Tag

EQKLISEEDL (SEQ ID NO: 24)
SEQ ID NO: 49—heavy chain variable domain CDR2 of certain antibodies of the disclosure, in accordance with CDRs as defined by Kabat

YISSGSSTIYYADSVKG

SEQ ID NO: 50—light chain variable domain CDR1 of certain antibodies of the disclosure, in accordance with CDRs as defined by Kabat

RASKSVSTSSYSYLA

SEQ ID NO: 51—light chain variable domain CDR2 of certain antibodies of the disclosure, in accordance with CDRs as defined by Kabat

YASYLQS

SEQ ID NO: 52—bovine GAA precursor protein (GenBank Accession No. NP_776338.1)

MMRWPPCSRPLLGVCTLLSLALLGHILLHDLEVVPRELRGFSQDEIHQAC
QPGASSPECRGSPRAAPTQCDLPPNSRFDCAPDKGITPQQCEARGCCYMP
AEWPPDAQMGQPWCFFPPSYPSYRLENLTTTETGYTATLTRAVPTFFPKD
IMTLRLDMLMETESRLHFTIKDPANRRYEVPLETPRVYSQAPFTLYSVEF
SEEPFGVVVRRKLDGRVLLNTTVAPLFFADQFLQLSTSLPSQHITGLAEH
LGSLMLSTNWTKITLWNRDIAPEPNVNLYGSHPFYLVLEDGGLAHGVFLL
NSNAMDVVLQPSPALSWRSTGGILDVYIFLGPEPKSVVQQYLDVVGYPFM
PPYWGLGFHLCRWGYSTSAITRQVVENMTRAYFPLDVQWNDLDYMDARRD
FTFNKDHFGDFPAMVQELHQGGRRYIMIVDPAISSSGPAGTYRPYDEGLR
RGVFITNETGQPLIGQVWPGLTAFPDFTNPETLDWWQDMVTEFHAQVPFD
GMWIDMNEPSNFVRGSVDGCPDNSLENPPYLPGVVGGTLRAATICASSHQ
FLSTHYDLHNLYGLTEALASHRALVKARGMRPFVISRSTFAGHGRYSGHW
TGDVWSNWEQLSYSVPEILLFNLLGVPLVGADICGFLGNTSEELCVRWTQ
LGAFYPFMRNHNALNSQPQEPYRFSETAQQAMRKAFTLRYVLLPYLYTLF
HRAHVRGETVARPLFLEFPEDPSTWTVDRQLLWGEALLITPVLEAEKVEV
TGYFPQGTWYDLQTVPMEAFGSLPPPAPLTSVIHSKGQWVTLSAPLDTIN
VHLRAGHIIPMQGPALTTTESRKQHMALAVALTASGEAQGELFWDDGESL
GVLDGGDYTQLIFLAKNNTFVNKLVHVSSEGASLQLRNVTVLGVATAPQQ
VLCNSVPVSNFTFSPDTETLAIPVSLTMGEQFVISWS

SEQ ID NO: 53 Nucleotide sequence encoding murine 3E10 light chain Genbank accession number L34051

GACATTGTGCTGACACAGTCTCCTGCTTCCTTAGCTGTATCTCTGGGGCA
GAGGGCCACCATCTCCTGCAGGGCCAGCAAAAGTGTCAGTACATCTAGCT
ATAGTTACATGCACTGGTACCAACAGAAACCAGGACAGCCACCCAAACTC
CTCATCAAGTATGCATCCTACCTAGAATCTGGGGTTCCTGCCAGGTTCAG
TGGCAGTGGGTCTGGGACAGACTTTCACCTCAACATCCATCCTGTGGAGG
AGGAGGATGCTGCAACATATTACTGTCAGCACAGTAGGGAGTTTCCGTGG
ACGTTCGGTGGAGGCACCAAGCTGGAGTTGAAA

SEQ ID NO: 54 Nucleotide sequence encoding murine heavy chain sequence (Genbank accession number L16982)

GAGGTGCAGCTGGTGGAGTCTGGGGGAGGCTTAGTGAAGCCTGGAGGGTC
CCGGAAACTCTCCTGTGCAGCCTCTGGATTCACTTTCAGTAACTATGGAA
TGCACTGGGTCCGTCAGGCTCCAGAGAAGGGGCTGGAGTGGGTTGCATAC
ATTAGTAGTGGCAGTAGTACCATCTACTATGCAGACACAGTGAAGGGCCG
ATTCACCATCTCCAGAGACAATGCCAAGAACACCCTGTTCCTGCAAATGA
CCAGTCTAAGGTCTGAGGACACAGCCATGTATTACTGTGCAAGGCGGGGG
TTACTACTTGACTACTGGGGCCAAGGCACCACTCTCACAGTCTCCTCA

SEQ ID NO: 55=The amino acid sequence of the human MBNL2 protein, isoform 1 (GenBank Accession No. NP_659002.1)

MALNVAPVRDTKWLTLEVCRQFQRGTCSRSDEECKFAHPPKSCQVENGRV
IACFDSLKGRCSRENCKYLHPPTHLKTQLEINGRNNLIQQKTAAAMLAQQ
MQFMFPGTPLHPVPTFPVGPAIGTNTAISFAPYLAPVTPGVGLVPTEILP
TTPVIVPGSPPVTVPGSTATQKLLRTDKLEVCREFQRGNCARGETDCRFA
HPADSTMIDTSDNTVTVCMDYIKGRCMREKCKYFHPPAHLQAKIKAAQHQ
ANQAAVAAQAAAAAATVMAFPPPGALHPLPKRQALEKSNGTSAVFNPSVLH
YQQALTSAQLQQHAAFIPTGSVLCMTPATSIVPMMHSATSATVSAATTPA
TSVPFAATATANQIILK

SEQ ID NO: 56=The amino acid sequence of the human MBNL2 protein, isoform 3 (GenBank Accession No. NP_997187.1)

MALNVAPVRDTKWLTLEVCRQFQRGTCSRSDEECKFAHPPKSCQVENGRV
IACFDSLKGRCSRENCKYLHPPTHLKTQLEINGRNNLIQQKTAAAMLAQQ
MQFMFPGTPLHPVPTFPVGPAIGTNTAISFAPYLAPVTPGVGLVPTEILP
TTPVIVPGSPPVTVPGSTATQKLLRTDKLEVCREFQRGNCARGETDCRFA
HPADSTMIDTSDNTVTVCMDYIKGRCMREKCKYFHPPAHLQAKIKAAQHQ
ANQAAVAAQAAAAAATVMAFPPPGALHPLPKRQALEKSNGTSAVFNPSVLH
YQQALTSAQLQQHAAFIPTDNSEIISRNGMECQESALRITKHCYCTYYPV
SSSIELPQTAC

SEQ ID NO: 57=The amino acid sequence of the human MBNL3 protein, isoform G (GenBank Accession No. NP_060858.2)

MTAVNVALIRDTKWLTLEVCREFQRGTCSRADADCKFAHPPRVCHVENGR
VVACFDSLKGRCTRENCKYLHPPPHLKTQLEINGRNNLIQQKTAAAMFAQ
QMQLMLQNAQMSSLGSFPMTPSIPANPPMAFNPYIPHPGMGLVPAELVPN
TPVLIPGNPPLAMPGAVGPKLMRSDKLEVCREFQRGNCTRGENDCRYAHP
TDASMIEASDNTVTICMDYIKGRCSREKCKYFHPPAHLQARLKAAHHQMN
HSAASAMALQPGTLQLIPKRSALEKPNGATPVFNPTVFHCQQALTNLQLP

-continued

QPAFIPAGPILCMAPASNIVPMMHGATPTTVSAATTPATSVPFAAPTTGN

QLKF

SEQ ID NO: 58=The amino acid sequence of the human MBNL3 protein, isoform R (GenBank Accession No. NP_597846.1)

MTAVNVALIRDTKWLTLEVCREFQRGTCSRADADCKFAHPPRVCHVENGR

VVACFDSLKGRCTRENCKYLHPPPHLKTQLEINGRNNLIQQKTAAAMFAQ

QMQLMLQNAQMSSLGSFPMTPSIPANPPMAFNPYIPHPGMGLVPAELVPN

TPVLIPGNPPLAMPGAVGPKLMRSDKLEVCREFQRGNCTRGENDCRYAHP

TDASMIEASDNTVTICMDYIKGRCSREKCKYFHPPAHLQARLKAAHHQMN

HSAASAMALTNLQLPQPAFIPAGPILCMAPASNIVPMMHGATPTTVSAAT

TPATSVPFAAPTTGNQIPQLSIDELNSSMFVSQM

SEQ ID NO: 59=Amino acids 1-116 of the human MBNL1 protein, isoform a (GenBank Accession No. NP_066368.2) or isoform b

MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVP

SEQ ID NO: 60—human kappa light chain

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

SEQ ID NO: 61—Exemplary signal sequence

MDMRVPAQLLGLLLLWLRGARC

SEQ ID NO: 62—Exemplary signal sequence

MEFGLSWLFLVAILKGVQC

SEQ ID NO: 63—Exemplary blunt end DNA substrate

5'-GGG TGA ACC TGC AGG TGG GCA AAG ATG TCC-3'

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An antibody or antigen-binding fragment, wherein the antibody or antigen-binding fragment comprises a light chain variable (VL) domain and a heavy chain variable (VH) domain; wherein the VH domain comprises:
   a VH CDR1 having the amino acid sequence of SEQ ID NO: 32;
   a VH CDR2 having the amino acid sequence of SEQ ID NO: 49; and
   a VH CDR3 having the amino acid sequence of SEQ ID NO: 34,
which CDRs are according to the Kabat system;
and the VL comprises:
   a VL CDR1 having the amino acid sequence of SEQ ID NO: 35 or 50;
   a VL CDR2 having the amino acid sequence of SEQ ID NO: 51; and
   a VL CDR3 having the amino acid sequence of SEQ ID NO: 37,
which CDRs are according to the Kabat system;
wherein the antibody or antigen-binding fragment binds DNA.

2. The antibody or antigen binding fragment of claim 1, wherein the VH domain and VL domain are humanized.

3. The antibody or antigen-binding fragment of claim 1, wherein the VL comprises the amino acid sequence set forth in SEQ ID NO: 40.

4. The antibody or antigen-binding fragment of claim 1, wherein the VL comprises the amino acid sequence set forth in SEQ ID NO: 8.

5. The antibody or antigen-binding fragment of claim 1, wherein the $V_H$ domain comprises the amino acid sequence set forth in SEQ ID NO: 39.

6. The antibody or antigen-binding fragment of claim 1, wherein the $V_H$ domain comprises the amino acid sequence set forth in SEQ ID NO: 10.

7. The antibody or antigen-binding fragment of claim 1, wherein the VH comprises the amino acid sequence set forth in SEQ ID NOs: 10, 38 or 39.

8. An antibody or antigen-binding fragment, wherein the antibody or antigen-binding fragment comprises a light chain variable ($V_L$) domain and a heavy chain variable ($V_H$) domain; wherein the $V_L$ domain comprises the amino acid sequence set forth in SEQ ID NO: 8; and the VH domain comprises the amino acid sequence set forth in SEQ ID NO: 10, wherein the antibody or antigen-binding fragment binds DNA and penetrates cells.

9. The antibody or antigen-binding fragment of claim 1, wherein the $V_H$ domain comprises one or more of the following amino acid alterations: V5Q, E6Q, L11V, V12I, K13Q, R18L, K19R, V37I, E42G, A49S, T63S, A75S, F80Y, T84N, S88A, M93V, T111L or L112V, as compared with and numbered with respect to the amino acid sequence of SEQ ID NO: 9.

10. The antibody or antigen-binding fragment of claim 1 wherein the $V_L$ domain comprises one or more of the following amino acid alterations: V3Q, L4M, A9S, A12S, V13A, L15V, Q17D, A19V, S22T, M37L, H38A, G45E, Q46K, P47A, E59Q, A64S, H76T, N78T, H80S, P81S, V82L, E83Q, E84P, A87V, A87F, or G104A, as compared with and numbered with respect to the amino acid sequence of SEQ ID NO: 7.

11. The antibody or antigen-binding fragment of claim 1, which is an scFv.

12. The antibody or antigen-binding fragment of claim 1, which is a Fab'.

13. The antibody or antigen-binding fragment of claim 1, which is a full length antibody comprising a heavy chain constant domain and a light chain constant domain.

14. The antibody or antigen-binding fragment of claim 1, wherein the antibody or antigen-binding fragment is conjugated to a heterologous agent.

15. A composition comprising the antibody or antigen-binding fragment of claim 1 formulated in a physiologically acceptable carrier.

16. The composition of claim 15, wherein the composition is pyrogen free.

* * * * *